US009249456B2

(12) United States Patent
Ehrich et al.

(10) Patent No.: US 9,249,456 B2
(45) Date of Patent: Feb. 2, 2016

(54) BASE SPECIFIC CLEAVAGE OF METHYLATION-SPECIFIC AMPLIFICATION PRODUCTS IN COMBINATION WITH MASS ANALYSIS

(75) Inventors: Mathias Ehrich, San Diego, CA (US); Dirk Johannes Van Den Boom, La Jolla, CA (US)

(73) Assignee: AGENA BIOSCIENCE, INC., San Diego, CA (US)

( * ) Notice: Subject to any disclaimer, the term of this patent is extended or adjusted under 35 U.S.C. 154(b) by 740 days.

(21) Appl. No.: 11/089,805

(22) Filed: Mar. 24, 2005

(65) Prior Publication Data
US 2005/0272070 A1   Dec. 8, 2005

Related U.S. Application Data

(60) Provisional application No. 60/556,632, filed on Mar. 26, 2004.

(51) Int. Cl.
*C12Q 1/68* (2006.01)

(52) U.S. Cl.
CPC ............ *C12Q 1/6848* (2013.01); *C12Q 1/6858* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,762,823 A | 8/1988 | Watanabe et al. |
| 4,826,360 A | 5/1989 | Iwasawa et al. |
| 4,851,018 A | 7/1989 | Lazzari et al. |
| 5,003,059 A | 3/1991 | Brennan |
| 5,079,342 A | 1/1992 | Alizon et al. |
| 5,118,937 A | 6/1992 | Hillenkamp et al. |
| 5,122,457 A | 6/1992 | Reim et al. |
| 5,173,418 A | 12/1992 | Molin et al. |
| 5,210,412 A | 5/1993 | Levis et al. |
| 5,252,478 A | 10/1993 | Margarit y Ros et al. |
| 5,264,563 A | 11/1993 | Huse |
| 5,387,518 A | 2/1995 | Sawayanagi et al. |
| 5,391,490 A | 2/1995 | Varshavsky et al. |
| 5,427,927 A | 6/1995 | Meyer et al. |
| 5,436,150 A | 7/1995 | Chandrasegaran |
| 5,440,119 A | 8/1995 | Labowsky |
| 5,453,247 A | 9/1995 | Beavis et al. |
| 5,453,613 A | 9/1995 | Gray et al. |
| 5,498,545 A | 3/1996 | Vestal |
| 5,503,980 A | 4/1996 | Cantor |
| 5,506,137 A | 4/1996 | Mathur |
| 5,536,649 A | 7/1996 | Fraiser et al. |
| 5,547,835 A | 8/1996 | Koster et al. |
| 5,578,443 A | 11/1996 | Santamaria et al. |
| 5,580,733 A | 12/1996 | Levis et al. |
| 5,604,098 A | 2/1997 | Mead et al. |
| 5,605,798 A | 2/1997 | Koster et al. |
| 5,622,824 A | 4/1997 | Koster |
| 5,631,134 A | 5/1997 | Cantor et al. |
| 5,635,713 A | 6/1997 | Labowsky |
| 5,646,020 A | 7/1997 | Swiggen et al. |
| 5,686,656 A | 11/1997 | Amirav et al. |
| 5,691,141 A | 11/1997 | Koster |
| 5,700,672 A | 12/1997 | Mathur et al. |
| 5,714,330 A | 2/1998 | Brenner et al. |
| 5,753,439 A | 5/1998 | Smith et al. |
| 5,777,324 A | 7/1998 | Hillenkamp |
| 5,786,146 A | 7/1998 | Herman et al. |
| 5,792,664 A | 8/1998 | Chait et al. |
| 5,795,714 A | 8/1998 | Cantor et al. |
| 5,807,522 A | 9/1998 | Brown et al. |
| 5,830,712 A | 11/1998 | Rampersad et al. |
| 5,837,832 A | 11/1998 | Chee et al. |
| 5,843,669 A | 12/1998 | Kaiser et al. |
| 5,849,542 A | 12/1998 | Reeve |
| 5,851,765 A | 12/1998 | Koster |
| 5,853,979 A | 12/1998 | Green et al. |
| 5,858,705 A | 1/1999 | Wei et al. |

(Continued)

FOREIGN PATENT DOCUMENTS

| | | | | |
|---|---|---|---|---|
| AU | 758454 B2 | 3/2003 | | |
| DE | WO03/080863 | * 10/2003 | ............... | C12Q 1/68 |

(Continued)

OTHER PUBLICATIONS

Vaughn et al. (Genetic Analysis: Biomolecular Engineering (1999) vol. 14, pp. 169-175).*
Sakai et al. (American Journal of Human Genetics, 1991, vol. 48, p. 880-888).*
Deng et al. (Cancer Research, 1999, vol. 59, p. 2029-2033).*
Chan et al. (Oncogene, 2003, 22, p. 924-934, IDS reference).*
Rand et al. (Methods, 2002, vol. 2, iss. 27, p. 114-120).*
Friso et al. (Anal Chem, 2002, 74, p. 4526-4531).*

(Continued)

*Primary Examiner* — Stephanie K Mummert
(74) *Attorney, Agent, or Firm* — Grant IP, Inc.

(57) ABSTRACT

Methods, combinations and kits are provided for identifying the methylation state of a target nucleic acid molecule, the methylation state of a nucleotide locus in a target nucleic acid molecule, or for identifying the locus of one or more methylated or unmethylated nucleotides in a target nucleic acid molecule. Methylation state identification is performed by treating a methylated target nucleic acid molecule with a reagent that modifies one or more nucleotides in the target nucleic acid molecule as a function of the methylation state of the target nucleic acid molecule, methylation specifically amplifying treated target nucleic acid molecule, fragmenting amplified products, and detecting one or more fragments to thereby identify the methylation state of a target nucleic acid molecule, the methylation state of a nucleotide locus in a target nucleic acid molecule, or the locus of one or more methylated or unmethylated nucleotides in a target nucleic acid molecule.

27 Claims, 2 Drawing Sheets

(56) References Cited

U.S. PATENT DOCUMENTS

Figure 1:
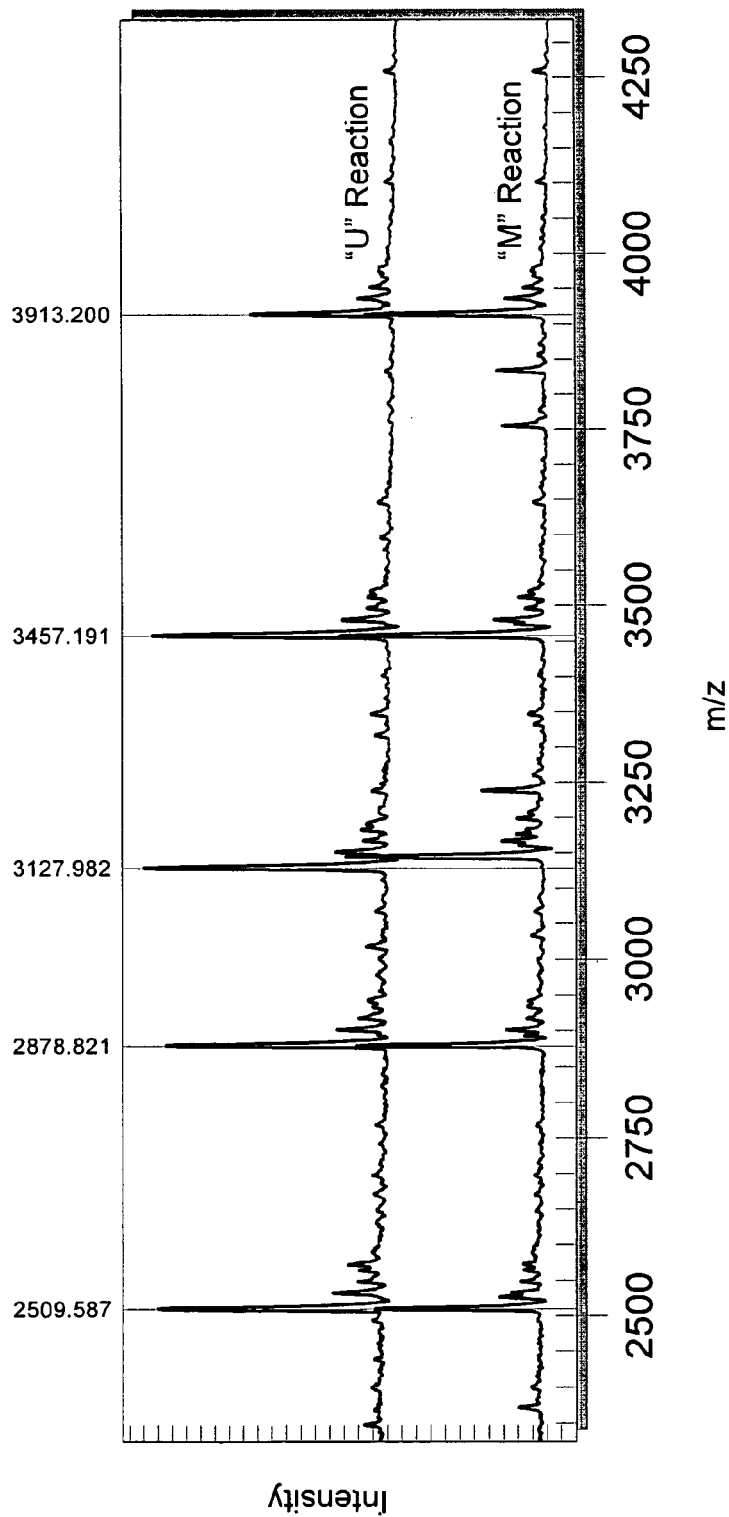

| | | | |
|---|---|---|---|
| 5,861,242 A | 1/1999 | Chee et al. |
| 5,864,137 A | 1/1999 | Becker et al. |
| 5,869,240 A | 2/1999 | Patterson |
| 5,869,242 A | 2/1999 | Kamb |
| 5,871,911 A | 2/1999 | Dahlberg et al. |
| 5,871,991 A | 2/1999 | Elrod et al. |
| 5,872,003 A | 2/1999 | Koster |
| 5,874,283 A | 2/1999 | Harrington et al. |
| 5,885,841 A | 3/1999 | Higgs, Jr. et al. |
| 5,888,795 A | 3/1999 | Hamilton |
| 5,900,481 A | 5/1999 | Lough et al. |
| 5,928,870 A | 7/1999 | Lapidus et al. |
| 5,928,906 A | 7/1999 | Koster et al. |
| 5,932,451 A | 8/1999 | Wang et al. |
| 5,948,902 A | 9/1999 | Honkanen et al. |
| 5,952,176 A | 9/1999 | McCarthy et al. |
| 5,965,363 A | 10/1999 | Monforte et al. |
| 5,975,492 A | 11/1999 | Brenes |
| 5,976,806 A | 11/1999 | Mahajan et al. |
| 6,017,704 A | 1/2000 | Herman et al. |
| 6,022,688 A | 2/2000 | Jurinke et al. |
| 6,024,925 A | 2/2000 | Little et al. |
| 6,043,031 A | 3/2000 | Koster et al. |
| 6,051,378 A | 4/2000 | Monforte et al. |
| 6,054,276 A | 4/2000 | Macavicz |
| 6,059,724 A | 5/2000 | Campell et al. |
| 6,074,823 A | 6/2000 | Koster et al. |
| 6,090,549 A | 7/2000 | Mirzabekov et al. |
| 6,090,558 A | 7/2000 | Butler et al. |
| 6,090,606 A | 7/2000 | Kaiser et al. |
| 6,099,553 A | 8/2000 | Hart et al. |
| 6,104,028 A | 8/2000 | Hunter et al. |
| 6,107,039 A | 8/2000 | Hanna |
| 6,110,426 A | 8/2000 | Shalon et al. |
| 6,111,251 A | 8/2000 | Hillenkamp |
| 6,111,261 A | 8/2000 | Bolza-Schunemann et al. |
| 6,112,161 A | 8/2000 | Dryden et al. |
| 6,113,436 A | 9/2000 | Kuwahara et al. |
| 6,133,436 A | 10/2000 | Koster et al. |
| 6,140,053 A | 10/2000 | Koster et al. |
| 6,146,854 A | 11/2000 | Koster et al. |
| 6,188,064 B1 | 2/2001 | Koster |
| 6,190,865 B1 | 2/2001 | Jendrisak et al. |
| 6,194,144 B1 | 2/2001 | Koster |
| 6,194,180 B1 | 2/2001 | Joyce |
| 6,197,498 B1 | 3/2001 | Koster |
| 6,200,756 B1 | 3/2001 | Herman et al. |
| 6,207,370 B1 | 3/2001 | Little et al. |
| 6,214,556 B1 * | 4/2001 | Olek et al. | 435/6.12 |
| 6,221,605 B1 | 4/2001 | Koster |
| 6,225,450 B1 | 5/2001 | Koster |
| 6,235,478 B1 | 5/2001 | Koster |
| 6,238,871 B1 | 5/2001 | Koster |
| 6,258,538 B1 | 7/2001 | Koster et al. |
| 6,265,167 B1 | 7/2001 | Carmichael et al. |
| 6,265,171 B1 | 7/2001 | Herman et al. |
| 6,265,716 B1 | 7/2001 | Hunter et al. |
| 6,268,131 B1 | 7/2001 | Kang et al. |
| 6,270,835 B1 | 8/2001 | Hunt et al. |
| 6,270,962 B1 | 8/2001 | Chamberlin et al. |
| 6,271,037 B1 | 8/2001 | Chait et al. |
| 6,277,573 B1 | 8/2001 | Koster et al. |
| 6,297,006 B1 | 10/2001 | Drmanac et al. |
| 6,300,076 B1 | 10/2001 | Koster |
| 6,309,833 B1 | 10/2001 | Edman et al. |
| 6,322,970 B1 | 11/2001 | Little et al. |
| 6,326,174 B1 | 12/2001 | Joyce et al. |
| 6,331,427 B1 | 12/2001 | Robison |
| 6,383,775 B1 | 5/2002 | Duff et al. |
| 6,423,965 B1 | 7/2002 | Hashimoto et al. |
| 6,423,966 B2 | 7/2002 | Hillenkamp et al. |
| 6,428,955 B1 | 8/2002 | Koster et al. |
| 6,436,635 B1 * | 8/2002 | Fu et al. | 435/7.24 |
| 6,440,705 B1 | 8/2002 | Stanton, Jr. et al. |
| 6,475,736 B1 | 11/2002 | Stanton, Jr. |
| 6,475,807 B1 | 11/2002 | Geysen et al. |
| 6,500,621 B2 | 12/2002 | Koster |
| 6,522,477 B2 | 2/2003 | Anhalt |
| 6,537,746 B2 | 3/2003 | Arnold et al. |
| 6,558,902 B1 | 5/2003 | Hillenkamp |
| 6,566,055 B1 | 5/2003 | Monforte et al. |
| 6,569,385 B1 | 5/2003 | Little et al. |
| 6,589,485 B2 | 7/2003 | Koster |
| 6,602,662 B1 | 8/2003 | Koster et al. |
| 6,884,586 B2 | 4/2005 | Van Ness |
| 6,994,960 B1 | 2/2006 | Foote et al. |
| 6,994,969 B1 | 2/2006 | Zabeau et al. |
| 7,332,275 B2 * | 2/2008 | Braun et al. | 435/6.11 |
| 7,608,394 B2 | 10/2009 | van den Boom et al. |
| 7,820,378 B2 | 10/2010 | van den Boom et al. |
| 2001/0008615 A1 | 7/2001 | Little et al. |
| 2002/0009394 A1 | 1/2002 | Koster et al. |
| 2002/0042112 A1 | 4/2002 | Koster et al. |
| 2002/0120127 A1 | 8/2002 | Church et al. |
| 2002/0155587 A1 | 10/2002 | Opalsky et al. |
| 2003/0013099 A1 | 1/2003 | Lasek et al. |
| 2003/0017483 A1 | 1/2003 | Ecker et al. |
| 2003/0027169 A1 | 2/2003 | Zhang et al. |
| 2003/0082600 A1 | 5/2003 | Olek et al. |
| 2003/0087235 A1 | 5/2003 | Darikee et al. |
| 2003/0129589 A1 | 7/2003 | Koster et al. |
| 2003/0180748 A1 | 9/2003 | Braun et al. |
| 2003/0180749 A1 | 9/2003 | Braun et al. |
| 2003/0180779 A1 | 9/2003 | Lofton-Day et al. |
| 2003/0190644 A1 | 10/2003 | Braun et al. |
| 2004/0014101 A1 | 1/2004 | Liu et al. |
| 2004/0029258 A1 | 2/2004 | Heaney et al. |
| 2004/0102905 A1 | 5/2004 | Adorjan et al. |
| 2004/0253141 A1 | 12/2004 | Schembri et al. |
| 2005/0009053 A1 | 1/2005 | Boecker et al. |
| 2005/0009059 A1 | 1/2005 | Shapero |
| 2005/0019762 A1 | 1/2005 | Olek |
| 2005/0026183 A1 | 2/2005 | Fan et al. |
| 2005/0064406 A1 | 3/2005 | Zabarovsky |
| 2005/0064428 A1 | 3/2005 | Berlin |
| 2005/0069879 A1 | 3/2005 | Berlin |
| 2005/0089904 A1 | 4/2005 | Beaulieu et al. |
| 2005/0112590 A1 | 5/2005 | van den Boom et al. |
| 2005/0153316 A1 | 7/2005 | Jeddeloh |
| 2005/0153347 A1 | 7/2005 | Shapero |
| 2005/0164193 A1 * | 7/2005 | Berlin | 435/6 |
| 2005/0164246 A1 * | 7/2005 | Fan et al. | 435/6 |
| 2005/0272070 A1 | 12/2005 | Ehrich et al. |
| 2006/0073501 A1 | 4/2006 | van den Boom et al. |
| 2006/0210992 A1 | 9/2006 | van den Boom et al. |
| 2006/0252061 A1 | 11/2006 | Zabeau et al. |

FOREIGN PATENT DOCUMENTS

| | | |
|---|---|---|
| EP | 0103677 | 3/1984 |
| EP | 0269520 | 1/1988 |
| EP | 0296781 | 6/1988 |
| EP | 0299652 | 7/1988 |
| EP | 0332435 | 9/1989 |
| EP | 0395481 | 4/1990 |
| EP | 0534858 | 3/1993 |
| EP | 0596205 | 5/1994 |
| EP | 0655501 | 5/1995 |
| EP | 1197567 | 4/2002 |
| EP | 1179589 | 12/2002 |
| FR | 2749662 | 12/1997 |
| GB | 2329475 | 8/1998 |
| GB | 2329475 | 3/1999 |
| JP | 2003-245087 | 9/2003 |
| WO | WO9213969 | 8/1992 |
| WO | WO 9315407 | 8/1993 |
| WO | WO 9321592 | 10/1993 |
| WO | WO9400562 | 1/1994 |
| WO | WO 9415219 | 7/1994 |
| WO | WO 9416101 | 7/1994 |
| WO | WO 9421663 | 9/1994 |
| WO | WO 9421822 | 9/1994 |
| WO | WO 9525281 | 9/1995 |
| WO | WO 9629431 | 9/1996 |

(56) References Cited

FOREIGN PATENT DOCUMENTS

| | | |
|---|---|---|
| WO | WO 9632504 | 10/1996 |
| WO | WO 96/36732 | 11/1996 |
| WO | WO 96/36986 | 11/1996 |
| WO | WO 9703210 | 1/1997 |
| WO | WO9708306 | 3/1997 |
| WO | WO 9708308 | 3/1997 |
| WO | WO9733000 | 9/1997 |
| WO | WO 9737041 | 10/1997 |
| WO | WO 9740462 | 10/1997 |
| WO | WO 9742348 | 11/1997 |
| WO | WO 9743617 | 11/1997 |
| WO | WO 97/47766 | 12/1997 |
| WO | WO 98/03684 | 1/1998 |
| WO | WO9812355 | 3/1998 |
| WO | WO 9812734 | 3/1998 |
| WO | WO 98/20453 | 5/1998 |
| WO | WO 9820019 | 5/1998 |
| WO | WO 9820020 | 5/1998 |
| WO | WO 9820166 | 5/1998 |
| WO | WO 9824935 | 6/1998 |
| WO | WO 9833808 | 8/1998 |
| WO | WO 9835609 | 8/1998 |
| WO | WO 98/40520 | 9/1998 |
| WO | WO9854571 | 12/1998 |
| WO | WO 9905323 | 2/1999 |
| WO | WO 9912040 | 3/1999 |
| WO | WO 99/028498 | 6/1999 |
| WO | WO 9931278 | 6/1999 |
| WO | WO 9950447 | 10/1999 |
| WO | WO 9954501 | 10/1999 |
| WO | WO 9957318 | 11/1999 |
| WO | WO 00/18967 | 4/2000 |
| WO | WO 00/22130 | 4/2000 |
| WO | WO0018967 | 4/2000 |
| WO | WO 0031300 | 6/2000 |
| WO | WO 0051053 | 8/2000 |
| WO | WO 0056446 | 9/2000 |
| WO | WO 0060361 | 11/2000 |
| WO | WO0066771 | 11/2000 |
| WO | WO 0127857 | 4/2001 |
| WO | WO 01/55455 | 8/2001 |
| WO | WO0213122 | 2/2002 |
| WO | WO0225567 | 3/2002 |
| WO | WO 02/37398 | 5/2002 |
| WO | WO 02/086163 | 10/2002 |
| WO | WO02086794 | 10/2002 |
| WO | WO 02101353 | 12/2002 |
| WO | WO 0300926 | 1/2003 |
| WO | WO 0302760 | 1/2003 |
| WO | WO 0331649 | 4/2003 |
| WO | WO 03/038726 | 5/2003 |
| WO | WO 03/044232 | 5/2003 |
| WO | WO 0338121 | 5/2003 |
| WO | WO 03/057909 | 7/2003 |
| WO | WO 03/078657 | 9/2003 |
| WO | WO 03/080863 | 10/2003 |
| WO | WO 2004/013284 | 2/2004 |
| WO | WO2004050839 | 6/2004 |
| WO | WO2004097369 | 11/2004 |
| WO | WO 2005/040399 | 5/2005 |
| WO | WO 2005/093095 | 10/2005 |
| WO | WO 2007/016668 | 2/2007 |

OTHER PUBLICATIONS

Aebersold and Mann, Nature, 422:198-207 (2003).
Anderson, S., Nucleic Acids Res., 9(13): 3015-3027 (1981).
Anker, R. at al., Hum. Mol. Genet., 1(2): 137 (1992).
Arnheim et al., Proc. Natl. Acad. Sci. USA, 82:6970-6974 (1985).
Bader and Hogue, BMC Bioinformatics. Jan. 13, 2003;4:2, Epub Jan. 13, 2003. http://www.biomedcentral.com/1471-2105/4/2.
Bains and Smith, J. Theoret. Biol., 135:303-307 (1988).
Banerjee, A. et al., Science, 263(5144): 227-230 (1994).
Barlow, D.P. and H. Leach, Trends Genet., 3: 167-171(1987).
Beaulieu et al., Am. J. Hum. Genet., 73(5):441- (2003).
Beckmann, J.S. and J.L. Weber, 12: 627-631 (1992).
Berkenkamp, S. et al., Proc. Natl.Acad. Sci. U.S.A., 93(14): 7003-7007 (1996).
Biemann, K., Methods in Enzymol., 193: 455-479(1990).
Bird, A., Genes and Development, 16(1): 6-21 (2002).
Bleczinski et al., Rapid Communications in Mass Spectrometry, 12:1737-1743(1998).
Bocker, S., Bioinformatics 19(Suppl. 1):i44-i53 (2003).
Boecker, Lect. Notes Comp. Sci. 2818:476-487 (2003) (http://gi.cebitec.uni-bielefeld.de/people/boecker/download/Preprint_2003-04_Sequencing_SBoecker.pdf).
Boecker, Technical Report (http://gi.cebitec.uni-bielefeld.de/people/boecker/download/Preprint_2003-07_WeightedSC_SBoecker.pdf).
Browne, K. A., J.Am. Chem. Soc., 124(27): 7950-7962 (2002).
Caldwell and Joyce, PCR Methods and Applications 2:28-33 (1992).
Cannistraro, V.J. and D. Kennell, Eur. J. Biochem., 181(2): 363-370 (1989).
Chait, B.T. and S.B.H. Kent, Science, 257(5078): 1885-1894(1992).
Chakrabarti, L. et al., Nature, 328(6130): 543-547 (1987).
Chechetkin et al., Biomol. Struct. Dyn., 18(1):83-101 (2000).
Chung, M.H. et al., Mutat. Res., 254(1): 1-12, (1991).
Clausen et al., J. Clinical Investigation, 98(5):1195-1209 (1998).
Cleveland, D.W. et al., J. Biol. Chem., 252(3): 1102-1106 (1977).
Database WPI, Derwent publication #007515331.
Dahl and Goldberg, Biogerontology, 4:233-250.
Dausset, J. et al., Genomics, 6(3): 575-577(1990).
Delagrave et al., Protein Engineering, 6:327-331 (1993).
Ding and Cantor, Proc. Natl. Acad. Sci. USA, 100(13):7449-7453 (2003).
Dunham, I. et al., Nature 402(6761): 489-495 (1999).
Edwards, M.C. et al.Nucleic Acids Res., 19(17): 4791 (1991).
Eggertsen et al., Clinical Chemistry 30(10):2125-2129 (1993).
Ehrlich, S.D. et al., Biochemistry 10(11):2000-2009 (1971).
Eitan et al., Nucleic Acids Res. 30(12):E62.1-E62.8 (2002).
Elso et al., Genome Res. 12(9)1428-1433 (2002).
Fel and Smith., Rapid Commun. Mass. Spectrom., 14(11):950-959 (2000).
German, J. and E. Passarge, Clin, Genet., 35: 57-69 (1989).
Gerrnino, J. and D. Bastis, Proc. Natl. Acad. Sci. U.S.A., 81(15):4692-(1984).
Gogos, J.A. et al., Nucleic Acids Res., 18(23): 6807-6817 (1990).
Goldman and Youvan, Biotechnology 10:1557-1561 (1992).
Graber et al., Genetic Analysis: Biomolecular Engineering, 14:215-219 (1999).
Gupta, R.C. and K. Randerath, Nucleic Acids Res., 4(6):1957-1978 (1977).
Gust, I.D. et al., Intervirology, 20:1-7 (1983).
Gut, I. G. and S. Beck, Nucleic Acids Res., 23(8): 1367-1373 (1995).
Guyader, M. et al., Nature, 326(6114): 662-669 (1987).
Haff and Smirnov, Genome Research, 7:378-388 (1997).
Haffey, M. L. et al., DNA,6(6): 565-571 (1987).
Hahner, S. et al., Nucleic Acids Res., 25(10): 1957-1964 (1997).
Hanish, J. and M. McClelland, Gene, Gene. Anal. Tech., 5: 105-107 (1988).
Harrington, J.J. and M.R. Lieber, Genes and Develop., 8(11): 1344-1355 (1994).
Hartmer et al., Nucleic Acids Res., 31(9):E47.1-E47.10 (2003).
Heym, B. et al., Lancet, 344(8918): 293-298 (1994).
Hillenkamp, F. and M. Karas, Anal. Chem., 63(24): 1193A-1202A (1991).
Hsu, I-C. et al., Carcinogenesis, 15(8): 1657-1662 (1994).
Huang, Z.-H. et al., Anal. Biochem., 268(2):305-317 (1999).
Jeffreys et al., Nature, 314:67-73 (1985).
Johnson, R. S. et al., Intl. J. Mass Spectrum. Ion Processes,86: 137-154 (1988).
Ju, L.-Y., et al., Electrophoresis 12(4):270-273 (1991).
Krebs et al., Nucleic Acids Res., 31(7):E37.1-E37.8 (2003).
Kruglyak and Nickerson., Nature Genetics. 27-234-236 (2001).
Kuchino, Y. and S. Nishimura, 180:154-163 (1989).
Lai. E. et al., Genomics. 54(1): 31-38 (1998).
Landegren et al., Genome Res., 8:769-776 (1998).

(56) References Cited

OTHER PUBLICATIONS

Lu, A.-L. and I.-C. Hsu, "Detection of Single DNA Base Mutations with MismatchRepair Enzymes", Genomics, 14(1): 249-255 (1992).
Marotta, C.A. et al., "Preferred sites of digestion of a ribonuclease fromEnterobacter species in the sequence analysis of Bacillus stearothermophilus 5Sribonucieic acid", Biochemistry, 12(15): 2901-2904 (1973).
Maxam, A.M. and W. Gilbert, "A new method for sequencing DNA", Proc. Natl.Acad. Sci. U.S.A., 74(2): 560-564(1977).
McClelland, M. et al., "A single buffer for all restriction endonucleases", NucleicAcid Res., 16(1): 364 (1988).
McKinnon, P.J., Hum. Genet., 75(3): 197-208 (1987).
McKinzie et al., Mutation Research, 517(1-2):209-220 (2002).
McLafferty, F.W., ,Acc. Chem. Res., 27(11): 379-386 (1994).
Minshull and Stemmer Cuff. Opin. Chem. Biol., 3(3):284-290 (1999).
Morris et al., J. Infect, Dis., 171: 954-960 (1995).
Muller et al., Human Molecular Genetics, 9(5):757-763, 2000.
Murante, R. S. et al., J. Biol. Chem., 269(2): 1191-1196 (1994).
Nagai, K. and H. C.Thogersen, Nature, 309: 810-812(1984).
Nakamura, Y: et al., Science, 235: 1616-1622 (1987).
Nikodem, V. and J.R. Fresco, "Protein Fingerprinting by SDS-Gel Electrophoresisafter Partial Fragmentation with CNBr", Anal. Biochem., 97(2): 382-386 (1979).
Nishimura, D.Y. and J.C. Murray, "A tetranucleotide repeat for the F13B locus",Nucleic Acids Res., 20(5): 1167 (1992).
Nordhoff, E. et al., "Ion stability of nucleic acids in infrared matrix-assisted laserdesorption/Ionization mass spectrometry", Nucleic Acids Res., 21(15): 3347-3357(1993).
Perlman, P.S. and R.A. Butow, "Mobile Introns and Intron-Encoded Proteins",Science, 246(4934): 1106-1109(1989).
Pevzner, J. Biomol. Struct. Dyn., 7:63-73 (1989).
Pevzner, PNAS USA, 98(17):9748-9753 (2001).
Ploos et al., "Tetranucleotide repeat polymorphism in the vWF gene", NuclelcAcids Res., 18(16): 4957 (1990).
Podhajska et al., Gene, 40:175-182 (1985).
Polettinl et al., Journal of Chromatography B 713; 265-279 (1998).
Polymeropoulos et al., "Tetranucleotide repeat polymorphism at the humanaromatase cytochrome P-450 gene (CYP19)", Nucl. Acids Res., 19(1): 195 (1991).
Polymeropoulos, M.H. et al., "Tetranucleotide repeat polymorphism at the humanc-fes/fps proto-oncogene (FES)", Nucleic Acids Res., 19(14): 4018 (1991).
Polymeropoulos, M.H. et al., Nucl. Acids Res., 19(15): 4306 (1991).
Polymeropoulos, M.H. et al.,, Nucl. Acids Res., 18(24): 7468 (1990).
Ratner, L. et al., "Complete nucleotide sequence of the AIDS virus, HTLV-III",Nature, 313: 227-284 (1985).
Rodi at al., Biotechniques 32(Suppl):S62-S69 (2002).
Rojo, M.A. et al., "Cusativin, a new cytidine-specific ribonuclease accumulated inseeds of Cucumis sativus L"; Planta, 194: 328-338 (1994).
Ross et al., Nature Biotechnology 16:1347-1351 (1998).
Santoro, S. W. and G. F. Joyce, "A general purpose RNA-cleaving DNA enzyrne",Proc. Natl. Acad. Sci. U.S.A., 94(9): 4262-4266 (1997).
Sargent, T.D. et al., "Isolation of Differentially Expressed Genes", MethodsEnzymol, 152: 423-432 (1987).
Saris, C.J.M. et al., "Hydroxylamine Cleavage of Proteins in Polyacrylamide Gels",Anal. Biochem., 132(1): 54-67 (1983).
Seela, F. and A. Kehne, "Palindromic octa- and dodecanucleotides containing 2'-deoxytubercidin: synthesis, hairpin formation, and recognition by the endodeoxyribonuclease EcoRI", Biochemistry, 26(8): 2232-2238 (1987).
Sequenom, Application Notes from company website: "SNP Discovery Using theMassARRAY System", http://www.sequenom.com/Assets/pdfs/appnotes/SNP_Discovery_Application_Note.pdf (accessed on Jun. 29, 2004).

Shchepinov et al., "Matrix-induced fragmentation of P3' -N5' -phosphoroamidatecontaining DNA: high-throughput MALDI-TOF analysis of genomic sequence polymorphisms", Nucleic Acids Res. 29(18):3864-3872 (2001).
Simoncsits et al., "New, rapid gel sequencing method for RNA", Nature, 269: 833-836 (1977).
Sluzdak, G., "The emergence of mass spectrometry in biochemical research", Proc. Natl. Acad. Sci, U.S.A., 91(24): 11290-11297 (1994).
Smith, D. B. and K. S. Johnson, "Single-step purification of polypeptides expressed in *Escherichia coli* as fusions with glutathione S-transferase", Gene, 67: 31-40 (1988).
Sommer et al., Biotechniques, 12(1):82-87 (1992).
SpectroCHIP BioArray Product Advertisement.
Springer, B. et al., "Two-laboratory collaborative study on identification of mycobacteria: molecular versus phenotypic methods", J. Clin. Microbiol., 34(2):296-303 (1996).
Stevens, A., "Pyrimidine-specific cleavage by an endoribonuclease of *Saccharomyces cerevisiae*", J. Bacteriol., 1641): 57-62 (1985).
Stults, J. T. et al., "Simplification of high-energy collision spectra of peptides byamino-terminal derivatization", Anal. Chem., 65(13): 1703-1708 (1993).
Tautz, D., "Hyperyariability of simple sequences as a general source forpolymorphic DNA markers . . . ", Nucleic Acids Res., 17(16): 6463-6471 (1989).
The International SNP Map Working Group, "A Map of human genome sequencevariation containing 1.42 million single nucleotide polymorphisms", Nature,409(6822): 928-933 (2001).
Vanfleteren, J.R. et al., "Peptide Mapping and Microsequencing of ProteinsSeparated by SDS-PAGE After Limited In Situ Acid Hydrolysis", BioTechniques,12(4): 550-557 (1992).
Vath, J. E. et al.,"Method for the derivatization of organic compounds at the sub?nanomole level with reagent vapor", Fresenius' Zeitschrfl fur analytische Chemie,331: 248-252 (1988).
Wagner, D. S. et al., "Derivatization of Peptides to Enhance Ionization Effiencyand Control Fragmentation During Analysis by Fast Atom Bombardment TandemMass Spectrometry", Biol. Mass Spectrom., 20(7): 419-425 (1991).
Wain-Hobson, S. et al., "Nucleotide sequence of the AIDS virus, LAV", Cell, 40:9-17 (1985).
Wang et al., Science, 280:1077-1082 (1998).
Weber, J.L and P.E. May, "Abundant class of human DNA polymorphisms whichcan be typed using the polymerase chain reaction", Am. J. Hum. Genet., 44: 388?396(1989).
Weissenbach et al., Nature, 359(6358):794-801 (1992).
Yates, J. Mass Spec., 33:1-19 (1998).
Yule, A., "Amplification-Based Diagnosis Target TB", Bio/Technology, 12: 1335?1337 (1994).
Zuliani, G. and H.H. Hobbs, "Tetranucleotide repeat polymorphism in the LPLgene", Nucleic Acids Res., 18(6): 4958 (1990).
Amir et al., Nature Genet. 23:185-188 (1999).
Arrand et al., J. Biol. Chem., 261.(20):9079-9082 (1986).
Badger et al., Proteins: Structure, Function, and Genetics, 35(11):25-33 (1999).
Beck et al. , Nucl. Acids Res., 17(13}:5115-5123 (1989).
Bertina et al., Nature, 64-67 (1994).
Bessho et al., Nucl. Acids Res. , 27(4):79-83 (1999).
Bjelland at al., Nucl. Acids Res., 15{7):2787-2801 (1987).
Braun et al., Clinical Chemistry, 43(7):1151-1158 (1997).
Braun et al., Genomics,46:18-23 (1997).
Breen, G., et al., BioTechniques, 28(3):464-470, (2000).
Bregman et al, J. Biol.Chem.. 266(11):7207-7213 (1991).
Bteczinski at al., Rapid Communications in Mass Spectrometry, 12:1737- 1743(1998).
Buetow, et al., Proc. Natl. Acad. Sci. USA, (2001), 581-584, 98(2).
Burton at al., Proc. Natl. Acad. Sci. USA, 94:11067-11072 (1997).
Cal et al., J. Chem. Inf. Comput. Sci 38: 1161-1170 (1998).
Carr et al., J. Biol. Chem., 287(19):13376-13382 (1992).
Carr et al., J. Biol.Chem., 266(22):14188-14192 (1991).
Cavalli-Sforza, L.I.,Trends in Genetics 14(2): 60-65 (1998).
Chiu et al, Clin. Chem., 45:1578 (1999).
Chiu of al., Nucl. Acids. Res., 28(8}:e31 (2000).
Clegg or al., Proc. Natl. Acad. Sci. USA, 85:3703-3707(1988).

(56) References Cited

OTHER PUBLICATIONS

Coghlan at al., Science, 267:108-111 (1995).
Cohen et al., Advanced Chromatography, 36:127-162 11996).
Colledge et al., Trends in Cell Biology, 8:216-221(1999).
Collins et al., Genome Research, 8:1229-1231 (1998).
Corder et al., Science, 261:921-923 (1993).
Costello et al., Nature Genet., 24:132-138 (2000).
Database WPI, Derwent publication # 011635345.
Dittmar, M., Anthropol Anz. 53(4): 289-315 (1995).
Dodgson et al., Poultry Science 76: 1108-1114 (1997).
Downes, Kate, et al., BioTechniques, (2004), 840-845, 36(5).
Eftedal et al., Nucl. Acids Res., 21191:2095-2101 (1993).
Faux et al., Trends Biochem., 21:312-315 (1996).
Foster et al., Genome Research, 8:755-757 (1998).
Fu et al., Genetic Analysis:Biomolecular Engineering, 12:137-142 (1996).
Fu et al., Nature Biotechnol., 16:381-384 (1998).
Fu et al., Proc. Natl. Acad. Sci. USA, 92:10162-10166 (1995).
Fu et al., Nucl. Acids Res. 25(3):677-679 (1997).
Gabbita et al., J Neurochemistry, 73(4):1660-1666 (1999).
Gardiner-Garden et al., J. Mol. Biol. 196:261-282 (1987).
Germer,et al, Genome Research, (2000), 258-266, 10, Cold Spring HarborLaboratory Press.
Glantz et al., J. Biol. Chem., 2681171:12796-12804 (1993).
Goldmacher et al, Bioconj. Chem., 3:104-107 (1992).
Griffin et al., Nature Biotechnology, 15:1368-1372 (1997).
Grunau et al., Nucl. Acid Res., 29:C65 (2001).
Guatelli et al, Proc. Natl. Acad. Sci. USA, 87:1874-1878 (1990).
Hausken et al., J. Biol. Chem., 271(46):29016-29022 (1996).
Hazum et al., in Pept., Proc. Eur. Pept. Symp., 16th, Brunfeldt, K., (Ed.), pp. 105-110 (1981).
Herman et al., Proc. Natl. Acad. Sci. 93:9821-26 (1996).
Hey, J., Trends in Genetics 14(8): 303-306 (1998) (with reply by L. Cavalli-Worn).
Higgins et al., BioTechniques, 23(4):710-714 (1997).
Higgins et al., Methods in Enzymology, 68:50-71(1979).
Higley et al., Mutation Research, DNA Repair, 294;109-116 (1993).
Hinton et al., Laboratory Automation & Information Management, vol. 21 No. 2103, pp. 223-227, Dec. 1, 1993.
Hoogendoorn, et al., Hum Genet. (2000) 107:488-493,.
Huang et al., Journal of Biological Chemistry, 272(12):8057-8064 (1997).
Huang et al., Proc. Natl. Acad. Sci. USA, 94:11184-11189 (1997).
Hubbard et al., Trends Biochem. Sci., 18:172-177 (1993).
Ikemoto, S., Nippon Hoigaku Zasshi 49(6): 419-431 (1995).
Jahnsen et al , J.Biol. Chem., 261(26):12352-12361 (1986).
Jiang-Baucom et al., Analytical Chemistry, 61:4894-4898 (1997).
Jurinke at el., Genetic Analysis: Biomolecular Engineering. 13:67-71(1996).
Jurinke et al , Genetic Analysis: Biomolecular Engineering, 14:97-102 (1998).
Jurinke et al., Anal. Biochem., 237:174-181 (1996).
Jurinke et al., Anal. Chem., 69:904-910 (1997).
Kario et al., Thromb. Haemost., 73:617-22 (1995).
Klauck et al., Science, 271:1589-1592 (1998).
Koster et al., Nucl. Acids Res., Symposium Series No. 24 (1991) 318-321.
Koster et al.,Nature Biotechnology, 14:1123-1128 (1996).
Kwoh et al., Proc. Natl. Acad. Sci. USA,:86:1173-1177 (1989).
Laken et al., Nature Biotechnology, 16:1352-1356 (1998).
Laken et al., Nature Genetics, 17:79-83 (1995).
Lam et al., Diabetologia, 41:760-766 (1998).
Lasko et al, Mutation Research, 236:277-287 (1990).
Le hellard, et al., Nucleic Acids Research, (2002) 1-10, 30(15).
Lee et al., Proc. Natl. Acad. Sci. USA, 80:3608-3612 (1983).
Lehman, I.R.,Science, 186:790-797(1974).
Li et al., Anal. Chem., 68(13):2090-2096 (1996).
Li et al., Cell, 69:915-926 (1992).
Li et al., Nucl. Acids Res., 22(4):632-638 (1994).
Li, J., Abstract—Eleventh IEEE Symposium on Computer-Based Medical Systems, pp. 252-255 (1998).
Lindahi et al, Annu. Rev. Biochem., 61:251-281 (1992).
Little et al., International Journal of Mass Spectrometry and ion Processes,169-170:323-330 (1997).
Little et al., Anal. Chem., 69:4540-4546 (1997).
Little et al., Eur. J. Clin. Chem. Clin. Biochem.,35(7),:545-548 (1997).
Little et al., J. Mol. Med., 75:745-750 (1997).
Little et al., Nature Medicine, 3:1413-1416 (1997).
Lizardi et al., BioTechnology, 6:1197-1202 (1988).
Miki et al., J. Biol. Chem., 273(51):34384-34390.
Miki et al., J. Biol. Chem.274(41):29057-29062 (1999).
Mochly-Rosen, D.,Science, 268:247-251 (1995).
Moskovitz at al., Proc. Natl. Acad. Sci. USA, 95:14071-14075 (1998).
Nagamura et al, Plant Molecular Biology 35: 79-87 (1997).
Nelson et al. , Journal of Magnetic Resonance 84:95-109 (1989).
Nilges et al., J. Mol. Biol., 269:408-422 (1997).
Nucleases 2nd ed., Linn, S.M. at al., (Eds.), Cold Spring Harbor Laboratory Press (1993).
Okano et al., Cell, 99: 247-257 (1999).
Olek et al., Nucl. Acid Res., 24:5064-5066 (1996).
Paterson, A.H., Genome Research 5(4): 321-333 (1995).
Pena et al., J. Mol. Med. 73: 555-564 (1995).
Polettini et al., Journal of Chromatography B 713; 265-279 (1998).
Reymer et al-, Nature Genetics, 10:28-34 (1995).
Risch,et al., Genome Research,(1998), 8:1273-1288.
Robertson et al., Nature Rev. Genet. 1:11-19 (2000).
Ross et al., Analytical Chemistry 69:4197-4202 (1997).
Ross et al., Analytical Chemistry 69:3966-3972 (1997).
Ross, et al., BioTechniques, (2000) 29(3):620-629.
Ruppert et al.,Anal. Biochem., 230:130-134 (1995).
Samson et al., Nature, 382:722-725 (1996).
Saparbaev et al., Nucl. Acids Res., 23(18):3750-3755 (1995).
Sarkar of al. , Moire Inst. Oswaldo Cruz, 93(51:693-694 (1998).
Sasaki, et al., Am. J. Hum, Genet. (2001) 68:214-218.
Schachter et al., Nature Genetics, 6:29-32 (1994).
Scott at al., J. BIoL Chem., 265(35):21561-21566 (1990).
Scott, J., 50:123-145(1991).
Senko et al., J. Am. Soc. Mass Spectrom., 6:52-56 (1995).
Senter et al., Photochem. Photobiol., 42:231-237 (1985).
Shriver et al., Am. J. Hum. Genet., 60:957-964 (1997).
Siegert et al., Anal. Biochem., 24 :55-65 (1996).
Smith, L.M., Nature Biotechnology, 14:1084-1085(1996).
Srinivasan et al. , Rapid Communications in Mass Spectrometry, 11:1144-1150 (1997).
Stanssens et al., Genomic Res., 14:126-133 (2004).
Sugisaki et al., Gene, 16:73-78 (1981).
Szybalski et al., Gene, 100:13-26 (19911.
Takio et al., Proc. Natl. Acad. Sci. USA, 79:2644-8(1982).
Tammen et al. J. Cromatogr. A. 852:285-295.
Tang et al., Nucl. Acids Res., 23(16):3126-3131 (1995).
Tang et al., Proc. Natl. Acad. Sci. USA, 96:10016-10020 (1999).
Taranenko et al, Genetic Analysis: Biomolecular Engineering. 13:87-94 (1996).
Thompson, Laboratory Automation and Information Management, 31:173-193 (1996).
Tost et al., Nucl. Acid Res., 31:C50 (2003).
van den Boom et al., Anal. .Biochem., 256:127-129 (1998).
van den Boom et al., J. Biochem. Biophys. Methods, 35:69-79 (1997).
Vaughan et al., Genetic Analysis: Biomolecular Engineering, 14:169-175 O.(1999).
Waga et al., J. Biol. Chem., 269(14):10923-10934 (1994).
Wang et al, J. Mol. Spectrosc., 194(20):256-268 (1999).
Weiler et al., Nucleic Acids Res., 25:2792-2799 (1997).
Wilson et al., Annu. Rev. Genet., 25:585-627(1991).
Yasuda et al. , Japanese Journal of Legal Medicine 51: 407-416 (1997).
Yen et al, Makromol. Chem., 190:69-82 (1989).
Zhou, et al., Nucl. Acids Res., (2001) , 29(19 e93):1-11.

(56) References Cited

OTHER PUBLICATIONS

Litz C. E. et al., "Methylation status of the major breakpoint cluster region in Philadelphia chromosone negative leukemias" Leukemia 6(1):35-41 (1992).
Tooke N. and Pettersson M. IVDT. Nov. 2004; 41.
Valk PJ et al. N. Engl J Med 350:1617-28 (2004).
Badger et al., "New features and enhancements in the X-PLOR computer program", Proteins: Structure, Function, and Genetics, 35(1):25-33, (1999).
Biazewicz et al., "On some properties on DNA graphics," Discrete Applied Mathematics, vol. 98, 1999, pp. 1-19.
Blazewicz et al., "On the recognition of de Bruijn graphs and their induced subgraphs," Discrete Applied Mathematics, vol. 245, 81-92 Feb. 28, 2002.
Boguski, M.S. et al., J. Biol Chem., 255(5): 2160-2163 (1980).
Buck et al., "Design Strategies and Performance of Custom DNA Sequencing Primers" BioTechniques. Sep. 1999, 27:528-536.
Chen et al., "Detectionin fecal DNA or colon cancer specitc methylation of the nonexpressed vimentin gene," J Natl Cancer Inst., Aug. 3, 2005;97(15):1124-1132.
Donis-Keller, H et al., Nucleic Acids Res., 4(8): 2527-2537 (1977).
Donis-Keller, H., Nucleic Acids Res., 8(14): 3133-3142 (1980).
Futscher, B., et al., "Role for DNA methylation in the control of cell type-specific maspin expression", Nature Genetics. 2002, 175-179, 31. USA.
Genbank Accession No. AF037439, Chatterjee et al. Dec. 1997
Gunderson et al., "Mutation detection by ligation to complete n-mer DNA Arrays," Genome Res. Nov. 1998:8(11):1142-1153.
Hurtubise, A. et al., "Evaluation of antineoplastic action of 5-aza-2rdeoxycytidine ,, , (Dacogen) and docetaxel (Taxotere) on . . . " Anti-Cancer Drugs, 2004. 161-1 67, 15, Canada.
Instrumentation: "Genesis 200/8" (200 cm with including an 8-tip arm) liquid handling systems; Tecan Ag of Switzerland ("Tecan"), Tecan Products for Diagnostics and Life Science, located at http://www.tecan.ch/index.htm.
Instrumentation, "Model CRS A 255" robot"Digital Servo Gripper""Plate Cube" system. "lid parking station""shaker"Robocon Labor-und lndustrieroboter Ges.m.b.H of Austria ("Robocon").
Instrumentation: "Multimek 96"automated pipettor; Beckman Coulter, Inc. located at http://www.coulter.com, Sep. 8, 1999.
Instrumentation; "Nano-Plotter" from GeSiM, Germany, located at http://www.gesim.de/np-intro.htm.
Instrumentation; Bar code systems, including one and two dimensional bar codes, readable and readable/writable codes and systems, Datalogic S.p.A. of Italy ("Datalogic") located at http://www.datalogic.com.
Instrumentation:"MJ Microseal" plate sealer; Thermal Cycler Accessories: Sealing Options, Sealing Products, MJ Research, located at http://www.mjresearch.com/html/consumables/ealing/sealing_products.html.
Jahnen et al., Biochem. Biophys. Res. Commun., 166 (1): 139-145 (1990).
Jurinke, C. et al., Adv. Biochem. Eng. Biotechnol., 77: 57-74 (2002).
Kirk, et al., "Single Mucleotide polymorphism seeking long term association with complex disease," Nuoleic Acids Res. 2002, vol. 30, No. 5, pp. 3295-3311.
Ling, X. et al., "Proteomics-Based Identification of Maspin Differential Expression in Bronchial Epithelia Immortalized . . . " Chinese J. of Cancer, 2003, 463-466, 22, China.
Liu, X, et al., "XAGE-1, A New Gene That is Frequently Expressed in Eqing's Sarcoma" Cancer Research, 2000, 4752-4755, 60, USA.
Luty, J.A. et al., Five Polymorphic Microsateliite VNTRs on the Human XChromosone Am. J Hum. Genet. 46: 776-783 (1990).
Maass, N. at at., "Decline in the expression of the serine proteinase inhibitor maspin is associated with tumour progression . . . " J. of Pathology, 2001, 321-326, 195, Germany.
Moon, C et al. "Aquaporin Expression in Human Lymphocytes and Dentritic Cells" American Journal of Hematotogy. 2004 128-133, 75, USA.

Murakami, J. et al., "Effects of dernethylating agent 5aza-2'deoxycytidine and histone deacetylase inhibitor FR901228 on maspin . . . " Oral Oncology 2004,597-603,40, Japan.
NCBI GenBank Accession Number: NM_002639.
Oshio, K. et al., "Aquaporin-1 expression in human glial tumors suggests a potential novel therapeutic target for tumor-associated . . ." Acta Neurochir, 2003, 494-502, 86, USA.
Risch, Neil, et al., The Relative Power of Family-Based and Case Control Design for Linkage Disequilibrium Studies of Complex Human Diseases I. DNA Pooling. Genome Research, (1998), 1278-1288, 8, Cold Spring Harbor Laboratory Press.
Saadoun, S. et al., "Increased aquaporin 1 water channel expression in human brain tumours", British J. of Cancer, 2002, 621-623,87, UK.
Sequenom and Gemini ldentify Genes Linked to Cardiovascular Disease, Press Release: Nov. 28, 2000, http://www/sequenom.com/ir/ir_prs.asp.
Sequenom Announces Publication of Results From Large-Scale SNP Study With the National Cancer Institute, Press Release: Jan. 16, 2001, http://www/sequenom.com/ir/ir_prs.asp.
Sequenom Completes Design of More Than 400,000 SNP Assays; Mass EXTENDTM Assay Portfolio Covers Majority of SNPs in the Public Domain, Press Sequenom: Technologies and Tools, located at http://www.squenom-san.com/tech/tools.html, dated Aug. 29, 1999.
Smith, S. et al., "Maspin-the most commonly-expressed gene of the 18q21.3 serpin cluster in lung cancer . . . " Oncogene, 2003, 8677-8687, 22, UK.
Stomakhin et ai., "DNA sequence analysis by hybridization with oligonucleotides microchips; MALDI mass spectrometry identificaiton of 5mers contiguously stacked to microchip oligonucleotides," Nucleic Acids Res. Mar. 1, 2000;28(5):1193-1198.
Takenawa J.et al., "Transcript Levels of Aquaporin 1 and Carbonic Anhydrase IV as Predictive indicators for Prognosis of Renel Cell . . . " Int. J. Cancer, 1998, 1-7, 79, Japan.
Vacca, A. et al., "Microvessel overexprssion of aquaporin 1 parallels bone marrow angiogenesis in patients with active . . . " British J. of Haematology, 2001,415-421, 113, Italy.
von Wintzingerode, F. et al., "Phylogenetic Analysis of an Anaerobic, Trichlorobenzene-Transforming Microbial Consortium", Appl. Environ. Mcrobiol., 65(1): 283-286 (1999).
Wada et al., "Detection of Single-nucleotide Mutations Including Substitutions and Deletions by Matrix-assisted Laser Desorption/Ionization Time-of-flight Mass Spectrometry," Rapid Communications in Mass Spectrometry, 11:1657-1660, (1997).
Wada, J. Mass Spectrometry, 33:187-192 (1998).
Zaia. J., in: Protein and Peptide Analysis by Mass Spectrometry. J. R. Chapman (ed.), pp. 29-41, Humana Press, Totowa, N.J., (1996).
Zendman, A. et al., "The XAGE Family of Cancer/Tetis-Associated Genes: Alignment and Expression Profile in Normal Tissues . . . " Int. J. Cancer, 2002,361-369,99 Netherlands.
Zhu et a., "Use of DNA Methylation for cancer detection and molecular classification," J Biochem Mol Biol. Mar. 31, 2007;40(2):135-141.
Tang et al., "Matrix-assisted Laser Desorption/Ionization of Restriction Enzyme-digested DNA," Rapid Communication in Mass Spectrometry, v. 8, pp. 183-186, 1994.
Aurup et al., Biochemistry, 31: 9636-9641 (1992).
Bachem et al., The Plant Journal, 9: 745-753 (1996).
Bonnin et al., J. Mol. Biol., 290: 241-251 (1999).
Bullinger, L., "Gene Expression Profiling in Acute Myloid Leukemia," J. Clinical Oncology. Sep. 10, 2005, vol. 23, No. 26, pp. 6296-6305.
Clayton et al., Curr. Opin. Microbiol., 1: 562-566 (1998).
Conrad et al., Nucleic Acids Res., 23: 1845-1853 (1995).
Contreras et al., FEBS Lett., 16: 281-283 (1971).
Crain et al., Curr. Opin. in Biotechnol., 9: 25-34 (1998).
Eckstein, Ann. Rev. Biochem., 54: 367-402 (1985).
Eng et al., Nature Biotechnol., 15: 422-426 (1997).
Fleischmann et al., Science, 269: 496-512 (1995).
Frommer et al., "A Genomic Sequencing Protocol that Yields a Positive Display of 5-Methylcytosine Residues in Individual DNA Strands," PNAS, vol. 89, Mar. 1, 1992 p. 1827-1831.

(56) References Cited

OTHER PUBLICATIONS

Gao et al., Proc. Natl. Acad. Sci. USA, 94: 407-411 (1997).
Gish et al., Nucleic Acids Symp. Ser., pp. 253-256 (1987).
Gish et al., Science, 240: 1520-1522 (1988).
Hertogs et al., Animicrob. Agents Chemother., 42: 269-276 (1998).
International Search Report and Written Opinion received in PCT/US2006/30256 mailed on: Aug. 14, 2008.
Isola et al., Anal. Chem., 71: 2266-2269 (1999).
Ivanova et al., Nucleic Acids Res., 23: 2954-2958 (1995).
Kato, Nucleic Res., 23: 3685-3690 (1995).
Lander et al., Science, 265: 2037-2048 (1994).
Lee et al.; Proc. Natl. Acad. Sci. USA, 92: 8303-8307 (1995).
Liang et al., Science, 257: 967-971 (1992).
Limbach, Mass Spectrom. Rev., 15: 297-336 (1996).
Lipshutz et al., Curr. Opin. in Struct. Biol., 4: 376-380 (1994).
Little et al., J. Am. Chem. Soc., 116: 4893-4897 (1994).
Loverix et al., Nature Struct. Biol., 5: 365-368 (1998).
Meador et al., Eur. J. Biochem., 187: 549-553 (1990).
Milligan et al., Nucleic Acids Res., 15: 8783-8798 (1987).
Murray, J. Mass Spectrom, 31: 1203-1215 (1996).
New England BioLabs Catalog, T4 DNA polymerase, T7 RNA polymerase, pp. 74-75, 1996/1997.
Nickerson et al., Nature Genet., 19: 233-240 (1998).
Nordhoff et al., J. Mass Spectrom., 30: 99-112 (1995).
Office Action mailed: Jan. 15, 2008 in U.S. Appl. No. 11/089,805, filed Mar. 24, 2005 Published as: US-2005-0272070 on Dec. 8, 2005.
Office Action mailed: Jan. 19, 2007 in U.S. Appl. No. 11/222,991, filed Sep. 8, 2005, Published as: US-2006-0073501A on Apr. 6, 2006.
Office Action mailed: Jan. 23, 2007 in U.S. Appl. No. 10/830,943, filed Apr. 22, 2004 Published as: US-2005-0009053A1 on Jan. 13, 2005.
Office Action mailed: Jan. 24, 2003 in U.S. Appl. No. 10/018,453, filed Oct. 30, 2001, Now U.S. Pat. No. 6,994,969 Issued on: Feb. 7, 2006.
Office Action mailed: Jan. 27, 2006 in U.S. Appl. No. 10/272,665, filed Nov. 15, 2002 Published as: US-2003-0180748A1 on Sep. 25, 2003, now U.S. Pat. No. 7,332,275 issued on Feb. 19, 2008.
Office Action mailed: Jan. 27, 2009 in U.S. Appl. No. 10/888/359, filed Jul. 9, 2004 Published as: US-2006-0210992A1 on Sep. 21, 2006.
Office Action mailed: Jan. 30, 2009 in U.S. Appl. No. 11/348,683, filed Feb. 7, 2006 Published as: US-2006-0252061A1 on Nov. 9, 2006.
Office Action mailed: Oct. 26, 2004 in U.S. Appl. No. 10/272,665, filed Nov. 15, 2002 Published as: US-2003-0180748A1 on Sep. 25, 2003, now U.S. Pat. No. 7,332,275 issued on Feb. 19, 2008.
Office Action mailed: Oct. 9, 2007 in U.S. Appl. No. 10/830,943, filed Apr. 22, 2004 Published as: US-2005-0009053A1 on Jan. 13, 2005.
Office Action mailed: Dec. 12, 2005 in U.S. Appl. No. 10/723,365, filed Nov. 26, 2003 Published as: US-2005-0112590A1 on May 26, 2005.
Office Action mailed: Dec. 16, 2008 in U.S. Appl. No. 11/222,991, filed Sep. 8, 2005, Published as: US-2006-0073501A on Apr. 6, 2006.
Office Action mailed: Dec. 2, 2005 in U.S. Appl. No. 10/933,611, filed Sep. 2, 2004 Published as: US-2005-0089904A1 on Apr. 28, 2005.
Office Action mailed: Dec. 27, 2006 in U.S. Appl. No. 10/933,611, filed Sep. 2, 2004 Published as: US-2005-0089904A1 on Apr. 28, 2005.
Office Action mailed: Dec. 5, 2006 in U.S. Appl. No. 10/723,365, filed Nov. 26, 2003 Published as: US-2005-0112590A1 on May 26, 2005.
Office Action mailed: Dec. 8, 2008 in U.S. Appl. No. 10/723,365, filed Nov. 26, 2003 Published as: US-2005-0112590A1 on May 26, 2005.
Office Action mailed: Feb. 17, 2009 in U.S. Appl. No. 10/933,611, filed Sep. 2, 2004 Published as: US-2005-0089904A1 on Apr. 28, 2005.
Office Action mailed: Feb. 2, 2009 in U.S. Appl. No. 11/089,805, filed Mar. 24, 2005 Published as: US-2005-0272070 on Dec. 8, 2005.
Office Action mailed: Feb. 29, 2008 in U.S. Appl. No. 10/723,365, filed Nov. 26, 2003 Published as: US-2005-0112590A1 on May 26, 2005.
Office Action mailed: Feb. 6, 2009 in U.S. Appl. No. 10/830,943, filed Apr. 22, 2004 Published as: US-2005-0009053A1 on Jan. 13, 2005.
Office Action mailed: Mar. 31, 2008 in U.S. Appl. No. 11/348,683, filed Feb. 7, 2006 Published as: US-2006-0252061A1 on Nov. 9, 2006.
Office Action mailed: Mar. 8, 2006 in U.S. Appl. No. 10/723,365, filed Nov. 26, 2003 Published as: US-2005-0112590A1 on May 26, 2005.
Office Action mailed: Apr. 17, 2008 in U.S. Appl. No. 10/933,611, filed Sep. 2, 2004 Published as: US-2005-0089904A1 on Apr. 28, 2005.
Office Action mailed: Apr. 19, 2005 in U.S. Appl. No. 10/018,453, filed Oct. 30, 2001, Now U.S. Pat. No. 6,994,969 Issued on: Feb. 7, 2006.
Office Action mailed: Apr. 2, 2008 in U.S. Appl. No. 11/222,991, filed Sep. 8, 2005, Published as: US-2006-0073501A on Apr. 6, 2006.
Office Action mailed: May 16, 2007 in U.S. Appl. No. 11/222,991, filed Sep. 8, 2005, Published as: US-2006-0073501A on Apr. 6, 2006.
Office Action mailed: May 2, 2007 in U.S. Appl. No. 11/089,805, filed Mar. 24, 2005 Published as: US-2005-0272070 on Dec. 8, 2005.
Office Action mailed: May 20, 2008 in U.S. Appl. No. 10/888,359, filed Jul. 9, 2004 Published as: US-2006-0210992A1 on Sep. 21, 2006.
Office Action mailed: Jun. 1, 2004 in U.S. Appl. No. 10/018,453, filed Oct. 30, 2001, Now U.S. Pat. No. 6,994,969 Issued on: Feb. 7, 2006.
Office Action mailed: Jul. 11, 2007 in U.S. Appl. No. 11/089,805, filed Mar. 24, 2005 Published as: US-2005-0272070 on Dec. 8, 2005.
Office Action mailed: Jul. 17, 2008 in U.S. Appl. No. 10/830,943, filed Apr. 22, 2004 Published as: US-2005-0009053A1 on Jan. 13, 2005.
Office Action mailed: Jul. 3, 2007 in U.S. Appl. No. 10/888/359, filed Jul. 9, 2004 Published as: US-2006-0210992A1 on Sep. 21, 2006.
Office Action mailed: Jul. 6, 2005 in U.S. Appl. No. 10/272,665, filed Nov. 15, 2002 Published as: US-2003-0180748A1 on Sep. 25, 2003, now U.S. Pat. No. 7,332,275 issued on Feb. 19, 2008.
Office Action mailed: Aug. 28, 2007 in U.S. Appl. No. 10/888/359, filed Jul. 9, 2004 Published as: US-2006-0210992A1 on Sep. 21, 2006.
Office Action mailed: Aug. 28, 2006 in U.S. Appl. No. 10/272,665, filed Nov. 15, 2002 Published as: US-2003-0180748A1 on Sep. 25, 2003, now U.S. Pat. No. 7,332,275 issued on Feb. 19, 2008.
Office Action mailed: Sep. 2, 2008 in U.S. Appl. No. 10/830,943, filed Apr. 22, 2004 Published as: US-2005-0009053A1 on Jan. 13, 2005.
Office Action mailed: Sep. 20, 2007 in U.S. Appl. No. 10/272,665, filed Nov. 15, 2002 Published as: US-2003-0180748A1 on Sep. 25, 2003, now U.S. Pat. No. 7,332,275 issued on Feb. 19, 2008.
Office Action mailed: Sep. 29, 2003 in U.S. Appl. No. 10/018,453 filed on Oct. 30, 2001, Now U.S. Pat. No. 6,994,969 Issued on: Feb. 7, 2006.
Parsons et al., Environmental and Molecular Mutagenisis, 1998, vol. 32, p. 200-2111.
Parsons et al., Mutagenesis, 1998, vol. 13, No. 6, p. 581-588.
Pieles et al., Nucleic Acids Res., 21: 3191-3196 (1993).
Prashar et al., Proc. Natl. Acad. Sci. USA, 93: 659-663 (1996).
Richterich et al., Nucleic Acids Res., 23: 4922-4923 (1995).
Risch et al., Science, 273: 1516-1517 (1996.
Sanger et al., Proc. Natl. Acad. Sci. USA, 74: 5463-5467 (1977).
Schena et al., Science, 270: 467-470 (1995).
Schinazi et al., Int. Antivir. News, 4: 95-107 (1996).
Sousa et al., EMBOL J. 14: 4609-4621 (1995).
Stevens, J. Bacteriol., 164: 57-62 (1985).
Steyaert, Eur. J. Biochem., 274: 1-11 (1997).
Stratagene Catalog (1998), p. 39. Published by Stratagene, 11011 North Torrey Pines Road, La Jolla, CA 92037, USA.
Supplemental European Search Report received in PCT/US2005/009929 mailed on Jan. 30, 2009.

(56) References Cited

OTHER PUBLICATIONS

Supplemental European Search Report received in PCT/US2005/032441 mailed on Nov. 28, 2008.
Tang et al., "Matrix-Assisted Laser Desorption/Ionization of Restriction Enzyme-digested DNA," Rapid Communications in Mass Spectrometry, vol. 8, pp. 183-186, 1994.
Tost et al., "Genotyping Single Nucleotide Polymorphisms by Mass Spectrometry," Mass Spectrometry Reviews, John Wiley and Sons, New York, vol. 21, No. 6, Nov. 1, 2002, p. 388-418.
Vos et al., Nucleic Acids Res., 23: 4407-4414 (1995).
Wodicka et al., Nature Biotechnol., 15: 1359-1367 (1997).
Graff et al., "Mapping Patters of CpG island methylation in normal and neoplasitc cells implicates both upstream and downstream regions in de novo methylation," Journal of Biological Chemistry, The American Society of Biological Chemists, Inc., Aug. 29, 1997, pp. 22322-22329.
Michalatos-Beloin et al., Nucleic Acids Research, 1996, 24(23):4841-4843.
Rein et al., "Identifying 5-methylcytosine and related modifications in DNA genomes," Nucleic Acids Research, Oxford University Press, Surrey GB, vol. 26, No. 10, Jan. 1, 1998 pp. 2255-2264.
Office Action mailed: Aug. 20, 2009 in U.S. Appl. No. 11/348,683, filed Feb. 7, 2006 and published as: US 2006/0252061 on Nov. 9, 2006.
Office Action mailed: Aug. 28, 2009 in U.S. Appl. No. 10/830,943, filed Apr. 22, 2004 Published as US-2005-0009053A1 on Jan. 13, 2005.
Office Action mailed: Jan. 27, 2009 in U.S. Appl. No. 10/888,359, filed Jul. 9, 2004 Published as: US-2006-0210992A1 on Sep. 21, 2006 and issued as 7,608,394 on Oct. 27, 2009.
Office Action mailed: Jun. 12, 2009 in U.S. Appl. No. 10/888,359, filed Jul. 9, 2004 Published as US-2006-0210992A1 on Sep. 21, 2006 and Issued as 7,608,394 on Oct. 27, 2009.
Office Action mailed: Sep. 3, 2009 in U.S. Appl. No. 10/723,365, filed Nov. 26, 2003 Published as: US-2005-0112590A1 on May 26, 2005 and issued as 7,820,378 on Oct. 26, 2010.
Office Action mailed: Jun. 14, 2010 in U.S. Appl. No. 10/723,365, filed Nov. 26, 2003 Published as US-2005-0112590A1 on May 26, 2005 and Issued as 7,820,378 on Oct. 26, 2010.
Office Action mailed: Oct. 1, 2009 in U.S. Appl. No. 10/933,611, filed Sep. 2, 2004 Published as: US2005-0089904A1 on Apr. 28, 2005.
Office Action mailed: May 12, 2010 in U.S. Appl. No. 10/933,611, filed Sep. 2, 2004 Published as: US-2005-0089904A1 on Apr. 28, 2005.
International Search Report and Written Opinion dated Nov. 8, 2006 in International Application No. PCT/US2005/32441, filed Sep. 8, 2005 and published as WO 06/031745 on: Mar. 23, 2006.
Supplemental European Search Report dated May 7, 2010 received in EP0379490 filed on: Nov. 26, 2003 based on PCT/US0337931.
Supplemental European Search Report dated Apr. 28, 2009 received in EP05768312 filed on: Jul. 6, 2005 based on PCT/US05/023846.
Extended European Search Report dated: Jul. 1, 2009 received in EP09157036 filed on Apr. 1, 2009.
European Search Report dated: Nov. 2, 2011 in EP11006184 filed: Mar. 24, 2005.
Office Action mailed: Oct. 17. 2012 in U.S. Appl. No. 11/348,683, filed Feb. 7, 2006 and published as: US 2006/0252061 on Nov. 9, 2006.
Office Action mailed: Mar. 20, 2012 in U.S. Appl. No. 10/933,611, filed Sep. 2, 2004 Published as: US-2005-0089904A1 on Apr. 28, 2005.
Office Action mailed: Feb. 28. 2013 in U.S. Appl. No. 10/933,611, filed Sep. 2, 2004 Published as: US-2005-0089904A1 on Apr. 28, 2005.
Clark, "Methylation Analysis," Mini-Review Jan. 1999, DNA Methylation Society.
Cline et al., Nucleic Acids Research, 1996, 24(18):3546-3551.
Ehrich et al., "Comparative Sequence Analysis by MALDI-TOF Mass Spectrometry—Utilizing the knows to Discover the New," Chapter 3, Perspectives in Bioanalysis, Voume 2, Chapter 3, p. 97-117.
Ellington et al., Current Protocols in Molecular Biology, 1988, 2.11.1-2.11.25.
Fraga et al., "DNA Methylation: A Profile of Methods and Applications," Review in Biotechniques, 33:632-649, Sep. 2002.
Genereux et al., "Errors in bisulfate conversion of DNA: modulating inappropriate- and failed-conversion frequencies," Nucleic Acid Research, Nov. 4, 2008, vol. 36, No. 22, e150, 1-19.
Harrison et al., "DNA Methylation: a timeline of Methods and Applications," Review Article in Frontiers in Genetics, Oct. 25, 2011, vol. 2, Article 74, p. 1-13.
Holland et al., PNAS, 1991, vol. 88, p. 7276-7280.
Mikeska et al, "The implications of heterogeneous DNA methylation for the accurate quantification of methylation," Epigenomics, (2010) 2(4), 561-573.
Model et al., "Feature Selection for DNA Methylation Based Cancer Classification" Bioinformatics, Oxford University Press, Surrey, GB, vol. 17, No. Suppl. 01, Jan. 1, 2001.
Rauch et al., "High-resolution mapping of DNA Hypermethylation and hypomethylation in lung cancer." PNAS, Jan. 8, 2008, vol. 105, No. 1, p. 257-252.
Singal et al., "DNA Methylation, Review Article." Blood, vol. 93, No. 12, Jun. 15, 1999, pp. 4059-4070.
Yang et al., "A simple method for estimating global DNA methylation using bisulfater PCR of repetitive DNA elements," Nucleic Acids Research, Feb. 18, 2004, vol. 32, No. 3, e38, 1-6.
Office Action mailed on Mar. 12, 2015 in U.S. Appl. No. 10/933,611, filed Sep. 2, 2004 and published as US 2005-0089904 on Apr. 28, 2005.
Knight et al., "In vivo characterization of regulatory polymorphisms by allele-specific quantification of RNA polymerase loading" Nature Genetics (2003) 33:469-475.
Griffin et al., "Direct genetic analysis by matrix-assisted laser desorption/ionization mass spectrometry" PNAS USA (1999) 96:6301-6306.
"Phosphodiesterase" from Wikipedia, the free encyclopedia, printed on Jun. 13, 2013.
"Restriction enzyme" from Wikipedia, the free encyclopedia, printed on Jun. 13, 2013.
Office Action mailed Jun. 20, 2013 in U.S. Appl. No. 11/348,683, filed Feb. 7, 2006 and published as US 2006-0252061 on Nov. 9, 2006.
Office Action mailed on Nov. 19, 2014 in U.S. Appl. No. 11/348,683, filed Feb. 7, 2006 and published as US 2006-0252061 on Nov. 9, 2006.
Office Action mailed Mar. 24, 2014 in U.S. Appl. No. 11/348,683, filed Feb. 7, 2006 and published as US 2006-0252061 on Nov. 9, 2006.
U.S. Appl. No. 11/997,402, filed Jan. 30, 2008, van den Boom.
Aoki E. et al., "Methylation status of the pl51NK4B gene in hematopoietic progenitors and peripheral blood cells in myelodysplastic syndromes", Leukemia 14(4):586-593 (2000).
Asimakopoulos FA et al., "ABL 1 methylation is a distinct molecular event associated with clonal evolution of chronic myeloid leukemia" Blood 94(7):2452-2460 (1999).
Bair and Tibshirani, PloS Biol 2:E108 (2004).
Bullinger L. et al. N Engl J Med 350:1605-16 (2004).
Chan et al., Oncogene 22:924-934 (2003).
Chen et al., Analytical Biochemistry, 1996, vol. 239, p. 61-69.
Colella et al. Biotechniques. Jul. 2003;35(1):146-50.
Costello et al., Nature Gent, 24:132-138 (2000).
Dohner et al. J Clin Oncol 20:3254-61 (2002).
Dupont JM, Tost J, Jammes H, and Gut IG. Anal Biochem, Oct. 2004; 333(1): 119-27.
Fajkusova L. et al., "Detailed Mapping of Methylcytosine Positions at the CpG Island Surrounding the Pa Promoter at the bcr-abl Locus in CML Patients and in Two Cell Lines, K562 and BV173" Blood Cells Mol. Dis. 26(3):193-204 (2000).
Feinberg, AP Nat Genet 27:9-10 (2001).
Frigola et al. Nat Genet. May 2006;38(5):540-9.

(56) References Cited

OTHER PUBLICATIONS

Frohling et al. Blood 100:4372-80 (2002).
Gebhard et al. Cancer Res. Jun. 15, 2006;66(12):6118-28.
Genebank Accession No. NM_153620.
Genebank Accession No. AB025106.
Genebank Accession No. AB040880.
Genebank Accession No. BC013998.
Genebank Accession No. NM_001031680.
Genebank Accession No. NM_001394.
Genebank Accession No. NM_001614.
Genebank Accession No. NM_003998.
Genebank Accession No. NM_004350.
Genebank Accession No. NM_004360.
Genebank Accession No. NM_005522.
Genebank Accession No. NM_005766.
Genebank Accession No. NM_033317.
Issa JP, Nat Rev Cancer 4:988-93 (2004).
Kaneko et al., Gut 52:641-646 (2003).
Laird, P.W. Nature Reviews Cancer 3, 253-266 (2003).
Litz C. E. et al., "Methylation status of the major breakpoint cluster region in Philadelphia chromosone negative leukemias", Cancer Res. 6(1):35-41 (1992).
Nosaka, K. et al., "Increasing methylation of the CDKN2A gene is associated with the progression of adult T-cell leukemia", Cancer Res. 60(4):1043-1048 (2000).
Puskas et al. Genome Research, 1995, vol. 5, p. 309-311.
Schuette et al. Journal of Parmaceutical and Biomedical Analysis, 1995, vol. 13, p. 1195-1203.
Strathdee, et al., Am. J. Pathol. 158:1121-1127 (2001).
Tooke N and Pettersson M. IVDT. Nov. 2004; 41.
Toyota, M. et al., Blood 97:2823-9 (2001).
Uhlmann, K. et al. Electrophoresis 23:4072-4079 (2002).
Valk PJ et al. N Engl J Med 350:1617-28 (2004).
Akiyama, Y. et al., "Cell-Type-Specific Repression of the Maspin Gene is Disrupted Frequently by Demethylation at the . . . " Amer. J. of Pathology, 2003, 1911-1919, 163, Japan.
Badger et al., "New features and enhancements in the X-PLOR computer program", Proteins: Structure, Function, and Genetics, 35(1):25-33, (1999).
Baylin and Bestor, "Altered methylation pattersn in cancer cell genomes: cause or consequence?" Cancer Cell. May 2002:1(4):299-305.
Blazewicz et al., "On some properties on DNA graphics," Discrete Applied Mathematics, vol. 98, 1999, pp. 1-19.
Blazewicz et al., "On the recognition of de Bruijn graphs and their induced subgraphs." Discrete Applied Mathematics, vol. 245, 81-92 Feb. 28, 2002.
Boguski, M.S. et al., J. Biol, Chem., 255(5): 2160-2163 (1980).
Buck et al., "Design Strategies and Performance of Custom DNA Sequencing Primers" BioTechniques. Sep. 1999. 27:528-536.
Caskey, C. T. et al., Science 256(5058): 784-789 (1992).
Chen et al., "Detectionin fecal DNA or colon cancer specific methylation of the nonexpressed vimentin gene," J Natl Cancer Inst., Aug. 3, 2005;97(15):1124-1132.
Costello, J. et al., "Methylation matters: a new spin on maspin" Nature Genetics, 2002, 123-124,31 USA.
De Noronha et al., (1992) PCR Methods and Applications, 2(2), p. 131-136.
Donis-Keller, H. et al., Nucleic Acids Res., 4(8): 2527-2537 (1977).
Donis-Keller. H., Nucleic Acids Res., 8(14): 3133-3142 (1980).
Egland, K. et al., "Characterization of Overlapping XAGE-1 Transcripts Encoding a Cancer Testis Antigen Expressed in . . . " Molecular Cancer Therapeutics, 2002,441-450, USA.
Fischer, "Red Tape: It's in You to Give: Last year the Canadian Blood Services' security measures weeded out 200,000 would-be donors. Doug Fischer looks at the reasons behind the red tape." Ottawa Citizen Saturday Final Edition Oct. 5, 2002.
Futscher, B. et al., "Aberrant Methylation of the Maspin Promoter is an Early Event in Human Breast Cancer" Neoplasia, 2004,380-389, 6, USA.
Futscher, B., et al., "Role for DNA methylation in the control of cell type-specific maspin expression", Nature Genetics, 2002,175-179,31. USA.
Genbank Accession AC005730.
Genbank Accession AF021833.
Genbank Accession AF096289.
Genbank Accession AJ242973.
Genbank Accession AW195104.
Genbank Accession AW874187.
Genbank Accession NM007202.
Genbank Accession No. AF037439, Chatterjee et al. Dec. 1997.
Genbank Accession X86173.
Gunderson et al., "Mutation detection by ligation to complete n-mer DNA Arrays," Genome Res. Nov. 1998;8(11):1142-1153.
Heighway, J. et al., "Expression profiling of primary non-small cell lung cancer for target identification", Oncogene, 2002, 7749-7763,21, UK.
Hurtubise, A. et al., "Evaluation of antineoplastic action of 5-aza-2rdeoxycytidine . . . (Dacogen) and docetaxel (Taxotere) on . . . " Anti-Cancer Drugs, 2004. 161-1 67,15, Canada.
Instrumentation; "Genesis 200/8" (200 cm with including an 8-tip arm) liquid handling systems; Tecan AG of Switzerland ("Tecan"), TECAN Products for Diagnostics and Life Science, located at http://www.tecan.ch/index.htm.
Instrumentation; "Model CRS A 255" robot "Digital Servo Gripper" "Plate Cube" system. "lid parking station" "shaker" Robocon Labor- und Industrieroboter Ges.m.b.H of Austria ("Robocon").
Instrumentation: "Multimek 96" automated pipettor; Beckman Coulter, Inc. located at http://www.coulter.com, Sep. 8, 1999.
Instrumentation; "Nano-Plotter" from GeSiM, Germany, located at http:/www.gesim.de/np-intro.htm.
Instrumentation; Bar code systems, including one and two dimensional bar codes, readable and readable/writable codes and systems: Datalogic S.p.A. of Italy ("Datalogic") located at http://www.datalogic.com.
Instrumentation; DYNABEADS, streptavidin-coated magnetic beads; from Dynal, Inc. Great Neck. NY and Oslo Norway.
Instrumentation:"MJ Microseal" plate sealer; Thermal Cycler Accessories; Sealing Options, Sealing Products, MJ Research, located at http://www.mjresearch.com/html/consumables/ealing/sealing_ products.html.
International Search Report for International Application No. PCT/US00/08111, Date of Mailing Nov. 13, 2000.
International Search Report for international Application No. PCT/US005/32441 Oct. 2, 2006.
Jahnen et al., Biochem. Biophys, Res. Commun.,166(1): 139-145 (1990).
Jurinke et al., "Detection of RET proto-oncogene codon 634 mutations using mass spectrometry", J. Mol. Med., 75:745-750, (1997).
Jurinke et al., (1998) Rapid Comm in Mass Spec., vol. 12, p. 50-52.
Jurinke, C. et al., Adv. Biochem, Eng. Biotechnol., 77: 57-74 (2002).
Jurinke, C. et al., Methods Mol. Biol., 187: 179-192 (2002).
Kim, S. et al., "Maspin Expression Is Transactivated by P63 and Is Critical for the Modulation of Lung Cancer Progression" Cancer Research, 2004, 6900-6905, 64, Korea.
Kirk, et al., "Single Mucleotide polymorphism seeking long term association with complex disease," Nucleic Acids Res. 2002. vol. 30, No. 5, pp. 3295-3311.
Kruglyak and Nickerson., Nature Genetics, 27-234-236 (2001).
Kuchino, Y. and S. Nishimura, 180: 154-163 (1989).
Kwok et al., Nucl. Acids Res.,18(4): 999-1005 (1990).
Ling, X. et al., "Proteomics-Based Identification of Maspin Differential Expression in Bronchial Epithelia Immortalized . . . " Chinese J. of Cancer, 2003,463-466, 22, China.
Litt, M. and J.A. Luty, Nucleic Acids Res., 18(14): 4301 (1990).
Litt, M. et al., NucleicAcids Res., 18(19): 5921 (1990).
Liu, X. et al., "XAGE-1, A New Gene That Is Frequently Expressed in Eqing's Sarcoma" Cancer Research, 2000, 4752-4755, 60, USA.
Luty, J.A. and M. Litt, "Dinucleotide repeat polymorphism at the D 14S45 locus",Nucleic Acids Res., 19(15): 4308 (1991).
Luty, J.A. et al.. "Five Polymorphic Microsatellite VNTRs on the Human XChromosome", Am. J. Hum. Genet., 46: 776-783 (1990).

(56) References Cited

OTHER PUBLICATIONS

Maass, N. et al., "Decline in the expression of the serine proteinase inhibitor maspin is associated with tumour progression . . . " J. of Pathology, 2001, 321-326,195, Germany.

Maass, N., et al., "Hyipermethylation and histone deacetylation lead to silencing of the maspin gene in human breast cancer . . . " BBRC, 2002, 125-128,297, USA.

Moon. C. et al. "Aquaporin Expression in Human Lymphocytes and Dentritic Cells" American Journal of Hematotogy, 2004 128,-133, 75, USA.

Moon, C. et al., "Involvement of aquaporins in colorectal carcinogenesis" Oncogene, 2003,6699-6703,22, USA.

Murakami, J. et al., "Effects of demethylating agent 5aza-2'deoxycytidine and histone deacetylase inhibitor FR901228 on maspin . . . " Oral Oncology 2004,597-603, 40, Japan.

NCBI GenBank Accession No. NM_002639.

Ogasawara, S. et al., "Disruption of cell-type-specific methylation at the Maspin gene promoter is frequently involved in . . . " Oncogene, 2004, 11 17-1 124, 23, Japan.

Oshio, K. et al., "Aquaporin-1 expression in human glial tumors suggests a potential novel therapeutic target for tumor-associated . . . " Acta Neurochir, 2003,494-502, 86, USA.

Risch, Neil, et al., The Relative Power of Family-Based and Case Control Design for Linkage Disequilibrium Studies of Complex Human Diseases I. DNA Pooling. Genome Research, (1998), 1278-1288. 8, Cold Spring Harbor Laboratory Press.

Saadoun, S. et al., "Increased aquaporin 1 water channel expression in human brain tumors", British J. of Cancer, 2002, 621-623, 87, UK.

Sarkar et al., Analytical Biochemistry 186:64-68 (1990).

Sarkar et al., Biotechniques 10(4):436-440 (1991).

Sato, N. et al. "Identification of maspin and S100P as novel hypomethylation targets in pancreatic cancer using global gene expression profiling", 2004, 1531-1538,23, USA.

Schächter et al., "Genetic associations with human longevity at the APOE and ACE loci", Nature Genetics, 6:29-32, (1994).

Sequenom Advances the Industrial Genomics Revolution with the Launch of Its DNA MassArray Automated Process Line, Press Release: Sep. 28, 1998, http://www.sequenom.com/pressrelease.htm.

Sequenom and Gemini Identify Genes Linked to Cardiovascular Disease, Press Release: Nov. 28, 2000, http://www/sequenom.com/ir/ir_prs.asp.

Sequenom Announces Publication of Results From Lange-Scale SNP Study With the National Cancer Institute, Press Release: Jan. 16, 2001, http://www/sequenom.com/ir/ir_prs.asp.

Sequenom Completes Design of More Than 400,000 SNP Assays; Mass EXTENDTM Assay Portfolio Covers Majority of SNPs in the Public Domain, Press Release; Oct. 10, 2000, http://www/sequenom.com/ir/ir_prs.asp.

Sequenom: Technologies and Tools, located at http://www.sequenom-san.com/tech/tools.html, dated Aug. 29, 1999.

Sheng et al., "Tagged probe interval graphs," Journal of Combinatorial Optimization. 2001 vol. 5, pp. 133-142.

Sigaloiti, L. et al., "Cancer testis antigens expression in mesothelioma:role of DNA methylation . . . " British J. of Cancer, 2002, 979-982, 86, UK.

Smith, S. et al., "Maspin-the most commonly-expressed gene of the 18q21.3 serpin cluster in lung cancer . . . " Oncogene, 2003, 8677-8687,22, UK.

Stomakhin et al., "DNA sequence analysis by hybridization with oligonucleotides microchips;MALDI mass spectrometry identificaiton of 5mers contiguously stacked to microchip oligonucleotides," Nucleic Acids Res. Mar. 1, 2000;28(5)1193-1198.

Takenawa, J.et al., "Transcript Levels of Aquaporin 1 and Carbonic Anhydrase IV as Predictive indicators for Prognosis of Renel Cell . . . " Int. J. Cancer, 1998, 1-7, 79, Japan.

Tang et al., Int. J. Mass. Spectrometry, 226(1):37-54 (2003).

Uracil-DNA Glycosylase (UDG), product description. New England Biolabs. http://circuit.neb.com/neb/products/mod_enzymes/280.html, (Dec. 21, 2000).

Uracil-DNA Glycosylase, product description. Roche Molecular Biochemicals Catalog Version 3, Nov. 1999 http:/biochem.roche.com/pack-insert/1269062a.pdf, (Dec. 21, 2000).

Vacca, A. et al., "Microvessel overexprssion of aquaporin 1 parallels bone marrow angiogenesis in patients with active . . . " British J. of Haematology, 2001,415-421,113, Italy.

van den Boom et al., Int. J. Mass Spectrom., 238(2):173-188 (2004).

von Wintzingerode, F. et al., "Base-specific fragmentation of amplified 16S rRNAgenes analyzed by mass spectrometry: A tool for rapid bacterial identification",Proc. Natl. Acad. Sci. U.S.A., 99(10): 7039-7044 (2002).

von Wintzingerode, F. et al., "Phylogenetic Analysis of an Anaerobic,Trichlorobenzene-Transforming Microbial Consortium", Appl. Environ. Mcrobiol.,65(1): 283-286 (1999).

Wada et al., "Detection of Single-nucleotide Mutations Including Substitutions and Deletions by Matrix-assisted Laser Desorption/Ionization Time-of-flight Mass Spectrometry," Rapid Communications in Mass Spectrometry, 11:1857-1660, (1997).

Wads, J. Mass Spectrometry, 33:187-192 (1998).

Wada, K. et al., "Aberrant Expression of the Maspin Gene Associated,with Epigenetic Modification," J. Invest Dermatol, 2004, 805-811, 122, Japan.

Xiong et al., "COBRA: a sensitive and quantitative DNA methylation assay," Nucleic Acids Res. Jun. 15, 1997;25(12):2532-2534.

Yatabe, Y. et al., "Maspin expression in normal lung and non-small-cell lung cancers: cellular property . . . " Oncogene, 2004,4041-4049, 23, Japan.

Zaia, J. and K. Biemann, "Comparison of Charged Derivatives for High EnergyCollision-Induced Dissociation Tandem Mass Spectrometry", J. Am. Soc. MassSpectrom., 6(5): 428-436 (1995).

Zaia, J., in: Protein and Peptide Analysis by Mass Spectrometry, J. R. Chapman (ed.). pp. 29-41, Humana Press, Totowa. N.J., (1996)

Zendman, A. et al., "The XAGE Family of Cancer/Testis-Associated Genes: Alignment and Expression Profile in Normal Tissues . . . " Int. J. Cancer, 2002,361-369,99 Netherlands.

Zhu et a., "Use of DNA Methylation for cancer detection and molecular classification," J Biochem Mol Biol. Mar. 31, 2007;40(2)135-141.

Zou et al., "Maspin, a serpin with tumor-suppressing activity in human mammary epithelial cells," Science, Jan. 28, 1994;263(5146):526-529.

\* cited by examiner

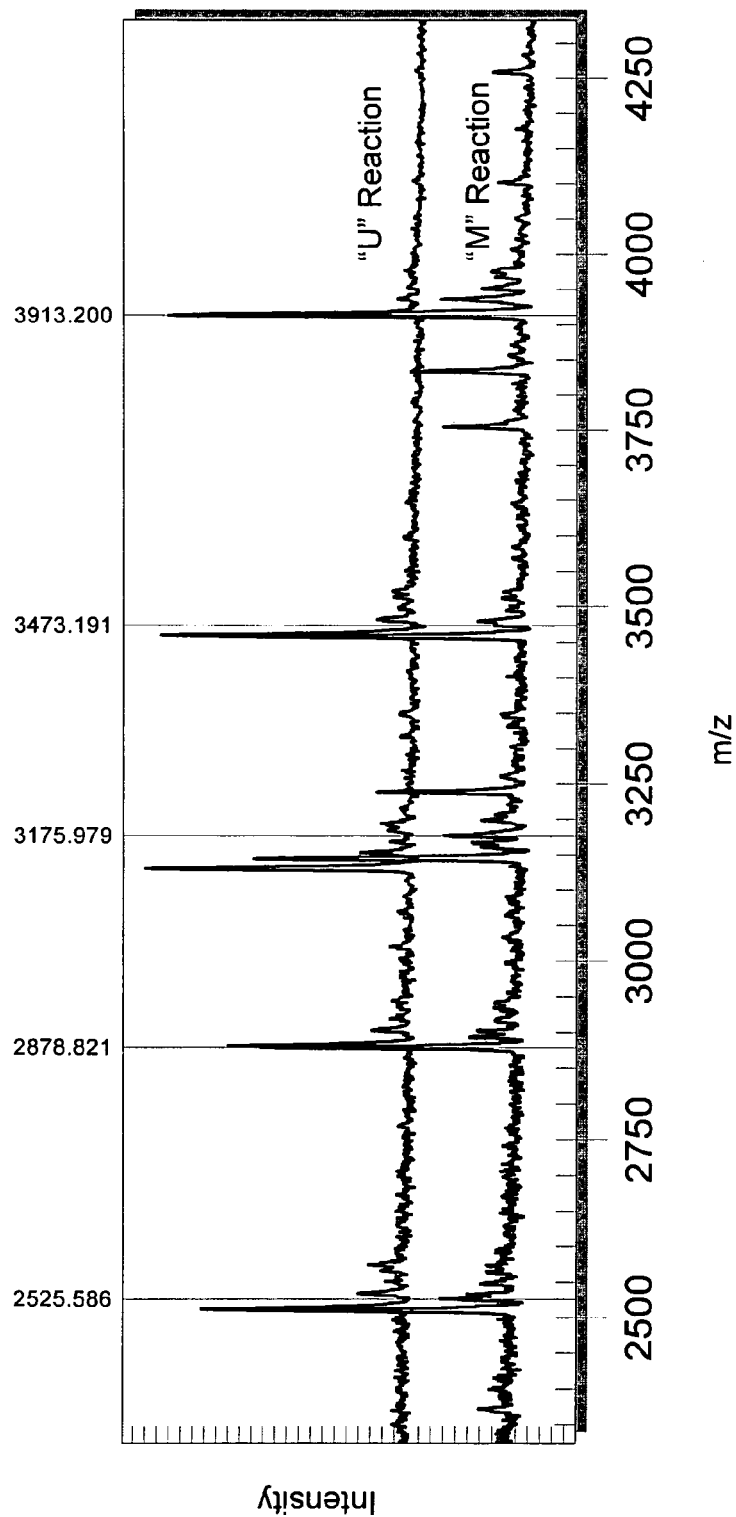

SEQUENCE LISTING

```
<160> NUMBER OF SEQ ID NOS: 5

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Synthetic
      T7 promoter sequence

<400> SEQUENCE: 1
cagtaatacg actcactata gggaga                                          26

<210> SEQ ID NO 2
<211> LENGTH: 56
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 2
cagtaatacg actcactata gggagaaggc tttttcctat cacaaaaata atccac         56

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aggaagagag gggattttta ttaagtgggt gttg                                 34

<210> SEQ ID NO 4
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cagtaatacg actcactata gggagaaggc tcttttccta tcacaaaaat aatccg         56

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aggaagagag gatttttatt aagcgggcgt c                                    31
```

BASE SPECIFIC CLEAVAGE OF METHYLATION-SPECIFIC AMPLIFICATION PRODUCTS IN COMBINATION WITH MASS ANALYSIS

RELATED APPLICATIONS

This application claims the benefit of U.S. Provisional Patent Application No. 60/556,632, filed on Mar. 26, 2004, entitled "BASE SPECIFIC CLEAVAGE OF METHYLATION-SPECIFIC AMPLIFICATION PRODUCTS IN COMBINATION WITH MASS ANALYSIS," to Mathias Ehrich and Dirk van den Boom, which hereby is incorporated by reference herein in its entirety. Subject matter in this application is related to U.S. application Ser. No. 10/272,665 to Andreas Braun, Christian Jurinke and Dirk van den Boom, filed Oct. 15, 2002, entitled "METHODS FOR GENERATING DATABASES AND DATABASES FOR IDENTIFYING POLYMORPHIC GENETIC MARKERS;" to subject matter in U.S. provisional application Ser. No. 10/723,365 to Dirk van den Boom and Sebastian Böcker, filed Nov. 27, 2003, entitled "FRAGMENTATION-BASED METHODS AND SYSTEMS FOR SEQUENCE VARIATION DETECTION AND DISCOVERY," and to U.S. provisional Ser. No. 60/466,006 to Sebastian Böcker and Dirk van den Boom, entitled "FRAGMENTATION-BASED METHODS AND SYSTEMS FOR DE NOVO SEQUENCING," filed Apr. 25, 2003. The subject matter and contents of each of these non-provisional and provisional applications as well as priority and parent applications thereof is incorporated by reference in its entirety.

FIELD OF THE INVENTION

Methods and products for assessing the methylation state of nucleic acids are provided.

BACKGROUND

Genetic information not only is stored in the sequential arrangement of four nucleotide bases, but also in covalent modification of selected bases (see, e.g., Robertson et al., *Nature Rev. Genet.* 1:11-19 (2000)). One of these covalent modifications is methylation of cytosine nucleotides, particularly cytosines adjacent to guanine nucleotides in "CpG" dinucleotides. Covalent addition of methyl groups to cytosine within CpG dinucleotides is catalyzed by proteins from the DNA methyltransferase (DNMT) family (Amir et al., *Nature Genet.* 23:185-88 (1999); Okano et al., *Cell* 99:247-57 (1999)). In the human genome, CpG dinucleotides are generally under represented, and many of the CpG dinucleotides occur in distinct areas called CpG islands. A large proportion of these CpG islands can be found in promoter regions of genes. The conversion of cytosine to 5'-methylcytosine in promoter associated CpG islands has been linked to changes in chromatin structure and often results in transcriptional silencing of the associated gene. Transcriptional silencing by DNA methylation has been linked to mammalian development, imprinting and X-Chromosome inactivation, suppression of parasitic DNA and numerous cancer types (see, e.g., Li et al., *Cell* 69:915-26 (1992); Okano et al., *Cell* 99:247-57 (1999)). Detected changes in the methylation status of DNA can serve as markers in the early detection of neoplastic events (Costello et al., Nature Genet. 24:132-38 (2000)).

Studies demonstrating the practical use of DNA methylation analysis in a clinical environment are scarce. This is due, at least in part, to the technical limitations facing DNA methylation research. A few DNA methylation analysis techniques have been used, but each method has its limitations. Some methods are prone to false positive results and are limited in accurate methylation assessment to a single cytosine position per analysis. Others require high amounts of high quality genomic DNA, are labor intensive, and are susceptible to false positive results.

Since DNA methylation has diagnostic and other uses, there is a need for reliable, cost effective, high throughput DNA methylation analysis tools and methods to evaluate potential methylated sites, to associate methylation sites with disease, and to develop prognostic methylation markers. Therefore, among the objects herein, it is an object herein to provide methylated nucleotide identification methods, and products therefor.

SUMMARY

Provided herein are methods, combinations and kits for identifying the methylation state of a target nucleic acid molecule. The methods can include treating a target nucleic acid molecule with a reagent that modifies nucleotides of the target nucleic acid molecule as a function of the methylation state of the target nucleic acid molecule, amplifying treated target nucleic acid molecule, fragmenting amplified target nucleic acid molecule, and detecting one or more amplified target nucleic acid molecule fragments, and based upon the fragments, such as size and/or number thereof, identifying the methylation state of a target nucleic acid molecule, or a nucleotide locus in the nucleic acid molecule, or identifying the nucleic acid molecule or a nucleotide locus therein as methylated or unmethylated.

Fragmentation can be performed, for example, by treating amplified products under base specific cleavage conditions. Detection of the fragments can be effected by measuring or detecting a mass of one or more amplified target nucleic acid molecule fragments, for example, by mass spectrometry such as MALDI-TOF mass spectrometry. Detection also can be effected, for example, by comparing the measured mass of one or more target nucleic acid molecule fragments to the measured mass of one or more reference nucleic acid, such as measured mass for fragments of untreated nucleic acid molecules. In an exemplary method, the reagent modifies unmethylated nucleotides, and following modification, the resulting modified target is specifically amplified.

Also provided herein are methods, combinations and kits for identifying one or more methylated or unmethylated nucleotides in a nucleic acid, by treating a target nucleic acid molecule with a reagent that modifies a selected nucleotide as a function of the methylation state of the selected nucleotide to produce a different nucleotide; contacting the treated target nucleic acid molecule with a primer containing one or more nucleotides complementary to the selected nucleotide, or one or more nucleotides complementary to the different nucleotide; treating the contacted target nucleic acid molecule under nucleic acid synthesis conditions, whereby nucleotides are synthesized onto primers hybridized to the target nucleic acid molecule; treating the synthesized products under base specific cleavage conditions; and detecting the products of the cleavage treatment, wherein a target nucleic acid molecule containing one or more methylated or unmethylated selected nucleotides is determined according to the number of cleavage products or according to a comparison between one or more cleavage products and one or more references.

Similarly provided herein are methods, combinations and kits for identifying one or more methylated or unmethylated nucleotides in a nucleic acid, by treating a target nucleic acid molecule with a reagent that modifies a selected nucleotide as a function of the methylation state of the selected nucleotide to produce a different nucleotide; amplifying the treated target nucleic acid molecule to form an amplification product; contacting the treated target nucleic acid molecule with a primer containing one or more nucleotides complementary to a nucleotide complementary to the selected nucleotide, or one or more nucleotides complementary to a nucleotide complementary to the different nucleotide; treating the contacted target nucleic acid molecule under nucleic acid synthesis conditions, whereby nucleotides are synthesized onto primers hybridized to the target nucleic acid molecule; treating the synthesized products under base specific cleavage conditions; and detecting the products of the cleavage treatment, wherein a target nucleic acid molecule containing one or more methylated or unmethylated selected nucleotides is determined according to the number of cleavage products or according to a comparison between one or more cleavage products and one or more references.

For example, the methods, combinations and kits provided herein include methods, combinations and kits for identifying methylated or unmethylated nucleotides in a nucleic acid, by treating a target nucleic acid molecule with a reagent selected from among a reagent that modifies an unmethylated selected nucleotide to produce a different nucleotide, and a reagent that modifies a methylated selected nucleotide to produce a different nucleotide; specifically amplifying the treated target nucleic acid molecule by a method selected from: (i) contacting the treated target nucleic acid molecule with a primer that specifically hybridizes to a target nucleic acid region containing one or more of the selected nucleotides or one or more of the different nucleotides, and treating the contacted target nucleic acid molecule under nucleic acid synthesis conditions, and (ii) amplifying the treated target nucleic acid molecule to form an amplification product, contacting the amplification product with a primer that specifically hybridizes to a target nucleic acid region containing one or more of the selected nucleotides, or one or more of the different nucleotides, and treating the contacted amplification product under nucleic acid synthesis conditions; treating the amplified products with base specific cleavage conditions; and detecting the products of the cleavage treatment, wherein a target nucleic acid molecule containing one or more methylated or unmethylated selected nucleotides is indicated by an observation selected from among: the presence of two or more cleavage products, the presence of only a single cleavage product, the presence of one or more cleavage products greater than the number of reference nucleic acid molecules, the presence of one or more cleavage products fewer than the number of reference nucleic acid molecules, the presence of the same number of cleavage products as reference nucleic acid molecules, a change in the mass of one or more cleavage products compared to a reference nucleic acid molecule mass, and one or more cleavage products that are the same mass as a reference nucleic acid molecule mass.

An example of methods, combinations and kits provided herein is a method, combination and kit for identifying a methylated nucleic acid molecule, by treating a target nucleic acid molecule with a reagent that modifies unmethylated cytosine to produce uracil; specifically amplifying the treated target nucleic acid molecule with a primer that contains one or more guanine nucleotides; base specifically cleaving the amplified products; and detecting the cleaved products, wherein the presence of two or more fragments indicates that the target nucleic acid molecule contains one or more methylated cytosines. Another example includes a method of identifying an unmethylated nucleic acid molecule, by treating a target nucleic acid molecule with a reagent that modifies unmethylated cytosine to produce uracil; specifically amplifying the treated target nucleic acid molecule with a primer that contains one or more adenine nucleotides; base specifically cleaving the amplified products; and detecting the cleaved products, wherein the presence of two or more fragments indicates that the target nucleic acid molecule contains one or more unmethylated cytosines.

Another exemplary method, combination and kit provided herein includes a method, combination and kit for identifying the nucleotide locus of a methylated nucleotide in a nucleic acid, by treating a target nucleic acid molecule with a reagent that modifies unmethylated cytosine to produce uracil; specifically amplifying the treated target nucleic acid molecule with a primer that contains one or more guanine nucleotides; base specifically cleaving the amplified products; and detecting the mass of the cleaved products, wherein: a change in mass of one or more cleaved products compared to a reference mass indicates that a nucleotide locus in a target is methylated. A similar exemplary method includes a method for identifying the nucleotide locus of an unmethylated nucleotide in a nucleic acid, by treating a target nucleic acid molecule with a reagent that modifies unmethylated cytosine to produce uracil; specifically amplifying the treated target nucleic acid molecule with a primer that contains one or more adenine nucleotides; base specifically cleaving the amplified products; and detecting the mass of the cleaved products, wherein: a change in mass of one or more cleaved products compared to a reference mass indicates that a nucleotide locus in a target is methylated.

Also provided herein are methods, combinations and kits for identifying the methylation state of a nucleotide locus in a methylated nucleic acid, by treating a target nucleic acid molecule to deaminate unmethylated cytosine nucleotides; specifically amplifying the treated target nucleic acid molecule with a primer that specifically hybridizes to a predetermined first region in the target nucleic acid molecule containing one or more cytosine nucleotides; base specifically cleaving the amplified products; and detecting the mass of the cleaved products, wherein: a change in mass of one or more cleaved products compared to a reference mass indicates that a nucleotide locus in a second region in a target is methylated, wherein the first region and second region do not overlap.

The methods, combinations and kits provided herein can be performed or used in conjunction with any of a variety of other procedures including, but not limited to, any procedures for modifying the target nucleic acid molecule according to the methylation state of the target nucleic acid molecule, any procedures for amplifying a target nucleic acid molecule, any procedures for fragmenting a target nucleic acid molecule, and any procedures for detecting target nucleic acid molecule fragments.

For example, provided herein are methods, combinations and kits for identifying the nucleotide locus of a methylated nucleotide in a nucleic acid, by treating a target nucleic acid molecule with a reagent that modifies unmethylated cytosine to produce uracil; specifically amplifying the treated target nucleic acid molecule with a primer that contains one or more guanine nucleotides; base specifically cleaving the amplified products; and cleaving or simulating cleavage of a reference nucleic acid with the same cleavage reagent(s); detecting the mass of the cleaved products; determining differences in the mass signals between the target nucleic acid molecule fragments and the reference fragments; and determining a reduced set of sequence variation candidates from the differences in the mass signals and thereby determining sequence variations in the target compared to the reference nucleic acid, wherein methylation of a nucleotide locus is indicated by the nucleotide locus of a sequence variation. In another example of the methods, combinations and kits provided herein, a method, combination and kit is provided for identifying the nucleotide locus of a methylated nucleotide in a nucleic acid, by treating a target nucleic acid molecule with a reagent that modifies unmethylated cytosine to produce uracil; amplifying the treated target nucleic acid molecule to form a first amplification product; specifically amplifying the first amplification product with a primer that contains one or more cytosine nucleotides to form a second amplification product; base specifically cleaving the second amplification products; cleaving or simulating cleavage of a reference nucleic acid with the same cleavage reagent(s); detecting the mass of the cleaved products; determining differences in the mass signals between the target nucleic acid molecule fragments and the reference fragments; and determining a reduced set of sequence variation candidates from the differences in the mass signals and thereby determining sequence variations in the target compared to the reference nucleic acid, wherein methylation of a nucleotide locus is indicated by the nucleotide locus of a sequence variation.

Also provided herein are methods, combinations and kits for identifying one or more methylated or unmethylated nucleotides in two or more nucleic acids, by, for example, treating two or more different target nucleic acid molecules with a reagent that modifies a selected nucleotide as a function of the methylation state of the selected nucleotide to produce a different nucleotide; contacting the treated target nucleic acid molecules with a primer containing one or more nucleotides complementary to the selected nucleotide, or one or more nucleotides complementary to the different nucleotide; treating the contacted target nucleic acid molecules under nucleic acid synthesis conditions, whereby nucleotides are synthesized onto primers hybridized to the target nucleic acid molecules; treating the synthesized products under base specific cleavage conditions; and detecting the products of the cleavage treatment, wherein target nucleic acid molecules containing one or more methylated or unmethylated selected nucleotides are determined according to a comparison between one or more cleavage products and one or more references.

Methods, combinations and kits also are provided for identifying one or more methylated or unmethylated nucleotides in a nucleic acid, by treating a target nucleic acid molecule with a reagent that modifies a selected nucleotide as a function of the methylation state of the selected nucleotide to produce a different nucleotide; contacting the treated target nucleic acid molecule with a primer containing one or more nucleotides complementary to the selected nucleotide, or one or more nucleotides complementary to the different nucleotide; treating the contacted target nucleic acid molecule under nucleic acid synthesis conditions, whereby nucleotides are synthesized onto primers hybridized to the target nucleic acid molecules; treating the synthesized products under fragmentation conditions; and detecting the products of the fragmentation treatment by mass spectrometry, wherein target nucleic acid molecules containing one or more methylated or unmethylated selected nucleotides are determined according to the number of fragmentation products or according to a comparison between one or more fragmentation products and one or more references. Similarly, methods are provided for identifying one or more methylated or unmethylated nucleotides in a nucleic acid, by treating a target nucleic acid molecule with a reagent that modifies a selected nucleotide as a function of the methylation state of the selected nucleotide to produce a different nucleotide; contacting the treated target nucleic acid molecule with a blocking oligonucleotide containing one or more nucleotides complementary to the selected nucleotide, or one or more nucleotides complementary to the different nucleotide; treating the contacted target nucleic acid molecule under nucleic acid synthesis conditions, wherein nucleotide synthesis is inhibited when the blocking oligonucleotide is hybridized to a target nucleic acid molecule; treating the synthesized products under base specific cleavage conditions; and detecting the products of the cleavage treatment, wherein a target nucleic acid molecule containing one or more methylated or unmethylated selected nucleotides are determined according to the number of cleavage products or according to a comparison between one or more cleavage products and one or more references.

Methods, combinations and kits also are provided herein for identifying one or more methylated or unmethylated nucleotides in a nucleic acid, by treating a target nucleic acid molecule with a reagent that modifies a selected nucleotide as a function of the methylation state of the selected nucleotide to produce a different nucleotide; contacting the target nucleic acid molecule with a cleavage reagent that selectively cleaves the target nucleic acid at a site containing one or more methylated selected nucleotides or one or more unmethylated selected nucleotides, or with a cleavage reagent that selectively cleaves the treated target nucleic acid at a site containing one or more selected nucleotides or one or more different nucleotides; treating the contacted target nucleic acid molecule under nucleic acid synthesis conditions, wherein a target nucleic acid molecule not cleaved is amplified; treating the amplified products under base specific cleavage conditions; and detecting the products of the cleavage treatment, wherein a target nucleic acid molecule containing one or more methylated or unmethylated selected nucleotides are determined according to the number of cleavage products or according to a comparison between one or more cleavage products and one or more references.

Also provided herein are methods, combinations and kits for identifying one or more methylated or unmethylated nucleotides in a nucleic acid, by contacting the target nucleic acid molecule with a primer and treating the contacted target nucleic acid molecule under nucleic acid synthesis conditions, wherein a strand complementary to the target nucleic acid molecule is synthesized; contacting the target nucleic acid-synthesized product duplex with a methyltransferase reagent whereby methylation in a CpG sequence of the target nucleic acid also is present in the complementary CpG sequence of the synthesized product; repeating the primer and methyltransferase reagent contacting steps to form a second synthesized product having the same sequence of nucleotides and methylation state of CpG nucleotides as present in the target nucleic acid molecule; treating synthesized products with a reagent that modifies a selected nucleotide as a function of the methylation state of the selected nucleotide to produce a different nucleotide; treating the reagent-treated products under base specific cleavage conditions; and detecting the products of the cleavage treatment, wherein a target nucleic acid molecule containing one or more methylated or unmethylated selected nucleotides are determined according to the number of cleavage products or according to a comparison between one or more cleavage products and one or more references.

Also provided herein are methods, combinations and kits for identifying one or more methylated or unmethylated nucleotides in a nucleic acid, where the amplified products are cleaved by base specific cleavage conditions selected from chemical conditions, physical conditions, enzymatic base specific cleavage conditions, and combinations thereof. For example, the amplified products can be cleaved by an RNase, a DNase, an alkaline compound, piperidine formate, piperidine, dimethyl sulfate, hydrazine, sodium chloride, and combinations thereof.

Also provided herein are methods, combinations and kits for identifying one or more methylated or unmethylated nucleotides in a nucleic acid, where the amplifying step includes transcription. In such methods, the nucleoside triphosphates incorporated into the transcript can include three rNTPs and one dNTP. For example, the one dNTP can be selected from dCTP, dTTP, dATP and dGTP. In another example, the one dNTP can be selected from dCTP and dTTP, and the transcript can be cleaved by RNase A.

Also provided herein are methods, combinations and kits for identifying one or more methylated or unmethylated nucleotides in a nucleic acid, where the intensity of one or more sample measured masses is compared to the intensity of one or more reference masses. Similarly, also provided herein are methods of identifying one or more methylated or unmethylated nucleotides in a nucleic acid, where two or more nucleic acid samples are pooled, and the intensity of one or more sample measured masses is compared to the intensity of one or more reference masses. In such methods an incompletely converted target nucleic acid molecule can be distinguished from a methylated target nucleic acid molecule.

The methods, combinations and kits provided herein can be used for a variety of different applications, including verifying specific amplification of methylated or unmethylated target nucleic acid molecules, determining a disease diagnosis, likely disease outcome or disease treatment regimen, and identifying an allele correlated with a methylation state.

The methods, combinations and kits can be used for distinguishing between a false positive methylation specific amplification and a true methylation specific amplification, by, for example, treating a target nucleic acid molecule with a reagent that modifies an unmethylated selected nucleotide to produce a different nucleotide; contacting the treated target nucleic acid molecule with a methylation state specific primer complementary to a first target nucleic acid region containing one or more of the selected nucleotides; treating the contacted target nucleic acid molecule under nucleic acid synthesis conditions; treating the synthesized products under base specific cleavage conditions; and detecting the mass of the cleaved products, wherein: a change in mass of one or more cleaved products compared to a reference mass indicates that a nucleotide locus in a second region in a target is methylated, wherein the second region does not overlap with the first region, whereby presence of one or more methylated loci in the second region confirms true methylation specific amplification.

The methods, combinations and kits can be used for identifying methylated nucleotides and thereby identify methylation patterns, which can be correlated with a disease, disease outcome, or outcome of a treatment regimen, by, for example, identifying methylated or unmethylated nucleotides, in accordance with the method of any of methods provided herein, in one or more nucleic acid molecules from one or more samples collected from one or more subjects having a known disease, disease outcome, or outcome of a treatment regimen; identifying methylated or unmethylated nucleotides, in accordance with the method of any of methods provided herein, in one or more nucleic acid molecules from one or more normal subjects; and identifying the differently methylated or unmethylated nucleotides between the one or more nucleic acid molecules of step (a) and the one or more nucleic acid molecules of step (b); whereby the differently methylated or unmethylated nucleotides identify methylation correlated with a disease, disease outcome, or outcome of a treatment regimen.

In another example, the methods, combinations and kits can be used for diagnosing a disease, deciding upon a treatment regimen, or determining a disease outcome in a subject, by, for example, identifying one or more methylated or unmethylated nucleotides in one or more nucleic acid molecules from one or more samples collected from a subject; and comparing the methylated or unmethylated nucleotides in the one or more nucleic acid molecules with one or more reference nucleic acid molecules correlated with a known disease, disease outcome, or outcome of a treatment regimen; whereby methylated or unmethylated nucleotides that are the same as the reference nucleic acid molecules identify the disease, disease outcome, or outcome of a treatment regimen in the subject. The methods, combinations and kits provided herein also can be used in deciding upon a treatment regimen, or determining a disease outcome in a subject, by, for example, identifying one or more methylated or unmethylated nucleotides in one or more nucleic acid molecules from one or more samples collected from a subject; and comparing the methylated or unmethylated nucleotides in the one or more nucleic acid molecules with one or more reference nucleic acid molecules correlated with a known disease, disease outcome, or outcome of a treatment regimen; whereby methylated or unmethylated nucleotides that are different from the reference nucleic acid molecules identify the disease, disease outcome, or outcome of a treatment regimen in the subject.

The methods, combinations and kits also can be used in determining a methylation state at one or more nucleotide loci correlated with an allele, by, for example, pooling nucleic acid molecules containing a known allele; identifying one or more methylated or unmethylated nucleotide loci in the nucleic acid molecules containing the known allele; identifying the methylation state of the corresponding nucleotide loci in nucleic acid molecules that do not contain the allele; and comparing the methylation state of the nucleotide loci in allele-containing nucleic acid molecules to the methylation state of nucleotide loci in allele-lacking nucleic acid molecules, whereby differences in methylation state frequency at one or more loci identify the different loci as correlated with the allele. Similarly, the methods. combinations and kits provided herein can be used for determining an allele correlated with a methylation state at one or more nucleotide loci, by forming a first pool of nucleic acid molecules containing one or more known methylated or unmethylated nucleotide loci, which loci were identified in accordance with the methods provided herein; identifying the frequency at which one or more alleles are present in the pooled nucleic acid samples; identifying the allele frequency at which one or more alleles are present in a second pool of nucleic acid molecules having nucleotide loci with different methylation state relative to the first pooled nucleic acid molecules; and comparing the allelic frequency in the first pool of nucleic acid molecules to the allelic frequency in the second pool of nucleic acid molecules, whereby differences in allelic frequency identify the one or more loci as correlated with the allele.

The methods, combinations and kits provided herein also can be used for determining the probable identity of one or more alleles, by, for example, identifying one or more methylated or unmethylated nucleotides a nucleic acid molecule; and determining the frequency of presence of one or more alleles with the presence of one or more methylated or unmethylated nucleotides where the probable identity of the allele is determined.

Also provided herein are combinations and kits for identifying the methylation state of a target nucleic acid molecule. Kits can include a reagent that modifies one or more nucleotides of the target nucleic acid molecule as a function of the methylation state of the target nucleic acid molecule, one or more methylation specific primers capable of specifically hybridizing to a treated target nucleic acid molecule, and one or more compounds capable of fragmenting an amplified target nucleic acid molecule. The one or more compounds capable of fragmenting amplified nucleic acid products can include an RNase, a DNase, an alkaline compound, piperidine formate, piperidine, dimethyl sulfate, hydrazine, sodium chloride, and combinations thereof. For example, kits provided herein can include one or more RNases.

DETAILED DESCRIPTION

A. Definitions
B. Methods for Determining Methylation of a Target Nucleic Acid Molecule
  1. Samples
    a. Source
    b. Preparation
  2. Target nucleic acid molecule
    a. Type of Nucleic Acid
    b. Structural or Biological Role of Target Nucleic Acid Molecule
    c. Size and Composition of Target Nucleic Acid Molecule
C. Methylation State-Specific Sequence Modification
  1. Reagents for Sequence Modification
  2. Modification of Cytosine with Bisulfite
  3. Resulting Nucleic Acid molecules
D. Amplification of Treated Target Nucleic Acid Molecule
  1. Methylation-specific primers
    a. Design of a Methylation Specific Primer
    b. Primer Composition
    c. Region Bound By Primer
    d. Primers Containing C or G Nucleotides
  2. Nucleic Acid Synthesis Methods
    a. Preliminary Amplification
    b. Synthesis of Complementary Strands
    c. Separating First Amplification Step from Later Steps
    d. Reaction Parameters
    e. Modified Nucleoside Triphosphates
    f. The Two Strands of the Treated Target Nucleic Acid Molecule
    g. Post-Amplification Steps
    h. Multiple Aliquots of Amplified Products
    i. Multiplexed Amplification
  3. Nucleotide Synthesis Blockers
    a. Composition and Properties of Nucleotide Synthesis Blockers
    b. Use of Nucleotide Synthesis Blockers
    c. Use of Multiple Nucleotide Synthesis Blockers
  4. Fragmentation in Conjunction with Nucleotide Synthesis
  5. Transcription
  6. Amplification of a Target Nucleic Acid Molecule While Maintaining the Methylated Sequence
E. Fragmentation of Nucleic Acid Molecules
  1. Enzymatic Fragmentation of Nucleic Acid Molecules
    a. Base-Specific Fragmentation
    b. Endonuclease Fragmentation of Nucleic Acid Molecules
    c. Nuclease Fragmentation
    d. Nucleic Acid Enzyme Fragmentation
  2. Physical Fragmentation of Nucleic Acid Molecules
  3. Chemical Fragmentation of Nucleic Acid Molecules
  4. Combinations of Fragmentation methods
    a. Base-Specific Fragmentation
      i. Absence of a Fragment
      ii. Presence of a Fragment
      iii. Comparison to a Reference
    b. Multiple Base Specific Cleavage Reactions
    c. Sequence Information and Methylation State Identification
F. Detection of Target Nucleic Acid Molecule Fragments
  1. Mass Spectrometric Analysis
    a. Mass Spectrometry Sample
      i. Characteristics of Nucleic Acid Molecules Measured
      ii. Conditioning
      iii. Multiplexing and Mass Modification
  2. Other Mass Measurement Methods
  3. Determining Mass Peak Characteristics
  4. Hybridization-Based Detection Methods
G. Fragment Measurement Analysis
  1. Methylation State Identification
    a. Identification Methods Without a Reference
    b. Identification Methods Using a Reference
      i. Nucleic Acid Molecule Sequence Known
      ii. Nucleic Acid Molecule Sequence Unknown
    c. Use of Mass Peak Characteristics
  2. Information Available from Analysis of Fragment Measurements
    a. Detection of Small Amounts of Methylated or Unmethylated Nucleic Acid
    b. Distinguishing Methylation State from Incomplete Conversion
    c. Methylation State Determination at Two or More Loci
    d. Confirmation of Specific Amplification
      i. Distinguishing from Mismatch Hybridization
      ii. Distinguishing from Incomplete Conversion
  3. Analysis of Both Target Nucleic Acid Molecule Strands
  4. Information in Cleavage Patterns
H. Applications
  1. Methylation Discovery
    a. Disease-Related Discovery
    b. Multiplex Analysis
    c. Target Nucleic Acid Molecule Fragments as Markers
  2. Methylation Analysis
    a. Disease-Related Analysis
    b. Organism Identification
    c. Pathogen Identification and Typing
    d. Haplotyping
    e. Determining Methylation Frequency
    f. Identifying Alleles
  3. Combinations and Kits
  A. Definitions Unless defined otherwise, all technical and scientific terms used herein have the same meaning as is commonly understood by one of skill in the art to which the invention(s) belong. All patents, patent applications, published applications and publications, GENBANK sequences, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information is known and can be readily accessed, such as by searching the internet and/or appropriate databases. Reference thereto evidences the availability and public dissemination of such information.

As used herein, a "target nucleic acid molecule" is a nucleic acid molecule that is examined using the methods disclosed herein. A target nucleic acid molecule includes a segment of genomic DNA, a segment of mitochondrial DNA or RNA and a segment of RNA. A target nucleic acid molecule can be examined, for example, for the presence or absence of one or more methylated nucleotides therein. In the context of methods of methylation identification, such as identifying the methylation state of a target nucleic acid or the methylation state of a nucleotide locus, a target nucleic acid molecule also can refer to an amplified product of a target nucleic acid molecule, including an amplified product of a treated target nucleic acid molecule, where the nucleotide sequence of such an amplified product reflects the methylation state of the target nucleic acid molecule. The intended target will be clear from the context or will be specified.

As used herein, the "methylation state" of a target nucleic acid molecule refers to the presence of absence of one or more methylated nucleotide bases in a target nucleic acid molecule. For example, a target nucleic acid molecule containing a methylated cytosine is considered methylated (i.e., the methylation state of the target nucleic acid molecule is methylated). A target nucleic acid molecule that does not contain any methylated nucleotides is considered unmethylated. Similarly, the methylation state of a nucleotide locus in a target nucleic acid molecule refers to the presence or absence of a methylated nucleotide at a particular locus in the target nucleic acid molecule. For example, the methylation state of a cytosine at the 7th nucleotide in a target nucleic acid molecule is methylated when the nucleotide present at the 7th nucleotide in the target nucleic acid molecule is 5-methylcytosine. Similarly, the methylation state of a cytosine at the 7th nucleotide in a target nucleic acid molecule is unmethylated when the nucleotide present at the 7th nucleotide in the target nucleic acid molecule is cytosine (and not 5-methylcytosine).

As used herein, "methylation state frequency" refers to the number of instances in which a molecule or locus is methylated relative to the number of instances the molecule or locus is unmethylated. Methylation state frequency can be used to describe a population of individuals or a sample from a single individual. For example, a nucleotide locus having a methylation state frequency of 50% is methylated in 50% of instances and unmethylated in 50% of instances. Such a frequency can be used, for example, to describe the degree to which a nucleotide locus or nucleic acid region is methylated in a population of individuals. Thus, when methylation in a first population or pool of nucleic acid molecules is different from methylation in a second population or pool of nucleic acid molecules, the methylation state frequency of the first population or pool will be different from the methylation state frequency of the second population or pool. Such a frequency also can be used, for example, to describe the degree to which a nucleotide locus or nucleic acid region is methylated in a single individual. For example, such a frequency can be used to describe the degree to which a group of cells from a tissue sample are methylated or unmethylated at a nucleotide locus or nucleic acid region.

As used herein, a "methylated nucleotide" or a "methylated nucleotide base" refers to the presence of a methyl moiety on a nucleotide base, where the methyl moiety is not present in a recognized typical nucleotide base. For example, cytosine does not contain a methyl moiety on its pyrimidine ring, but 5-methylcytosine contains a methyl moiety at position 5 of its pyrimidine ring. Therefore, cytosine is not a methylated nucleotide and 5-methylcytosine is a methylated nucleotide. In another example, thymine contains a methyl moiety at position 5 of its pyrimidine ring; however, for purposes herein, thymine is not considered a methylated nucleotide when present in DNA since thymine is a typical nucleotide base of DNA. Typical nucleoside bases for DNA are thymine, adenine, cytosine and guanine. Typical bases for RNA are uracil, adenine, cytosine and guanine.

As used herein, a "methylated nucleic acid molecule" refers to a nucleic acid molecule that contains one or more methylated nucleotides that are not typically methylated.

As used herein a "nucleotide locus" refers to the location of a nucleotide in a nucleic acid molecule. A nucleotide locus of a methylated nucleotide refers to the location of a methylated nucleotide in a nucleic acid molecule.

A "CpG island" as used herein refers to a G:C-rich region of genomic DNA containing an increased number of CpG dinucleotides relative to total genomic DNA. A CpG island can be at least 200 base pairs in length, where the G:C content of the region is at least 50% and the ratio of observed CpG frequency over expected frequency is 0.6; typically a CpG island can be at least 500 base pairs in length, where the G:C content of the region is at least 55% and the ratio of observed CpG frequency over expected frequency is 0.65. The observed CpG frequency over expected frequency can be calculated according to the method provided in Gardiner-Garden et al., *J. Mol. Biol.* 196:261-281 (1987). For example, the observed CpG frequency over expected frequency can be calculated according to the formula:

$$R=(A\times B)/(C\times D)$$

where R is the ratio of observed CpG frequency over expected frequency, A is the number of CpG dinucleotides in an analyzed sequence, B is the total number of nucleotides in the analyzed sequence, C is the total number of C nucleotides in the analyzed sequence, and D is the total number of G nucleotides in the analyzed sequence.

As used herein, a reagent that modifies a nucleotide of the target nucleic acid molecule as a function of the methylation state of the target nucleic acid molecule, or a methylation-specific reagent, refers to a compound or composition or other agent that can change the nucleotide sequence of a target nucleic acid molecule in a manner that reflects the methylation state of the target nucleic acid molecule. Methods of treating a target nucleic acid molecule with such a reagent can include contacting the target nucleic acid molecule with the reagent, coupled with additional steps, if desired, in order to accomplish the desired change of nucleotide sequence. Such a change in the target nucleic acid molecule's nucleotide sequence can result in a target nucleic acid molecule in which each methylated nucleotide is modified to a different nucleotide. Such a change in the target nucleic acid nucleotide sequence can result in a target nucleic acid molecule in which each unmethylated nucleotide is modified to a different nucleotide. Such a change in the target nucleic acid nucleotide sequence can result in a target nucleic acid molecule in which each of a selected nucleotide which is unmethylated (e.g., each unmethylated cytosine) is modified to a different nucleotide. Use of such a reagent to change the target nucleic acid nucleotide sequence can result in a target nucleic acid molecule in which each of a selected nucleotide which is methylated nucleotide (e.g., each methylated cytosine) is modified to a different nucleotide.

As used herein, use of a reagent that modifies a selected nucleotide refers to a reagent that modifies one nucleotide of the four typically occurring nucleotides in a nucleic acid molecule (C, G, T and A for DNA and C, G, U and A for RNA), such that the reagent modifies the one nucleotide without modifying the other three nucleotides. In one exemplary embodiment, such a reagent modifies an unmethylated selected nucleotide to produce a different nucleotide. In another exemplary embodiment, such a reagent can deaminate unmethylated cytosine nucleotides. An exemplary reagent is bisulfite.

As used herein, a "selected nucleotide" refers to one nucleotide of the four typically occurring nucleotides in a nucleic acid molecule (C, G, T and A for DNA and C, G, U and A for RNA), and can include methylated derivatives of the typically occurring nucleotides (e.g., when C is the selected nucleotide, both methylated and unmethylated C are included within the meaning of a selected nucleotide), whereas a methylated selected nucleotide refers specifically to a methylated typically occurring nucleotide and an unmethylated selected nucleotides refers specifically to an unmethylated typically occurring nucleotide.

As used herein, a "different nucleotide" refers to a nucleotide that is chemically different from a selected nucleotide, typically such that the different nucleotide has Watson-Crick base-pairing properties that differ from the selected nucleotide, whereby the typically occurring nucleotide that is complementary to the selected nucleotide is not the same as the typically occurring nucleotide that is complementary to the different nucleotide. For example, when C is the selected nucleotide, U or T can be the different nucleotide, which is exemplified by the complementarity of C to G and the complementarity of U or T to A.

As used herein, a nucleotide that is complementary to the selected nucleotide or that is complementary to the different nucleotide refers to a nucleotide that base-pairs, under high stringency conditions, with the selected nucleotide or different nucleotide with higher affinity than the complementary nucleotide's base-paring with three of the four typically occurring nucleotides. An example of complementarity is Watson-Crick base pairing in DNA (e.g., A-T and C-G) and RNA (e.g., A-U and C-G). Thus, for example, G base-pairs, under high stringency conditions, with higher affinity to C than G base-pairs to G, A or T, and, therefore, when C is the selected nucleotide, G is a nucleotide complementary to the selected nucleotide. Also included are non-natural or atypical nucleotides that have similar base-pairing properties. For example, a non-natural or atypical nucleotide complementary to C is a non-natural or atypical nucleotide that is similar to G in that it base-pairs with C with higher affinity than it base pairs with G, A or T.

As used herein: stringency of hybridization in determining percentage mismatch is as follows:
1) high stringency: 0.1×SSPE, 0.1% SDS, 65° C.
2) medium stringency: 0.2×SSPE, 0.1% SDS, 50° C.
3) low stringency: 1.0×SSPE, 0.1% SDS, 50° C.

Those of skill in this art know that the washing step selects for stable hybrids and also know the ingredients of SSPE (see, e.g., Sambrook, E. F. Fritsch, T. Maniatis, in: *Molecular Cloning, A Laboratory Manual*, Cold Spring Harbor Laboratory Press (1989), vol. 3, p. B. 13, see, also, numerous catalogs that describe commonly used laboratory solutions). SSPE is pH 7.4 phosphate-buffered 0.18 M NaCl. Further, those of skill in the art recognize that the stability of hybrids is determined by $T_m$, which is a function of the sodium ion concentration and temperature ($T_m$=81.5° C.-16.6($\log_{10}$ [Na$^+$])+0.41(% G+C)−600/l)), so that the only parameters in the wash conditions critical to hybrid stability are sodium ion concentration in the SSPE (or SSC) and temperature. Specific hybridization typically occurs under conditions of high stringency.

As used herein, a nucleotide that is complementary to the complement of a selected nucleotide or is complementary to the complement of a different nucleotide refers to a nucleotide that base-pairs under high stringency conditions with the nucleotide that is complementary to the selected nucleotide or that is complementary to the different nucleotide, with higher affinity than the complementary nucleotide's base-paring with three of the four typically occurring nucleotides. For example, when C is the selected nucleotide, G can be the complement of the selected nucleotide, and a C or C analog nucleotide can be a nucleotide that is complementary to the complement of the selected nucleotide. In another example, U can be the different nucleotide, and A can be the complement to the different nucleotide, and T can be the nucleotide complementary to the complement of the different nucleotide.

As used herein, a target nucleic acid molecule having a pre-determined region, or a treated target nucleic acid molecule having a pre-determined region, and variations thereof, refers to a particular region of a target nucleic acid molecule that has been treated with a reagent that modifies one or more nucleotides of the target nucleic acid molecule as a function of the methylation state of the target nucleic acid molecule, where the resulting nucleotide sequence of the region is a known or expected nucleotide sequence. For example, a primer that hybridizes to a pre-determined region in a target nucleic acid molecule can be a primer with a nucleotide sequence that is complementary to a target nucleic acid molecule region having a known nucleotide sequence. When the primer and reagent-treated target nucleic acid molecule are complementary, the hybridization is specific. As used in the context of such a primer, "pre-determined" can refer to a known nucleotide sequence in at least part of the target nucleic acid. Pre-determined also refers to an expected sequence of nucleotides in at least part of the treated target nucleic acid when treatment with a methylation specific reagent results in a change in nucleotide sequence, and such a nucleotide sequence change of the region is calculated, permitting design of a primer complementary to the region having a changed sequence of nucleotides.

As used herein, "treat" or "treating" refers to the process of exposing an analyte, typically a nucleic acid molecule, to conditions under which physical or chemical analyte modification or other chemical reactions (including enzymatic reactions) can occur. For example, treating a target nucleic acid with a reagent that modifies a target nucleic acid as a function of the methylation state of the target nucleic acid can include adding a reagent such as bisulfite to a solution containing a target nucleic acid molecule, where any unmethylated selected nucleotide, such as any unmethylated C nucleotide, present in the target nucleic acid molecule can be chemically modified, such as deaminated; however, if the target nucleic acid molecule contains no unmethylated selected nucleotide, such as no unmethylated C nucleotide, then a target nucleic acid molecule treated with such a reagent may not be chemically modified at all. In another example, treating a target nucleic acid molecule under fragmentation or cleavage conditions can include adding a cleavage reagent such as RNase T1, such that in selected target nucleic acid molecules, such as target nucleic acid molecules containing G nucleotides, cleavage can occur. Cleavage, however, need not occur, such as with target nucleic acid molecules not containing G nucleotides, cleavage with RNase T1 may not occur. In another example, treating a target nucleic acid molecule under nucleic acid synthesis conditions can include adding a DNA or RNA polymerase and NTPs, such that nucleic acid synthesis can occur if, for example, a primer is hybridized to a target nucleic acid molecule; however, no nucleic acid synthesis is necessary if, for example, no primer is hybridized to a target nucleic acid molecule.

As used to herein, mixing samples or other analyte-containing compositions "prior to treating" the samples refers to first combining samples into a single mixture and then performing one or more treatment steps such as, for example, nucleic acid synthesis or fragmentation or bisulfite treatment. In contrast, when two or more samples or compositions are "separately treated", the samples or compositions are added to each other, if at all, after one or more treatment steps.

As used herein, an "aliquot" is a portion less than the total amount of a sample or other analyte-containing composition. Multiple aliquots are not required to be identical to each other in size or amount.

As used herein, a treated target nucleic acid molecule "formed from" or "arising from" an untreated target nucleic acid molecule refers to a treated target nucleic acid molecule having a nucleotide sequence related to the nucleotide sequence of the untreated target nucleic acid molecule, which reflects the methylation state of the untreated target nucleic acid molecule.

As used herein, a "methyltransferase reagent" refers to a reagent that can transfer or catalyze transfer of a methyl moiety to a compound such as a nucleotide or nucleic acid molecule. Typically a methyltransferase reagent can transfer the methyl moiety with base specificity. Exemplary methyltransferase reagents are DNA methyltransferases, as known in the art.

As used herein, the phrase "hybridizing," or grammatical variations thereof, refers to binding of a first nucleic acid molecule to a second nucleic acid molecule under low, medium or high stringency conditions, or under nucleic acid synthesis conditions. Hybridizing can include instances where a first nucleic acid molecule binds to a second nucleic acid molecule, where the first and second nucleic acid molecules are complementary.

As used herein, "specifically hybridizes" refers to preferential hybridization under nucleic acid synthesis conditions of a probe or primer to a nucleic acid molecule having a sequence complementary to the probe or primer compared to hybridization to a nucleic acid molecule not having a complementary sequence. For example, specific hybridization includes the hybridization of a probe to a target sequence that is complementary to the probe.

As used herein, nucleotide synthesis conditions in the context of primer hybridization refer to conditions in which a primer anneals to the nucleic acid molecule to be amplified. Exemplary nucleotide synthesis conditions are 10 mM Tris HCl pH 8.3, 1.5 mM $MgCl_2$, 50 mM KCl, 62° C. Other exemplary nucleotide synthesis conditions are 16.6 mM ammonium sulfate, 67 mM Tris pH 8.8, 6.7 mM $MgCl_2$, 10 mM 2-mercaptoethanol, 60° C. Those of skill in the art are familiar with parameters that affect hybridization; such as temperature, probe or primer length and composition, buffer composition and pH, and salt concentration can readily adjust these parameters to achieve specific hybridization of a nucleic acid to a target sequence.

As used herein, complementary base pairs refers to Watson-Crick base pairs (e.g., G-C and A-T in DNA and G-C and A-U in RNA), or the equivalent thereof when non-natural or atypical nucleotides are used. Two nucleic acid strands that are complementary contain complementary base pairing. In some embodiments, a probe can contain universal or semi-universal bases or other components that can base pair or otherwise interact with more than one nucleotide base; in such cases, the probe can still be complementary despite containing base pairs that are not the typical C-G or A-T base pairs. A probe is not complementary when mismatches such as G-T, G-A, C-T or C-A arise when a probe or primer hybridizes to a target nucleic acid molecule.

As used herein "substantially" complementary refers to primers that are sufficiently complementary to hybridize with target nucleic acid molecules having a desired sequence under nucleic acid synthesis conditions. Primers should have sufficient complementarity to hybridize to a desired target nucleic acid molecule and permit amplification of the target nucleic acid molecule. For example, a primer used in the methods disclosed herein can be 100% complementary with the target nucleic acid molecule desired to be amplified. In another example, a primer can have 1, 2, 3, or more mismatches, provided that the primer can be used to amplify at least one target nucleic acid molecule desired to be amplified. For example, a target nucleic acid molecule can have 3 cytosine nucleotides in the region with which a primer hybridizes; when only one of the 3 C nucleotides are methylated, treatment with bisulfite can convert the 2 unmethylated C nucleotides to U nucleotides, and a primer 100% complementary to a target nucleic acid molecule having 3 C nucleotides can still hybridize to a target nucleic acid molecule having only 1 C nucleotide, such that the target nucleic acid molecule having only 1 C nucleotide can still be amplified.

As used herein "nucleic acid" refers to polynucleotides such as deoxyribonucleic acid (DNA) and ribonucleic acid (RNA). The term also includes, as equivalents, derivatives, variants and analogs of either RNA or DNA made from nucleotide analogs, single-stranded (sense or antisense) and double-stranded polynucleotides, including PNA (peptide nucleic acids). Deoxyribonucleotides include deoxyadenosine, deoxycytidine, deoxyguanosine and deoxythymidine. For RNA, the base portion of uridine is uracil.

As used herein, "detecting" a nucleic acid molecule or fragment thereof refers to determining the presence of the nucleic acid molecule, typically when the nucleic acid molecule or fragment thereof has been fully or partially separated from other components of a sample or composition, and also can include determining the charge-to-mass ratio, the mass, the amount, the absorbance, the fluorescence, or other property of the nucleic acid molecule or fragment thereof.

As used herein, "mass spectrometry" encompasses any suitable mass spectrometric format known to those of skill in the art. Such formats include, but are not limited to, Matrix-Assisted Laser Desorption/Ionization, Time-of-Flight (MALDI-TOF), Electrospray (ES), IR-MALDI (see, e.g., published International PCT application No. 99/57318 and U.S. Pat. No. 5,118,937), Ion Cyclotron Resonance (ICR), Fourier Transform and combinations thereof. MALDI, particularly UV and IR, are among the formats known in the art.

As used herein, the phrase "mass spectrometric analysis" refers to the determination of the charge to mass ratio of atoms, molecules or molecule fragments.

As used herein, mass spectrum refers to the presentation of data obtained from analyzing a biopolymer or fragment thereof by mass spectrometry either graphically or encoded numerically or otherwise presented.

As used herein, pattern with reference to a mass spectrum or mass spectrometric analyses, refers to a characteristic distribution and number of signals, peaks or digital representations thereof.

As used herein, signal, peak, or measurement, in the context of a mass spectrum and analysis thereof refers to the output data, which can reflect the charge to mass ratio of an atom, molecule or fragment of a molecule, and also can reflect the amount of the atom, molecule, or fragment thereof, present. The charge to mass ratio can be used to determine the mass of the atom, molecule or fragment of a molecule, and the amount can be used in quantitative or semi-quantitative methods. For example, in some embodiments, a signal peak or measurement can reflect the number or relative number of molecules having a particular charge to mass ratio. Signals or peaks include visual, graphic and digital representations of output data.

As used herein, intensity, when referring to a measured mass, refers to a reflection of the relative amount of an analyte present in the sample or composition compared to other sample or composition components. For example, an intensity of a first mass spectrometric peak or signal can reported relative to a second peak of a mass spectrum, or can be reported relative to the sum of all intensities of peaks. One skilled in the art can recognize a variety of manners of reporting the relative intensity of a peak. Intensity can be represented as the peak height, peak width at half height, area under the peak, signal to noise ratio, or other representations known in the art.

As used herein, comparing measured masses or mass peaks refers to analyzing one or more measured sample mass peaks to one or more sample or reference mass peaks. For example, measured sample mass peaks can be analyzed by comparison with a calculated mass peak pattern, and any overlap between measured mass peaks and calculated mass peaks can be determined to identify the sample mass or molecule. A reference mass peak is a representation of the mass of a reference atom, molecule or fragment of a molecule.

As used herein, a reference mass is a mass with which a measured sample mass can be compared. A comparison of a sample mass with a reference mass can identify a sample mass as the same as or different from the reference mass. Such a reference mass can be calculated, can be present in a database or can be experimentally determined. A calculated reference mass can be based on the predicted mass of a nucleic acid. For example, calculated reference masses can be based on a predicted fragmentation pattern of a target nucleic acid molecule of known or predicted sequence and known or predicted methylation state. An experimentally derived reference mass can arise from a measured mass of any nucleic acid sample. For example, experimentally derived masses can be masses measured after treating nucleic acid molecule with a methylation-specific reagent, amplifying the treated target nucleic acid molecule, and base specifically cleaving the amplification product. A database of reference masses can contain one or more reference masses where the reference masses can be calculated or experimentally determined; a database can contain reference masses corresponding to the calculated or experimentally determined fragmentation pattern of a target nucleic acid molecule; a database can contain reference masses corresponding to the calculated or experimentally determined fragmentation patterns of two or more target nucleic acid molecules.

As used herein, a reference nucleic acid molecule refers to a nucleic acid molecule known to be methylated or unmethylated, or a nucleic acid molecule in which the methylation state of one or more nucleotide loci of the nucleic acid molecule is known. A reference nucleic acid can be used to calculate or experimentally derive reference masses. A reference nucleic acid used to calculate reference masses is typically a nucleic acid containing a known sequence with known methylated nucleotide loci. A reference nucleic acid used to experimentally derive reference masses can have, but is not required to have, a known sequence or known methylated nucleotide loci; methods such as those disclosed herein or otherwise known in the art can be used to identify a reference nucleic acid as methylated even when the reference nucleic acid does not have a known sequence.

As used herein, a "correlation" between one or more sample masses (or one or more sample mass peak characteristics) and one or more reference masses (or one or more reference mass peak characteristics), and grammatical variants thereof, refers to a comparison between or among one or more sample masses (or one or more sample mass peak characteristics) and one or more reference masses (or one or more reference mass peak characteristics), where an increasing similarity of masses is indicative of an increasing likelihood that the a mass property, such as methylation of a sample target nucleic acid molecule is the same as the mass property, such as methylation, of the reference nucleic acid. Such a correlation can be used to identify a target nucleic acid molecule, such as to identify it as methylated, to identify the number of methylated nucleotides in a target nucleic acid molecule, to identify the methylation state of one or more nucleotide loci, or to identify one or more nucleotide loci as methylated.

As used herein, a correlation between a target nucleic acid molecule and a reference, including a correlation between a nucleotide locus in a target nucleic acid molecule and a nucleotide locus in a reference, refers to a similarity or identity of the methylation state of a target nucleic acid molecule or nucleotide locus to that of a reference, such that the target nucleic acid molecule and the reference are expected to have at least one undefined locus with the same methylation state. For example, when the methylation state of fewer than all nucleotide loci of a target nucleic acid molecule have been identified, and when there is a correlation between a reference nucleic acid and a target nucleic acid, one or more of the unidentified loci of the target nucleic acid molecule can be expected to have the same methylation state as the corresponding nucleotide locus in the reference. In another example, when there is a correlation between a reference nucleic acid and a target nucleic acid, one or more of the loci of the target nucleic acid molecule located in the region of primer hybridization can be expected to have the same methylation state as the corresponding nucleotide locus in the reference. A lack of such a correlation can refer to insufficient correlation to provide expectation of an unidentified methylation state in the target nucleic acid molecule, or can refer to an anti-correlation, where the methylation state in the target nucleic acid molecule is expected to be the opposite (i.e., unmethylated or methylated) of the methylation state in the reference.

As used herein, "analysis" refers to the determination of particular properties of a single oligonucleotide, or of mixtures of oligonucleotides. These properties include, but are not limited to, the nucleotide composition and complete sequence of an oligonucleotide or of mixtures of oligonucleotides, the existence of one or more methylated nucleotides in a oligonucleotide, the masses and the lengths of oligonucleotides and the presence of a molecule or sequence within molecule in a sample.

As used herein, "multiplexing," "multiplexed," "a multiplexed reaction," or grammatical variations thereof, refers to the simultaneous assessment or analysis of more than one molecule, such as a biomolecule (e.g., an oligonucleotide molecule) in a single reaction or in a single mass spectrometric or other mass measurement, e.g., a single mass spectrum.

As used herein, "pooling" refers to mixing samples from two or more sources. Such pooling can be, for example, a mixing of nucleic acid samples from cells collected from the same organism, a mixing of nucleic acid samples from different organisms of the same species, or a mixing of nucleic acid samples from different species.

As used herein, nucleic acid synthesis refers to a chemical or biochemical reaction in which a phosphodiester bond is formed between one nucleotide and a second nucleotide or an oligonucleotide. Nucleic acid synthesis can include enzymatic reactions such as DNA replication reactions such as PCR or transcription, or chemical reactions such as solid phase synthesis. Nucleic acid synthesis conditions refers to conditions of a nucleic acid molecule-containing solution in which nucleotide phosphodiester bond formation is possible. For example, a target nucleic acid molecule can be contacted with a primer, and can be treated under nucleic acid synthesis reactions, which can include, for example, PCR or transcription conditions, and, when the primer hybridizes to the target nucleic acid molecule, nucleotides can be synthesized onto the primer, that is, nucleotides can be enzymatically added via phosphodiester linkage to the 3' end of primer; however, when no primer is hybridized to the target nucleic acid molecule, it is possible that no nucleotides are synthesized onto the primer.

As used herein, amplifying refers to increasing the amount of a biopolymer, especially nucleic acids. Amplification includes a one or more steps of forming additional biopolymers, such as one or more cycles of PCR. Based on the 5' and 3' primers that are chosen, amplification also serves to narrow and define the region of the nucleic acid which is subject to analysis. Amplification can be by any means known to those skilled in the art, including use of the polymerase chain reaction (PCR), transcription, and other such methods. Amplification, such as PCR, can be done quantitatively, such as when the frequency of methylated nucleotides is to be determined.

As used herein, specifically amplifying refers to increasing the amount of a particular biopolymer on the basis of one or more properties of the biopolymer. For example, a nucleic acid can be specifically amplified based upon the nucleotide sequence of the nucleic acid, or based upon the nucleotide sequence of a portion of the nucleic acid. An example of specific amplification of a nucleic acid based on a portion of the sequence of the nucleic acid is amplification, using for example, PCR, of a nucleic acid using specific hybridization of one or two primers to one or two regions of the nucleic acid. Typically, specifically amplifying includes nucleic acid synthesis of a target nucleic acid molecule where a primer hybridizes with complete complementarity to a nucleotide sequence in the target nucleic acid molecules. In a specifically amplifying reaction, some primers can unintendedly hybridize to a sequence of nucleotides with which the primers are partially mismatched, resulting in unintended or false positive amplification products. Methods provided herein can be used to distinguish between true products of a specific amplification and false positive products.

As used herein a "primer" is a polynucleotide such as DNA or RNA that contains a 3' hydroxyl group. A primer can be used, for example, as a precursor for phosphoester or phosphodiester bond formation at the 3' hydroxyl group, by, for example, nucleotide synthesis reactions such as transcription or DNA replication. A primer can hybridize to a template nucleic acid, whereupon an enzyme can catalyze addition of one or more nucleotides to the 3' end of the primer.

As used herein, a "methylation specific primer" or "methylation state specific primer" refers to a primer that can specifically hybridize with a target nucleic acid molecule or a methylation-specific reagent-treated target nucleic acid molecule in accordance with the methylation state of the target nucleic acid molecule. For example, a target nucleic acid molecule can be treated with a methylation-specific reagent, resulting in a change in the nucleotide sequence of the target nucleic acid molecule as a function of the methylation state of the target nucleic acid molecule; and a methylation state specific primer can specifically hybridize to the treated methylated target nucleic acid molecule, without hybridizing to a treated unmethylated target nucleic acid molecule or without hybridizing to a treated, differently methylated target nucleic acid molecule. In another example, a target nucleic acid molecule can be treated with a methylation-specific reagent, resulting in a change in the nucleotide sequence of the target nucleic acid molecule as a function of the methylation state of the target nucleic acid molecule; and a methylation state specific primer can specifically hybridize to the treated unmethylated target nucleic acid molecule, without hybridizing to a treated methylated target nucleic acid molecule or without hybridizing to a treated, differently unmethylated target nucleic acid molecule. In other examples, methylation specific primers do not always hybridize solely with the perfectly complementary sequence, but also unintendedly bind to a nucleotide sequence that is at least partially mismatched with the methylation state specific primer. While this less efficient mismatched hybridization can result in non-methylation specific amplification, the methods provided herein can be used to distinguish between amplification products resulting from perfectly complementary hybridization and amplification products resulting from mismatched hybridization. Methylation specific primers that hybridize to a target nucleic acid molecule then can serve as primers for subsequent nucleotide synthesis reactions, such as PCR.

As used herein, an "amplification blocker" or "nucleotide synthesis blocker" refers to a compound, typically an oligonucleotide, that binds a nucleotide sequence on a nucleic acid molecule and reduces or inhibits the ability of an enzyme, such as DNA or RNA polymerase, to catalyze nucleotide synthesis. In one example, the amplification blocker binds to a nucleotide sequence along which the enzyme would pass in catalyzing nucleotide synthesis. In another example, an amplification blocker can compete with a primer for binding to a nucleic acid molecule nucleotide sequence at which nucleotide synthesis would begin. Typically, an amplification blocker is an oligonucleotide, where such a blocking oligonucleotide does not contain a 3'-hydroxy group so that additional nucleotides cannot be added to the amplification blocker during a nucleotide synthesis reaction.

As used herein, inhibiting nucleotide synthesis refers to a reduction in the amount of synthesized nucleic acid molecules produced from all or a selected subset of nucleic acid molecules in a sample or composition. Nucleotide synthesis can be inhibited, for example, by reducing the ability of a primer to hybridize to a nucleotide sequence, or by physically blocking the processive path of a nucleic acid polymerase. Typically, nucleotide synthesis is inhibited for nucleic acid molecules that do not contain a desired sequence, such as, for example, nucleic acid molecules that might otherwise be amplified despite partial mismatch with a methylation specific primer.

As used herein, a query region of a nucleic acid molecule refers to a region of the nucleic acid molecule whose nucleotide sequence is under examination. A primer query region of a nucleic acid molecule refers to a region of the nucleic acid molecule whose nucleotide sequence is to be examined to determine whether a primer hybridizes to that region of the nucleic acid molecule. For example, a methylation specific primer can specifically hybridize under nucleic acid synthesis conditions to a target nucleic acid molecule at the primer query region when the primer query region is complementary to the primer. Similarly, a non-primer query region of target nucleic acid molecule is a region in a nucleic acid molecule to which a methylation specific primer will not specifically hybridize. Typically, a non-primer query region of a target nucleic acid molecule is the nucleotide region that does not overlap with the primer query region, such as, for example, the region located between two primer hybridization sites, including the nucleotide region located between two primer query regions of a target nucleic acid molecule. A non-methylation specific primer query region of a target nucleic acid molecule typically is the nucleotide region that does not overlap with a methylation specific primer query region, although it can overlap with a primer hybridization region when the primer is not a methylation specific primer.

As used herein, a pre-determined region refers to a region of a nucleic acid molecule that contains a defined nucleotide sequence. For example, a primer can be created that has a known, particular nucleotide sequence. A region of a target nucleic acid molecule that hybridizes to such a primer with complete complementarity can be defined in terms of the known, particular nucleotide sequence of the primer. Thus, a pre-determined region can be a region of a nucleic acid molecule that hybridized with complete complementarity to such a primer.

As used herein, a first region that does not overlap with a second region refers to portions of a nucleic acid molecule that do not encompass any of the same nucleotide loci. For example, a first region that does not overlap with a primer hybridization region is a first region that does not encompass any of the nucleotide loci with which a primer hybridizes.

As used herein, an amplified product is any product of a nucleotide synthesis reaction using a target nucleic acid molecule as the template. Thus, a single-stranded nucleic acid molecule complementary to the treated target nucleic acid molecule and formed in the first amplification step is an amplified product. In addition, products of subsequent nucleotide synthesis reactions which contain the same sequence as the treated target nucleic acid molecule, or the complement thereof, are amplification products. An amplification product can be a single-stranded nucleic acid molecule or a double-stranded nucleic acid molecule.

As used herein, "fragmentation" or "cleavage" refers to a procedure or conditions in which a nucleic acid molecule, such as a target nucleic acid molecule or amplified product thereof, is severed into two or more smaller nucleic acid molecules. Such fragmentation or cleavage can be sequence specific, base specific, or nonspecific, and can be accomplished by any of a variety of methods, reagents or conditions, including, for example, chemical, enzymatic, physical fragmentation.

As used herein, fragmentation conditions refer to chemical, enzymatic or physical conditions under which fragmentation or cleavage of a nucleic acid molecule can, but are not required to, be achieved. Cleavage conditions or cleavage reaction conditions can include one or more cleavage reagents that are used to perform actual or simulated cleavage reactions, and other parameters of the reactions including, but not limited to, time, temperature, pH, or choice of buffer or ions. For example, fragmentation conditions can refer to a buffer containing a sequence-specific endonuclease, where nucleic acid molecules containing the recognized sequence are cleaved, and nucleic acid molecules not containing the recognized sequence are not cleaved.

As used herein, a cleavage reagent is any compound that can cause cleavage of a nucleic acid molecule, including, for example, nucleases and chemicals, such as a strong base, that cleave nucleic acid molecules.

As used herein, "fragments," "cleavage products," "cleaved products" or grammatic variants thereof, refers to nucleic acid molecules resultant from a fragmentation or cleavage of a target nucleic acid molecule or amplified product thereof. While such fragments or cleaved products can refer to all nucleic acid molecules resultant from a cleavage reaction, typically such fragments or cleaved products refer only to nucleic acid molecules resultant from a fragmentation or cleavage of a target nucleic acid molecule or the portion of an amplified product thereof containing the corresponding nucleotide sequence of a target nucleic acid molecule. For example, it is within the scope of the present methods, compounds and compositions, that an amplified product can contain one or more nucleotides more than the amplified nucleotide region of the target nucleic acid sequence (e.g., a primer can contain "extra" nucleotides such as a transcriptional initiation sequence, in addition to nucleotides complementary to a target nucleic acid molecule, resulting in an amplified product containing "extra" nucleotides or nucleotides not corresponding to the amplified nucleotide region of the target nucleic acid molecule). In such an example, the fragments or cleaved products corresponding to the nucleotides not arising from the target nucleic acid molecule will typically not provide any information regarding methylation in the target nucleic acid molecule. One skilled in the art can therefore understand that the fragments of an amplified product used to provide methylation information in the methods provided herein are fragments containing one or more nucleotides arising from the target nucleic acid molecule, and not fragments containing nucleotides arising solely from a sequence other than that in the target nucleic acid molecule. Accordingly, one skilled in the art will understand the fragments arising from methods, compounds and compositions provided herein to be include fragments arising from portions of amplified nucleic acid molecules containing, at least in part, nucleotide sequence information from a or based or representative target nucleic acid molecule.

As used herein, base specific cleavage refers to selective cleavage of a nucleic acid at the site of a particular base (e.g., A, C, U or G in RNA or A, C, T or G in DNA) or of a particular base type (e.g., purine or pyrimidine). For example, C-specific cleavage refers to cleavage of a nucleic acid at every C nucleotide in the nucleic acid.

As used herein, the phrase "non-specifically cleaved," in the context of nucleic acid cleavage, refers to the cleavage of target nucleic acid molecule at random locations throughout, such that various cleaved fragments of different size and nucleotide sequence content are randomly generated. Cleavage at random locations, as used herein, does not require absolute mathematical randomness, but instead only a lack of sequence-based preference in cleavage. For example, cleavage by irradiative or shearing means can cleave DNA at nearly any position; however, such methods can result in cleavage at some locations with slightly more frequency than other locations. Nevertheless, cleavage at nearly all positions with only a slight sequence preference is still random for purposes herein. Non-specific cleavage using the methods described herein can result in the generation of overlapping nucleotide fragments.

As used herein, the term "complete cleavage" or "total cleavage" refers to a cleavage reaction in which all the cleavage sites recognized by a particular cleavage reagent are cut to completion.

As used herein, the term "partial cleavage," "partial fragmentation" or "incomplete cleavage," or grammatical variations thereof, refers to a reaction in which only a fraction of the respective cleavage sites for a particular cleavage reagent are actually cut by the cleavage reagent. Partial cleavage can refer to total cleavage of a particular locus, but less than total cleavage at one or more other loci of the same target nucleic acid molecule; or partial cleavage can refer to cleavage of some, but not all, target nucleic acid molecules at one or more loci. The cleavage reagent can be, but is not limited to an enzyme, a chemical cleavage reagent, or mechanical or physical force. As set forth herein, exemplary of a method for achieving partial cleavage is to produce a biomolecule and include cleavable or non-cleavable nucleotides or amino acids during its production, such that a particular cleavage site contains uncleavable nucleotides or amino acids. This renders the resulting target biomolecule partially cleaved, even when the cleavage reaction is run to completion. For example, if an uncleaved target biomolecule has 4 potential cleavage sites therein, then the resulting mixture of products from partial cleavage can have any combination of fragments of the target biomolecule resulting from: a single cleavage at a first, second, third or fourth cleavage site; double cleavage at any one or more combinations of 2 cleavage sites; or triple cleavage at any one or more combinations of 3 cleavage sites.

As used herein, uncleaved cleavage sites means cleavage sites that are known recognition sites for a cleavage reagent but that are not cut by the cleavage reagent under the conditions of the reaction, e.g., time, temperature, or modifications of the bases at the cleavage recognition sites to prevent cleavage by the reagent.

As used herein, complementary cleavage reactions refers to cleavage reactions that are performed or simulated on the same target or reference nucleic acid or protein using different cleavage reagents or by altering the cleavage specificity of the same cleavage reagent such that alternate cleavage patterns of the same target or reference nucleic acid or protein are generated.

As used herein, the phrase "overlapping fragments" refers to fragments that have one or more nucleotide loci from the native target nucleic acid molecule in common.

As used herein, the phrase "statistically range in size" refers to the size range for a majority of the fragments generated using cleavage methods known in the art or disclosed herein, such that some of the fragments can be substantially smaller or larger than most of the other fragments within the particular size range. An example of such a statistical range in sizes of fragments is a Poisson distribution. For example, the statistical size range of 12-30 bases also can include some oligonucleotides as small as 1 nucleotide or as large as 300 nucleotides or more, but these particular sizes statistically occur relatively rarely. In some embodiments, there is no limit to the statistical range of fragments. In other embodiments, a statistical range of fragments can specify a range such that 10% of the fragments are within the specified size range, where 20% of the fragments are within the specified size range, where 30% of the fragments are within the specified size range, where 40% of the fragments are within the specified size range, where 50% of the fragments are within the specified size range, where 60% or more of the fragments are within the specified size range, where 70% or more of the fragments are within the specified size range, where 80% or more of the fragments are within the specified size range, where 90% or more of the fragments are within the specified size range, or where 95% or more of the fragments are within the specified size range.

As used herein, matrix or support particles refers to support materials that are in the form of discrete particles. The particles have any shape and dimensions, but typically have at least one dimension that is 100 mm or less, 50 mm or less, 10 mm or less, 1 mm or less, 100 µm or less, 50 µm or less, 10 µm or less, 5 µm or less, 1 µm or less, 0.5 µm or less, and typically have a size that is 100 mm$^3$ or less, 50 mm$^3$ or less, 10 mm$^3$ or less, and 1 mm$^3$ or less, 100 µm$^3$ or less and can be on the order of cubic microns; typically the particles have a diameter of more than about 1.5 microns and less than about 15 microns, such as about 4-6 microns. Such particles are collectively called "beads."

As used herein, "substrate" refers to an insoluble support that can provide a surface on which or over which a reaction can be conducted and/or a reaction product can be retained at identifiable loci. Support can be fabricated from virtually any insoluble or solid material. For example, silica gel, glass (e.g., controlled-pore glass (CPG)), nylon, Wang resin, Merrifield resin, Sephadex, Sepharose, cellulose, a metal surface (e.g., steel, gold, silver, aluminum, silicon and copper), a plastic material (e.g., polyethylene, polypropylene, polyamide, polyester, polyvinylidenedifluoride (PVDF)). Exemplary substrates include, but are not limited to flat supports such as glass fiber filters, glass surfaces, metal surfaces (steel, gold, silver, aluminum, copper and silicon), and plastic materials. The solid support is in any form suitable for mounting on the cartridge base, including, but not limited to: a plate, membrane, wafer, a wafer with pits, a porous three-dimensional substrate, and other geometries and forms known to those of skill in the art. Exemplary supports are flat surfaces designed to receive or link samples at discrete loci, such as flat surfaces with hydrophobic regions surrounding hydrophilic loci for receiving, containing or binding a sample.

As used herein, "a non-specific RNase" refers to an enzyme that cleaves a RNA molecule irrespective of the sequence of nucleotides present at the cleavage site. An exemplary non-specific RNase is RNase I.

As used herein, "a non-specific DNase" refers to an enzyme that cleaves a DNA molecule irrespective of the sequence of nucleotides present at the cleavage site. An exemplary non-specific DNase is DNase I.

As used herein, the term "single-base cutter" refers to a restriction enzyme that recognizes and cleaves a particular base (e.g., A, C, T or G for DNA or A, C, U or G for RNA), or a particular type of base (e.g., purines or pyrimidines).

As used herein, the term "1¼-cutter" refers to a restriction enzyme that recognizes and cleaves a 2 base stretch in the nucleic acid, in which the identity of one base position is fixed and the identity of the other base position is any three of the four typically occurring bases.

As used herein, the term "1½-cutter" refers to a restriction enzyme that recognizes and cleaves a 2 base stretch in the nucleic acid, in which the identity of one base position is fixed and the identity of the other base position is any two out of the four typically occurring bases.

As used herein, the term "double-base cutter" or "2 cutter" refers to a restriction enzyme that recognizes and cleaves a specific nucleic acid site that is 2 bases long.

As used herein, the phrase "set of mass signals" or a "mass peak pattern" refers to two or more mass determinations made for each of two or more nucleic acid fragments of a nucleic acid molecule. A "mass pattern" refers to two or more masses corresponding to two or more nucleic acid fragments of a nucleic acid molecule.

As used herein, scoring or a score refers to a calculation of the probability that a particular methylated nucleotide or sequence candidate is actually present in the target nucleic acid molecule or protein sequence. The value of a score is used to determine the methylated nucleotide or sequence candidate that corresponds to the actual target sequence. Usually, in a set of samples of target sequences, the highest score represents the most likely methylated nucleotide or sequence in the target molecule, but other rules for selection also can be used, such as detecting a positive score, when a single target sequence is present.

As used herein, simulation (or simulating) refers to the calculation of a fragmentation pattern based on the nucleotide sequence and location of methylated nucleotides in a nucleic acid and the predicted cleavage sites in the nucleic acid for a particular specific cleavage reagent. The fragmentation pattern can be simulated as a table of numbers (for example, as a list of masses corresponding to the masses of fragments of a reference biomolecule), as a mass spectrum, as a pattern of bands on a gel, or as a representation of any technique that measures mass distribution. Simulations can be performed in most instances by a computer program.

As used herein, simulating cleavage refers to an in silico process in which a target molecule or a reference molecule is virtually cleaved.

As used herein, in silico refers to research and experiments performed using a computer. In silico methods include, but are not limited to, molecular modelling studies, biomolecular docking experiments, and virtual representations of molecular structures and/or processes, such as molecular interactions.

As used herein, a subject includes, but is not limited to, an animal, plant, bacterium, virus, parasite and any other organism or entity that has nucleic acid. Among subjects are mammals, including primates, such as humans.

As used herein, a disease treatment regimen refers to steps taken in management of a disease, including, for example, behavioral modification, surgery, or medication. Treatment includes regimen that ameliorates or eliminates the symptoms of a disease or the disease.

As used herein, normal, when referring to a nucleic acid molecule or sample source, such as an individual or group of individuals, refers to a nucleic acid molecule or sample source that was not selected according to any particular criterion, and typically refers to a typical nucleotide sequence of a nucleic acid molecule or health condition of a sample source (e.g., one or more healthy subjects or one or more subjects not diagnosed with a disease). For example, a normal methylation state of a particular nucleotide locus can be the wild type methylation state of the nucleotide locus. In another example, a group of normal subjects can be a group of subjects not having a particular phenotype (such as a disease).

As used herein, a phenotype refers to a set of parameters that includes any distinguishable trait of an organism. A phenotype can be physical traits and can be, in instances in which the subject is an animal, a mental trait, such as emotional traits.

As used herein, a methylation or methylation state correlated with a disease, disease outcome or outcome of a treatment regimen refers to a methylation state of a nucleic acid region or nucleotide locus that is present or absent more frequently in subjects with a known disease, disease outcome or outcome of a treatment regimen, relative to the methylation state of a nucleic acid region or nucleotide locus in normal subjects.

As used herein, an allele refers to any particular one of two or more nucleotide variations that occur at a genetic locus. For example, an allele can be a deletion of one or more nucleotides, a SNP, or a mutation of a plurality of nucleotides, any of a variety of a variety of repeats in a microsatellite, or loss of heterozygosity. A known allele is an allele that has been characterized in accordance with the methods used by those skilled in the art.

As used herein, a nucleic acid molecule or locus lacking an allele is a nucleic acid molecule or locus that does not contain a particular allele (e.g., a particular number of microsatellite repeats), but can contain any of the other allelic variations at that locus.

As used herein, an allele frequency is the fraction or percentage of loci containing a particular allele within a population, where the population can be any group, including, for example, a plurality of individuals, normal or sharing a similar phenotype.

As used herein, a methylation state that is correlated with an allele is a methylation state where the presence or absence of methylation and the presence of the allele are more frequently observed in the same nucleic acid molecule than would otherwise be expected for unrelated methylation state/allele pairings.

As used herein, a methylation state that is correlated with a disease, disease outcome or outcome of a treatment regimen, is a methylation state where the presence or absence of methylation and the disease, disease outcome or outcome of a treatment regimen are more frequently observed in the same individual nucleic acid molecule than otherwise occur in a larger population of individuals (e.g., a population of all individuals).

As used herein, "assignment" refers to a determination that the position of a nucleic acid fragment indicates a particular molecular weight and a particular terminal nucleotide.

As used herein, "a" refers to one or more.

As used herein, "plurality" refers to two or more polynucleotides, each of which has a different sequence or methylation state. Such a difference can be due to a naturally occurring variation among the polynucleotides, for example, to differential methylation in a polynucleotide, or can be due to the introduction of particular modifications into various polynucleotides, for example, the differential incorporation of a particular nucleotide into each polynucleotide as a result of treatment with a methylation-specific reagent.

As used herein, "unambiguous assignment" refers to the unique assignment of peaks or signals corresponding to a particular sequence variation or methylation state in a target molecule and, in the event that a number of molecules are multiplexed, that the peaks representing a particular sequence variation or methylation state can be uniquely assigned to each molecule.

As used herein, a data processing routine refers to a process, that can be embodied in software, that determines the biological significance of acquired data (i.e., the ultimate results of the assay). For example, the data processing routine can make a genotype determination based upon the data collected. In the systems and methods herein, the data processing routine also can control the instrument and/or the data collection routine based upon the results determined. The data processing routine and the data collection routines can be integrated and provide feedback to operate the data acquisition by the instrument, and hence provide assay-based judging methods.

As used herein, a plurality of genes or a plurality of target nucleic acid molecules includes at least two, five, 10, 25, 50, 100, 250, 500, 1000, 2,500, 5,000, 10,000, 100,000, 1,000,000 or more genes or target nucleic acid molecules. A plurality of genes or target nucleic acid molecules can include complete or partial genomes of an organism or even a plurality thereof. Selecting the organism type determines the genome from among which the gene or target nucleic acid molecules are selected. Exemplary organisms for gene or target nucleic acid molecule selection include animals, such as mammals, including human and rodent, such as mouse; insects; yeast; bacteria; parasites; and plants.

As used herein, "sample" refers to a composition containing a material to be detected. Samples include "biological samples," which refer to any material obtained from a living source, for example, an animal such as a human or other mammal, a plant, a bacterium, a fungus, a protist or a virus or a processed form, such as amplified or isolated material. The biological sample can be in any form, including a solid material such as a tissue, cells, a cell pellet, a cell extract, or a biopsy, or a biological fluid such as urine, blood, interstitial fluid, peritoneal fluid, plasma, lymph, ascites, sweat, saliva, follicular fluid, breast milk, non-milk breast secretions, serum, cerebral spinal fluid, feces, seminal fluid, lung sputum, amniotic fluid, exudate from a region of infection or inflammation, a mouth wash containing buccal cells, synovial fluid, or any other fluid sample produced by the subject. In addition, the sample can be solid samples of tissues or organs, such as collected tissues, including bone marrow, epithelium, stomach, prostate, kidney, bladder, breast, colon, lung, pancreas, endometrium, neuron, muscle, and other tissues. Samples can include organs, and pathological samples such as a formalin-fixed sample embedded in paraffin. If desired, solid materials can be mixed with a fluid or purified or amplified or otherwise treated. Samples examined using the methods described herein can be treated in one or more purification steps in order to increase the purity of the desired cells or nucleic acid in the sample, Samples also can be examined using the methods described herein without any purification steps to increase the purity of desired cells or nucleic acid. In particular, herein, the samples include a mixture of matrix used for mass spectrometric analyses and a biopolymer, such as a nucleic acid.

As used herein, a sample derived from another refers to a sample that has been processed, such as by purification or isolation and/or amplification of nucleic acid molecules.

As used herein, a composition refers to any mixture. It can be a solution, a suspension, liquid, powder, a paste, aqueous, non-aqueous or any combination thereof.

As used herein, a combination refers to any association between two or among more items.

As used herein, the term "false positives" refers to results that are above background noise but are not generated from an expected event or sequence or methylation state. For example, a false positive can arise when mismatch hybridization occurs, or when a fragment is formed by a process other than specific cleavage of a nucleic acid, or when treatment with a methylation-specific reagent is incomplete (i.e., not all nucleotides that could be converted by the reagent are actually converted).

The term "true" or "true positive" refers to results that are above background noise and are generated from an expected event or sequence or methylation state. For example, a true positive can arise when completely complementary hybridization occurs, or when a fragment is formed by specific cleavage of a nucleic acid, or when treatment with a methylation-specific reagent is complete (i.e., all nucleotides that could be converted by the reagent are actually converted).

As used herein, the term "false negatives" refers to actual signals that are missing from an actual measurement, but were otherwise expected. For example, a false negative can arise when mass signals not present in an actual mass spectrum were calculated to arise in a corresponding simulated spectrum.

As used herein, "incomplete conversion" and grammatic variants thereof, refers to a step of modifying the sequence of a nucleic acid molecule as a function of the methylation state of the nucleic acid molecule, where fewer than all nucleotides that can be modified are actually modified. Subsequent to the treatment step, mass measurement methods provided herein can be used to distinguish between a fragment arising as a result of incomplete conversion from a fragment arising as a result of an actual methylated nucleotide.

As used herein, fluid refers to any composition that can flow. Fluids thus encompass compositions that are in the form of semi-solids, pastes, solutions, aqueous mixtures, gels, lotions, creams and other such compositions.

As used herein, a cellular extract refers to a preparation or fraction which is made from a lysed or disrupted cell.

As used herein, a kit is combination in which components are packaged optionally with instructions for use, reagents and/or apparatus for use with the combination.

As used herein, a system refers to a combination of elements with software and/or whit any other elements for controlling and directing methods.

As used herein, software refers to computer readable program instructions that, when executed by a computer, performs computer operations. Typically, software is provided on a program product containing program instructions recorded on a computer readable medium, such as but not limited to, magnetic media including floppy disks, hard disks, and magnetic tape; and optical media including CD-ROM discs, DVD discs, magneto-optical discs, and other such media on which the program instructions can be recorded.

As used herein, "array" refers to a collection of elements, such as nucleic acids. Typically an array contains three or more members. An addressable array is one in which the members of the array are identifiable, typically by position on a solid support. Hence, in general the members of the array will be immobilized to discrete identifiable loci on the surface of a solid phase. Arrays include a collection on elements on a single solid phase surface, such as a collection of nucleotides on a chip.

B. Methods for Determining Methylation of a Target Nucleic Acid Molecule

Provided herein are methods for determining the methylation state of a target nucleic acid molecule. Methylated nucleic acid molecules such as DNA contain methylated nucleotides. Methylated nucleotides have a number of functions. For example, they play a role in gene expression, and have been linked to diseases including cancer. The methods provided herein can be used to determine whether or not a nucleic acid molecule is methylated (i.e., contains methylated nucleotides). The methods provided herein can be used to determine the locus of a methylated or unmethylated nucleotide in a nucleic acid molecule. The methods provided herein can be used to determine whether or not a nucleotide locus in a nucleic acid molecule is methylated. Additional methods and combinations, kits and systems for practicing the methods also are provided.

In one method, the methylation state of a nucleic acid molecule can be identified by treating a target nucleic acid molecule with a reagent that modifies the target nucleic acid molecule nucleotide sequence as a function of the methylation state of the target nucleic acid molecule, amplifying the treated target nucleic acid molecule using one or more primers, cleaving the amplified product, and detecting one or more of the cleaved products. In one embodiment, the amplification method includes methylation specific amplification, such as methylation specific PCR. In another embodiment, the step of detecting the cleaved products is performed by measuring the mass of the target nucleic acid molecule fragments, by, for example, mass spectrometry. In yet another embodiment masses of one or more cleaved products are compared to one or more masses of a reference nucleic acid molecule.

In another method, the locus of a methylated or unmethylated nucleotide in a nucleic acid molecule can be identified by treating a target nucleic acid molecule with a reagent that modifies the target nucleic acid molecule nucleotide sequence as a function of the methylation state of the target nucleic acid molecule, amplifying the treated target nucleic acid molecule using one or more primers, cleaving the amplified product, and detecting one or more of the cleaved products. In one embodiment, the amplification method includes methylation specific amplification, such as methylation specific PCR. In another embodiment, the step of detecting the cleaved products is performed by measuring the mass of the target nucleic acid molecule fragments, using, for example, mass spectrometry. In yet another embodiment masses of one or more cleaved products are compared to one or more masses of a reference nucleic acid molecule.

In another method, the methylation state of a nucleotide locus in a nucleic acid molecule can be determined by treating a target nucleic acid molecule with a reagent that modifies the target nucleic acid molecule nucleotide sequence as a function of the methylation state of the target nucleic acid molecule, amplifying the treated target nucleic acid molecule using one or more primers, cleaving the amplified product, and detecting one or more of the cleaved products. In one embodiment, the amplification method includes methylation specific amplification, such as methylation specific PCR. In another embodiment, the step of detecting the cleaved products is performed by measuring the mass of the target nucleic acid molecule fragments, using, for example, mass spectrometry. In yet another embodiment masses of one or more cleaved products are compared to one or more masses of a reference nucleic acid molecule.

The methods of identifying a methylated or unmethylated nucleic acid molecule or the locus of a methylated or unmethylated nucleotide in a nucleic acid molecule can be used for a variety of applications such as methylation discovery, disease diagnosis, mode of treatment determination, and organism identification, as described further herein.

A methylated nucleotide that has been correlated with disease is methylated cytosine, such as 5-methylcytosine. In some instances, the presence of methylated cytosine is correlated with disease. In other instances the absence of methylated cytosine, or the presence of unmethylated cytosine, is correlated with disease. The methods provided herein can be used to determine whether or not a nucleic acid molecule contains methylated or unmethylated cytosine. The methods provided herein also can be used to identify the locus of a methylated or unmethylated cytosine in a nucleic acid molecule. The methods provided herein also can be used to determine whether or not a cytosine at a particular nucleotide locus in a nucleic acid molecule is methylated.

1. Samples

The methods described herein can be applied to samples from any of a variety of sources, for any of a variety of purposes. Typically the methods used herein are used to determine information regarding a subject, or to determine a relationship between nucleic acid methylation and disease. The samples used in the methods described herein will be selected according to the purpose of the method to be applied. For example, samples can contain nucleic acid from a plurality of different organisms when a phenotype of the organisms is to be correlated with the presence or absence of a methylated nucleic acid molecule or nucleotide locus. In another example, samples can contain nucleic acid from one individual, where the sample is examined to determine the disease state or tendency toward disease of the individual. One skilled in the art can use the methods described herein to determine the desired sample to be examined.

a. Source

A sample can be from any subject, including animal, plant, bacterium, virus, parasite, bird, reptile, amphibian, fungus, fish, and other plants and animals. Among subjects are mammals, typically humans.

A sample from a subject can be in any form, including a solid material such as a tissue, cells, a cell pellet, a cell extract, or a biopsy, or a biological fluid such as urine, blood, interstitial fluid, peritoneal fluid, plasma, lymph, ascites, sweat, saliva, follicular fluid, breast milk, non-milk breast secretions, serum, cerebral spinal fluid, feces, seminal fluid, lung sputum, amniotic fluid, exudate from a region of infection or inflammation, a mouth wash containing buccal cells, synovial fluid, or any other fluid sample produced by the subject. In addition, the sample can be collected tissues, including bone marrow, epithelium, stomach, prostate, kidney, bladder, breast, colon, lung, pancreas, endometrium, neuron, and muscle. Samples can include tissues, organs, and pathological samples such as a formalin-fixed sample embedded in paraffin.

b. Preparation

As one of skill in the art will recognize, some samples can be used directly in the methods provided herein. For example, samples can be examined using the methods described herein without any purification or manipulation steps to increase the purity of desired cells or nucleic acid molecules.

If desired, a sample can be prepared using known techniques, such as that described by Maniatis, et al. (*Molecular Cloning: A Laboratory Manual*, Cold Spring Harbor, N.Y., pp. 280-281 (1982)). For example, samples examined using the methods described herein can be treated in one or more purification steps in order to increase the purity of the desired cells or nucleic acid in the sample. If desired, solid materials can be mixed with a fluid.

Methods for isolating nucleic acid in a sample from essentially any organism or tissue or organ in the body, as well as from cultured cells, are well known. For example, the sample can be treated to homogenize an organ, tissue or cell sample, and the cells can be lysed using known lysis buffers, sonication, electroporation and methods and combinations thereof. Further purification can be performed as needed, as will be appreciated by those skilled in the art. In addition, sample preparation can include a variety of reagents which can be included in subsequent steps. These include reagents such as salts, buffers, neutral proteins (e.g., albumin), detergents, and such reagents, which can be used to facilitate optimal hybridization or enzymatic reactions, and/or reduce non-specific or background interactions. Also, reagents that otherwise improve the efficiency of the assay, such as, for example, protease inhibitors, nuclease inhibitors and anti-microbial agents, can be used, depending on the sample preparation methods and purity of the target nucleic acid molecule.

2. Target Nucleic Acid Molecule

The methods provided herein are used to determine methylation states, including whether a target nucleic acid molecule contains a methylated or unmethylated nucleotide, whether a nucleotide locus in a target nucleic acid molecule is methylated, and the nucleotide locus of a methylated or unmethylated nucleotide in a target nucleic acid. Thus, target nucleic acid molecules used in the methods provided herein include any nucleic acid molecule. One or more methods provided herein can be practiced to provide information regarding methylated nucleotides in the target nucleic acid molecule.

a. Type of Nucleic Acid

The methods provided herein permit any nucleic acid-containing sample or specimen, in purified or nonpurified form, to be used. Thus, the process can employ, for example, DNA or RNA, including messenger RNA, wherein DNA or RNA can be single stranded or double stranded. In addition, a DNA-RNA hybrid that contains one strand of each can be examined. A mixture of nucleic acids also can be employed, as can nucleic acids that contain nucleotide analogs and mixtures of ribo and deoxy nucleotides. The specific nucleic acid sequence to be examined, i.e., the target nucleic acid molecule, can be a fraction of a larger molecule or can be present initially as a discrete molecule, so that the specific target nucleic acid molecule constitutes the entire nucleic acid component of a sample. It is not necessary that the target nucleic acid molecule to be examined be present initially in a pure form; it can be a minor fraction of a complex mixture, such as contained in whole organism DNA. The target nucleic acid molecule for which methylation status is to be determined can be an isolated molecule or part of a mixture of nucleic acid molecules. The target nucleic acid molecule to be analyzed can represent only a minor fraction of a complex of nucleic acid molecules. Also, the target nucleic acid molecule can constitute a portion or essentially all of a polynucleotide in a sample.

b. Structural or Biological Role of Target Nucleic Acid Molecule

The target nucleic acid molecule to be analyzed can include one or more protein-encoding regions of genomic DNA or a portion thereof. The target nucleic acid molecule can contain one or more gene promotor regions, one or more CpG islands, one or more sequences related to chromatin structure, or other regions of cellular nucleic acid. The target nucleic acid molecule can be methylated or unmethylated at individual nucleotides, such as cytosines; at small groups of nucleotides, such as cytosine-rich sequences, or at one or more CpG islands.

c. Size and Composition of Target Nucleic Acid Molecule

The length of the target nucleic acid molecule that can be used in the current methods can vary according to the sequence of the target nucleic acid molecule, the particular methods used for methylation identification, and the particular methylation state identification desired, but will typically be limited to a length at which fragmentation and detection methods disclosed herein can be used to identify the methylation state of one or more nucleotide loci of the target nucleic acid molecule. For example, the length of the target nucleic acid molecule can be limited to a length in which the methylation state of at least about 1%, at least about 3%, at least about 5%, at least about 10%, at least about 20%, at least about 30%, at least about 40%, at least about 50%, at least about 60%, at least about 70%, at least about 80%, at least about 85%, at least about 90%, at least about 95%, at least about 98%, at least about 99%, or all of the target nucleic acid molecule can be measured using the fragmentation and detection methods disclosed herein.

In one embodiment, the target nucleic acid molecule is of a length in which the methylation state of two or more nucleotide loci can be identified. For example, the length of the target nucleic acid molecule can be limited to a length in which the methylation state of at least about 1%, at least about 3%, at least about 5%, at least about 10%, at least about 20%, at least about 30%, at least about 40%, at least about 50%, at least about 60%, at least about 70%, at least about 80%, at least about 85%, at least about 90%, at least about 95%, at least about 98%, at least about 99%, or all nucleotide loci in question can be identified using the fragmentation and detection methods disclosed herein. For example, a target nucleic acid molecule can be at least about 20, 25, 30, 35, 40, 50, 60, 70, 80, 90, 100, 120, 140, 160, 180, 200, 225, 250, 275, 300, 350, 400, 450, 500, 550, 600, 700, 800, 900, 1000, 1200, 1400, 1600, 1800, 2000, 2500 or 3000 bases in length. Typically, a target nucleic acid molecule will be no longer than about 10,000, 5000, 4000, 3000, 2500, 2000, 1500, 1000, 900, 800, 700, 600, 500, 450, 400, 350, 280, 260, 240, 220, 200, 190, 180, 170, 160, 150, 140, 130, 120, 110 or 100 bases in length.

A target nucleic acid molecule examined using the methods disclosed herein can contain one or more methylated nucleotides, but is not required to contain any methylated nucleotides. The methods disclosed herein can be used to identify whether or not a target nucleic acid molecule contains methylated or unmethylated nucleotides, and also can be used to identify the nucleotide locus of a methylated or unmethylated nucleotide in the target nucleic acid molecule.

The methylation state of the target nucleic acid molecule or of a nucleotide locus in the target nucleic acid molecule can be identified using the methods provided herein. Methylated nucleotides can be present in clusters, such that a nucleic acid region contains numerous methylated nucleotides; in addition, methylated nucleotides can be present in single, unclustered loci. A target nucleic acid molecule can include all or a portion of a nucleic acid region where clusters of methylated nucleotides may be present. A target nucleic acid can also include a nucleic acid region in which only one nucleotide locus may be methylated.

A nucleotide that has been identified as methylated in genomic DNA is cytosine. Methylated cytosines can be present in any of a variety of regions of genomic DNA. The methods provided herein can be used to determine the methylation state of a cytosine in any of a variety of genomic DNA regions. For example, methylcytosine is commonly found in cytosine-guanine dinucleotides termed "CpG" dinucleotides. In one embodiment, the methylation state of a cytosine nucleotide in one or more CpG dinucleotides in the target nucleic acid molecule is identified. Such dinucleotides are enriched in some regions of the genome, where these enriched regions are termed CpG islands. CpG islands can be found near promotor regions for some genes, including promotor regions for tumor suppressor genes, oncogenes, developmental regulatory genes, and housekeeping genes. Thus, the methods disclosed herein can be used to identify the methylation state of a cytosine in a CpG dinucleotide in a target nucleic acid molecule where the CpG nucleotide is located in a gene promotor region, such as a tumor suppressor gene, oncogene, developmental regulatory gene, or housekeeping gene promotor region. The methods disclosed herein also can be used to identify the methylation state of a one or more cytosines in a CpG island in a target nucleic acid molecule.

The methods provided herein can be used to identify the methylation state of a plurality of nucleotide loci. Accordingly, methylation state of one or more, up to all, nucleotide loci of a large target nucleic acid can be identified using the methods provided herein. For example, the methylation state of a plurality of nucleotide loci, up to all nucleotide loci of an entire CpG island can be identified using the methods provided herein.

C. Methylation State-Specific Sequence Modification

Nucleic acid molecules can contain nucleotides with modifications, such as methylation, that do not change the nucleotide sequence of the nucleic acid molecule. Amplification of a nucleic acid molecule containing such a modified nucleotide can result in an amplified product complementary to the unmodified nucleotide, resulting in the amplified product not containing the information regarding the nucleotide modification. For example, the amplified product of a nucleic acid molecule containing a methylated cytosine will result in an amplified product containing either an unmodified guanine (for the complementary strand) or an unmodified cytosine at the location of the methylated cytosine. Reagents are known that can modify the nucleotide sequence of a target nucleic acid molecule according to the presence or absence of modifications in one or more nucleotides, where the modification itself does not change the nucleotide sequence. For example, bisulfite can be used in a process to convert unmethylated cytosine into uracil, thus resulting in a modification of the nucleotide sequence of a target nucleic acid molecule according to the presence of unmethylated cytosines in the target nucleic acid molecule.

In performing the methods disclosed herein, the target nucleic acid molecule is treated with a reagent that can modify the target nucleic acid molecule as a function of the methylation state of the target nucleic acid molecule. The treated target nucleic acid molecule can have a resulting sequence that reflects the methylation state of the untreated target nucleic acid molecule. In one embodiment, the reagent can be used to modify an unmethylated selected nucleotide to produce a different nucleotide. For example, the reagent can be used to modify unmethylated cytosine to produce uracil. In some embodiments, a nucleic acid is contacted with one or more modification reagents in one reaction vessel (e.g., reaction tube), where one or more amplification, cleavage and/or detection steps also are carried out in the reaction vessel. In such embodiments, modified and unmodified nucleic acids can be detected from one reaction vessel. In certain embodiments, a nucleic acid sample is split into two or more reaction vessels, where one of the reaction vessels is contacted with a modification reagent and another of the reaction vessels is not contacted with a modification reagent.

1. Reagents for Sequence Modification

A variety of reagents for modifying the nucleotide sequence of nucleic acid molecules are known in the art and can be used in conjunction with the methods provided herein. Reagents and conditions such as known mutagens or mutagenic agents can be selected from a variety of chemicals or other procedures. Mutagenic chemical reagents include methylmethane sulfonate, ethylmethane sulfonate, diethylsulfate, nitrosoguanidine (N-methyl-N'-nitro-N-nitrosoguanidine), nitrous acid, di-(2-chloroethyl)sulfide, di-(2-chloroethyl)methylamine, 2-aminopurine, t-bromouracil, hydroxylamine, sodium bisulfite, hydrazine, formic acid, and sodium nitrite. Enzymes that can change the nucleotide sequence of a nucleic acid molecule can also be used in the methods provided herein, including, for example, 5-methylcytosine DNA glycosylase. In addition, conditions such as high temperature, ultraviolet radiation, x-radiation, can induce changes in the sequence of a nucleic acid molecule.

A method for determining the methylation state of a nucleic acid molecule or nucleotide locus includes contacting a target nucleic acid molecule-containing sample with a reagent that can modify the target nucleic acid molecule nucleotide sequence as a function of the methylation state of the target nucleic acid molecule. For example, a target nucleic acid molecule can be contacted with a reagent that modifies methylated bases, such as methylated cytosines, such that the nucleotide sequence of the target nucleic acid molecule is modified at the location of a methylated base such as a methylated cytosine. Any reagent that modifies a base can be employed. An exemplary reagent that modifies methylated bases is 5-methylcytosine DNA glycosylase. Heat also can be used to modify methylated cytosine to thymine.

In another example, a target nucleic acid molecule can be contacted with a reagent that modifies unmethylated bases but not methylated bases, such as unmethylated cytosines but not methylated cytosines, in such a manner that the nucleotide sequence of the target nucleic acid molecule is modified at the location of an unmethylated base but not at the location of the methylated base, such as at the location of an unmethylated cytosine but not at the location of a methylated cytosine. An exemplary reagent that modifies unmethylated bases but not methylated bases is sodium bisulfite, which modifies unmethylated cytosines but not methylated cytosines.

Methods for modifying a target nucleic acid molecule in a manner that reflects the methylation pattern of the target nucleic acid molecule are known in the art, as exemplified in U.S. Pat. No. 5,786,146 and U.S. patent publications 20030180779 and 20030082600.

2. Modification of Cytosine with Bisulfite

In one embodiment, the reagent can be used to modify unmethylated cytosine to uracil. An exemplary reagent used for modifying unmethylated cytosine to uracil is sodium bisulfite. Sodium bisulfite ($NaHSO_3$) reacts with the 5,6-double bond of cytosine to form a sulfonated cytosine reaction intermediate which is susceptible to deamination, giving rise to a sulfonated uracil. The sulfonate group of the sulfonated uracil can be removed under alkaline conditions, resulting in the formation of uracil. Uracil is recognized as a thymine by DNA polymerase enzymes such as Taq polymerase, and, therefore, upon amplification of the target nucleic acid molecule using methods such as PCR, the resultant amplified target nucleic acid molecule contains thymine at positions where unmethylated cytosine occurs in the starting template target nucleic acid molecule, and the complementary strand contains adenine at positions complementary to positions where unmethylated cytosine occurs in the starting target nucleic acid molecule. Further, amplification methods such as PCR can yield an amplified target nucleic acid molecule containing cytosine where the starting target nucleic acid molecule contains 5-methylcytosine, and the complementary strand maintains guanine at positions complementary to positions where methylated cytosine occurs in the starting target nucleic acid molecule. Thus, in amplification methods such as PCR, cytosine in the amplified product can mark the location of 5-methylcytosine, and thymine in the amplified product can mark the location of unmethylated cytosine. Similarly, in the amplified product strands complementary to the treated target nucleic acid molecule, guanine can mark the location of 5-methylcytosine and adenine can mark the location of unmethylated cytosine.

Exemplary methods for bisulfite treatment of target DNA can include contacting denatured DNA with a bisulfite solution that also can contain urea and hydroquinone, and incubating the mix for 30 seconds at 95° C. and 15 minutes at 55° C., for 20 cycles. In one alternative method, the bisulfite treatment can be performed in agarose, and precipitation steps can be replaced with dialysis steps (U.S. Pat. No. 6,214,556 and Olek et al., *Nucl. Acids Res.* 24:5064-66 (1996)). Variations of bisulfite treatment of a target nucleic acid molecule are known in the art as exemplified in U.S. Pats. Nos. 5,786,146 and 6,214,556, U.S. patent publication 20030082600, Tost et al., *Nucl. Acids. Res.* 31:e50 (2003), Olek et al., *Nucl. Acids Res.* 24:5064-66 (1996), and Grunau et al., *Nucl. Acids Res.* 29:e65 (2001).

3. Resulting Nucleic Acid Molecules

In the methods provided herein, a methylation-specific reagent-treated target nucleic acid molecule can have a different nucleotide sequence compared to the nucleotide sequence of the target nucleic acid molecule prior to treatment. Since the methylation-specific reagent modifies the nucleotide sequence of a target nucleic acid molecule as a function of the methylation state of the target nucleic acid molecule, the treated target nucleic acid molecule will have a nucleotide sequence related to the nucleotide sequence of the untreated target nucleic acid molecule, which reflects the methylation state of the untreated target nucleic acid molecule.

D. Amplification of Treated Target Nucleic Acid Molecule

The methods provided herein also can include a step of amplifying the treated target nucleic acid molecule using one or more primers. In one embodiment, at least one primer is a methylation specific primer. In another embodiment, the primer contains one or more nucleotides complementary to the nucleotide treated using the methylation-specific reagent. For example, bisulfite is cytosine specific; when bisulfite is used, a primer used in a method of identifying methylated nucleotides can contain one or more guanine nucleotides. The amplification methods can serve to selectively amplify target nucleic acid molecules complementary to the primers while not amplifying one or more other nucleic acid molecules in a nucleic acid sample.

1. Methylation-specific Primers

Methylation-specific primers, which are also referred to herein as methylation state specific primers, are designed to distinguish between nucleotide sequences of treated target nucleic acid molecules based on the methylation state of one or more nucleotides in the untreated target nucleic acid molecule. For example, methylation specific primers can be designed to hybridize to a nucleotide sequence of a reagent-treated target nucleic acid molecule arising from a target nucleic acid molecule that contained methylated nucleotides in preference to hybridizing to a nucleotide sequence of a reagent-treated target nucleic acid molecule arising from a target nucleic acid molecule that contained unmethylated nucleotides. In another example, methylation specific primers can be designed to hybridize to a nucleotide sequence of a reagent-treated target nucleic acid molecule arising from a target nucleic acid molecule that contained unmethylated nucleotides in preference to hybridizing to a nucleotide sequence of a reagent-treated target nucleic acid molecule arising from a target nucleic acid molecule that contained methylated nucleotides.

The primers used for amplification of the treated target nucleic acid molecule in the sample can hybridize to the treated target nucleic acid molecule under conditions in which a nucleotide synthesis reaction, such as PCR, can occur. Typically, two or more nucleotide synthesis reaction cycles are performed to produce sufficient quantities of target nucleic acid molecule for subsequent steps including fragmentation and detection. In methods of selectively amplifying a target nucleic acid molecule using a methylation specific primer, at least one primer used in the amplification method will be methylation specific. In some embodiments, two primers used in the amplification method will be methylation specific.

In one embodiment, treated target nucleic acid molecule formed from a methylated untreated target nucleic acid molecule is amplified in preference to treated target nucleic acid molecule formed from unmethylated untreated target nucleic acid molecule. For example, a methylation specific primer can specifically hybridize to a treated target nucleic acid molecule formed from a methylated target nucleic acid molecule, while the methylation specific primer does not selectively hybridize to a treated target nucleic acid molecule formed from an unmethylated target nucleic acid molecule. In another embodiment, treated target nucleic acid molecule formed from an unmethylated untreated target nucleic acid molecule is amplified in preference to treated target nucleic acid molecule formed from a methylated untreated target nucleic acid molecule. For example, a methylation specific primer can specifically hybridize to a treated target nucleic acid molecule formed from an unmethylated target nucleic acid molecule, while the methylation specific primer does not selectively hybridize to a treated target nucleic acid molecule formed from a methylated target nucleic acid molecule.

In another embodiment, treated target nucleic acid molecule formed from an untreated target nucleic acid molecule containing methylated nucleotides at one or more selected nucleotide loci is amplified in preference to a treated target nucleic acid molecule formed from an untreated target nucleic acid molecule containing unmethylated nucleotides at one or more selected nucleotide loci. For example, a methylation specific primer can specifically hybridize to a treated target nucleic acid molecule formed from a target nucleic acid molecule containing methylated nucleotides at one or more nucleotide loci, while the methylation specific primer does not selectively hybridize to a treated target nucleic acid molecule formed from a target nucleic acid molecule not having methylated nucleotides at one or more target nucleotide loci. In another embodiment, treated target nucleic acid molecule formed from an untreated target nucleic acid molecule containing unmethylated nucleotides at one or more selected nucleotide loci is amplified in preference to a treated target nucleic acid molecule formed from an untreated target nucleic acid molecule containing methylated nucleotides at one or more selected nucleotide loci. For example, a methylation specific primer can specifically hybridize to a treated target nucleic acid molecule formed from a target nucleic acid molecule containing unmethylated nucleotides at one or more nucleotide loci, while the methylation specific primer does not selectively hybridize to a treated target nucleic acid molecule formed from a target nucleic acid molecule not having unmethylated nucleotides at one or more target nucleotide loci.

a. Design of a Methylation Specific Primer

Methylation specific primers are designed to distinguish between nucleotide sequences of treated target nucleic acid molecules based on the methylation state of one or more nucleotides in the untreated target nucleic acid molecule. Methylation specific primers can be designed to selectively hybridize to a treated target nucleic acid molecule arising from an unmethylated target nucleic acid molecule. Methylation specific primers also can be designed to selectively hybridize to a treated target nucleic acid molecule arising from a methylated target nucleic acid molecule. Methylation specific primers also can be designed to bind to a pre-defined nucleotide sequence of a treated target nucleic acid molecule, where the pre-defined sequence can arise from a methylated or an unmethylated target nucleic acid molecule.

Design of a methylation specific primer will be influenced by the methylation state of the nucleotide in the target nucleic acid molecule intended to be selectively amplified (e.g., choosing to amplify a target nucleic acid molecule containing a methylated nucleotide locus, and to not amplify a target nucleic acid molecule containing the nucleotide locus unmethylated), and by the reagent used to modify the nucleotide sequence of the target nucleic acid molecule as a function of the methylation state of the target nucleic acid molecule (e.g., bisulfite, which can be used to convert unmethylated cytosine to uracil). For example, a primer designed to amplify a bisulfite treated target nucleic acid molecule containing methylated cytosine will typically contain one or more guanine nucleotides. Design of a methylation specific primer can also be influenced by any knowledge of the nucleotide sequence of the region of the target nucleic acid molecule to which the primer hybridizes. For example, when the entire nucleotide sequence of a target nucleic acid molecule is known, the primer hybridization site can be selected (and thereby pre-defined) by designing a primer containing a nucleotide sequence that is complementary to the pre-defined site.

In one example, a methylation specific primer can be designed to selectively bind a target nucleic acid molecule that has a pre-defined site that is unmodified by the methylation state specific reagent in favor of a target nucleic acid molecule that has a pre-defined site modified by the methylation state specific reagent. In another example, one or more methylation specific primers can selectively bind a target nucleic acid molecule that has a pre-defined site modified by the methylation state specific reagent in favor of a target nucleic acid molecule that has an pre-defined site unmodified by the methylation state specific reagent.

b. Primer Composition

Primers used in the methods disclosed herein are of sufficient length and appropriate sequence to permit specific primer extension using a target nucleic acid molecule template. The primers are typically designed to be complementary to each strand of the target nucleic acid molecule to be amplified. The primer can be an oligodeoxyribonucleotide, an oligoribonucleotide, or an oligonucleotide containing both deoxyribonucleotides and ribonucleotides; in some embodiments, a primer can contain one or more nucleotide analogs. The length of primer can vary, depending on any of a variety of factors, including temperature, buffer, desired selectivity and nucleotide composition. The primer can contain at least about 5, 8, 10, 15, 20, 25, 30, 40, 50, 60, 70 or 80 nucleotides, and typically contains no more than about 120, 110, 100, 90, 70, 60, 50, 40, 30, 20 or 10 nucleotides.

In one embodiment, the primers used in nucleic acid synthesis methods also can contain a moiety that does not hybridize to the target nucleic acid molecule. This moiety can include any of a variety of compounds or compositions, and can serve any of a variety of functions. For example, such a moiety can be additional nucleotides that do not hybridize with the target nucleic acid molecule, such as a transcriptional initiation sequence. The moiety also can be a moiety that permits identification or isolation of the primer or of a nucleic acid into which the primer is incorporated. Such a moiety can be, for example, a bindable moiety such as biotin, polyhistidine, magnetic bead, or other composition or compound used for specific binding. Such a moiety also can be a fluorescent compound, a compound containing a radionuclide, colloidal metal, a quantum dot, or other composition or compound used for detection.

The oligonucleotide primers used herein can be prepared using any suitable method, such as conventional phosphotriester and phosphodiester methods or automated embodiments thereof. In one such automated embodiment, diethylphosphoramidites are used as starting materials and can be synthesized as described by Beaucage, et al. *Tetrahedron Letters* 22:1859-1862 (1981). Methods for synthesizing oligonucleotides on a solid support are known in the art, as exemplified in U.S. Pat. No. 4,458,066.

c. Region Bound By Primer

A primer used in accordance with the disclosed amplification and nucleic acid synthesis methods can specifically hybridize to a target nucleic acid molecule. Typically, the methylation specific primer can specifically hybridize to a target nucleic acid molecule having a pre-defined or pre-determined sequence. The portion of the target nucleic acid molecule to which the methylation specific primer specifically hybridizes can be termed the primer query region.

In methods provided herein, the nucleotide sequence of a target nucleic acid molecule can be modified as a function of the methylation state of the target nucleic acid molecule. Accordingly, the primer query region of a methylation-specific reagent-treated target nucleic acid molecule that corresponds to a methylation state of a region of an untreated target nucleic acid molecule can be a primer query region whose nucleotide sequence reflects the methylation state of that region in the untreated target nucleic acid molecule. For example, a region of an untreated target nucleic acid molecule that contains a methylcytosine at the 4th nucleotide and an unmethylated cytosine at the 7th nucleotide can be treated with bisulfite, which will convert the cytosine at the 7th nucleotide to uracil without changing the methylcytosine at the 4th nucleotide; thus, a primer query region of the treated target nucleic acid molecule that corresponds to that region of the untreated target nucleic acid molecule will contain a cytosine at the 4th nucleotide and a uracil (or thymine) at the 7th nucleotide, and a primer complementary to such a primer query region will contain an adenine at the locus complementary to the 4th nucleotide and a guanine at the locus complementary to the 7th nucleotide.

In one embodiment of the methylation specific amplification methods disclosed herein, a methylation specific primer can specifically hybridize to a primer query region of a target nucleic acid molecule when the primer query region contains a sequence that is complementary to the methylation specific primer. Further in accordance with this embodiment, a methylation specific primer does not specifically hybridize to a primer query region of a target nucleic acid molecule when the primer query region does not contain a sequence that is complementary to the methylation specific primer. For example, a target nucleic acid molecule containing one or more methylated loci can be treated with bisulfite, and a primer query region of the treated target nucleic acid molecule can contain one or more cytosine nucleotides; a methylation specific primer can be designed such that the methylation specific primer specifically hybridizes to the one or more cytosine nucleotides present in the primer query region of the treated target nucleic acid molecule, and the primer can thereby specifically hybridize to the primer query region of the treated methylated target nucleic acid molecule. Similarly, in another example, a target nucleic acid molecule containing one or more unmethylated loci can be treated with bisulfite, and a primer query region of the treated target nucleic acid molecule can contain no cytosine nucleotides; a methylation specific primer can be designed such that the methylation specific primer specifically hybridizes to one or more cytosine nucleotides present in the primer query region of the treated target nucleic acid molecule, and the primer thereby does not specifically hybridize to the treated unmethylated target nucleic acid molecule.

In another example, a target nucleic acid molecule containing one or more unmethylated loci can be treated with bisulfite, and a primer query region of the treated target nucleic acid molecule can contain one or more uracil nucleotides; a methylation specific primer can be designed such that the methylation specific primer specifically hybridizes to the one or more uracil nucleotides present in the primer query region of the treated target nucleic acid molecule, and the primer can thereby specifically hybridize to the primer query region of the treated unmethylated target nucleic acid molecule. Similarly, in another example, a target nucleic acid molecule containing one or more methylated loci can be treated with bisulfite, and a primer query region of the treated target nucleic acid molecule can contain no uracil nucleotides; a methylation specific primer can be designed such that the methylation specific primer specifically hybridizes to one or more uracil nucleotides present in the primer query region of the treated target nucleic acid molecule, and the primer thereby does not specifically hybridize to the treated methylated target nucleic acid molecule.

The methods provided herein can be used to determine the methylation state of a non-primer query region of a target nucleic acid molecule. The methods provided herein also can be used to determine the methylation state of one or more nucleotide loci in the non-primer query region of a target nucleic acid molecule. The methods provided herein also can be used to determine the locus of a methylated or unmethylated nucleotide in the non-primer query region of a target nucleic acid molecule. In one example, the non-primer query region of a treated target nucleic acid molecule can contain one or more cytosine nucleotides; identification of a non-primer query region of the treated target nucleic acid molecule as containing one or more cytosine nucleotides can serve to identify the non-primer query region of the target nucleic acid molecule as containing one or more methylated nucleotides. In another example, one or more nucleotide loci in the non-primer query region of a treated target nucleic acid molecule can be identified as containing a cytosine nucleotide; in such an identification, one or more nucleotide loci in the non-primer query region of the treated target nucleic acid molecule can be identified as methylated. The methods provided herein also can be used to determine the locus of the methylated cytosine nucleotide.

In another example, the non-primer query region of a treated target nucleic acid molecule can contain one or more uracil nucleotides; identification of a non-primer query region of the treated target nucleic acid molecule as containing one or more uracil nucleotides can serve to identify the non-primer query region of the target nucleic acid molecule as containing one or more unmethylated nucleotides. In another example, one or more nucleotide loci in the non-primer query region of a treated target nucleic acid molecule can be identified as containing a uracil nucleotide; in such an identification, one or more nucleotide loci in the non-primer query region of the treated target nucleic acid molecule can be identified as unmethylated. The methods provided herein also can be used to determine the locus of the unmethylated cytosine nucleotide.

Thus, the methods provided herein can be used to identify the methylation state of the non-primer query region of a target nucleic acid molecule, and can be used to identify the methylation state of one or more nucleotide loci in the non-primer query region of a target nucleic acid molecule, and also can be used to determine the locus of a methylated or unmethylated nucleotide.

In one embodiment, the primer query region of the target nucleic acid molecule can contain one or more cytosine nucleotides. Typically, when a methylated target nucleic acid molecule is treated with a methylation-specific reagent such as bisulfite, unmethylated cytosine nucleotides can be converted to uracil, whereas methylated cytosine nucleotides are not. Accordingly, methylated target nucleic acid molecules that are treated with bisulfite can contain one or more cytosine nucleotides, where the cytosine nucleotides correspond to methylated cytosine nucleotides in the untreated target nucleic acid molecule. In one embodiment, one or more cytosine nucleotides are located near the 5' end of the primer query region of the target nucleic acid molecule. For example, the 5' half of the primer query region can contain one or more cytosine nucleotides, where the 5' half refers to the nucleotides located between and including the 5' end of the primer query region and the midpoint of the primer query region. In another embodiment, the primer query region of the target nucleic acid molecule contains a cytosine nucleotide at the 5' end of the primer query region.

Similarly, an amplification product complementary to the treated target nucleic acid molecule can contain one or more guanine nucleotides in a primer query region. In one embodiment, one or more guanine nucleotides are located near the 5' end of the primer query region of the complementary amplification product. For example, the 5' half of the primer query region can contain one or more guanine nucleotides, where the 5' half refers to the nucleotides located between and including the 5' end of the primer query region and the midpoint of the primer query region. In another embodiment, the primer query region of the complementary amplification product contains a guanine nucleotide at the 5' end of the primer query region.

In another embodiment, the primer query region of the target nucleic acid molecule can contain one or more uracil nucleotides. Target nucleic acid molecules containing one or more unmethylated cytosines that are treated with bisulfite can contain one or more uracil nucleotides, where at least some uracil nucleotides can correspond to unmethylated cytosine nucleotides in the untreated target nucleic acid molecule. In one embodiment, one or more uracil nucleotides are located near the 5' end of the primer query region of the target nucleic acid molecule. For example, the 5' half of the primer query region can contain one or more uracil nucleotides. In another embodiment, the primer query region of the target nucleic acid molecule contains a uracil nucleotide at the 5' end of the primer query region.

Similarly, an amplification product complementary to the treated target nucleic acid molecule can contain one or more adenine nucleotides in a primer query region. In one embodiment, one or more adenine nucleotides are located near the 5' end of the primer query region of the complementary amplification product. For example, the 5' half of the primer query region can contain one or more adenine nucleotides. In another embodiment, the primer query region of the complementary amplification product contains an adenine nucleotide at the 5' end of the primer query region.

A target nucleic acid molecule containing one or more primer query regions to which methylation specific primers can specifically hybridize also can contain one or more non-primer query regions. Non-primer query regions are portions of the target nucleic acid molecule that do not play a role in methylation specific amplification. For example, non-primer query regions can be regions of a target nucleic acid molecule to which a methylation specific primer does not specifically hybridize. The non-primer query region of a target nucleic acid molecule can contain the portion of the target nucleic acid molecule located between, but excluding, two primer query regions; for example, the non-primer query region can be located between and excluding primer hybridization regions, and can be located between and excluding methylation specific primer hybridization regions. Further contemplated herein are methods in which a first primer is a methylation specific primer and a second primer is not (i.e., the second primer does not selectively hybridize to the treated target nucleic acid molecule as a function of the methylation state of the untreated target nucleic acid molecule). In such methods, the non-methylation specific primer query region includes the region located between the primer hybridization regions and also includes the region two which the second (non-methylation specific) primer hybridizes.

d. Primers Containing C or G Nucleotides

A methylation specific primer can contain any combination of nucleotides, according to the intended use of the primer. As will be understood by one skilled in the art, a primer can contain a plurality of regions, including one or more regions that do not hybridize to the target nucleic acid molecule (e.g., a transcriptional initiation sequence); accordingly, discussion regarding nucleotide composition of a primer, unless otherwise indicated refers to the nucleotide composition of the region that hybridizes with the target nucleic acid molecule and does not refer to the nucleotide composition of the primer regions that do not hybridize with the target nucleic acid molecule. In one example, a methylation specific primer can contain one or more guanine nucleotides (i.e., the target nucleic acid molecule binding region contains one or more guanine nucleotides). A methylation specific primer can contain one or more cytosine nucleotides (i.e., the target nucleic acid molecule binding region contains one or more cytosine nucleotides). A treated target nucleic acid molecule, or amplification product thereof that has the same nucleotide sequence, can contain one or more cytosine nucleotides. Methylation specific primers that are complementary to such a treated target nucleic acid molecule or amplification product thereof can contain one or more guanine nucleotides. An amplification product complementary to a treated target nucleic acid molecule can contain one or more guanine nucleotides. Methylation specific primers that are complementary to such an amplification product can contain one or more cytosine nucleotides.

In another example, a methylation specific primer can contain one or more thymine or uracil nucleotides (i.e., the target nucleic acid molecule binding region contains one or more thymine or uracil nucleotides). A methylation specific primer can contain one or more adenine nucleotides (i.e., the target nucleic acid molecule binding region contains one or more adenine nucleotides). A treated target nucleic acid molecule, or amplification product thereof that has the same nucleotide sequence, can contain one or more thymine or uracil nucleotides. Methylation specific primers that are complementary to such a treated target nucleic acid molecule or amplification product thereof can contain one or more adenine nucleotides. An amplification product complementary to a treated target nucleic acid molecule can contain one or more adenine nucleotides. Methylation specific primers that are complementary to such an amplification product can contain one or more thymine or uracil nucleotides.

In one embodiment in which bisulfite is used as the reagent to treat the target nucleic acid molecule, the target nucleic acid molecule can contain few methylated cytosines, and, as a consequence, methylation specific primers contain relatively few Cs or Gs in the sequence since the Cs will be mostly absent in the primer for one strand and the Gs mostly absent in the primer for the complementary strand due to the fact that the unmethylated Cs become modified to U (uracil) which is amplified as T (thymidine) in the amplification product, and the complementary amplified strand will therefore have an A instead of a G at each site corresponding to a modified C.

In other embodiments, a target nucleic acid molecule can contain a numerous methylated cytosines. In these embodiments, methylation specific primers can contain relatively few, relatively many, or any relative number therebetween, Cs or Gs in the sequence.

In one embodiment, primers can be designed to decrease the likelihood of amplification from non-specific hybridization. One or more guanine nucleotides can be located near the 3' end of the primer. For example, the 3' half of the primer can contain one or more guanine nucleotides, where the 3' half refers to the nucleotides located between and including the 3' end of the primer and the midpoint of the primer. A target nucleic acid molecule or amplification product thereof can contain one or more cytosine nucleotides to which such a primer specifically hybridizes. Under some conditions, a primer can non-specifically hybridize to a nucleic acid molecule that does not contain one or more cytosine nucleotides; however, a primer in which the 3' half contains one or more guanine nucleotides will have one or more mismatched base pairs over its 3' half. Since primer extension occurs at the 3' end, mismatched base pairing at or near the 3' end (i.e., over the 3' half) can decrease the likelihood of primer extension relative to the same degree of mismatching at the 5' end. Thus, using primers containing one or more guanine nucleotides in the 3' half of the primer will increase the likelihood of extending specifically hybridized primers and not mismatched primers, In another embodiment, when the amplification product complementary to the treated target nucleic acid is hybridized to a primer, one or more cytosine nucleotides can be located near the 3' end of the primer. For example, the 3' half of the primer can contain one or more cytosine nucleotides.

In another embodiment, when the methylation specific primer is used to selectively amplify unmethylated target nucleic acid, one or more adenine nucleotides can be located near the 3' end of the primer. For example, the 3' half of the primer can contain one or more adenine nucleotides. Similarly, when the amplification product complementary to the treated target nucleic acid is hybridized to a primer, one or more thymine or uracil nucleotides can be located near the 3' end of the primer. For example, the 3' half of the primer can contain one or more thymine or uracil nucleotides.

In another embodiment, the 3' nucleotide of a methylation specific primer can specifically distinguish between treated target nucleic acid molecules that are methylated at one locus, and treated target nucleic acid molecules that are non-methylated at that locus by selectively hybridizing, at the 3' end of the primer, a nucleotide arising from a methylated nucleotide. For example, a methylation specific primer can have a guanine (G) at the 3' end, and, upon hybridization with the target nucleic acid molecule, presence of a C nucleotide at the position corresponding to the primer 3'G nucleotide locus results in amplification of the target nucleic acid molecule, whereas presence of a U or T nucleotide at the position corresponding to the primer 3'G nucleotide locus does not result in amplification of the target nucleic acid molecule. In another example, a methylation specific primer can have a C at the 3' end, and, upon hybridization with the target nucleic acid molecule, presence of a G nucleotide at the position corresponding to the primer 3° C. nucleotide results in amplification of the target nucleic acid molecule, whereas presence of an A nucleotide at the position corresponding to the primer 3° C. nucleotide results in no amplification of the target nucleic acid molecule.

In another embodiment, a primer can be used to selectively hybridize, at the 3' end of the primer, with a nucleotide arising from an unmethylated nucleotide. For example, a methylation specific primer can have an adenine (A) at the 3' end, and, upon hybridization with the target nucleic acid molecule, presence of a T or U nucleotide at the position corresponding to the primer 3'G nucleotide locus results in amplification of the target nucleic acid molecule, whereas presence of a C nucleotide at the position corresponding to the primer 3'G nucleotide locus does not result in amplification of the target nucleic acid molecule. In another example, a methylation specific primer can have a T or U at the 3' end, and, upon hybridization with the target nucleic acid molecule, presence of an A nucleotide at the position corresponding to the primer 3° C. nucleotide results in amplification of the target nucleic acid molecule, whereas presence of a G nucleotide at the position corresponding to the primer 3° C. nucleotide results in no amplification of the target nucleic acid molecule.

2. Nucleic Acid Synthesis Methods

The methylation specific primers described herein or known in the art can be used in methods to specifically amplify target nucleic acid molecules according to the methylation state of the target nucleic acid molecule, and to thereby selectively increase the amount of target nucleic acid in a sample. The amplified products of the methylation state specific amplification can be examined for further methylation information in accordance with the fragmentation and fragment detection methods provided herein. Methylation state specific amplification methods include one or more nucleic acid synthesis steps, using one or more methylation specific primers. In one embodiment, methylation specific amplification is performed using one methylation specific primer and one primer that does not specifically bind according to the methylation state of a target nucleic acid molecule. In another embodiment, methylation specific amplification is performed using two methylation specific primers. In another embodiment, a preliminary amplification step can be performed prior to performing methylation specific amplification.

In accordance with the methods disclosed herein, a target nucleic acid sequence can serve as a template for one or more steps of nucleic acid synthesis. The nucleic acid synthesis step or steps can include primer extension, DNA replication, polymerase chain reaction (PCR), reverse transcription, reverse transcription polymerase chain reaction (RT-PCR), rolling circle amplification, whole genome amplification, strand displacement amplification (SDA), and transcription based reactions.

a. Preliminary Amplification

In one embodiment, prior to nucleic acid synthesis steps that use methylation specific primers, an amplification step can be performed that can amplify one or more nucleic acids without distinguishing between methylated and unmethylated nucleic acid molecules or loci. Such an amplification step can be performed, for example, when the amount of nucleic acid in a sample is very low and detection of methylated target nucleic acid molecules can be improved by a preliminary amplification step that does not distinguish methylated target nucleic acid molecules from unmethylated target nucleic acid molecules or other nucleic acids in the sample. Typically, such an amplification step is performed subsequent to treating the nucleic acid sample with a reagent that modifies the nucleotide sequence of nucleic acid molecules as a function of the methylation state of the nucleic acid molecules. Although this method does not distinguish according to methylation state, the primers used in such a preliminary amplification step nevertheless can be used to increase the amount of nucleic acid molecules of a particular target nucleic acid region to be examined relative to the total amount of nucleic acid in a sample. For example, primers can be designed to hybridize to a pre-determined region of a target nucleic acid molecule in order to increase the relative amount of that target nucleic acid molecule in the sample, but without amplifying the target nucleic acid molecule according to the methylation state of the target nucleic acid molecule. One skilled in the art can determine the primer used in such a preamplification step according to various known factors and including the desired selectivity of the preamplification step and any known nucleotide sequence information.

b. Synthesis of Complementary Strands

In the methods of nucleic acid synthesis using a double-stranded nucleic acid molecule, the strands are first separated before any nucleic acid synthetic steps. Following strand separation, one or more primers can be hybridized to one or more treated single-stranded nucleic acid molecules to be amplified, and nucleotide synthesis can be performed to add nucleotides to each primer to form a strand complementary to the strand of the target nucleic acid molecule. In one embodiment, nucleic acid synthesis can be performed to selectively amplify one of two strands of a treated target nucleic acid molecule. In another embodiment, the step of synthesizing a strand complementary to each strand of a double-stranded treated target nucleic acid molecule is performed in the presence of two or more primers, such that at least one primer can hybridize to each strand and prime additional nucleotide synthesis.

In the methods of nucleic acid synthesis using a single-stranded nucleic acid molecule, a primer can be hybridized to the single-stranded nucleic acid molecule to be amplified, and nucleotide synthesis can be performed to add nucleotides to the primer to form a strand complementary to the single-stranded nucleic acid molecule. In one embodiment, the step of synthesizing a strand complementary to a single-stranded nucleic acid molecule is performed in the presence of two or more primers, such that one primer can hybridize to the nucleotide sequence of the strand of the target nucleic acid molecule, and one primer can hybridize to the synthesized complementary strand and prime additional nucleotide synthesis. For example, after synthesis of the complementary strand, PCR amplification of the nucleic acid molecule can be immediately performed without further manipulation of the sample.

c. Separating First Amplification Step from Later Steps

In another embodiment, the step of synthesizing a strand complementary to a single-stranded nucleic acid molecule is performed separately from additional nucleotide synthetic reactions. For example, the complementary strand can be synthesized to form a double-stranded nucleic acid molecule, and the sample can be subjected to one or more intermediate steps prior to amplifying the double-stranded nucleic acid molecule. Intermediate steps can include any of a variety of methods of manipulating a nucleic acid sample, including increasing the purity of the nucleic acid molecule, removing excess primers, changing the reaction conditions (e.g., the buffer conditions, enzyme or reactants present in the sample), and other parameters. In one example, the sample can be subjected to one or more purification steps of the nucleic acid molecule. For example, the primer used to create the strand complementary to the nucleic acid molecule can contain a moiety at its 5' end that permits identification or isolation of the primer or of a nucleic acid into which the primer is incorporated. Such a moiety can be, for example, a bindable moiety such as biotin, polyhistidine, magnetic bead, or other suitable substrate, whereby contacting the sample with the binding partner of the bindable moiety can result in selective binding of nucleic acid molecule into which the primer has been incorporated. Such selective binding can be used to separate the nucleic acid molecule from sample impurities, thereby increasing the purity of the nucleic acid molecule. After performing one or more intermediate steps, such as purity enhancing steps, the nucleic acid molecule can be amplified according to the methods provided herein and as known in the art.

In one variation of this embodiment, subsequent to synthesis of the complementary strand, one or more second methylation specific primers can be hybridized to the complementary strand synthesized in the preceding step, and nucleic acid synthesis can be performed. This embodiment can be used, for example, when a first methylation specific primer hybridizes specifically to target nucleic acid molecules that contain different nucleotide sequences in the region to which the first methylation specific primer does not hybridize. By using different second methylation specific primers, the target nucleic acid molecules that contain different nucleotide sequences can be separated. For example, attachment of bindable moieties to the second primers, can be used to separate nucleic acid molecules according to the sequence at a second position in the nucleic acid molecule to which the second primers hybridized. In another variation, the product of the first amplification step can be separated into two or more aliquots and different second primers can be added to each aliquot where some or all of the second primers can be methylation specific primers. An embodiment using two or more second primers that are methylation specific primers can be used to methylation specifically amplify target nucleic acids at a variety of different second primer query regions.

d. Reaction Parameters

After formation of the strand complementary to the single-stranded target nucleic acid molecules, subsequent target nucleic acid molecule amplification steps can be performed in which the complementary strands are separated, primers are hybridized to the strands, and the primers have added thereto nucleotides to form a new complementary strand. Strand separation can be effected either as a separate step or simultaneously with the synthesis of the primer extension products. This strand separation can be accomplished using various suitable denaturing conditions, including physical, chemical, or enzymatic means, the word "denaturing" includes all such means. One physical method of separating nucleic acid strands involves heating the target nucleic acid molecule until it is denatured. Typical heat denaturation can involve temperatures ranging from about 80° C. to 105° C., for times ranging from about 1 to 10 minutes. Strand separation also can be accomplished by chemical means, including high salt conditions or strongly basic conditions. Strand separation also can be induced by an enzyme from the class of enzymes known as helicases or by the enzyme RecA, which has helicase activity, and in the presence of riboATP, is known to denature DNA. The reaction conditions suitable for strand separation of nucleic acids with helicases are described by Kuhn Hoffmann-Berling, *CSH-Quantitative Biology*, 43:63 (1978) and techniques for using RecA are reviewed in C. Radding, *Ann. Rev. Genetics* 16:405-437 (1982).

After each amplification step, the amplified product will be double stranded, with each strand complementary to the other. The complementary strands of can be separated, and both separated strands can be used as a template for the synthesis of additional nucleic acid strands. This synthesis can be performed under conditions allowing hybridization of primers to templates to occur. Generally synthesis occurs in a buffered aqueous solution, typically at about a pH of 7-9, such as about pH 8. Typically, a molar excess of two oligonucleotide primers can be added to the buffer containing the separated template strands. In some embodiments, the amount of target nucleic acid is not known (for example, when the methods disclosed herein are used for diagnostic applications), so that the amount of primer relative to the amount of complementary strand cannot be determined with certainty.

In an exemplary method, deoxyribonucleoside triphosphates dATP, dCTP, dGTP, and dTTP can be added to the synthesis mixture, either separately or together with the primers, and the resulting solution can be heated to about 90° C.-100° C. from about 1 to 10 minutes, typically from 1 to 4 minutes. After this heating period, the solution can be allowed to cool to about room temperature. To the cooled mixture can be added an appropriate enzyme for effecting the primer extension reaction (called herein "enzyme for polymerization"), and the reaction can be allowed to occur under conditions known in the art. This synthesis (or amplification) reaction can occur at room temperature up to a temperature above which the enzyme for polymerization no longer functions. For example, the enzyme for polymerization also can be used at temperatures greater than room temperature if the enzyme is heat stable. In one embodiment, the method of amplifying is by PCR, as described herein and as is commonly used by those of skill in the art. Alternative methods of amplification have been described and also can be employed. A variety of suitable enzymes for this purpose are known in the art and include, for example, *E. coli* DNA polymerase I, Klenow fragment of *E. coli* DNA polymerase I, T4 DNA polymerase, other available DNA polymerases, polymerase muteins, reverse transcriptase, and other enzymes, including thermostable enzymes (i.e., those enzymes which perform primer extension at elevated temperatures, typically temperatures that cause denaturation of the nucleic acid to be amplified).

e. Modified Nucleoside Triphosphates

In one embodiment, nucleic acid synthesis reactions performed according to the methods disclosed herein or known in the art can use one or more modified nucleoside triphosphates. The modifications can, for example, confer or alter cleavage specificity of the target nucleic acid molecule sequence by the respective cleavage methods, or can alter the detection of cleaved target nucleic acid molecules. For example, one or more of the nucleoside triphosphates can be substituted with an analog that creates a selectively non-hydrolyzable bond between nucleotides. For example, a nucleoside can be substituted with an α-thio-substrate and the phosphorothioate internucleoside linkages can subsequently be modified by alkylation using reagents such as an alkyl halide (e.g., iodoacetamide, iodoethanol) or 2,3-epoxy-1-propanol. Other exemplary nucleosides that can be selectively non-hydrolyzable include 2'fluoro nucleosides, 2'deoxy nucleosides and 2'amino nucleosides.

Other exemplary modified nucleoside triphosphates include mass modified nucleoside triphosphates can be used such as mass modified deoxynucleoside triphosphates, mass modified dideoxynucleoside triphosphates, and mass modified ribonucleoside triphosphates. The mass modified nucleoside triphosphates can be modified on the base, the sugar, and/or the phosphate moiety, and are introduced through an enzymatic step, chemically, or a combination of both. In one aspect, the modification can include 2' substituents other than a hydroxyl group. In another aspect, the internucleoside linkages can be modified e.g., phosphorothioate linkages or phosphorothioate linkages further reacted with an alkylating agent. In yet another aspect, the modified nucleoside triphosphate can be modified with a methyl group, e.g., 5-methyl cytosine or 5-methyl uridine.

In another embodiment, the target nucleic acid molecules are amplified using nucleoside triphosphates that are naturally occurring, but that are not normal precursors of the target nucleic acid molecule. For example, uridine triphosphate, which is not normally present in DNA, can be incorporated into an amplified DNA molecule by amplifying the DNA in the presence of normal DNA precursor nucleotides (e.g., dCTP, dATP, and dGTP) and dUTP. Such an incorporation of uridine into DNA can facilitate base-specific cleavage of DNA. For example, when amplified uridine-containing DNA is treated with uracil-DNA glycosylase (UDG), uracil residues are cleaved. Subsequent chemical treatment of the products from the UDG reaction results in the cleavage of the phosphate backbone and the generation of base specific cleavage fragments.

f. The Two Strands of the Treated Target Nucleic Acid Molecule

In one embodiment, upon treatment with a reagent that modifies a target nucleic acid molecule as a function of the methylation state of the target nucleic acid molecule, the two strands of treated double-stranded target nucleic acid molecules will not remain perfectly complementary. For example, when a double-stranded target nucleic acid molecule is treated with bisulfite, unmethylated C nucleotides on both strands of the target nucleic acid molecule can be converted to U nucleotides. The complementary G nucleotides of the two strands are not modified. Accordingly, each methylation-based sequence modification of a target nucleic acid molecule can create a mismatch between complementary strands of the target nucleic acid molecule.

Methods of manipulating a target nucleic acid molecule subsequent to methylation based sequence modification treatment, such as amplification and fragmentation, can be performed using only one strand of the treated target nucleic acid molecule, or using both strands of the treated target nucleic acid molecule. For example, primers used for amplification steps can be complementary to only one strand of the treated target nucleic acid molecule, or can be complementary to both strands of the treated nucleic acid. Accordingly, amplification steps can be performed to create at least two different amplified double-stranded products, where both strands of the treated target nucleic acid molecule is amplified into separate double-stranded products.

Alternatively, amplification can be performed such that only one of the two strands of the treated target nucleic acid molecule is amplified. For example, when amplification is performed using at least one primer that is selective for the sequence of one of the two strands, the strand hybridized to the primer can be selectively amplified. For example, since after reagent treatment, the two strands are no longer perfect complements, a methylation specific primer can be designed to be specifically hybridize to a nucleotide sequence of a first treated strand, but not to the corresponding nucleotide sequence of the complement to the second treated strand. Thus, at least one primer will selectively hybridize to a nucleotide sequence arising uniquely from one of the two treated target nucleic acid molecule strands. Similarly, a second primer also can be designed to selectively hybridize with only one of two treated target nucleic acid molecule strands. Alternatively, a second primer can be designed to hybridize to either strand, but, when used in conjunction with a first strand-selective primer, will still result in the selective amplification of only one of two treated target nucleic acid molecule strands.

g. Post-Amplification Steps

After one or more steps of amplification, the amplified products can be subjected to one or more manipulation steps prior to additional amplification steps or prior to cleavage steps. For example, amplified products can be subjected to one or more purification steps prior to additional amplification or prior to cleavage. Amplified products also can be subjected to one or more steps that modify the amplified product.

Methods for purifying nucleic acid molecules are known in the art and include precipitation, dialysis or other solvent exchange, gel electrophoresis, enzymatic degradation of impurities (e.g., protease treatment, or RNase treatment for a DNA target nucleic acid molecule sample), liquid chromatography including ion exchange chromatography and affinity chromatography, and other methods of specifically binding target nucleic acid molecules to separate them from impurities (e.g., hybridization, biotin binding). Purification steps also can include separating complementary strands of amplification products. One skilled in the art will know to select which, if any, purification steps to use according to desired level of purity and/or desired sample composition for subsequent amplification, modification or cleavage steps.

Steps that modify the amplified product can include any method that changes the composition of the product. Such steps can include separating the two strands of a double stranded product, hybridizing a nucleic acid to a single strand of a product, adding or removing moieties (e.g., fluorescent dyes, biotin, signal sequences, and other moieties disclosed herein or known in the art) from the 5' or 3' end of the amplified product, modifying nucleotide bases, modifying phosphodiester linkages, or modifying sugar moieties.

h. Multiple Aliquots of Amplified Products

Methods for determining methylation in a target nucleic acid can include methods in which a single sample is treated in one or more steps, and then the single sample can be divided into two or more aliquots for parallel treatment in subsequent steps. The parallel treatment of sample aliquots can provide complementary information regarding methylation in the target nucleic acid molecule. For example, a single sample can be treated in a step of contacting the sample with a reagent that modifies the sequence of a target nucleic acid molecule according to the methylation state of the target nucleic acid molecule; the single sample can then be amplified; and then the single sample can be divided into two or more aliquots prior to fragmentation such that each different aliquot is treated under different fragmentation conditions. The different fragmentation patterns of the two aliquots can be detected, for example, by mass spectrometry, where the mass spectra from each can provide information complementary to the information provided by the mass spectra of the other aliquots. Thus, by separating a single sample into two or more aliquots, complementary information can be obtained regarding methylation in the target nucleic acid molecule.

Amplified products can be split into two or more aliquots after amplification. For example, amplified products can be split into two or more aliquots after amplification but prior to cleaving the amplified products; amplified products can split into two or more aliquots after amplification and subjected to further steps such as one or more amplified product purification steps or amplified product modification steps.

When amplified products are split into two or more aliquots prior to cleavage, different cleavage methods can be applied to each of the two or more aliquots. For example, a first target nucleic acid molecule aliquot can be base specifically fragmented with RNase A, while a second target nucleic acid molecule aliquot can be base specifically fragmented with RNase T1. In another example, amplified target nucleic acid molecule can be split into four aliquots and each aliquot can be treated with a different base-specific reagent to produce four different sets of base specifically cleaved target nucleic acid molecule fragments. Separation into two or more aliquots permits different cleavage reactions to be performed on the same amplification product. Use of different cleavage reactions on the same amplification product is further described in the cleavage methods provided herein.

In another embodiment, treated target nucleic acid molecules or amplified products thereof can be separated into two or more aliquots and two or more different amplification steps can be performed to yield two or more different amplified products from the same treated target nucleic acid. For example, two or more different transcription steps can be performed on the PCR product of a treated target nucleic acid. An example of two different transcription steps is where a first transcription reaction incorporates rATP, rGTP, rCTP and dTTP into the transcript, while a second transcription reaction incorporates rATP, rGTP, rTTP and dCTP into the transcript, so that the two resultant transcripts have different deoxynucleotides incorporated therein.

Different amplification steps can include use of different enzymes in different aliquots, use of different reaction conditions in different aliquots, use of different nucleosides or nucleoside analogs in different aliquots, and can be designed to amplify one specific strand of a treated target nucleic acid molecule or of an amplified product of one strand of a treated target nucleic acid molecule. For example, different amplification reactions can contain nucleotides that are different in mass, chemical composition, or typical occurrence (typical versus non-typical nucleoside), as disclosed herein and known in the art. Different amplification steps can be used to yield amplification products that are cleaved at different nucleotide loci, have different cleavage product masses, or can be detected by different methods.

Typically two or more different amplification steps will yield different amplified products, and, typically, different amplified products will have different fragmentation properties. Different amplified products will typically be target nucleic acid molecules that differ by at least one atom. For example, a first amplified product can contain a deoxycytosine nucleotide while a second amplified product can contain a ribonucleic cytosine nucleotide, where the difference between the two amplified products is the presence of an oxygen atom bonded to the 2' carbon of the nucleotide sugar moiety. Amplified products that have different fragmentation properties will typically be amplified products that yield dissimilar sets of cleaved products when treated under the same cleavage conditions. For example, a transcript that contains one or more deoxycytosine nucleotides will have a different RNAse A cleavage pattern than a transcript containing one or more deoxythymine nucleotides.

A sample can be divided into two or more aliquots in specifically amplifying different strands of a target nucleic acid molecule in different aliquots. For example, a treated target nucleic acid molecule can have non-complementary strands that can be separately treated with different primers such as different methylation state specific primers in separately amplifying the different strands in different aliquots. In another embodiment, complementary strands of an amplified target nucleic acid molecule can be separately amplified in different aliquots, according to the primers used in each aliquot. For example, a sample of amplified target nucleic acid molecules can be separated into two or more aliquots, where the forward strand is transcribed in a first set of aliquots and the reverse strand is transcribed in a second set of aliquots. As will be appreciated by one skilled in the art, a sample can be divided into any of a plurality of aliquots in which any combination of the parallel reactions described herein can be performed.

i. Multiplexed Amplification

Amplification methods can be performed on two or more target nucleic acid molecules simultaneously, for example, by multiplex PCR methods. In this embodiment, a primer can act as a methylation specific primer for one or more target nucleic acid molecules. Typically, each target nucleic acid molecule can be hybridized with a different methylation specific primer to permit amplification of a plurality of different target regions. Multiplexed target nucleic acids or amplicates thereof can be subjected to fragmentation conditions, including, for example, base specific cleavage.

Multiplexing also can be performed on target nucleic acid molecules in detecting fragments produced from one or more fragmentation reactions. In one embodiment of fragment detecting, multiplexing can be performed when the masses to be measured and used in methylation identification methods do not overlap. When the mass fragmentation and measured masses of two or more target nucleic acids are known or can be calculated, overlap of the resultant masses can be measured or predicted. In this context, overlap refers to a difference in mass or measured mass of two or more fragments that is sufficient to separately determine the presence of the two or more fragments. When the mass fragments do not overlap, multiplexing can be performed, and the resultant masses can be associated with the appropriate target nucleic acid in methods of methylation identification. For example, based on knowledge of the target nucleic acid molecule nucleotide sequences and primer design, fragmentation patterns from two or more amplified products can be predicted to yield fragments that do not have the same mass; mass measurement of these fragments can be performed in one mass spectrometric measurement, and the resultant measured masses can be associated with the appropriate target nucleic acid according to the calculated fragmentation patterns.

When the nucleotide sequences of the target nucleic acid molecules are known, primers and fragmentation methods can be designed to reduce overlap of fragments by, for example, increasing the differences in nucleotide composition of the predicted fragments. Primers and fragmentation methods that reduce overlap will be a function of the nucleotide sequences of the target nucleic acids and can be readily determined by one skilled in the art.

In another multiplexing embodiment, some fragment masses can overlap, but methylation identification methods can still be performed using non-overlapping peaks. In this embodiment, a subset of the fragmentation pattern can be non-overlapping for target nucleic acid molecules, and masses from this non-overlapping subset can be used in the methylation identification methods provided herein. One skilled in the art can determine whether or not the non-overlapping fragment masses will be suitable for methylation identification methods by determining whether or not a mass shift, new fragment mass or missing fragment mass can be detected and associated with a methylation state of a target nucleic acid molecule.

In other embodiments, masses of two or more target nucleic acid molecule fragments containing methylation state information can overlap. In such embodiments, fragments from the two or more target nucleic acid molecules can still be used in multiplexing methods by using one or more of a variety of methods. For example, overlapping fragments can be made to no longer overlap by modifying the masses of fragments of one or more of the target nucleic acid molecules. Methods for mass modification of nucleic acid molecules are described herein. For example, overlapping fragment masses from two target nucleic acid molecules can be separated by RNA incorporation of rCTP, rGTP, rUTP and rATP into a first transcript and incorporation of rCTP, rGTP, dTTP and rATP into a second transcript.

Nucleic acid molecules used in multiplexed measurements can be from any of a variety of sources. For example, multiplexed nucleic acid molecules can be nucleic acid molecules from different chromosome or genomic regions of the same individual, forward and reverse strands of a treated target nucleic acid molecule (where treatment of the target nucleic acid molecule has rendered the two strands non-complementary), forward and reverse complementary strands of a nucleic acid molecule, different ge4nomic or chromosome regions of different individuals, or any other different sequences that can be separately measured in the herein disclosed methods.

Nucleic acid molecules used in multiplexed measurements also can include nucleic acid molecules having the same nucleotide sequences. Typically such multiplexing can be used to determine the relative amounts of methylated and unmethylated nucleotides or nucleotide loci present in a sample. For example, samples can contain nucleic acid molecules of the same genomic region from a plurality of individuals. Such multiplexing can be used for determining frequency of methylation in the pool of individuals. In another example, multiplexing can contain both copies of diploid DNA from a single individual, where the methylation state of both copies of the diploid DNA is to be determined.

3. Nucleotide Synthesis Blockers

Methylation specific amplification of a target nucleic acid molecule can be performed using a primer specific for a region of a treated target nucleic acid molecule containing a desired nucleotide sequence, such as a nucleotide sequence that reflects one or more methylated or unmethylated nucleotides in the untreated target nucleic acid molecule. In addition, methylation specific amplification of a target nucleic acid molecule can be performed using an oligonucleotide that does not serve as a primer and instead serves to inhibit amplification of the target nucleic acid molecule to which it hybridizes. Such oligonucleotides, termed herein nucleotide synthesis blockers or amplification blockers, can bind to a target nucleic acid molecule containing an undesired sequence, such as a nucleotide sequence that reflects only unmethylated nucleotides or selected methylated nucleotides in the untreated target nucleic acid molecule. For example, when a target nucleic acid molecule is treated with bisulfite, an amplification blocker can be used that hybridizes with a region of the treated target nucleic acid where one or more cytosine nucleotides has been converted to uracil. In another example, when a target nucleic acid molecule is treated with bisulfite, an amplification blocker can be used that hybridizes with a region of the treated target nucleic acid containing one or more cytosine nucleotides. Thus, the methods provided herein for nucleotide synthesis described herein also can have added thereto one or more nucleotide synthesis blockers. Additional use of amplification blockers are known in the art, as provided, for example, in U.S. Pat. Pub. No. 20030082600.

a. Composition and Properties of Nucleotide Synthesis Blockers

A nucleotide synthesis blocker or amplification blocker is an oligonucleotide that hybridizes to one or more nucleic acids in a sample that are not to be amplified. Typically, an amplification blocker does not contain a 3'-hydroxy group so that additional nucleotides cannot be added to the amplification blocker during a nucleotide synthesis reaction. In one embodiment, amplification blockers bind to at least one nucleotide locus of a nucleic acid in which the methylation state of the nucleotide locus is under examination. For example, when a sample is treated with bisulfite, an amplification blocker can bind to a U (or T) nucleotide in a nucleic acid, where the U/T nucleotide arose as a result of bisulfite-based conversion of a C nucleotide to a U nucleotide. In another example, when a sample is treated with bisulfite, an amplification blocker can bind to a C nucleotide in a nucleic acid that was not converted to a U (or a T) nucleotide as a result of bisulfite treatment.

Amplification blockers can be added that bind specifically to regions of nucleic acids, including regions of target nucleic acid molecules or amplification products, depending on whether or not the nucleic acids were methylated or unmethylated prior to the treatment with a methylation-specific reagent such as bisulfite. In one use of amplification blockers, a treated target nucleic acid molecule having a desired sequence is amplified when one or more amplification blockers bind less effectively to the desired target nucleic acid molecules than to background DNA or nucleic acid molecules not having the desired sequence. That is, the amplification blockers can selectively block the amplification of background DNA and nucleic acid molecules not having the desired sequence. For example, amplification blockers can bind to nucleic acid molecules having nucleotide sequences that reflect unmethylated nucleotides (e.g., when bisulfite is used, bind a sequence containing U/T when the U/T arises from bisulfite conversion of unmethylated cytosine to uracil). In another example, amplification blockers can bind to nucleic acid molecules having nucleotide sequences that reflect methylated nucleotide loci (e.g., when bisulfite is used, bind a sequence containing C that is not converted to U by bisulfite treatment).

In the context of using an amplification blocker, a target nucleic acid molecule or amplified product having a desired sequence refers to a nucleic acid molecule that contains a nucleotide sequence which reflects one or more methylated or unmethylated nucleotides in an untreated target nucleic acid molecule. One skilled in the art can determine the desirability of the nucleotide sequence according to the experimental design. For example, when one or more unmethylated cytosine loci in a target nucleic acid are to be determined, the desired bisulfite-treated sequence contains one or more U/T nucleotides in the place of one or more C nucleotides, and the desired nucleic acid molecules to be amplified contain these U/T nucleotides. In another example, when one or more methylated cytosine loci in a target nucleic acid are to be determined, the desired bisulfite-treated sequence contains one or more C nucleotides not converted by bisulfite treatment, and the desired nucleic acid molecules to be amplified contain these C nucleotides. Typically, an amplification blocker will bind more readily to a nucleic acid molecule having an undesired sequence relative to binding to a nucleic acid molecule having a desired sequence.

The amplification blockers can be as short as two nucleotides, such as CG, TG or CA dinucleotides, or the amplification blockers can be larger than two nucleotides. For example, the amplification blockers can contain 3, 4, 5, 6, 7, 8, 9, 10 or more nucleotides, and can bind to specific sequences to inhibit amplification of a sequence with which the amplification blocker hybridizes. The nucleotide composition of the amplification blocker can be selected according to the methylation state to be determined and the methylation specific reagent used to treat the target nucleic acid molecule. For example, when bisulfite is used and methylated cytosines are to be determined, amplification blockers designed to bind directly to treated target nucleic acid molecules can contain A, C and T/U nucleotides, but do not contain G nucleotides. Amplification blockers designed to bind to the nucleic acids complementary to bisulfite-treated target nucleic acid molecules can contain A, G and T/U nucleotides, but do not contain C nucleotides. In another example, when bisulfite is used and unmethylated cytosines are to be determined, amplification blockers designed to bind directly to treated target nucleic acid molecules can contain G, C and T/U nucleotides, but do not necessarily contain A nucleotides. Amplification blockers designed to bind to the nucleic acids complementary to bisulfite-treated target nucleic acid molecules can contain A, G and C nucleotides, but do not necessarily contain U/T nucleotides.

In one embodiment, an amplification blocker can be designed to bind specifically to nucleic acid molecules having an undesired sequence (e.g., a bisulfite treated target nucleic acid molecule sequence having at the site of amplification blocker hybridization one or more uracils) while binding with much less specificity or affinity to a target nucleic acid molecule having a desired sequence (e.g., a bisulfite treated target nucleic acid molecule sequence having cytosines). In one example, an amplification blocker can specifically hybridize to a target nucleic acid molecule sequence containing only A, T and G nucleotides, without specifically hybridizing to a target nucleic acid molecule sequence containing one or more C nucleotides. Such amplification blockers will typically not contain G nucleotides. Similarly, when an amplification blocker hybridizes to the sequence complementary to a treated target nucleic acid molecule, the amplification blocker can specifically hybridize to a nucleotide sequence containing only, A, T and C nucleotides, without specifically hybridizing to a target nucleic acid molecule sequence containing one or more G nucleotides. Such amplification blockers will typically not contain C nucleotides.

Some exemplary amplification blockers can specifically hybridize to region in nucleic acid molecules containing TG or CA dinucleotide sequences. Such nucleic acid molecules contain a nucleotide sequence that reflects bisulfite treated, unmethylated CpG dinucleotide sequences, or the sequence complementary thereto. Thus, an amplification blocker can contain TG or CA dinucleotide sequences. In one embodiment, an amplification blocker contains two or more TG or CA dinucleotide sequences, which can bind, for example, bisulfite treated, unmethylated CpG islands, or the sequence complementary thereto.

Other exemplary amplification blockers can specifically hybridize to region in nucleic acid molecules containing GC or CG dinucleotide sequences. Such nucleic acid molecules contain a nucleotide sequence that reflects bisulfite treated, methylated CpG dinucleotide sequences, or the sequence complementary thereto. Thus, an amplification blocker can contain CG or GC dinucleotide sequences. In one embodiment, an amplification blocker contains two or more CG or GC dinucleotide sequences, which can bind, for example, bisulfite treated, methylated CpG islands, or the sequence complementary thereto.

Amplification blockers can have the property that they cannot be elongated by an enzyme used in a nucleotide synthesis reaction. This can be done by using 3'-deoxyoligonucleotides or oligonucleotides with other functions at the 3' position, for example, 3'-O-acetyl oligonucleotides. Additionally, amplification blockers are typically not readily hydrolyzed by the enzyme used in the amplification reaction. This can be accomplished using an enzyme without nuclease activity or using modified non-hydrolyzable oligonucleotides, which can have, for example, thioate bridges at the 5' terminal which confers resistance to hydrolysis.

b. Use of Nucleotide Synthesis Blockers

Methylation specific amplification can be performed in the presence of methylation specific amplification blockers in conjunction with either methylation specific primers or primers not specific for methylation. Thus, use of amplification blockers can permit use of a wide variety of primers in methylation specific amplification reactions. In one embodiment, amplification blockers are used in conjunction with methylation specific primers. In this embodiment, the amplification blockers can suppress amplification of background DNA and nucleic acid molecule having undesired sequences, while the methylation specific primers can preferentially amplify the nucleic acid molecule having the desired sequence. In this method, potentially very high relative amounts of background DNA and nucleic acid molecule having undesired sequences can be present in a target nucleic acid molecule sample, and nevertheless only the target nucleic acid molecule having the desired sequence is amplified.

In one embodiment, the amplification blockers can be directed to a primer query region of unmethylated nucleic acid molecules, where the primer query region is the site of methylation specific primer binding in methylated nucleic acid molecules. In this embodiment, the methylation specific primers can be used in the initial nucleic acid synthesis reaction steps, and amplification blockers can be subsequently added to inhibit amplification due to unintended hybridization (e.g., to prevent amplifying nucleic acids hybridized to, but mismatched with, methylation specific primers). Using methylation specific primers, the first two nucleic acid synthesis reaction steps can selectively yield nucleic acids complementary to single-stranded treated target nucleic acid molecules of a desired sequence, and to selectively replicate the single-stranded treated target nucleic acid molecules. Some amplification can arise from unintended hybridization (typically hybridization to a sequence arising from one or more mismatched base pairs) of a nucleic acid molecule having an undesired sequence in the primer hybridization region, and after a few amplification cycles, the methylation specific primers cannot select against such sequences due to incorporation of the primers into the amplified products. In the first few amplification steps, the amount of primer-incorporated amplified product is relatively small to the amount after numerous steps. Thus, by using amplification blockers after one or two nucleotide synthesis steps, the blockers will hybridize to non-primer incorporated regions of nucleic acids with undesired sequences to inhibit their amplification. Amplification blockers can thereby be used to decrease the amount of unintended hybridization of methylation specific primers with nucleic acids having an undesired sequence, resulting in a decrease in amplified products arising from undesired sequences.

In another embodiment, the amplification blockers can be specific for a region of the nucleic acid molecule or other nucleic acid that is different from the region to which the methylation specific primer hybridizes. In this embodiment, amplification blockers can serve to inhibit amplification of a nucleic acid having an undesired sequence during each amplification step. Thus, methylation specific primers can, in the initial steps of nucleic acid synthesis, be used to selectively amplify nucleic acids, typically target nucleic acid molecules of a desired sequence, while the amplification blockers can further serve to selectively inhibit, at each amplification step, amplification of nucleic acids having an undesired sequence.

In another embodiment, a combination of methylation specific primers with amplification blockers can be used when a target nucleic acid molecule contains two regions to be used for selectivity in methylation specific amplification, and the desired total size target nucleic acid molecule to be examined for its methylation state is larger than the nucleic acid portion between and including the two selective regions to be used for methylation specific amplification. This can occur, for example, when the two regions used for methylation specific amplification are close together, relative to the total length of the target nucleic acid molecule to be examined. For example, a target nucleic acid molecule to be examined can be 200 nucleotides in length, but can have two particular regions separated by 20 nucleotides which are to be used for selective amplification of the target nucleic acid molecule. In this instance, one of the selective regions can be targeted by a methylation specific primer, and the other selective region targeted by an amplification blocker. For example, one primer can be a methylation specific primer, and the other primer can be a methylation non-specific primer, and additional methylation specificity can be conferred by the use of one or more amplification blockers.

c. Use of Multiple Nucleotide Synthesis Blockers

In one embodiment, two or more amplification blockers can be used. In contrast to use of methylation specific primers, in which typically no more than two primers are used to select for a particular target nucleic acid molecule, the number of amplification blockers that can be used is not limited. For example, methylation specificity can be conferred using 1, 2, 3, 4, 5, 6, 7, 8, 9, 10 or more amplification blockers. Each amplification blocker can have a different number of nucleotides, and use of multiple amplification blockers can include use of amplification blockers that share common sequences (e.g., use of an amplification blocker trinucleotide having the sequence TTA, and an amplification blocker tetranucleotide having the sequence TTAA). In one example, at least one amplification blocker binds to a sequence of a nucleic acid in order to inhibit unintended hybridization of a methylation specific primer with the nucleic acid. In another example, at least one amplification blocker binds to a sequence of a nucleic acid other than a sequence with which a methylation specific primer can unintendedly hybridize. In another example, methylation specificity is conferred solely using amplification blockers (e.g., methylation specific amplification is performed using methylation specific amplification blockers and methylation non-specific primers). In another example, two or more regions of a target nucleic acid molecule can be targeted by amplification blockers. When fewer than two primers used in amplification are methylation specific primers, the amplification can use one or more methylation non-specific primers. When methylation specificity is determined solely by the use of one or more amplification blockers, both amplification primers can be methylation non-specific primers.

In one embodiment, amplification blockers are not used in the first methylation specific nucleic acid synthesis reaction. For example, amplification blockers can be omitted when a treated single-stranded target nucleic acid molecule is contacted with a methylation specific primer and nucleic acid synthesis adds nucleotides to the primer to form a strand complementary to the treated target nucleic acid molecule. Amplification blockers also can be omitted in the step following the complementary strand synthesis. Thus, amplification blockers can be omitted in the first, second, or both first and second, nucleic acid synthesis reactions. Following nucleic acid synthetic reactions without amplification blockers, amplification blockers then can be added during the nucleic acid amplification reactions. For example, methylation specific primers can be used for initial methylation specific synthesis of target nucleic acid molecules having the desired sequence; then during subsequent amplification steps amplification blockers can be used to prevent amplification of nucleic acids other than target nucleic acid molecules having the desired sequence.

4. Fragmentation in Conjunction with Nucleotide Synthesis

Selective nucleotide synthesis also can be performed in conjunction with fragmentation. A target nucleic acid amplified through a plurality of nucleic acid synthesis cycles will utilize primers hybridizing to two separate regions of the target nucleic acid molecule. Fragmentation of a target nucleic acid molecule in the center region in between the two primer hybridization sites will prevent amplification of the target nucleic acid molecule. Hence selective fragmentation of the center region of nucleic acid molecules can result in selective amplification of a target nucleic acid molecule even if the primers used in the nucleic acid synthesis reactions are not selective.

In one example, the sample can be treated with fragmentation conditions prior to being treated with nucleic acid synthesis conditions, and prior to being treated with a reagent that modifies the target nucleic acid molecule sequence as a function of the methylation state of the target nucleic acid. In such an example, the fragmentation conditions can be selective for methylated or unmethylated nucleotides. For example, an a sample can have added thereto a methylation sensitive endonuclease, such as HPAII, which cleaves at an unmethylated recognition site but not at a methylated recognition site. This results in a sample containing intact target nucleic acid molecules that are methylated at the recognition site and cleaved target nucleic acid molecules that are unmethylated at the recognition site. The sample then can be treated with nucleic acid synthesis conditions using primers designed so that only uncleaved target nucleic acid molecules are amplified. As a result of the cleavage, amplification will be selective for target nucleic acid molecules that are methylated at the recognition site.

In another example, the sample can be treated with fragmentation conditions prior to treatment with nucleic acid synthesis conditions, but subsequent to treatment with a reagent that modifies the target nucleic acid molecule sequence as a function of the methylation state of the target nucleic acid. For example, a sample can have added thereto an endonuclease that cleaves at a recognition site that includes a C nucleotide at a particular locus, but not a recognition site that contains a T or U nucleotide at that particular locus. Or vice versa, a sample can have added thereto an endonuclease that cleaves at a recognition site that includes a T or U nucleotide at a particular locus, but not a recognition site that contains a C nucleotide at that particular locus. The sample can first be treated with a reagent that modifies the target nucleic acid molecule sequence as a function of the methylation state of the target nucleic acid molecule, and then treated with such an endonuclease. The resulting sample will contain in tact target nucleic acid molecules that have the desired methylation state at the recognition site and cleaved target nucleic acid molecules that have the undesired methylation state at the recognition site. The sample then can be treated with nucleic acid synthesis conditions using primers designed so that only uncleaved target nucleic acid molecules are amplified. As a result of the cleavage, amplification will be selective for target nucleic acid molecules that are methylated at the recognition site.

Fragmentation conditions that can be used in such a method include any fragmentation conditions that can selectively cleave methylated nucleic acid molecules or unmethylated nucleic acid molecules, including endonucleases that can selectively cleave methylated nucleic acid molecules or unmethylated nucleic acid molecules. Additional fragmentation conditions that can be used include any fragmentation condition that can cleave by sequence specificity; for example, an endonuclease that selectively cleaves a nucleotide sequence containing a C nucleotide at a particular locus, or an endonuclease that selectively cleaves a nucleotide sequence containing a U or T nucleotide at a particular locus.

Fragmentation in conjunction with nucleic acid synthesis additionally can be combined with other methylation specific methods, including those provided herein. For example, fragmentation with nucleic acid synthesis can be performed using methylation specific primers, and fragmentation with nucleic acid synthesis can be performed using amplification blockers. Any combination of the methods provided herein can be combined, as will be understood by one skilled in the art.

5. Transcription

Transcription methods, which use a template DNA molecule to form an RNA molecule, can serve to amplify target nucleic acid molecules and to modify target nucleic acid molecule from DNA form to RNA form. Exemplary template DNA includes an amplified product target nucleic acid molecule and treated, unamplified target nucleic acid molecule.

As described herein, a treated target nucleic acid molecule is subjected to one or more nucleic acid synthesis reactions. The nucleic acid synthesis reactions can serve to amplify the treated target nucleic acid molecule and/or to modify the form of a nucleic acid molecule. In one embodiment, a treated target nucleic acid molecule or PCR product is transcribed.

Transcription of template DNA such as a target nucleic acid molecule, or an amplified product thereof, can be performed for one strand of the template DNA or for both strands of the template DNA. In one embodiment, the nucleic acid molecule to be transcribed contains a moiety to which an enzyme capable of performing transcription can bind; such a moiety can be, for example, a transcriptional promotor sequence.

Transcription reactions can be performed using any of a variety of methods known in the art, using any of a variety of enzymes known in the art. For example, mutant T7 RNA polymerase (T7 R&DNA polymerase; Epicentre, Madison, Wis.) with the ability to incorporate both dNTPs and rNTPs can be used in the transcription reactions. The transcription reactions can be run under standard reaction conditions known in the art, for example, 40 mM Tris-Ac (pH 7.5), 10 mM NaCl, 6 mM $MgCl_2$, 2 mM spermidine, 10 mM dithiothreitol, 1 mM of each rNTP, 5 mM of dNTP (when used), 40 nM DNA template, and 5 U/µL T7 R&DNA polymerase, incubating at 37° C. for 2 hours. After transcription, shrimp alkaline phosphatase (SAP) can be added to the cleavage reaction to reduce the quantity of cyclic monophosphate side products. Use of T7 R&DNA polymerase is known in the art, as exemplified by U.S. Pat. Nos. 5,849,546, 6,107,037, and Sousa et al., EMBO J. 14:4609-4621 (1995), Padilla et al., Nucl. Acid Res. 27:1561-1563 (1999), Huang et al., Biochemistry 36:8231-8242 (1997), and Stanssens et al., Genome Res., 14:126-133 (2004).

In addition to transcription with the four regular ribonucleotide substrates (rCTP, rATP, rGTP and rUTP), reactions can be performed replacing one or more ribonucleoside triphosphates with nucleoside analogs, such as those provided herein and known in the art, or with corresponding deoxyribonucleoside triphosphates (e.g., replacing rCTP with dCTP, or replacing rUTP with either dUTP or dTTP). In one embodiment, one or more rNTPs are replaced with a nucleoside or nucleoside analog that, upon incorporation into the transcribed nucleic acid, is not cleavable under the fragmentation conditions applied to the transcribed nucleic acid.

In one embodiment, transcription is performed subsequent to one or more nucleic acid synthesis reactions, including one or more nucleic acid synthesis reactions using methylation specific primers. For example, transcription of an amplified product can be performed subsequent to amplification of a target nucleic acid molecule, including methylation specific amplification of the target nucleic acid molecule.

In another embodiment, the treated target nucleic acid molecule is transcribed without any preceding nucleic acid synthesis steps. Transcription can be performed in the absence of amplification blockers described herein, or can be performed in the presence of amplification blockers. For example, transcription can be performed in the presence of one or more methylation specific amplification blockers.

6. Amplification of a Target Nucleic Acid Molecule While Maintaining the Methylated Sequence Also provided herein is a method for amplifying a methylated target nucleic acid molecule in a manner that preserves the methylation of any methylated residues. In this example, a methylated target nucleic acid molecule can serve as a template strand in a step of nucleic acid synthesis such as the nucleic acid synthesis methods described herein or as known in the art. The double stranded product will contain one methylated strand and one unmethylated strand. The newly synthesized, unmethylated strand of the double stranded target nucleic acid molecule then can be selectively methylated. The methylation reaction can be performed on specific cytosine bases of the newly synthesized strand by reference to the methylation state of the template strand of the nucleic acid. For example, where a CpG dinucleotide is methylated on the template strand, the cytosine on the newly synthesized strand, which is hybridized to the guanine of the methylated dinucleotide, can be methylated at the 5' position. In one embodiment, this method is performed by contacting the double stranded nucleic acid with a methyltransferase enzyme and a methyl donor molecule under conditions conducive to the methylation of the synthesized strand. The methylase activity of the enzyme can be such that the CpG dinucleotides within the synthesized strand can be methylated to reflect methylation in the corresponding CpG dinucleotide on the template strand, thereby preserving the genomic methylation pattern of the template strand.

Upon completion of the methylation reaction, the two methylated strands can be separated and the separated strands can be subjected to further nucleic acid synthesis reaction steps. Upon completion of the nucleic acid synthesis each double-stranded nucleic acid will contain one methylated strand and one unmethylated strand. The unmethylated strand then can be subjected to a step of methylation as described herein or known in the art. As a result of the second cycle of nucleic acid synthesis and methylation, duplicates of the template target nucleic acid strand can be produced that accurately maintain the methylation state of CpG dinucleotides in the original template target nucleic acid strand.

Methylation enzymes that can be used in methylation steps include those enzymes capable of methylating a cytosine at the 5' position according to the methylation status of the cytosine within the corresponding CpG dinucleotide on the template strand. When a cytosine within a CpG of the template strand is methylated, the corresponding CpG of the synthesized strand to which it is hybridized can be methylated at the 5' position of the cytosine nucleotide by action of the methylase enzyme. If the cytosine within the CpG of the template strand is unmethylated, the corresponding CpG on the synthesized strand will remain unmethylated. The reaction can be performed using appropriate buffers and other reagents and reaction conditions as recommended by the supplier of the selected enzyme. Such conditions can include a methyl donor molecule such as S-adenosylmethionine. In one embodiment, the methyl group added to the synthesized strand carries a detectable label, including a mass label, which is incorporated into the cytosine of the synthesized nucleic acid strand according to the methods described herein and known in the art.

The enzyme can be from any of a variety of sources, e.g., human, mouse, recombinant, and other sources of enzymes. In one embodiment, for example, the methyltransferase is DNA (cytosine-5) Methyltransferase (DNMT 1). Several species of methyltransferases are known, such as the family of maintenance methyltransferases that propagate the methylation pattern of hemimethylated DNA within the unmethylated strand, for example recombinant human DNMT1 (see Pradhan, S., Bacolla, A., Wells, R. D., Roberts, R. J. "Recombinant Human DNA (Cytosine-5) Methyltransferase. I. Expression, Purification and comparison of de novo and maintenance methylation." *J. Biol. Chem.* 274:33002-33010, and Bacolla A, Pradhan S, Roberts R. J., Wells, R. D., "Recombinant human DNA (cytosine-5) methyltransferase. II. Steady-state kinetics reveal allosteric activation by methylated DNA" *J. Biol. Chem.* 274:33011-33019). In one embodiment, the methyltransferase is a maintenance methyltransferase. Amplification/methylation methods described herein and reagents for performing such methods are known in the art, as exemplified in the publications U.S. 20030180779 and WO 02/101353.

Methylated amplified products can be used in the methods disclosed herein. For example, methylated amplified products can be treated with a reagent that modifies the sequence of the methylated amplified product as a function of the methylation of the methylated amplified product. Treated methylated amplified product then can be further amplified, then the further amplified products can be fragmented and the masses of the fragments can be measured. Alternatively, treated methylated amplified product can be fragmented without further amplification, and the masses of the fragments can be measured.

E. Fragmentation of Nucleic Acid Molecules

The methods provided herein also include steps of fragmentation and/or cleavage of target nucleic acid molecules or amplified products. Any method for cleaving a nucleic acid molecule into fragments with a suitable fragment size distribution can be used to generate the nucleic acid fragments. Fragmentation of nucleic acid molecules is known in the art and can be achieved in many ways. For example, nucleic acid molecules composed of DNA, RNA, analogs of DNA and RNA or combinations thereof, can be fragmented physically, chemically, or enzymatically. In one embodiment, enzymatic cleavage at one or more specific cleavage sites can be used to produce the nucleic acid molecule fragments utilized herein. Typically, cleavage is effected after amplification such that once a sufficient quantity of amplified products is generated using the methods provided herein, the amplified products can be cleaved into two or more fragments.

In embodiments where restriction enzymes are used, depending on the number and type of restriction enzymes used and the particular reaction conditions selected, the average length of fragments generated can be controlled within a specified range. In particular embodiments, fragments of nucleic acid molecules prepared for use herein can range in size from the group of ranges including 1-50 bases, 2-40 bases, 3-35 bases, and 5-30 bases. Yet other size ranges contemplated for use herein include between about 50 to about 150 bases, from about 25 to about 75 bases, or from about 12-30 bases. In one particular embodiment, fragments of about 3 to about 35 bases are used. Generally, fragment size range will be selected so that the mass of the fragments can be accurately determined using the mass measurement methods described herein and known in the art; also in some embodiments, size range is selected in order to facilitate the desired desorption efficiencies in MALDI-TOF MS.

1. Enzymatic Fragmentation of Nucleic Acid Molecules

Nucleic acid molecule fragments can result from enzymatic cleavage of single or multi-stranded nucleic acid molecules. Multistranded nucleic acid molecules include nucleic acid molecule complexes containing more than one strand of nucleic acid molecules, including for example, double and triple stranded nucleic acid molecules. Depending on the enzyme used, the nucleic acid molecules are cut non-specifically or at specific nucleotide sequences. Any enzyme capable of cleaving a nucleic acid molecule can be used, including but not limited, to endonucleases, exonucleases, single-strand specific nucleases, double-strand specific nucleases, ribozymes, and DNAzymes. A variety of enzymes for fragmenting nucleic acid molecules are known in the art and are commercially available, such as nuclease BAL-31, mung bean nuclease, exonuclease I, exonuclease III, exonuclease VIII, lambda exonuclease, T7 exonuclease, exonuclease T, RecJ, RNase I, RNase III, RNase A, RNase U2, RNase T1, RNase H ShortCut RNase III, Acc I, BasA I, BtgZ I, Mfe I, Sac I, N.BbvC IA, N.BbvC IB, N.BstNBI, I-Ceul, I-Scel, PI-PspI, PI-Scel, McrBC, and other known enzymes (see, e.g., New England Biolabs, Inc. Catalog; Sambrook, J., Russell, D. W., *Molecular Cloning: A Laboratory Manual,* 3rd ed., Cold Spring Harbor Laboratory Press, Cold Spring Harbor, N.Y., 2001). Enzymes also can be used to degrade large nucleic acid molecules into smaller fragments.

Also contemplated herein is the use of two or more "double-base cutters" or the use of a preferentially-cleaving endonuclease (like RNase PhyM), which is rendered more specific by the use of non-cleavable nucleotides (which at the same time increases the average fragment size). In another embodiment, cleavage can be performed using single- and/or double-base cutters. Once fragments are generated, the fragments can optionally be subjected to gel electrophoresis to isolate fragments having a specific size range.

a. Base-Specific Fragmentation

Target nucleic acid molecules can be fragmented using nucleases that selectively cleave at a particular base (e.g., A, C, T or G for DNA and A, C, U or G for RNA) or base type (i.e., pyrimidine or purine). In one embodiment, RNases that specifically cleave 3 RNA nucleotides (e.g., U, G and A), 2 RNA nucleotides (e.g., C and U) or 1 RNA nucleotide (e.g., A), can be used to base specifically cleave transcripts of a target nucleic acid molecule. For example, RNase T1 cleaves ssRNA (single-stranded RNA) at G ribonucleotides, RNase U2 digests ssRNA at A ribonucleotides, RNase CL3 and cusativin cleave ssRNA at C ribonucleotides, PhyM cleaves ssRNA at U and A ribonucleotides, and RNAse A cleaves ssRNA at pyrimidine ribonucleotides (C and U). The use of mono-specific RNases such as RNase $T_1$ (G specific) and RNase $U_2$ (A specific) is known in the art (Donis-Keller et al., *Nucleic Acids Res.* 4:2527-2537 (1977); Gupta and Randerath, *Nucleic Acids Res.* 4:1957-1978 (1977); Kuchino and Nishimura, *Methods Enzymol.* 180:154-163 (1989); and Hahner et al., *Nucl. Acids Res.* 25(10):1957-1964 (1997)). Another enzyme, chicken liver ribonuclease (RNase CL3) has been reported to cleave preferentially at cytidine, but the enzyme's proclivity for this base has been reported to be affected by the reaction conditions (Boguski et al., *J. Biol.*

Chem. 255:2160-2163 (1980)). Reports also claim cytidine specificity for another ribonuclease, cusativin, isolated from dry seeds of *Cucumis sativus* L (Rojo et al., Planta 194:328-338 (1994)). Alternatively, the identification of pyrimidine residues by use of RNase PhyM (A and U specific) (Donis-Keller, H. *Nucleic Acids Res.* 8:3133-3142 (1980)) and RNase A (C and U specific) (Simoncsits et al., *Nature* 269: 833-836 (1977); Gupta and Randerath, *Nucleic Acids Res.* 4:1957-1978 (1977)) has been demonstrated. Examples of such cleavage patterns are given in Stanssens et al., WO 00/66771.

In addition, bases can be targeted, for example, by incorporating a modified nucleotide into the nucleic acid, and excising the base of the nucleotide; subsequent treatment of the nucleic acid under the appropriate conditions or with an enzyme, can result in fragmentation of the nucleic acid at the site of the excised base. For example, dUTP can be incorporated into DNA, and base specific fragmentation can be accomplished by removing the uracil base using UDG, and subsequently cleaving the DNA under known cleavage conditions. In another example, methyl-cytosine can be incorporated into DNA, and base specific fragmentation can be accomplished using methyl cytosine deglycosylase to remove the methyl cytosine, followed by treatment under known conditions to result in DNA fragmentation. Base-specific fragmentation can be used in partial cleavage reactions (including partial cleavage reactions performed to completion when the target nucleic acid molecules contain non-cleavable nucleotides incorporated therein), and total cleavage reactions.

Base specific cleavage reaction conditions using an RNase are known in the art, and can include, for example 4 mM Tris-Ac (pH 8.0), 4 mM KAc, 1 mM spermidine, 0.5 mM dithiothreitol and 1.5 mM $MgCl_2$.

In one embodiment, amplified product can be transcribed into a single stranded RNA molecule and then cleaved base specifically by an endoribonuclease. Treatment of the target nucleic acid, for example using bisulfite which converts unmethylated cytosine to uracil without modifying methylated cytosine, can be used to generate differences in base specific cleavage patterns that can be analyzed by mass analysis methods, such as mass spectrometry, and can be used for identification of methylated sites. In one embodiment, transcription of a target nucleic acid molecule can yield an RNA molecule that can be cleaved using specific RNA endonucleases. For example, base specific cleavage of the RNA molecule can be performed using two different endoribonucleases, such as RNAse T1 and RNAse A. RNAse T1 specifically cleaves G nucleotides, and RNAse A specifically cleaves pyrimidine ribonucleotides (i.e., cytosine and uracil residues). In one embodiment, when an enzyme that cleaves more than one nucleotide, such as RNAse A, is used for cleavage, non-cleavable nucleosides, such as dNTP's can be incorporated during transcription of the target nucleic acid molecule or amplified product. For example, dCTPs can be incorporated during transcription of the amplified product, and the resultant transcribed nucleic acid can be subject to cleavage by RNAse A at U ribonucleotides, but resistant to cleavage by RNAse A at C deoxyribonucleotides. In another example, dTTPs can be incorporated during transcription of the target nucleic acid molecule, and the resultant transcribed nucleic acid can be subject to cleavage by RNAse A at C ribonucleotides, but resistant to cleavage by RNAse A at T deoxyribonucleotides. By selective use of non-cleavable nucleosides such as dNTPs, and by performing base specific cleavage using RNases such as RNAse A and RNAse T1, base cleavage specific to three different nucleotide bases can be performed on the different transcripts of the same target nucleic acid sequence. For example, the transcript of a particular target nucleic acid molecule can be subjected to G-specific cleavage using RNAse T1; the transcript can be subjected to C-specific cleavage using dTTP in the transcription reaction, followed by digestion with RNAse A; and the transcript can be subjected to T-specific cleavage using dCTP in the transcription reaction, followed by digestion with RNAse A.

In another embodiment, the use of dNTPs, different RNAses, and both orientations of the target nucleic acid molecule can allow for six different cleavage schemes. For example, a double stranded target nucleic acid molecule can yield two different single stranded transcription products, which can be referred to as a transcript product of the forward strand of the target nucleic acid molecule and a transcript product of the reverse strand of the target nucleic acid molecule. Each of the two different transcription products can be subjected to three separate base specific cleavage reactions, such as G-specific cleavage, C-specific cleavage and T-specific cleavage, as described herein, to result in six different base specific cleavage reactions. The six possible cleavage schemes are listed in Table 1. Use of four different base specific cleavage reactions can yield information on all four nucleotide bases of one strand of the target nucleic acid molecule. That is, by taking into account that cleavage of the forward strand can be mimicked by cleaving the complementary base on the reverse strand, base specific cleavage can be achieved for each of the four nucleotides of the forward strand by reference to cleavage of the reverse strand. For example, the three base-specific cleavage reactions can be performed on the transcript of the target nucleic acid molecule forward strand, to yield G-, C- and T-specific cleavage of the target nucleic acid molecule forward strand; and a fourth base specific cleavage reaction can be a T-specific cleavage reaction of the transcript of the target nucleic acid molecule reverse strand, the results of which will be equivalent to A-specific cleavage of the transcript of the target nucleic acid molecule forward strand. One skilled in the art will appreciate that base specific cleavage to yield information on all four nucleotide bases of one target nucleic acid molecule strand can be accomplished using a variety of different combinations of possible base specific cleavage reactions, including cleavage reactions provided in Table 1 for RNases T1 and A, and additional cleavage reactions for forward or reverse strands and/or using non-hydrolyzable nucleotides can be performed with other base specific RNases known in the art or disclosed herein.

TABLE 1

|  | Forward Primer | Reverse Primer |
|---|---|---|
| RNase T1 | G specific cleavage | G specific cleavage |
| RNase A; dCTP | T specific cleavage | T specific cleavage |
| RNase A; dTTP | C specific cleavage | C specific cleavage |

In one example, RNAse U2 can be used to base specifically cleave target nucleic acid molecule transcripts. RNAse U2 can base specifically cleave RNA at A nucleotides. Thus, by use of RNAses T1, U2 and A, and by use of the appropriate dNTPs (in conjunction with use of RNase A), all four base positions of a target nucleic acid molecule can be examined by base specifically cleaving transcript of only one strand of the target nucleic acid molecule. In some embodiments, non-cleavable nucleoside triphosphates are not required when base specific cleavage is performed using RNAses that base specifically cleave only one of the four ribonucleotides. For example, use of RNAse T1, RNase CL3, cusativin, or RNAse U2 for base specific cleavage does not require the presence of a non-cleavable nucleotides in the target nucleic acid molecule transcript. Use of RNAses such as RNAse T1 and RNAse U2 can yield information on all four nucleotide bases of a target nucleic acid molecule. For example, transcripts of both the forward and reverse strands of a target nucleic acid molecule or amplified product can be synthesized, and each transcript can be subjected to base specific cleavage using RNAse T1 and RNAse U2. The resulting cleavage pattern of the four cleavage reactions will yield information on all four nucleotide bases of one strand of the target nucleic acid molecule. In such an embodiment, two transcription reactions can be performed: a first transcription of the forward target nucleic acid molecule strand and a second of the reverse target nucleic acid molecule strand.

Also contemplated for use in the methods are a variety of different base specific cleavage methods. A variety of different base specific cleavage methods are known in the art and are described herein, including enzymatic base specific cleavage of RNA, enzymatic base specific cleavage of modified DNA, and chemical base specific cleavage of DNA. For example enzymatic base specific cleavage, such as cleavage using uracil-deglycosylase (UDG) or methylcytosine deglycosylase (MCDG), are known in the art and described herein, and can be performed in conjunction with the enzymatic RNAse-mediated base specific cleavage reactions described herein.

b. Endonuclease Fragmentation of Nucleic Acid Molecules

Endonucleases are an exemplary class of enzymes useful for fragmenting nucleic acid molecules. Endonucleases cleave the bonds within a nucleic acid molecule strand. Endonucleases can be specific for either double-stranded or single-stranded nucleic acid molecules. Cleavage can occur randomly within the nucleic acid molecule or at specific sequences. Endonucleases that randomly cleave double-strand nucleic acid molecules often make interactions with the backbone of the nucleic acid molecule. Specific fragmentation of nucleic acid molecules can be accomplished using one or more enzymes in sequential reactions or contemporaneously. Homogenous or heterogenous nucleic acid molecules can be cleaved.

Restriction endonucleases are a subclass of endonucleases which recognize specific sequences within double-strand nucleic acid molecules and typically cleave both strands either within or close to the recognition sequence. One commonly used enzyme in DNA analysis is HaeIII, which cuts DNA at the sequence 5'-GGCC-3'. Other exemplary restriction endonucleases include Acc I, Afl III, Alu I, Alw44 I, Apa I, Asn I, Ava I, Ava II, BamH I, Ban II, Bcl I, Bgl I, Bgl II, Bin I, Bsm I, BssH II, BstE II, Cfo I, Cla I, Dde I, Dpn I, Dra I, EcIX I, EcoR I, EcoR I, EcoR H, EcoR V, Hae II, Hae III, Hind III, Hind III, Hpa I, Hpa II, Kpn I, Ksp I, Mlu I, MluN I, Msp I, Nci I, Nco I, Nde I, Nde II, Nhe I, Not I, Nru I, Nsi I, Pst I, Pvu I, Pvu II, Rsa I, Sac I, Sal I, Sau3A I, Sca I, ScrF I, Sfi I, Sma I, Spe I, Sph I, Ssp I, Stu I, Sty I, Swa I, Taq I, Xba I, Xho I. The cleavage sites for these enzymes are known in the art. Also contemplated are Type IIS restriction endonucleases, which cleave downstream from their recognition sites.

Depending on the enzyme used, the cut in the nucleic acid molecule can result in one strand overhanging the other also known as "sticky" ends. For example, BamH I generates cohesive 5' overhanging ends, and Kpn I generates cohesive 3' overhanging ends. Alternatively, the cut can result in "blunt" ends that do not have an overhanging end. For example, Dra I cleavage generates blunt ends. Restriction enzymes can cleave sequences containing one or more methylated nucleotides while not cleaving the unmethylated equivalent sequence, can specifically cleave sequences containing no methylated nucleotides while not cleaving the equivalent sequence containing one or more methylated nucleotides, or can cleave a sequence regardless of the methylation state of one or more nucleotides in the sequence. In one example, cleavage recognition sites can be masked by methylation.

Restriction endonucleases can be used to generate a variety of nucleic acid molecule fragment sizes. For example, CviJ I is a restriction endonuclease that recognizes between a two and three base DNA sequence. Complete digestion with CviJ I can result in DNA fragments averaging from 16 to 64 nucleotides in length. Partial digestion with CviJ I can therefore fragment DNA in a "quasi" random fashion similar to shearing or sonication. CviJ I normally cleaves RGCY sites between the G and C leaving readily cloneable blunt ends, wherein R is any purine and Y is any pyrimidine. In the presence of 1 mM ATP and 20% dimethyl sulfoxide the specificity of cleavage is relaxed and CviJ I also cleaves RGCN and YGCY sites. Under these "star" conditions, CviJ I cleavage generates quasi-random digests. Digested or sheared DNA can be size selected at this point.

In another embodiment, CviJ I can be used to specifically cleave nucleic acid sequences having methylated CpG repeats. In this embodiment, CviJ I can be used under the "star" conditions such that most NGCY and RGCN sequences are cleaved by CviJ I. When, for example, the target nucleic acid molecule or amplified product is treated with bisulfite, presence of a GC dinucleotide in the treated target nucleic acid molecule or amplified product can imply the presence of a methylated C nucleotide; thus, cleavage at NGCY or RGCN can indicate the presence of a methylated C at the cleavage site.

Methods for using restriction endonucleases to fragment nucleic acid molecules are widely known in the art. In one exemplary protocol a reaction mixture of 20-50 μL is prepared containing: DNA 1-3 μg; restriction enzyme buffer 1×; and a restriction endonuclease 2 units for 1 μg of DNA. Suitable buffers also are known in the art and include suitable ionic strength, cofactors, and optionally, pH buffers to provide optimal conditions for enzymatic activity. Specific enzymes can require specific buffers which are generally available from commercial suppliers of the enzyme. An exemplary buffer is potassium glutamate buffer (KGB). Hannish, J. and M. McClelland, "Activity of DNA modification and restriction enzymes in KGB, a potassium glutamate buffer," *Gene Anal. Tech* 5:105 (1988); McClelland, M. et al. "A single buffer for all restriction endonucleases," *Nucl. Acids Res.* 16:364 (1988). The reaction mixture is incubated at 37° C. for 1 hour or for any time period needed to produce fragments of a desired size or range of sizes. The reaction can be stopped by heating the mixture at 65° C. or 80° C. as needed. Alternatively, the reaction can be stopped by chelating divalent cations such as $Mg^{2+}$ with for example, EDTA.

In particular embodiments, more than one enzyme can be used to fragment the nucleic acid molecule. Multiple enzymes can be used in the same reaction provided the enzymes are active under similar conditions such as ionic strength, temperature, or pH; or, multiple enzymes can be used in sequential reactions. Typically, multiple enzymes are used with a standard buffer such as KGB. When restriction enzymes are used, the nucleic acid molecules can be either partially or completely digested.

DNAses also can be used to generate nucleic acid molecule fragments. Anderson, S., "Shotgun DNA sequencing using cloned DNase I-generated fragments," *Nucl. Acids Res.* 9:3015-3027 (1981). DNase I (Deoxyribonuclease I) is an endonuclease that non-specifically digests double- and single-stranded DNA into poly- and mono-nucleotides. The enzyme is able to act upon single as well as double-stranded DNA and on chromatin.

Deoxyribonuclease type II is used for many applications in nucleic acid research including DNA sequencing and digestion at an acidic pH. Deoxyribonuclease II from porcine spleen has a molecular weight of 38,000 daltons. The enzyme is a glycoprotein endonuclease with dimeric structure. Optimum pH range is 4.5-5.0 at ionic strength 0.15 M. Deoxyribonuclease II hydrolyzes deoxyribonucleotide linkages in native and denatured DNA yielding products with 3'-phosphates. It also acts on p-nitrophenylphosphodiesters at pH 5.6-5.9. Ehrlich, S. D. et al. "Studies on acid deoxyribonuclease. IX. 5'-Hydroxy-terminal and penultimate nucleotides of oligonucleotides obtained from calf thymus deoxyribonucleic acid," *Biochemistry* 10(11):2000-2009 (1971).

Endonucleases can be specific for particular types of nucleic acid molecules. For example, endonuclease can be specific for DNA or RNA, or for single-stranded or double-stranded nucleic acid molecules. Endonucleases can be sequence specific or non-sequence specific. For example, ribonuclease H is an endoribonuclease that specifically degrades the RNA strand in an RNA-DNA hybrid. Ribonuclease A is an endoribonuclease that specifically attacks single-stranded RNA at C and U residues. Ribonuclease A catalyzes cleavage of the phosphodiester bond between the 5'-ribose of a nucleotide and the phosphate group attached to the 3'-ribose of an adjacent pyrimidine nucleotide. The resulting 2',3'-cyclic phosphate can be hydrolyzed to the corresponding 3'-nucleoside phosphate. RNase T1 digests RNA at only G ribonucleotides, cleaving between the 3'-hydroxy group of a guanylic residue and the 5'-hydroxy group of the flanking nucleotide. RNase $U_2$ digests RNA at only A ribonucleotides. Examples of base-specific digestion can be found in the publication by Stanssens et al., WO 00/66771.

Benzonase™, nuclease P1, and phosphodiesterase I are nonspecific endonucleases that are suitable for generating nucleic acid molecule fragments ranging from 200 base pairs or less. Benzonase™ (Novagen, Madison, Wis.) is a genetically engineered endonuclease which degrades all forms of DNA and RNA (single stranded, double stranded, linear and circular) and can be used in a wide range of operating conditions. The enzyme completely digests nucleic acids to 5'-monophosphate terminated oligonucleotides 2-5 bases in length. The nucleotide and amino acid sequences for Benzonase™ is provided in U.S. Pat. No. 5,173,418. Fragmentation of nucleic acids for the methods as provided herein also can be accomplished by dinucleotide ("2 cutter") or relaxed dinucleotide ("1½ cutter" or "1¼ cutter") cleavage specificity. Dinucleotide-specific cleavage reagents are known to those of skill in the art (see, e.g., WO 94/21663; Cannistraro et al., *Eur. J. Biochem.* 181:363-370 (1989); Stevens et al., *J. Bacteriol.* 164:57-62 (1985); Marotta et al., *Biochemistry* 12:2901-2904 (1973).

Nucleotide-specific cleavage can be controlled through enzymatic and/or chemical modification of the target nucleic acid molecule or amplified product. For example, transcripts of the target nucleic acid molecule of interest can be synthesized with a mixture of regular and α-thio-substrates and the phosphorothioate internucleoside linkages can subsequently be modified by alkylation using reagents such as an alkyl halide (e.g., iodoacetamide, iodoethanol) or 2,3-epoxy-1-propanol. The phosphothioester bonds formed by such modification are not expected to be substrates for RNAses. Other exemplary nucleotides that are not cleaved by RNAses include 2'fluoro nucleotides, 2'deoxy nucleotides and 2'amino nucleotides. In one example of using this procedure, the cleavage specificity of RNAse A can be restricted to CpN or UpN dinucleotides through incorporation of a non-hydrolyzable nucleotide, such as a 2'-modified form of a C nucleotide or U nucleotide, depending on the desired cleavage specificity. Thus, in an example of making RNAse A specific for CpG nucleotides, a transcript (target molecule) can be prepared by incorporating αS-dUTP, αS-ATP, αS-CTP and GTP nucleotides into the transcript. The repertoire of useful dinucleotide-specific cleavage reagents can be further expanded by using additional RNAses, such as RNAse-U2 and RNAse-T1. In the case of a mono-specific RNAse, such as RNAse-T1, use of non-cleavable nucleotides can limit cleavage of GpN bonds to any three, two or one out of the four possible GpN bonds depending on which nucleotide are selected to be non-cleavable. These selective modification strategies also can be used to prevent cleavage at every base of a homopolymer tract by selectively modifying some of the nucleotides within the homopolymer tract to render the modified nucleotides less resistant or more resistant to cleavage.

c. Nuclease Fragmentation

Large single-stranded nucleic acid molecules can be fragmented into small nucleic acid molecules using nucleases that remove various lengths of bases from the end of a nucleic acid molecule. Exemplary nucleases for removing the ends of single-stranded nucleic acid molecules include but are not limited to S1, Bal 31, and mung bean nucleases. For example, mung bean nuclease degrades single-stranded DNA to mono or polynucleotides with phosphate groups at their 5' termini. Double-stranded nucleic acids can be digested completely if exposed to very large amounts of this enzyme.

Exonucleases are proteins that also cleave nucleotides from the ends of a nucleic acid molecule, for example a DNA molecule. There are 5' exonucleases (cleave the DNA from the 5'-end of the DNA chain) and 3' exonucleases (cleave the DNA from the 3'-end of the chain). Different exonucleases can hydrolyze single-strand or double-strand DNA. For example, Exonuclease III is a 3' to 5' exonuclease, releasing 5'-mononucleotides from the 3'-ends of DNA strands; it is a DNA 3'-phosphatase, hydrolyzing 3'-terminal phosphomonoesters; and it is an AP endonuclease, cleaving phosphodiester bonds at apurinic or apyrimidinic sites to produce 5'-termini that are base-free deoxyribose 5'-phosphate residues. In addition, the enzyme has an RNase H activity; it will preferentially degrade the RNA strand in a DNA-RNA hybrid duplex, presumably exonucleolytically. In mammalian cells, the major DNA 3'-exonuclease is DNase III (also called TREX-1). Thus, fragments can be formed by using exonucleases to degrade the ends of nucleic acid molecules.

d. Nucleic Acid Enzyme Fragmentation

Catalytic DNA and RNA are known in the art and can be used to cleave nucleic acid molecules to produce nucleic acid molecule fragments. Santoro, S. W. and Joyce, G. F. "A general purpose RNA-cleaving DNA enzyme," *Proc. Natl. Acad. Sci. USA* 94:4262-4266 (1997). DNA as a single-stranded molecule can fold into three dimensional structures similar to RNA, and the 2'-hydroxy group is dispensable for catalytic action. As ribozymes, DNAzymes also can be made, by selection, to depend on a cofactor. This has been demonstrated for a histidine-dependent DNAzyme for RNA hydrolysis. U.S. Pat. Nos. 6,326,174 and 6,194,180 disclose deoxyribonucleic acid enzymes, catalytic and enzymatic DNA molecules, capable of cleaving nucleic acid sequences or molecules, particularly RNA.

The use of ribozymes for cleaving nucleic acid molecules is known in the art. Ribozymes are RNAs that catalyze a chemical reaction, e.g., cleavage of a covalent bond. Uhlenbeck demonstrated a small active ribozyme, the hammerhead ribozyme, in which the catalytic and substrate strands were separated (Uhlenbeck, Nature 328:596-600 (1987)). Such ribozymes bind substrate RNAs through base-pairing interactions, cleave the bound target RNA, release the cleavage products, and are recycled so that they can repeat this process multiple times. Haseloff and Gerlach enumerated general design rules for simple hammerhead ribozymes capable of acting in trans (Haseloff et al., Nature, 334:585-591 (1988)). A variety of different hammerhead ribozymes with high cleavage specificity have been developed, and general approaches for design of hammerhead ribozymes having desired substrate specificity are known in the art, as exemplified by U.S. Pat. Nos. 5,646,020 and 6,096,715. Another type if ribozyme with trans-cleavage activity are the δ ribozymes derived from the genome of hepatitis δ virus. Ananvoranich and Perrault have described the factors for substrate specificity of δ ribozyme cleavage (Ananvoranich et al., J. Biol. Chem. 273:13812-13188 (1998)). Hairpin ribozymes also can be used for trans-cleavage, and the principles for substrate specificity for hairpin ribozymes also are known (see, e.g., Perez-Ruiz et al., J. Biol. Chem. 274:29376-29380 (1999)). One skilled in the art can use the known principles of substrate specificity to select the ribozyme and design the ribozyme sequence to achieve the desired nucleic acid molecule cleavage specificity.

A DNA nickase, or DNase, can be used to recognize and cleave one strand of a DNA duplex. Numerous nickases are known. Among these, for example, are nickase NY2A nickase and NYS1 nickase (Megabase) with the following cleavage sites:

NY2A: 5' . . . R AG . . . 3'
 3' . . . Y TC . . . 5' where R=A or G and Y=C or T
NYS1: 5' . . . CC[A/G/T] . . . 3'
 3' . . . GG[T/C/A] . . . 5'.

Subsequent chemical treatment of the products from the nickase reaction results in the cleavage of the phosphate backbone and the generation of fragments.

The Fen-1 fragmentation method involves the enzymes Fen-1 enzyme, which is a site-specific nuclease known as a "flap" endonuclease (U.S. Pat. Nos. 5,843,669, 5,874,283, and 6,090,606). This enzyme recognizes and cleaves DNA "flaps" created by the overlap of two oligonucleotides hybridized to a target DNA strand. This cleavage is highly specific and can recognize single base variations, permitting detection of a single methylated base at a nucleotide locus of interest. Fen-1 enzymes can be Fen-1 like nucleases e.g., human, murine, and *Xenopus* XPG enzymes and yeast RAD2 nucleases or Fen-1 endonucleases from, for example, *M jannaschii, P. furiosus*, and *P. woesei*.

Another technique that can be used is cleavage of DNA chimeras. Tripartite DNA-RNA-DNA probes are hybridized to target nucleic acid molecules, such as *M tuberculosis*-specific sequences. Upon the addition of RNAse H, the RNA portion of the chimeric probe is degraded, releasing the DNA portions (Yule, *Bio/Technology* 12:1335 (1994)).

2. Physical Fragmentation of Nucleic Acid Molecules

Fragmentation of nucleic acid molecules can be achieved using physical or mechanical forces including mechanical shear forces and sonication. Physical fragmentation of nucleic acid molecules can be accomplished, for example, using hydrodynamic forces. Typically nucleic acid molecules in solution are sheared by repeatedly drawing the solution containing the nucleic acid molecules into and out of a syringe equipped with a needle. Thorstenson, Y. R. et al. "An Automated Hydrodynamic Process for Controlled, Unbiased DNA Shearing," *Genome Research* 8:848-855 (1998); Davison, P. F. *Proc. Natl. Acad. Sci.* USA 45:1560-1568 (1959); Davison, P. F. *Nature* 185:918-920 (1960); Schriefer, L. A. et al. "Low pressure DNA shearing: a method for random DNA sequence analysis," *Nucl. Acids Res.* 18:7455-7456 (1990). Shearing of DNA, for example with a hypodermic needle, typically generates a majority of fragments ranging from 1-2 kb, although a minority of fragments can be as small as 300 bp.

Devices for shearing nucleic acid molecules, including for example genomic DNA, are commercially available. An exemplary device uses a syringe pump to create hydrodynamic shear forces by pushing a DNA sample through a small abrupt contraction. Thorstenson, Y. R. et al. "An Automated Hydrodynamic Process for Controlled, Unbiased DNA Shearing," *Genome Research* 8:848-855 (1998). The volume for shearing is typically 100-250 μL, and processing time to less than 15 minutes. Shearing of the samples can be completely automated by computer control.

The hydrodynamic point-sink shearing method developed by Oefner et al. is one method of shearing nucleic acid molecules that utilizes hydrodynamic forces. Oefner, P. J. et al. "Efficient random subcloning of DNA sheared in a recirculating point-sink flow system," *Nucl. Acids Res.* 24(20):3879-3886 (1996). "Point-sink" refers to a theoretical model of the hydrodynamic flow in this system. The rate-of-strain tensor describes the force on a molecule and therefore, its breakage. DNA breakage was attributed to the "shearing" terms of this tensor, and this class of method of fragmenting was referred to as shearing. Breakage can be caused by both the shearing terms (when the fluid is inside the narrow tube or orifice) and the extensional strain terms (when the fluid approaches the orifice). Point-sink shearing is accomplished by forcing nucleic acid molecules, for example DNA, through a very small diameter tubing by applying pressure with a pump, for example a HPLC pump. The resulting fragments have a tight size range with the largest fragments being about twice as long as the smallest fragments. The size of the fragments are inversely proportional to the flow rate.

Nucleic acid molecule fragments also can be obtained by agitating large nucleic acid molecules in solution, for example by mixing, blending, stirring, or vortexing the solution. Hershey, A. D. and Burgi, E. *J. Mol. Biol.* 2:143-152 (1960); Rosenberg, H. S. and Bendich, A. *J. Am. Chem. Soc.* 82:3198-3201 (1960). The solution can be agitated for various lengths of time until fragments of a desired size or range of sizes are obtained. The addition of beads or particles to the solution can assist in fragmenting the nucleic acid molecules.

One suitable method of physically fragmenting nucleic acid molecules is based on sonicating the nucleic acid molecule. Deininger, P. L. "Approaches to rapid DNA sequence analysis," *Anal. Biochem.* 129:216-223 (1983). The generation of nucleic acid molecule fragments by sonication is typically performed by placing a microcentrifuge tube containing buffered nucleic acid molecules into an ice-water bath in a sonicator, for example a cup-horn sonicator, and sonicating for a varying number of short bursts using maximum output and continuous power. The short bursts can be about 10 seconds in duration. See for example Bankier, A. T. et al. "Random cloning and sequencing by the M13/dideoxynucleotide chain termination method," *Meth. Enzymol.* 155:51-93 (1987). In one exemplary sonication protocol, sonication of large nucleic acid molecules resulted in fragments in the range of 300-500 bp or 2-10 kb depending on conditions of sonication such as duration and sonication intensity. Kawata, Y. et al. "Preparation of a Genomic Library Using TA Vector," *Prep. Biochem & Biotechnol.* 29(1):91-100 (1999).

During sonication, temperature increases can result in uneven fragment distribution patterns, and for that reason, the temperature of the bath can be monitored carefully, and fresh ice-water can be added when necessary. An exemplary sonication protocol to determine specific conditions for sonication includes distributing approximately 100 μg of nucleic acid molecule sample, in 350 μl of a suitable buffer, into ten aliquots of 35 μl, five of which are subjected to sonication for increasing numbers of 10 second bursts. The nucleic acid molecule samples are cooled by placing the tubes in an ice-water bath for at least 1 minute between each 10 second burst. The ice-water bath in the sonicator can be replaced between each sample as needed. The samples can be centrifuged to reclaim condensation and an aliquot electrophoresed on a agarose gel versus a size marker. Based on the fragment size ranges detected from agarose gel electrophoresis, the remaining 5 tubes can be sonicated accordingly to obtain the desired fragment sizes.

Fragmentation of nucleic acid molecules also can be achieved using a nebulizer. Bodenteich, A., Chissoe, S., Wang, Y.-F. and Roe, B. A. (1994) In Adams, M. D., Fields, C. and Venter, J. C. (eds) *Automated DNA Sequencing and Analysis*. Academic Press, San Diego, Calif. Nebulizers are known in the art and commercially available. An exemplary protocol for nucleic acid molecule fragmentation using a nebulizer includes placing 2 ml of a buffered nucleic acid molecule solution (approximately 50 μg) containing 25-50% glycerol in an ice-water bath and subjecting the solution to a stream of gas, for example nitrogen, at a pressure of 8-10 psi for 2.5 minutes. It will be appreciated that any gas can be used, particularly inert gases. Gas pressure is the primary determinant of fragment size. Varying the pressure can produce various fragment sizes. Use of an ice-water bath for nebulization can be used to generate evenly distributed fragments. Similarly, fragments can be generated using a high pressure spray atomizer. Cavalieri, L. F. and Rosenberg, B. H., *J. Am. Chem. Soc.* 81:5136-5139 (1959).

Another method for fragmenting nucleic acid molecule employs repeatedly freezing and thawing a buffered solution of nucleic acid molecules. The sample of nucleic acid molecules can be frozen and thawed as necessary to produce fragments of a desired size or range of sizes. Additionally, nucleic acid molecules can be bombarded with ions or particles to generate fragments of various sizes. For example, nucleic acid molecules can be exposed to an ion extraction beamline under vacuum. Ions are extracted from an electron beam ion trap at 7 kV*q and directed onto the target nucleic acid molecules. The nucleic acid molecules can be irradiated for any length of time, typically for a few hours until, for example, a total fluence of 100 ions/μm$^2$ is achieved.

Nucleic acid molecule fragmentation also can be achieved by irradiating the nucleic acid molecules. Typically, radiation such as gamma or x-ray radiation will be sufficient to fragment the nucleic acid molecules. The size of the fragments can be adjusted by adjusting the intensity and duration of exposure to the radiation. Ultraviolet radiation also can be used. The intensity and duration of exposure also can be adjusted to minimize undesirable effects of radiation on the nucleic acid molecules.

Boiling nucleic acid molecules also can produce fragments. Typically a solution of nucleic acid molecules is boiled for a couple hours under constant agitation. Fragments of about 500 bp can be achieved. The size of the fragments can vary with the duration of boiling.

3. Chemical Fragmentation of Nucleic Acid Molecules

Chemical fragmentation can be used to fragment nucleic acid molecules either with base specificity or without base specificity. Nucleic acid molecules can be fragmented by chemical reactions including for example, hydrolysis reactions including base and acid hydrolysis. Alkaline conditions can be used to fragment nucleic acid molecules containing nicks or RNA because RNA (or unpaired bases) is unstable under alkaline conditions. See Nordhoff et al. "Ion stability of nucleic acids in infrared matrix-assisted laser desorption/ ionization mass spectrometry," *Nucl. Acids Res.* 21(15):3347-3357 (1993). DNA can be hydrolyzed in the presence of acids, typically strong acids such as 6M HCl. The temperature can be elevated above room temperature to facilitate the hydrolysis. Depending on the conditions and length of reaction time, the nucleic acid molecules can be fragmented into various sizes including single base fragments. Hydrolysis can, under rigorous conditions, break both of the phosphate ester bonds and also the N-glycosidic bond between the deoxyribose and the purines and pyrimidine bases.

An exemplary acid/base hydrolysis protocol for producing nucleic acid molecule fragments are known (see, e.g., Sargent et al. *Meth. Enz* 152:432 (1988)). Briefly, 1 g of DNA is dissolved in 50 mL 0.1 N NaOH. 1.5 mL concentrated HCl is added, and the solution is mixed quickly. DNA will precipitate immediately, and should not be stirred for more than a few seconds to prevent formation of a large aggregate. The sample is incubated at room temperature for 20 minutes to partially depurinate the DNA. Subsequently, 2 mL 10 N NaOH(OH— concentration to 0.1 N) is added, and the sample is stirred until DNA redissolves completely. The sample is then incubated at 65° C. for 30 minutes to hydrolyze the DNA. Typical sizes range from about 250-1000 nucleotides but can vary lower or higher depending on the conditions of hydrolysis.

Chemical cleavage also can be specific. For example, selected nucleic acid molecules can be cleaved via alkylation, particularly phosphorothioate-modified nucleic acid molecules (see, e.g., K. A. Browne, "Metal ion-catalyzed nucleic Acid alkylation and fragmentation," *J. Am. Chem. Soc.* 124 (27):7950-7962 (2002)). Alkylation at the phosphorothioate modification renders the nucleic acid molecule susceptible to cleavage at the modification site. I. G. Gut and S. Beck describe methods of alkylating DNA for detection in mass spectrometry. I. G. Gut and S. Beck, "A procedure for selective DNA alkylation and detection by mass spectrometry," *Nucl. Acids Res.* 23(8):1367-1373 (1995).

Various additional chemicals and methods for base-specific and base non-specific chemical cleavage of oligonucleotides are known in the art, and are contemplated for use in the fragmentation methods provided herein. For example, base-specific cleavage can be accomplished using chemicals such as piperidine formate, piperidine, dimethyl sulfate, hydrazine and sodium chloride, hydrazine. For example, DNA can be base-specifically cleaved at G nucleotides using dimethyl sulfate and piperidine; DNA can be base-specifically cleaved at A and G nucleotides using dimethyl sulfate, piperidine and acid; DNA can be base-specifically cleaved at C and T nucleotides using hydrazine and piperidine; DNA can be base-specifically cleaved at C nucleotides using hydrazine, piperidine and sodium chloride; and DNA can be base-specifically cleaved at A nucleotides, with a lower specificity for C nucleotides using a strong base.

4. Combinations of Fragmentation Methods

Fragments also can be formed using any combination of fragmentation methods described herein, using e.g., a combination of base-specific cleavage methods, a combination of enzymes or shearing combined with a sequence-specific enzyme. Methods for producing specific fragments can be combined with methods for producing random fragments. Further, different methods for producing random fragments can be combined, and different methods for producing specific fragments can be combined. For example, one or more enzymes that cleave a nucleic acid molecule at a specific site can be used in combination with one or more enzymes that specifically cleave the nucleic acid molecule at a different site. In another example, enzymes that cleave specific kinds of nucleic acid molecules can be used in combination, for example, an RNase in combination with a DNase or a single-strand specific nuclease can be used in combination with a double-strand specific nuclease, or an exonuclease can be used in combination with an endonuclease. In still another example, an enzyme that cleaves nucleic acid molecules randomly can be used in combination with an enzyme that cleaves nucleic acid molecules specifically. Use of fragmentation in combination refers to performing one or more methods after another or contemporaneously, on a nucleic acid molecule.

As contemplated herein, use in combination also can encompass using a first fragmentation method on a first fraction of a nucleic acid molecule sample, using a second fragmentation method on a second fraction of the nucleic acid molecule sample. The two samples can be separately analyzed in subsequent detection and mass measurement methods, or the two samples can be pooled together and simultaneously analyzed in subsequent detection and mass measurement methods. Combinations of fragmentation methods can include 2 or more fragmentation methods, 3 or more fragmentation methods, or 4 or more fragmentation methods.

a. Base-Specific Fragmentation

Sequence modification of a target nucleic acid molecule or amplified product as a function of the methylation state of a target nucleic acid molecule can result in a base specific cleavage pattern that reflects the methylation state of the target nucleic acid molecule. Thus, a difference in the methylation state of two nucleic acid molecules having the same nucleotide sequence can result in a difference in the base specific cleavage pattern of the two nucleic acid molecules. Types changes in the base specific cleavage pattern that can reflect changes in the methylation state of a target nucleic acid molecule include: methylation or lack of methylation of a nucleotide, which can introduce a new cleavable site in the nucleic acid molecule, and result in formation of two shorter fragments instead of one larger fragment; methylation or lack of methylation of a nucleotide, which can introduce a non-cleavable site in the target nucleic acid molecule, and result in a single larger fragment instead of two shorter fragments; and methylation or lack of methylation, which can result in a change in the nucleotide composition of a fragment, which can result in a mass shift. These three changes in base specific cleavage patterns are exemplified in Table 2 for base specific cleavage of transcripts formed from bisulfite treated nucleic acid molecules. Each of these changes in the base specific cleavage patterns can contain information that can be used in DNA methylation analysis, as described herein.

TABLE 2

|  | Non-methylated TAAATGTAT | Type of change | Methylated TAAACGTAT |
|---|---|---|---|
| RNAse A C specific cleavage | TAAATGTAT | New Signal | TAAAC GTAT |
| RNAse A T specific cleavage | T AAAT GT AT | Connecting Signals | T AAACGT AT |
| RNAse T1 G specific cleavage | TAAATG TAT | Mass Shift | TAAACG TAT |

Theoretical cleavage fragments of a specified nucleotide sequence TAAACGCAT, which will through bisulphite treatment be converted to TAAACGTAT if methylated at the Cytosine on position five and to TAAATGTAT if not methylated.

Fragment mass patterns that can be used in methylation state identification include the presence of a fragment, the absence of a fragment, and the mass of a fragment relative to a reference. Methylation state identification using fragment masses can be performed by comparing the fragment masses to reference nucleic acid sequences, reference fragment masses or calculated fragment masses. Methylation state identification using fragment masses can be performed in conjunction with nucleotide sequence determination of all or part of the target nucleic acid molecule. Methylation state identification using fragment masses also can be performed by only measuring fragment masses, without comparing to a reference or a nucleotide sequence.

i. Absence of a Fragment

Absence of a fragment can identify the target nucleic acid as methylated or unmethylated, or as containing one or more methylated or unmethylated nucleotides, and also can serve to identify the number of methylated or unmethylated nucleotides in the target nucleic acid molecule. Absence of a fragment can identify the locus of a methylated or unmethylated nucleotide, or can identify the methylation state of a nucleotide locus.

A single base specific cleavage reaction can be performed to determine whether or not any nucleotide bases of the target nucleic acid molecule are methylated or unmethylated. In one example, a base specific cleavage reaction that specifically cleaves at U ribonucleotides (or at A ribonucleotides for a transcript of the reverse strand) can result in N target nucleic acid molecule fragments (where N=two or more) when a target nucleic acid molecule contains one or more unmethylated C nucleotides and is treated with bisulfite. In this example, presence of the maximum number of possible fragments (i.e., N=M+Q+1 fragments, where M is the total number of C nucleotides present in the nucleic acid molecule and Q is the total number of U nucleotides present in the nucleic acid molecule) can indicate that each C nucleotide of a target nucleic acid molecule is unmethylated. Presence of fewer than the maximum number of fragments (i.e., N<M+Q+1) can indicate that one or more C nucleotides is methylated (e.g., number of methylated C nucleotides=(Q+M+1)−N).

It also is possible to identify absent fragments, and to use the identity of the fragments to identify the loci of methylated or unmethylated nucleotides, and to thereby determine the methylation state of one or more nucleotide loci. In such a method, one or more missing fragments can be compared to reference fragment masses, to reference nucleotide sequences such as the target nucleic acid sequence, or to a database of fragment masses and/or sequences, and by such a comparison, the location of the one or more absent fragments in the target nucleic acid sequence can be identified. For example, U-specific cleavage of a bisulfite treated target nucleic acid molecule can result in a cleavage pattern where one or more fragments are absent relative to a reference. An absent reference fragment can indicate the presence of one or two methylated cytosine loci at the 5' and/or 3' ends of the sequence of the absent fragment. Identification of the location of the absent fragment in the target nucleic acid sequence and the locus/loci within the fragment of methylated nucleotides can identify methylated nucleotide loci in the target nucleic acid. In addition, some observed fragments can arise as a result of a lack of cleavage, and, thus be present instead of two or more absent fragments. Comparison of observed fragments and absent fragments to reference fragments can be used to determine the number and locations of absent fragments, and thus, the number and loci of methylated nucleotides represented by the observed fragment (e.g., when the observed fragment is present in the place of two absent fragments, one nucleotide can be methylated; when the observed fragment is present in the place of three absent fragments, two nucleotides can be methylated). Thus, identification of the location of absent fragments in the target nucleic acid sequence and the locus/loci within the fragment of methylated nucleotides can identify methylated nucleotide loci in the target nucleic acid sequence, and also can serve to determine that loci are methylated.

Absence of a first fragment can result in absence of a second fragment and presence of a third fragment (e.g., the third fragment arises when there is no cleavage between the first and second fragments). Using methods such as those described herein, one skilled in the art can use any or all of such information resulting from absence of a fragment in identifying the location of one or more missing fragments, identifying the location of a new fragment, to thereby identify: a target nucleic acid molecule as methylated or unmethylated or as containing one or more methylated or unmethylated nucleotides; the number of methylated or unmethylated nucleotides in the target nucleic acid molecule; the locus of a methylated or unmethylated nucleotide; or the methylation state of a nucleotide locus.

In another example, absence of one or more fragments can indicate the presence of one or more unmethylated nucleotides in a target nucleic acid molecule. When a target nucleic acid molecule is treated with bisulfite and then subjected to C-specific cleavage, the number of peaks will be one greater than the number of methylated cytosines present in the target nucleic acid. When fewer than the maximum number of fragments are present, the number of fragments absent can be equal to the number of unmethylated cytosines. Further, comparison of absent and present fragments of C-specific cleavage to a reference can be used to identify the loci of the unmethylated cytosines.

Absence of a fragment also can be used to identify the methylation state of a particular nucleotide locus even without identifying the portion of the nucleotide sequence of a reference nucleic acid molecule represented by the fragment. For example, when a target nucleic acid molecule having a single C nucleotide at a known nucleotide locus is treated with bisulfite, absence of a fragment (i.e., presence of only one "fragment" instead of two fragments) after C-specific cleavage can identify the nucleotide locus as unmethylated. In another example, when a target nucleic acid molecule contains no T nucleotides and only one C nucleotide, absence of a fragment (i.e., presence of only one "fragment" instead of two fragments) after U-specific cleavage can identify the nucleotide locus as methylated.

ii. Presence of a Fragment

Presence of a fragment mass can identify the target nucleic acid as methylated or unmethylated, or as containing a methylated or unmethylated nucleotides, and also can serve to identify the number of methylated or unmethylated nucleotides in the target nucleic acid molecule. Presence of a fragment mass also can identify the locus of a methylated or unmethylated nucleotide, or can identify the methylation state of a nucleotide locus.

In one example, when a bisulfite treated target nucleic acid molecule containing one or more methylated C nucleotides is base specifically cleaved in a reaction that specifically cleaves at C ribonucleotides (or at G ribonucleotides for a reverse transcript), two or more nucleic acid molecule fragments can result. In this example, the number of fragments present can indicate the number of different C nucleotides that are methylated in the target nucleic acid molecule (typically N-1 methylated C nucleotides where N is the number different nucleic acid molecule fragments). For example, when performing a C-specific cleavage reaction, a completely non-methylated target nucleic acid molecule can result in a nucleic acid molecule that does not have any cleavage sites, does not generate any cleavage products, and, therefore, results in only one "fragment" (i.e., the full-length nucleic acid molecule). When a target nucleic acid molecule containing one methylated cytosine is used, the nucleic acid molecule is cleaved once to generate two cleavage fragments. Thus, a single base specific cleavage reaction of a nucleic acid molecule, followed by detection of the cleaved fragments, can serve to identify the target nucleic acid molecule as methylated, or as containing methylated nucleotides, and also can serve to identify the number of methylated nucleotides in the target nucleic acid molecule. This methylation state identification can be made with or without comparing the fragment masses to a reference nucleic acid sequence or fragment measurements or calculations arising from a reference nucleic acid, or nucleotide sequence determination of the target nucleic acid molecule.

Presence of fragments also can be used to identify unmethylated nucleotides and the number of unmethylated nucleotides also can be identified. For example, when performing U-specific cleavage of a bisulfite treated target nucleic acid molecule, any unmethylated C nucleotides will be converted to U/T, and will be cleaved in the U-specific cleavage reaction. Presence of two or more fragments more than the number of U nucleotides present in a target nucleic acid can indicate the presence of one or more unmethylated cytosines in the target nucleic acid molecule (i.e., $M=N-(Q+1)$ fragments, where M is the number of unmethylated C nucleotides present in the nucleic acid molecule, N is the number of fragments, and Q is the total number of U nucleotides present in the nucleic acid molecule). Thus, fragments present can indicate the that a target nucleic acid molecule contains unmethylated cytosines, and also can indicate the number of unmethylated cytosines in the target nucleic acid molecule.

It also is possible to identify present fragments, and to use the identity of the fragments to identify the loci of a methylated or unmethylated nucleotides, and to thereby determine the methylation state of the nucleotide loci. In such a method, one or more present fragments can be compared to reference fragment masses, to reference nucleotide sequences such as the target nucleic acid sequence, or to a database of fragment masses and/or sequences, and by such a comparison, the location of one or more present fragments in the target nucleic acid sequence can be identified. For example, a reference fragment present among the observed sample fragments can indicate the presence of one or two methylated or unmethylated cytosine loci at the 5' and/or 3' ends of the sequence of the absent fragment. Some observed fragments can arise as a result of a lack of cleavage, and, thus be present instead of two or more absent fragments. Comparison of observed fragments and absent fragments to reference fragments can be used to determine the number of methylated or unmethylated nucleotides represented by the observed fragment. Thus, identification of the location of the observed fragment in the target nucleic acid sequence and the locus/loci within the fragment of methylated or unmethylated nucleotide can identify methylated or unmethylated nucleotide loci in the target nucleic acid sequence, can serve to determine that loci are methylated or unmethylated, and can serve to identify the methylation state of one or more nucleotide loci.

Presence of a first fragment also can result in presence of a second fragment and absence of a third fragment (e.g., the first and second fragments arise when there is cleavage of the third fragment). Using methods such as those described herein, one skilled in the art can use any or all of such information resulting from presence of a fragment in identifying the location of one or more additional fragments, identifying the location of a missing fragment, to thereby identify: a target nucleic acid molecule as methylated or unmethylated or as containing one or more methylated or unmethylated nucleotides; the number of methylated or unmethylated nucleotides in the target nucleic acid molecule; the locus of a methylated or unmethylated nucleotide; or the methylation state of a nucleotide locus.

Presence of a fragment also can be used to identify the methylation state of a particular nucleotide locus even without identifying the portion of the nucleotide sequence of a reference nucleic acid molecule represented by the fragment. For example, when a target nucleic acid molecule having a single C nucleotide at a known nucleotide locus is treated with bisulfite, presence of two or more fragments after C-specific cleavage can identify the nucleotide locus as methylated. In another example, when a target nucleic acid molecule contains no T nucleotides and only one C nucleotide, presence of two or more fragments after U-specific cleavage can identify the nucleotide locus as unmethylated.

iii. Comparison to a Reference

The mass or relative mass of a fragment can be determined by comparison with a reference mass, where the reference mass can be a molecular weight representation of a reference nucleic acid molecule or of a fragment of a reference nucleic acid molecule. A shift in fragment mass relative to the reference mass, or a fragment mass the same as a reference mass can identify the target nucleic acid as methylated or unmethylated, or as containing a methylated or unmethylated nucleotide, or can serve to identify the number of methylated or unmethylated nucleotides in the target nucleic acid molecule. In another embodiment, a shift in fragment mass relative to a reference or a fragment mass the same as a reference can identify the locus of a methylated or unmethylated nucleotide, or can identify the methylation state of a nucleotide locus.

In one example, base specific cleavage that specifically cleaves at G ribonucleotides (or at C ribonucleotides for a transcript of the reverse strand) can result in fragments containing C nucleotide loci. When one or more C nucleotide loci are unmethylated in the target nucleic acid molecule, the fragments will contain U or T nucleotides at those loci. When one or more C nucleotide loci are methylated in the target nucleic acid molecule, the fragments will contain C nucleotides at those loci. The mass difference between C and U nucleotides is 1 Da (when both are deoxyribonucleotides or both are ribonucleotides), and the mass difference between C and T nucleotides is 15 Da (when both are deoxyribonucleotides or both are ribonucleotides). Thus, presence of one U or T in the place of C will result in a mass shift for the fragment of 1 Da or 15 Da, respectively. When a fragment contains a plurality of C nucleotide loci, the mass shift resultant from the presence of one or more U or T nucleotides in the place of C nucleotides can result in a determination of the number of methylated and unmethylated C nucleotide loci in the target nucleic acid molecule. For example, for an RNA fragment containing five C nucleotide loci in the target nucleic acid molecule where three of the C nucleotide loci are unmethylated, a mass shift of 3 Da will be observed relative to a reference representing five methylated C nucleotide loci, and a mass shift of 2 Da will be observed relative to a reference representing five unmethylated C nucleotide loci.

Although the masses of C and U differ only by 1 Da, any of a variety of the methods disclosed herein or known in the art can be used to increase the difference in mass between nucleotides representing C and nucleotide representing U, such that mass shifts are more readily measured. Alternatively, T can be used in place of U to increase the mass difference relative to C.

Use of a reference sequence or fragment or a database can serve to indicate that a measured fragment has the same or different composition as the reference sequence/fragment. For example, a reference fragment with the same mass as a measured fragment can identify the measured fragment as having the same nucleotide composition as the reference fragment. In another example, a reference fragment having a mass that is different from the mass of the measured fragment can identify the measured fragment as having a different nucleotide composition relative to the reference fragment. In addition, the difference in mass between the reference and measured fragments can be used to identify the nucleotide composition of the measured fragment. For example, an increase in mass of 2 Da for a reference fragment relative to a measured fragment can indicate that the reference fragment contains two additional U nucleotides relative to the measured fragment and the measured fragment contains two additional cytosines relative to the reference fragment. Thus, a measured fragment having the same mass as a reference fragment can serve to identify a target nucleic acid as methylated or unmethylated, or as containing a methylated or unmethylated nucleotide, to identify the number of methylated or unmethylated nucleotides in the target nucleic acid molecule, to identify the locus of a methylated or unmethylated nucleotide, or to identify the methylation state of a nucleotide locus. In addition, a measured fragment having a mass shift relative to a reference fragment can serve to identify a target nucleic acid as methylated or unmethylated, or as containing a methylated or unmethylated nucleotide, to identify the number of methylated or unmethylated nucleotides in the target nucleic acid molecule, to identify the locus of a methylated or unmethylated nucleotide, or to identify the methylation state of a nucleotide locus.

A base specific cleavage reaction can be performed to identify the loci of one or more methylated or unmethylated nucleotides in a target nucleic acid molecule. Base specific cleavage and comparison of the fragments with a reference can be used to identify all methylated or unmethylated loci, or to identify the methylation state for all loci in a target nucleic acid molecule. For example, a single base specific cleavage reaction can be performed and the resultant fragments can be compared to the fragments arising from a reference nucleic acid. Comparison of the measured nucleic acid molecule fragments to the reference nucleic acid fragments can be used to identify the loci of the methylated or unmethylated nucleotides in the target nucleic acid molecule. In another example, when a target nucleic acid molecule fragmentation pattern matches with a reference nucleic acid with known methylation state of cytosine nucleotide loci, the reference nucleic acid loci can be used to identify the methylation state of the cytosine loci in the target nucleic acid molecule. In another example, a single base specific cleavage reaction can be performed and the resultant fragments can be compared to the sequences or cleavage patterns of two or more reference nucleic acids. In this example, a sequence of a reference nucleic acid molecule whose cleavage pattern matches the measured fragment masses can be identified as the same sequence as the target nucleic acid molecule sequence. Reference nucleic acid fragments and fragmentation patterns can be determined experimentally or can be calculated by methods known in the art and described herein.

In one embodiment, two measured fragments from the same measurement (e.g., two mass peaks from the same mass spectrum) can serve as reference fragments for each other. This method can be used, for example, when the nucleic acid sample contains heterogenous nucleic acids (e.g., when the sample contains genomic DNA from multiple organisms). In this embodiment, one or more base specific cleavage reactions can be performed to form nucleic acid molecule fragments, where a mass shift in one or more fragments can indicate the presence or absence of one or more methylated nucleotides, such as a methylated cytosine. For example, amplified products can be subjected to G-specific cleavage using RNase T1. When the target nucleic acid molecules all are methylated at a particular C nucleotide, the fragments containing that particular nucleotide locus can have the same first mass. When all the target nucleic acid molecules all are unmethylated at that particular C nucleotide, the fragments containing that nucleotide locus can have the same second mass. When a sample contains a mixture of nucleic acid molecules that are methylated at the particular C nucleotide locus and at that are unmethylated at that C nucleotide locus, fragmentation can result in fragments of a first mass and a second mass. These fragments can be compared to each other as reference fragments to determine the amount of methylated nucleotide relative to unmethylated nucleotide at a particular nucleotide locus. For example, determination of the ratio of the sizes of the peaks for the first mass and second mass can result in a determination of the number of nucleic acid molecules methylated at that C nucleotide relative to the number of nucleic acid molecules unmethylated at that C nucleotide. A hemi-methylated DNA sample (e.g., DNA from a diploid cell where one of the two related nucleic acid regions contains a methylated nucleotide and the other contains an unmethylated nucleotide) can result in comparable amounts of both methylated and unmethylated nucleic acid molecule fragments (i.e., the ratio will be approximately 50/50).

In another embodiment, fragments from different mass measurements measurement (e.g., two mass peaks each from a different mass spectrum) can serve as reference fragments for each other. This method can be used, for example, to compare the relative amounts of methylated target nucleic acid molecules in two or more samples, such as two or more heterogenous samples. Alternatively, fragments from different mass measurements can be compared where one fragment corresponds to a unknown or test sample and the other fragment corresponds to a known reference. In these embodiments, one or more base specific cleavage reactions can be performed to form nucleic acid molecule fragments, where a mass shift in one or more fragments can indicate the presence or absence of one or more methylated nucleotides, such as a methylated cytosine. For example, amplified products can be subjected to G-specific cleavage using RNase T1. When the target nucleic acid molecules all are methylated at a particular C nucleotide, the fragments containing that particular nucleotide locus can have the same first mass. When all the target nucleic acid molecules all are unmethylated at that particular C nucleotide, the fragments containing that nucleotide locus can have the same second mass. When a sample contains a mixture of nucleic acid molecules that are methylated at the particular C nucleotide locus and at that are unmethylated at that C nucleotide locus, fragmentation can result in fragments of a first mass and a second mass. In such an example, one or both fragments can be compared to fragments of another sample or of a reference to determine the amount of methylated nucleotide relative to unmethylated nucleotide at a particular nucleotide locus. For example, determination of the ratio of the sizes of the peaks for the fragment of a first sample, and second fragment of a second sample or of a reference can result in a determination of an increased or decreased degree of methylation relative to a second sample or a reference, or a determination of the number of nucleic acid molecules methylated at that C nucleotide relative to the number of nucleic acid molecules unmethylated at that C nucleotide. In one example, the intensities of the fragments that are compared are normalized. For example, two samples or a sample and a reference, can have added thereto a known amount of a marker nucleic acid or can be normalized to a marker nucleic acid molecule that is relatively constant in the particular sample, such as a constitutively expressed housekeeping gene. In this example, the intensities of fragments to be compared are first normalized to the marker nucleic acid molecule, and the amounts of fragments relative to the marker then can be compared to each other in determining the relative amounts of methylation in two samples or in a sample relative to a reference, or in determining the number of nucleic acid molecules methylated at that C nucleotide relative to the number of nucleic acid molecules unmethylated at that C nucleotide.

In another embodiment, relative amounts can be measured by comparing three fragments. When presence of a methylated nucleotide results in cleavage where absence of methylation does not result in cleavage, there will be two smaller methylated nucleic acid molecule fragments and one larger unmethylated nucleic acid molecule fragment. In such a case, the measured amounts of the two fragments can be compared to the measured amount of the one fragment to calculate the ratio of methylated nucleotide to unmethylated nucleotide. In another embodiment, one larger fragment arises when a nucleotide is methylated and two smaller fragments are formed when a nucleotide is unmethylated; in such a case, the measurement of the one fragment is compared to the measurement of the two fragments to calculate the ratio of methylated nucleotide to unmethylated nucleotide.

b. Multiple Base Specific Cleavage Reactions

In other embodiments, two or more base specific cleavage reactions can be used to provide information on the methylation status of a particular nucleotide locus in a target nucleic acid molecule. For example, a first base specific cleavage reaction can be used to identify the methylation status of a particular nucleotide locus (i.e., whether or not any target nucleic acid molecule is methylated at that nucleotide locus), and a second base specific cleavage reaction can be used to determine the amount of methylated nucleotides relative to unmethylated nucleotides at that nucleotide locus.

Two or more base specific cleavage reactions also can be used to provide redundant information that can be used to confirm the identification of a nucleotide locus as methylated or unmethylated, and also can be used to provide additional information for quantitative measurements, such as determining the ratio of methylated to unmethylated nucleotides present at a particular nucleotide locus of a target nucleic acid molecule. Two or more base specific cleavage reactions also can be used to determine the methylation state of a large target nucleic acid molecule. For example, a target nucleic acid molecule can be so large that accurate mass measurement cannot be made of all nucleic acid molecule fragments from a single base specific cleavage reaction, and, thus, the methylation state of some nucleotides of the target nucleic acid molecule may not be determinable. When one or more additional base specific cleavage reactions are used to create one or more additional sets of nucleic acid molecule fragments, nucleic acid molecule fragments of each base specific cleavage reaction covering different regions of the target nucleic acid molecule can be measured, and can provide information regarding the methylation state of a larger number of target nucleic acid molecule nucleotide loci than can be provided from a single base specific cleavage reaction. In one embodiment, when two or more base specific cleavage reactions are performed, the methylation state of all nucleotide loci in question can be determined.

One skilled in the art can determine the number of cleavages necessary to achieved the desired level of completeness and redundancy of methylation state identification using, for example, methods that entail nucleotide sequence determination based on fragmentation and mass measurement of nucleic acid molecules. Exemplary methods for nucleotide sequence determination using cleavage and mass measurement are described herein, and can be found in copending U.S. provisional Ser. Nos. 60/466,006, filed Apr. 25, 2003 and 60/429,895, filed Nov. 27, 2002, and are known in the art, as exemplified in Stanssens et al., Genome Res. 14:126-133 (2004).

c. Sequence Information and Methylation State Identification

One or more methylated or unmethylated nucleotide loci of a target nucleic acid molecule can be identified subsequent to, or simultaneous with, identification of the target nucleic acid molecule nucleotide sequence. When the methylated or unmethylated nucleotide loci are identified subsequent to nucleotide sequence determination, the nucleotide sequence can be obtained by known sequencing methods or by referring to a database, such as a public database, that contains the target nucleic acid nucleotide sequence.

Nucleotide sequence determination methods also can be based on the fragmentation and mass measurement methods provided herein, and, hence, methylation state identification and nucleotide sequence determination can be performed simultaneously. When using methylation-specific reagents that modify the sequence as a function of the methylation state of the target nucleic acid molecules, such as bisulfite, sequence determination of the treated target nucleic acid molecule is performed in conjunction with sequence determination of a second target nucleic acid molecule. Such second nucleic acid molecules can include the reverse strand of the treated target nucleic acid molecule or an untreated target nucleic acid molecule. In this way, the pre-treatment nucleotide sequence (which can be determined subsequent to determining the sequence of the treated nucleotide sequence) can be used to distinguish unmodified nucleotides from modified nucleotides arising from methylated nucleotides (e.g., T nucleotides arising in wild type target nucleic acid molecule nucleotide sequence can be distinguished from T nucleotides arising from bisulfite treatment of unmethylated C nucleotides).

Exemplary nucleotide sequence determination methods include constructing and traversing sequencing graphs; scoring candidate sequences and determining sequence variations; and other methods known in the art. For example, when partial or random fragmentation is performed, methods for target nucleic acid molecule sequence determination can include steps such as fragmenting the target nucleic acid molecule, determining the molecular weights of the at least two fragments, determining the possible compositions of the at least two fragments, ordering the possible compositions of the at least two fragments according to the number of cleavage sites that are not cleaved in each fragment, constructing at least one sequencing graph that is a theoretical representation of the ordered compositions for the at least two fragments, scoring the one or more underlying sequence candidates and determining the rank order of fitness, and traversing the at least one sequencing graph to reconstruct one or more underlying sequence candidates of the target biomolecule. Exemplary methods for nucleotide sequence determination using partial or random cleavage can be found in copending U.S. provisional Ser. No. 60/466,006, filed Apr. 25, 2003.

In another example, when total fragmentation is performed, methods for target nucleic acid molecule sequence determination can include steps such as cleaving the target nucleic acid molecules into fragments by contacting the molecules with one or more specific cleavage reagents, cleaving or simulating cleavage of one or more reference nucleic acid molecules into fragments using the same cleavage reagents, determining the mass signals of target nucleic acid molecule and reference nucleic acid fragments, identifying fragments that are different between the target nucleic acid molecules and the one or more reference nucleic acid molecules, determining compomers, which are nucleotide base compositions of fragments, corresponding to the different fragments that are compomer witnesses, determining the sequence variations that are candidate sequences corresponding to each compomer witness, scoring the candidate sequences, and determining the sequence variations in the plurality of target nucleic acid molecules. Exemplary methods for nucleotide sequence determination using total cleavage can be found in copending U.S. provisional Ser. No. 60/429,895, filed Nov. 27, 2002.

F. Detection of Target Nucleic Acid Molecule Fragments

As set forth herein, the methods for methylation state identification can include of nucleic acid molecule detection methods. Such detection methods include those known in the art. Nucleic acid molecule detection methods include gel electrophoresis, capillary electrophoresis, hybridization methods such as Southern or Northern blot analysis, nucleic acid array hybridization, mass spectrometry and other such methods. In one embodiment, the nucleic acid molecules are detected by determining the molecular mass of one or more target nucleic acid molecule fragments formed using the methods disclosed herein or known in the art. For example, the mass of one or more target nucleic acid molecules can be determined using mass spectrometry, including MALDI-TOF mass spectrometry.

1. Mass Spectrometric Analysis

In the methods provided herein, mass spectrometric analysis can be performed to determine the charge to mass ratio of atoms, molecules or molecule fragments. Typically, a mass spectrometer can be used to detect the mass of an atom, molecule or molecule fragment. Any of a variety of mass spectrometric formats can be used, including any ion source, configuration and detector. Such formats include, but are not limited to, Matrix-Assisted Laser Desorption/Ionization, Time-of-Flight (MALDI-TOF), Electrospray ionization (ESi), IR-MALDI (see, e.g., published International PCT application No. 99/57318 and U.S. Pat. No. 5,118,937), Ion Cyclotron Resonance (ICR), Fourier Transform, Linear/Reflectron (RETOF), and combinations thereof (see, for example, Aebersold and Mann, Mar. 13, 2003, Nature, 422: 198-207 (e.g., at FIG. 2) for a review of exemplary methods for mass spectrometry suitable for use in the methods provided herein). MALDI methods typically include UV-MALDI or IR-MALDI. Nucleic acids can be analyzed by detection methods and protocols known in the art that rely on mass spectrometry (see, e.g., U.S. Pat. Nos. 5,605,798, 6,043, 031, 6,197,498, 6,428,955, 6,268,131, and International Patent Application No. WO 96/29431, International PCT Application No. WO 98/20019, and U.S. Patent Publication 20030129589). These methods can be automated by methods and devices known in the art (see, e.g., U.S. Publication 2002 0009394, which describes an automated process line).

Medium resolution instrumentation, including but not exclusively curved field reflectron or delayed extraction time-of-flight MS instruments, also can result in improved DNA detection for sequencing or diagnostics. Either of these are capable of detecting a 9 Da ($\Delta$m(A–T)) shift in ≥30-mer strands.

a. Mass Spectrometry Sample

When analyses are performed using mass spectrometry, such as MALDI, nanoliter volumes of sample can be loaded on chips. Use of such volumes can permit quantitative or semi-quantitative mass spectrometric results. For example, the area under the peaks in the resulting mass spectra are proportional to the relative concentrations of the components of the sample. Methods for preparing and using such chips are known in the art, as exemplified in U.S. Pat. No. 6,024,925, U.S. Publication 2001 0008615, and PCT Application No. PCT/US97/20195 (WO 98/20020); methods for preparing and using such chips also are provided in co-pending U.S. application Ser. Nos. 08/786,988, 09/364,774, and 09/297, 575. Chips and kits for performing these analyses are commercially available from SEQUENOM under the trademark MassARRAY™. MassARRAY™ systems contain a miniaturized array such as a SpectroCHIP® useful for MALDI-TOF (Matrix-Assisted Laser Desorption Ionization-Time of Flight) mass spectrometry to deliver results rapidly. It accurately distinguishes single base changes in the size of DNA fragments relating to genetic variants without tags.

i. Characteristics of Nucleic Acid Molecules Measured

In one embodiment, the mass of all nucleic acid molecule fragments formed in the step of fragmentation is measured. The measured mass of a target nucleic acid molecule fragment or fragment of an amplification product also can be referred to as a "sample" measured mass, in contrast to a "reference" mass which arises from a reference nucleic acid fragment.

In another embodiment, the length of nucleic acid molecule fragments whose mass is measured using mass spectroscopy is no more than 75 nucleotides in length, no more than 60 nucleotides in length, no more than 50 nucleotides in length, no more than 40 nucleotides in length, no more than 35 nucleotides in length, no more than 30 nucleotides in length, no more than 27 nucleotides in length, no more than 25 nucleotides in length, no more than 23 nucleotides in length, no more than 22 nucleotides in length, no more than 21 nucleotides in length, no more than 20 nucleotides in length, no more than 19 nucleotides in length, or no more than 18 nucleotides in length.

In another embodiment, the length of the nucleic acid molecule fragments whose mass is measured using mass spectroscopy is no less than 3 nucleotides in length, no less than 4 nucleotides in length, no less than 5 nucleotides in length, no less than 6 nucleotides in length, no less than 7 nucleotides in length, no less than 8 nucleotides in length, no less than 9 nucleotides in length, no less than 10 nucleotides in length, no less than 12 nucleotides in length, no less than 15 nucleotides in length, no less than 18 nucleotides in length, no less than 20 nucleotides in length, no less than 25 nucleotides in length, no less than 30 nucleotides in length, or no less than 35 nucleotides in length.

In one embodiment, the nucleic acid molecule fragment whose mass is measured is RNA. In another embodiment the target nucleic acid molecule fragment whose mass is measured is DNA. In yet another embodiment, the target nucleic acid molecule fragment whose mass is measured contains one modified or atypical nucleotide (i.e., a nucleotide other than deoxy-C, T, G or A in DNA, or other than C, U, G or A in RNA). For example, a nucleic acid molecule product of a transcription reaction can contain a combination of ribonucleotides and deoxyribonucleotides. In another example, a nucleic acid molecule can contain typically occurring nucleotides and mass modified nucleotides, or can contain typically occurring nucleotides and non-naturally occurring nucleotides.

ii. Conditioning

Prior to mass spectrometric analysis, nucleic acid molecules can be treated to improve resolution. Such processes are referred to as conditioning of the molecules. Molecules can be "conditioned," for example to decrease the laser energy required for volatilization and/or to minimize fragmentation. A variety of methods for nucleic acid molecule conditioning are known in the art. An example of conditioning is modification of the phosphodiester backbone of the nucleic acid molecule (e.g., by cation exchange), which can be useful for eliminating peak broadening due to a heterogeneity in the cations bound per nucleotide unit. In another example, contacting a nucleic acid molecule with an alkylating agent such as alkyloidide, iodoacetamide, $\beta$-iodoethanol, or 2,3-epoxy-1-propanol, can transform a monothio phosphodiester bonds of a nucleic acid molecule into a phosphotriester bond. Likewise, phosphodiester bonds can be transformed to uncharged derivatives employing, for example, trialkylsilyl chlorides. Further conditioning can include incorporating nucleotides that reduce sensitivity for depurination (fragmentation during MS) e.g., a purine analog such as N7- or N9-deazapurine nucleotides, or RNA building blocks or using oligonucleotide triesters or incorporating phosphorothioate functions which are alkylated, or employing oligonucleotide mimetics such as PNA.

iii. Multiplexing and Mass Modification

For some applications, simultaneous detection of more than one nucleic acid molecule fragment can be performed. In other applications, parallel processing can be performed using, for example, oligonucleotide or oligonucleotide mimetic arrays on various solid supports. "Multiplexing" can be achieved by several different methodologies. For example, fragments from several different nucleic acid molecules can be simultaneously subjected to mass measurement methods. Typically, in multiplexing mass measurements, the nucleic acid molecule fragments should be distinguishable enough so that simultaneous detection of the multiplexed nucleic acid molecule fragments is possible. Nucleic acid molecule fragments can be made distinguishable by ensuring that the masses of the fragments are distinguishable by the mass measurement method to be used. This can be achieved either by the sequence itself (composition or length) or by the introduction of mass-modifying functionalities into one or more nucleic acid molecules.

In one embodiment, the nucleic acid molecule to be mass-measured contains attached thereto one or more mass-modifying moieties. Mass-modifying moieties are known in the art and can be attached to the 3' end or 5' end of a nucleic acid molecule fragment, can be attached to a nucleobase or to a sugar moiety of a nucleotide, or can be attached to or substitute for the phospho diester linkage between nucleotides. A simple mass-modification can be achieved by substituting H for halogens like F, Cl, Br and/or I, or pseudohalogens such as SCN, NCS, or by using different alkyl, aryl or aralkyl moieties such as methyl, ethyl, propyl, isopropyl, t-butyl, hexyl, phenyl, substituted phenyl, benzyl, or functional groups such as $N_3$, $CH_2F$, $CHF_2$, $CF_3$, $Si(CH_3)_3$, $Si(CH_3)_2$ $(C_2H_5)$, Si(CH$_3$)(C$_2$H$_5$)$_2$, Si(C$_2$H$_5$)$_3$. Yet another mass- modification can be obtained by attaching homo- or heteropeptides through the nucleic acid molecule (e.g., detector (D)) or nucleoside triphosphates. One example useful in generating mass-modified species with a mass increment of 57 is the attachment of oligoglycines, e.g., mass-modifications of 74, 131, 188, 245 are achieved. Simple oligoamides also can be used, e.g., mass-modifications of 74, 88, 102, 116 . . . , are obtainable.

Mass-modifications also can include oligo-/polyethylene glycol derivatives. The oligo/polyethylene glycols also can be monoalkylated by a lower alkyl such as methyl, ethyl, propyl, isopropyl, t-butyl and other suitable substituents. Other chemistries also can be used in the mass-modified compounds (see, e.g., those described in Oligonucleotides and Analogues, A Practical Approach, F. Eckstein, editor, IRL Press, Oxford, 1991).

Mass modifying moieties can be attached, for instance, to either the 5'-end of the oligonucleotide, to the nucleobase (or bases), to the phosphate backbone, to the 2'-position of the nucleoside (nucleosides), and/or to the terminal 3'-position. Examples of mass modifying moieties include, for example, a halogen, an azido, or of the type, XR, wherein X is a linking group and R is a mass-modifying functionality. A mass-modifying functionality can, for example, be used to introduce defined mass increments into the oligonucleotide molecule, as described herein. Modifications introduced at the phosphodiester bond such as with alpha-thio nucleoside triphosphates, have the advantage that these modifications do not interfere with accurate Watson-Crick base-pairing and additionally allow for the one-step post-synthetic site-specific modification of the complete nucleic acid molecule e.g., via alkylation reactions (see, e.g., Nakamaye et al., *Nucl. Acids Res.* 16:9947-9959 (1988)). Exemplary mass-modifying functionalities are boron-modified nucleic acids, which can be efficiently incorporated into nucleic acids by polymerases (see, e.g., Porter et al. *Biochemistry* 34:11963-11969 (1995); Hasan et al., *Nucl. Acids Res.* 24:2150-2157 (1996); Li et al. *Nucl. Acids Res.* 23:4495-4501 (1995)).

Furthermore, the mass-modifying functionality can be added so as to affect chain termination, such as by attaching it to the 3'-position of the sugar ring in the nucleoside triphosphate. For those skilled in the art, it is clear that many combinations can be used in the methods provided herein. In the same way, those skilled in the art will recognize that chain-elongating nucleoside triphosphates also can be mass-modified in a similar fashion with numerous variations and combinations in functionality and attachment positions.

Different mass-modified nucleotides can be used to simultaneously detect a variety of different nucleic acid fragments simultaneously. In one embodiment, mass modifications can be incorporated during the amplification process. In another embodiment, multiplexing of different target nucleic acid molecules can be performed by mass modifying one or more target nucleic acid molecules, where each different target nucleic acid molecule can be differently mass modified, if desired.

2. Other Mass Measurement Methods

Additional mass measurement methods known in the art can be used in the methods of mass measurement, including electrophoretic methods such as gel electrophoresis and capillary electrophoresis, and chromatographic methods including size exclusion chromatography and reverse phase chromatography.

3. Determining Mass Peak Characteristics

Using methods of mass analysis such as those described herein, information relating to mass of the target nucleic acid molecule fragments can be obtained. Additional information of a mass peak that can be obtained from mass measurements include signal to noise ratio of a peak, the peak area (represented, for example, by area under the peak or by peak width at half-height), peak height, peak width, peak area relative to one or more additional mass peaks, peak height relative to one or more additional mass peaks, and peak width relative to one or more additional mass peaks. Such mass peak characteristics can be used in the present methylation identification methods, for example, in a method of identifying the methylation state of a nucleotide locus of a target nucleic acid molecule by comparing at least one mass peak characteristic of an amplification fragment with one or more mass peak characteristics of one or more reference nucleic acids.

4. Hybridization-Based Detection Methods

Hybridization-based detection methods can be employed in the methods herein. Generally, such methods detect the presence of a nucleic acid having a particular nucleotide sequence by detecting hybridization between a probe oligonucleotide and a sample nucleic acid, such as a target nucleic acid molecule, a target nucleic acid molecule fragment, where the probe oligonucleotide can be labelled with a detectable or bindable moiety or can be attached to a substrate or solid support. A large variety of hybridization-based nucleic acid detection methods are known in the art and include, but are not limited to, Southern blot analysis, Northern blot analysis, chip-based hybridization methods and in situ hybridization. Probe oligonucleotides can be attached to a substrate or a solid support such as a bead, a membrane or a plate; can contain a detectable moiety such as a fluorescent compound, chemiluminescent compound, radionuclide, cleavable mass marker; or can contain a bindable moiety such as biotin, magnetic bead or polyhistidine.

In one embodiment, the sequence of the nucleic acid molecule or nucleic acid molecule fragment to be detected by hybridization is a known sequence. Thus, probe oligonucleotides can be designed to hybridize to particular sequences of a nucleic acid molecule or nucleic acid molecule fragment. Hybridization of a probe oligonucleotide to a nucleic acid molecule or nucleic acid molecule fragment can be used to identify the target nucleic acid molecule as containing one or more methylated nucleotides, to identify one or more methylated nucleotide loci on the target nucleic acid molecule, or to identify the methylation state of one or more nucleotide loci of a target nucleic acid molecule. Hybridization of a probe oligonucleotide to a nucleic acid molecule or nucleic acid molecule fragment can be also used to identify a target nucleic acid molecule as not containing any methylated nucleotides or to identify one or more unmethylated nucleotide loci on the target nucleic acid molecule.

G. Fragment Measurement Analysis

Target nucleic acid molecules can be amplified according to the methylation state of the target nucleic acid molecule, and then fragmented according to the methods provided herein, and the presence of the fragments can be measured according to the methods provided herein, such as by mass spectrometry. Measurements of the fragments, such as measurement of fragment masses can provide a variety of information regarding methylation in the target nucleic acid molecule. For example, the fragment masses can inform whether or not a target nucleic acid molecule contains methylated nucleotides, whether or not a nucleotide locus is methylated, and the location of a methylated or unmethylated nucleotide locus. Fragment measurements can be compared to a reference, which can include reference masses, or the simply number of fragments can provide information regarding methylation in the target nucleic acid molecule. Different fragmentation patterns of the same target nucleic acid molecule can provide additional and/or overlapping information about methylation in the target nucleic acid molecule.

1. Methylation State Identification

Fragment measurements can be used to identify the methylation state of a target nucleic acid molecule or to identify the methylation state of a particular nucleotide locus of a target nucleic acid molecule. Fragment measurements can be used to identify whether or not a target nucleic acid molecule contains one or more methylated or unmethylated nucleotides, such as methylcytosine or cytosine, respectively; to determine the number of methylated or unmethylated nucleotides such as methylcytosine or cytosine, respectively, present in a target nucleic acid molecule; to identify whether or not a nucleotide locus, such as a cytosine locus, is methylated or unmethylated in a target nucleic acid molecule; to identify the nucleotide locus of a methylated or unmethylated nucleotide, such as methylcytosine or cytosine, respectively, in a target nucleic acid molecule; to determine the ratio of methylated target nucleic acid molecule relative to unmethylated target nucleic acid molecule in a sample; to determine the ratio of methylated nucleotide at a particular nucleotide locus on a target nucleic acid molecule relative to unmethylated nucleotide at that locus; and to provide redundant information to further confirm any of the determinations provided herein.

Fragment measurements can be used to identify whether or not a target nucleic acid molecule contains methylated or unmethylated nucleotides, or to identify the number of methylated or unmethylated nucleotides present in a target nucleic acid molecule, where the target nucleic acid molecule or amplified product is fragmented in a single base specific cleavage reaction. Fragment measurements can be used to identify whether or not two or more target nucleic acid molecules contain methylated or unmethylated nucleotides, or to identify the number of methylated or unmethylated nucleotides present in two or more target nucleic acid molecules, where the target nucleic acid molecules or amplified products are fragmented in a single base specific cleavage reaction. Fragment measurements can be used to identify whether or not a target nucleic acid molecule contains methylated or unmethylated nucleotides, or to identify the number of methylated or unmethylated nucleotides present in a target nucleic acid molecule, where the target nucleic acid molecule or amplified product is fragmented in two or more base specific cleavage reactions. Fragment measurements can be used to identify whether or not two or more target nucleic acid molecules contain methylated or unmethylated nucleotides, or to identify the number of methylated or unmethylated nucleotides present in two or more target nucleic acid molecules, where the target nucleic acid molecules or amplified products are fragmented in two or more base specific cleavage reactions.

a. Identification Methods without a Reference

Fragment measurements can be used to identify whether or not a target nucleic acid molecule contains methylated or unmethylated nucleotides, or to identify the number of methylated or unmethylated nucleotides present in a target nucleic acid molecule, with or without comparison of the fragment measurements to one or more reference molecules, sequences, fragments or masses. For example, when a target nucleic acid molecule is treated with bisulfite, and then subjected to a C-specific cleavage reaction, presence of two or more different fragment masses can, without reference to any other nucleotide molecule or sequence or fragment or mass (e.g., without comparing to a reference nucleotide mass or reference nucleotide sequence), indicate that one or more C nucleotides of the target nucleic acid molecules are methylated. In another example, when a target nucleic acid molecule is treated with bisulfite, and then subjected to a C-specific cleavage reaction, presence of two or more different fragment masses can, without reference to any other nucleotide molecule or sequence or fragment or mass, indicate the number of C nucleotides that are methylated in the target nucleic acid molecule.

b. Identification Methods Using a Reference

In other embodiments, one or more references can be used for methylation identification methods. In some cases, a previously known sequence (e.g., public database sequence) can exist for the region in which the target nucleic acid molecule is located. In these cases, reference nucleic acids can be experimentally obtained and fragment masses can be experimentally measured using methods known in the art or disclosed herein. In such cases, reference nucleic acid fragment sequences and masses also can be calculated for a particular reference nucleic acid composition, methylation-specific reagent, and fragmentation method.

In other cases, nucleic acid fragment mass patterns of the region encompassed by the target nucleic acid molecule can be known, even if the sequence of the target nucleic acid molecule is not known. For example, known nucleic acid fragment mass patterns can be mass patterns arising from base specific cleavage of a particular nucleic acid molecule with known methylation state and/or with a known number of methylated or unmethylated nucleotides. In one example, a portion of a chromosome of one individual can have a known methylation state or known number of methylated or unmethylated nucleotides, and a known set of fragment masses, but the nucleotide sequence of this portion is partially or fully unknown. In such a case, methylation identification methods can compare measured masses of the target nucleic acid molecule or amplified product fragments to one or more experimentally determined reference mass patterns to determine the methylation state of the target nucleic acid or the number of methylated or unmethylated nucleotides in the target nucleic acid.

i. Nucleic Acid Molecule Sequence Known

When the sequence of the target nucleic acid molecule is known, calculations or experimental methods can identify one or more fragment measurements that can be used in methylation identification methods. Experimental methods can be performed on a reference nucleic acid molecule known to contain methylated nucleotides, a reference nucleic acid known to not contain methylated nucleotides, or known to contain methylated or unmethylated nucleotides at particular loci. Such a reference nucleic acid molecule can be treated with a methylation-specific reagent, cleaved, and mass fragments can be measured. Calculations can be generated using a reference nucleic acid molecule sequence with defined methylated or unmethylated nucleotide loci, and predicting the mass fragments that arise as a result of treatment with a methylation-specific reagent and cleavage. For example, a reference nucleic acid molecule having a methylated cytosine at a known nucleotide locus can be treated with bisulfite, transcribed, the transcript base specifically cleaved with RNase T1, and the masses of the cleaved fragments can be measured. Using either the known nucleotide sequence information or comparison to cleavage of an unmethylated reference nucleic acid molecule, the masses of fragments indicative of the methylated cytosine can be identified. Fragment masses arising from a target nucleic acid molecule treated with bisulfite and RNase T1 can be compared to the reference fragment masses to indicate the presence or absence of the methylated cytosine.

In the case of either experimental determination or calculation, the reagent, nucleotide composition (e.g., RNA, DNA, mass-modified nucleotides), and base-specific cleavage used will be the same as those used for the target nucleic acid molecule. For example, both reference and target nucleic acid molecules are treated with bisulfite, transcribed, and base specifically cleaved with RNase T1.

The methods provided herein also include the use of one or more, but fewer than all fragment masses in methylation identification methods. For example, one reference nucleic acid fragment mass can be used to identify a target nucleic acid molecule as containing at least one methylated or unmethylated nucleotide, one reference nucleic acid fragment can be used to identify the methylation state of a target nucleic acid molecule nucleotide locus, one reference nucleic acid fragment can be used to identify a nucleotide locus as methylated or unmethylated.

Calculations can be made to predict fragmentation patterns to identify masses that are the same as or different from one or more of measured mass peak characteristics of target nucleic acid molecule or amplified product fragments. Such calculation methods can generate any or all of the characteristics of mass peaks, including mass, peak area, and signal to noise ratio of the mass peak. One or more measured mass peak characteristics of target nucleic acid molecule or amplified product fragments that differ from the calculated mass peak characteristics of fragments from an unmethylated reference nucleotide sequence can identify the target nucleic acid molecule as methylated and can provide the loci of one or more methylated nucleotides. One or more measured mass peak characteristics of target nucleic acid molecule or amplified product fragments that differ from the calculated mass peak characteristics of fragments from a methylated reference nucleotide sequence can identify the target nucleic acid molecule as unmethylated and can provide the loci of one or more unmethylated nucleotides. One or more measured mass peak characteristics of target nucleic acid molecule or amplified product fragments that are the same as the calculated mass peak characteristics of fragments from an unmethylated reference nucleotide sequence can identify the target nucleic acid molecule as unmethylated and can provide the loci of one or more unmethylated nucleotides. One or more measured mass peak characteristics of target nucleic acid molecule or amplified product fragments are the same as the calculated mass peak characteristics of fragments from a methylated reference nucleotide sequence can identify the target nucleic acid molecule as methylated and can provide the loci of one or more methylated nucleotides.

By repeating these calculations for differently methylated reference nucleic acid molecules, it is possible to generate several differing (and mutually exclusive) fragment mass patterns and several different collections of one or more mass peak characteristics that can be used to identify a target nucleic acid molecule as methylated or unmethylated and can provide the loci of one or more methylated or unmethylated nucleotides. Measurement of sample nucleic acid molecule fragments can generate sample fragment masses, of which all fragment masses or a subset containing one or more sample fragment masses can be compared to one or more collections of the calculated methylation state-indicative fragment masses, and the one or more collections of the calculated methylation state-indicative fragment masses can be correlated to the experimental fragment mass peaks. The methylation state of the sample target nucleic acid molecule then can be identified as the methylation state of the reference nucleic acid whose collection of calculated fragment masses most closely correlate to the experimental mass peaks, provided, optionally, that the correlation is above a user-defined threshold amount.

Correlation of sample masses (or peak characteristic)s and reference masses (or peak characteristics) can be performed in any of a variety of ways known to those of skill in the art. For example, one reference mass having a particular observed or calculated mass and intensity (e.g., peak area or signal to noise ratio) may be present in only one of a variety of reference mass patterns. Detection of a sample mass having essentially the same mass and intensity (e.g., the same mass and intensity, within experimental error) can serve to identify a nucleotide locus in the sample target nucleic acid molecule as having the same methylation state as that of the nucleotide locus of the reference nucleic acid. Correlations between sample masses and reference masses can be performed using statistical methods including regression methods such as linear or non-linear regression, and other methods known for data correlation.

In one embodiment, a user can define a threshold which sets a minimum correlation required for the reference nucleic acid to, with sufficient likelihood, identify methylation or lack of methylation in a target nucleic acid molecule. When no correlation occurs that is above the threshold value, none of the reference nucleic acids can, with sufficient likelihood, identify methylation or lack of methylation in a target nucleic acid molecule. When correlation between one or more reference masses and sample target nucleic acid molecule masses occurs that is above the threshold value, the reference nucleic acid with the highest correlation can identify methylation or lack of methylation in a target nucleic acid molecule.

Experimentally determined masses and mass peak characteristics can be used in the same manner as the herein-described use of calculated masses and mass peak characteristics in target nucleic acid methylation identification methods. In addition, a database of reference masses and/or mass peak characteristics can be derived from experimental determinations, calculations, or both experimental determinations and calculations of reference nucleic acid molecules, and can be used in the same manner as the herein-described use of calculated masses and mass peak characteristics in target nucleic acid methylation identification methods.

ii. Nucleic Acid Molecule Sequence Unknown

In one embodiment, the presence of methylated or unmethylated nucleotides in a target nucleic acid molecule can be identified using a pattern of the masses of nucleic acid molecule fragments without knowledge of the sequence of the target nucleic acid molecule. For example, the measured masses of nucleic acid molecule fragments can be compared to one or more reference nucleic acid molecule fragments, including reference mass patterns such as a mass spectrum containing a plurality of mass peaks, where the presence or absence of methylated or unmethylated nucleotides in the reference nucleic acid molecule is known, where a reference mass or reference mass pattern that is the same as a measured mass or measured mass pattern identifies the target nucleic acid molecule as having the same methylated or unmethylated nucleotides as the reference nucleic acid molecule, and a reference mass or reference mass pattern that is different from the measured mass or measured mass pattern identifies the target nucleic acid molecule as having nucleotides whose methylation state is different from the reference nucleic acid molecule. In such methods, the nucleotide sequence of neither the target nucleic acid nor the reference nucleic acid is necessary to identify the presence of methylated or unmethylated nucleotides in the target nucleic acid molecule.

Experimental methods can be performed on a reference nucleic acid molecule having unknown nucleotide sequence, but known to contain methylated nucleotides or known to contain unmethylated nucleotides. Such a reference nucleic acid molecule can be treated with a methylation-specific reagent, cleaved, and mass fragments can be measured. Such reference nucleic acid fragment masses can be used to determine whether or not a target nucleic acid molecule contains methylated or unmethylated nucleotides and the amount of methylated or unmethylated nucleotides present in a target nucleic acid molecule. Such determinations can be accomplished by comparing one or more masses (or mass peak characteristics) of target nucleic acid molecule fragments with one or more masses (or mass peak characteristics) from one or more reference nucleic acid fragments.

In an exemplary method, one or more or more characteristics of mass peaks measured from a sample target nucleic acid molecule fragments can be compared to one or more characteristics of mass peaks measured from one or more fragments of one or more reference nucleic acid molecules, and the mass peaks of the one or more reference molecules can be correlated to the sample target nucleic acid molecule mass peaks. The methylation state of the sample target nucleic acid molecule is then identified as corresponding to the methylation state of the reference nucleic acid having one or more mass peaks that most closely correlate to the sample target nucleic acid molecule mass peaks, and optionally, provided that the correlation is above a user-defined threshold amount. Thus, when the nucleotide sequence of the region encompassing the target nucleic acid molecule is unknown, identification of the methylation state of a target nucleic acid molecule can be accomplished by identifying a particular reference nucleic acid as having the same methylation state, even if neither the sequence nor location of the portions in question is known.

c. Use of Mass Peak Characteristics

The measured masses can have three or more identifying characteristics, including measured mass, peak area (e.g., area under the mass peak), and signal to noise ratio of the mass signal. It is contemplated herein that as few as 1 or as few as 2 characteristics of a mass peak can be used in target nucleic acid molecule methylation identification methods disclosed herein. When the nucleotide sequence for the target nucleic acid molecule is known, a collection of one or more mass peaks that demonstrate one or more predicted mass peak characteristics as a result of the nucleotide sequence and the predicted methylation state of the target nucleic acid molecule can be used to identify the methylation state of a nucleotide of a target nucleic acid molecule.

In one embodiment, two or more characteristics of mass peaks are used to identify the methylation state of a target nucleic acid molecule. In such a method, the collection of two or more characteristics of mass peaks is referred to as a "pattern." For example, a pattern can the masses of two or more nucleic acid molecule fragments. In another example, a pattern can be the masses and intensities of two or more nucleic acid molecule fragments. The pattern of mass peak characteristics of the target nucleic acid molecule fragments can be used according to the methylation identification methods disclosed herein. For example, the pattern arising from the sample target nucleic acid molecule fragments can be compared to one or more reference nucleic acid molecule fragment patterns, and a reference fragment pattern that correlates most closely to the sample target nucleic acid molecule fragment pattern is indicative that the methylation in the target nucleic acid molecule corresponds to the methylation in the matching reference nucleic acid molecule.

2. Information Available from Analysis of Fragment Measurements

The methods provided herein can be used to provide any of a variety of different types of information regarding a sample. For example, the methods can be used to detect a small amount of methylated or unmethylated target nucleic acid molecule in a sample, to detect incomplete cytosine conversion, and to identify the methylation state of multiple nucleotide loci a target nucleic acid molecule.

a. Detection of Small Amounts of Methylated or Unmethylated Nucleic Acid

In one embodiment, the methods provided herein can be used to detect a small amount of methylated or unmethylated target nucleic acid molecule in a sample. Methylated or unmethylated target nucleic acid molecules can be present in small amounts in any of a variety of samples as a result of any of a variety of factors. For example, methylated or unmethylated target nucleic acid molecules can be present in small amounts because the sample itself is very small or because the amount of methylated or unmethylated target nucleic acid molecules is small relative to the total amount of nucleic acid in a sample. Thus, the present methods can be used to detect methylated or unmethylated target nucleic acid molecule in a small sample and can be used to detect methylated or unmethylated target nucleic acid molecule in a sample containing relatively large amounts of background nucleic acid.

In another example, methylated target nucleic acid molecules can be present in small amounts in tissue samples containing a small amount of neoplastic cells, where the methylated target nucleic acid molecules are present only in the neoplastic cells. Thus, methylated target nucleic acid molecules can be present in small amounts relative to the total amount of DNA or total amount of nucleic acid molecules present in a sample. When the methylated target nucleic acid molecules are present in relatively small amounts, amplification of the target nucleic acid molecule sequence by methods that are not methylation specific can result in a pool of amplified nucleic acid molecules, where the amplified nucleic acid molecules resultant from the methylated target nucleic acid molecule are present in such relatively small amounts that the amplified methylated target nucleic acid molecules cannot be detected or detection of the amplified methylated target nucleic acid molecules is not greater than a signal to noise ratio required to confirm the presence of methylated target nucleic acid molecules.

Methylated target nucleic acid molecule can be present in small amounts in a sample because, for example, the sample contains heterogenous DNA. Heterogenous DNA can arise from a DNA sample containing the DNA of two or more organisms. Heterogenous DNA also can arise from a DNA sample containing DNA from two or more cells of a single organism where the epigenetic state of the two or more cells is different.

In accordance with the embodiment where a small amount of methylated target nucleic acid molecule is present in a sample, the methods herein can be used to detect the methylated target nucleic acid molecule. For example, methylation specific amplification methods provided herein can be used to increase the relative amount of methylated or unmethylated target nucleic acid molecules or to increase both the total amount and the relative amount of nucleic acid molecule arising from treatment of methylated target nucleic acid molecule with a reagent that modifies target nucleic acid molecule according to its methylation state (in this embodiment, target nucleic acid molecules and nucleic acid molecules arising from treated target nucleic acid molecules are used interchangeably). That is, amplification of methylated or unmethylated target nucleic acid molecules can be used to increase the total amount of methylated or unmethylated target nucleic acid molecules present in a sample, and, thereby to increase the amount of methylated or unmethylated target nucleic acid molecule fragments that can be detected using the mass measurement methods provided herein. Further, methylation specific amplification of methylated or unmethylated target nucleic acid molecules can serve to selectively increase the amount of methylated or unmethylated target nucleic acid molecule present in a sample without increasing the amount of background or undesired nucleic acid molecules or other nucleic acids present in the sample, thereby increasing the relative amount of methylated or unmethylated target nucleic acid molecule fragments that can be detected in the mass measurement methods provided herein. Thus, using the methods provided herein, methylated or unmethylated target nucleic acid molecule can be detected, even when present in small amounts. The methods provided herein can be used to detect a methylated or unmethylated target nucleic acid molecule present in a sample in quantities as small as 1 pg, 5 pg, 10 pg, 50 pg, 100 pg, 500 pg, or 1 ng. The methods provided herein can be used to detect a methylated or unmethylated target nucleic acid molecule present in a sample in relative amounts as small as 0.001%, 0.005%, 0.01%, 0.05%, or 0.1%.

b. Distinguishing Methylation State from Incomplete Conversion

In another embodiment, the methods provided herein can be used to distinguish fragments arising as a result of a target nucleic acid molecule containing methylated nucleotides from fragments arising as a result of incomplete conversion of unmethylated nucleotides in a target nucleic acid molecule. Methods for modifying the sequence of a nucleic acid molecule as a function of the methylation state of the nucleic acid molecule can be incomplete, resulting in a heterogenous mixture of treated unmethylated nucleic acid molecules, where a fraction of the treated unmethylated nucleic acid molecules has the same nucleotide sequence as treated methylated nucleic acid molecule or where a fraction of an unmethylated locus on a treated nucleic acid molecule has the same sequence as a methylated locus on a treated nucleic acid molecule. Such sequence-modifying reactions can be incomplete, the results of which can be also referred to as incomplete conversion. Subsequent to the treatment step, mass measurement methods provided herein can be used to distinguish between a fragment arising as a result of incomplete conversion from a fragment arising as a result of an actual methylated nucleotide.

Incomplete conversion of a homogenous mixture of nucleic acid molecules results in a heterogenous mixture of treated nucleic acid molecules. If a site of incomplete conversion is not located at the amplification primer hybridization site, the site of incomplete conversion will remain heterogenous during any subsequent amplification steps, and will result in a heterogenous mixture of nucleic acid molecule fragments detected by mass measurement. The heterogenous nucleic acid molecule fragments will contain nucleic acid fragments indicative of methylation at a particular nucleotide despite the fact that the nucleotide was unmethylated (i.e., fragments having nucleotides that were not converted) as well as nucleic acid fragments indicative of non-methylation at that nucleotide (i.e., fragments having nucleotides that were converted). The heterogenous nucleic acid molecule fragments also can contain nucleic acid fragments in which a particular nucleotide is consistently identified as methylated.

Mass measurement methods can be used to distinguish between partial conversion and an actual methylated nucleotide by detecting nucleic acid molecule fragments indicative of non-methylation at a particular nucleotide. Presence of both nucleic acid molecule fragments indicative of non-methylation and nucleic acid molecule fragments indicative of methylation at the same nucleotide locus can indicate that the conversion of the nucleotide at that locus was incomplete, and the nucleotide at that locus is not methylated in the sample target nucleic acid molecule. In contrast, presence of target nucleic acid molecule fragments consistently indicative of methylation at a nucleotide locus can indicate that the nucleotide locus is methylated in the sample nucleic acid molecule.

In one embodiment, fragments arising from a methylated nucleotide or a methylated locus are not necessarily homogenous. That is, some of the fragments in a fragmentation pattern can reflect methylated nucleotide at a locus while other fragments reflect unmethylated nucleotide at the locus, even if the locus is always methylated. This can arise in homogenous samples when, for example, when fragmentation is incomplete. This also can arise when the sample is not completely homogenous. The methods provided herein can be used to identify a locus as methylated even if heterogenous fragments are present. In one example, when the number of fragments reflecting a methylated locus is greater than the number of fragments reflecting an unmethylated locus, the locus in the target nucleic acid is methylated; and when the number of fragments reflecting a methylated locus is smaller than the number of fragments reflecting an unmethylated locus, the locus in the target nucleic acid is unmethylated. Thus, the ratio of fragments reflecting methylation relative to fragments reflecting no methylation can be used to determine methylation at a particular locus. In one example, a locus is methylated if the ratio of methylation fragments to non-methylation fragments is greater than 1, and vice versa. In another example, a locus is methylated if the ratio of methylation fragments to non-methylation fragments is greater than 2, 3 or 4; and a locus is unmethylated if the ratio of methylation fragments to non-methylation fragments is less than ½, ⅓ or ¼. In the latter example, ratios of about 1 can result in an ambiguous result where the methylation state of a particular locus cannot be identified.

In another embodiment, the fragments of a target nucleic acid molecule are compared to a reference nucleic acid molecule. For example, a target nucleic acid molecule can be treated with bisulfite, amplified and fragmented, and the fragments can reflect incomplete bisulfite conversion of one or more cytosine loci. The fragmentation of the target nucleic acid molecule can be compared to a reference nucleic acid molecule having loci with known methylation state that also has been bisulfite treated, amplified and fragmented. When, for example, the reference nucleic acid contains only unmethylated cytosines, the fragmentation pattern can reflect the baseline amount of incomplete conversion at one or more loci. Within the scope of these methods, each nucleotide locus can be converted in different amounts, and, thus, the baseline amount of incomplete conversion reflected in the fragmentation pattern can vary for each nucleotide locus. In comparing the reference nucleic acid molecule fragmentation pattern to a target nucleic acid molecule, when one or more fragments of the target nucleic acid molecule are greater than or less than the baseline amount, one or more loci can be identified as at least partially methylated. A reference nucleic acid that establishes a baseline for incomplete conversion can be used, for example, in methods where the target nucleic acid molecules are in a heterogenous nucleic acid sample, such as a tissue sample containing normal and tumorous cells, pooled samples from multiple individuals, or heterogenous diploid DNA from a single organism or a single cell. In such a case, the amount to which one or more fragments are greater than or less than the baseline amount established with the reference nucleic acid, reflects the relative amount of nucleotides that are methylated at one or more loci. Such methods also can be used for homogenous nucleic acid samples to similarly correct for incomplete conversion.

c. Methylation State Determination at Two or More Loci

In another embodiment, the methods provided herein can be used to identify the methylation state of two or more nucleotide loci in a target nucleic acid molecule. Target nucleic acid molecules that can be used in the methods provided herein can contain two or more nucleotide loci whose methylation state is in question. For example, target nucleic acid molecules can contain one or more nucleotide loci whose methylation state is in question and that are located in the primer hybridization region (or amplification blocker hybridization region) of the target nucleic acid molecule; and such a target nucleic acid molecule also can contain one or more nucleotide loci whose methylation state is in question and that are located in the region that does not hybridize to a primer (or an amplification blocker). The methods disclosed herein provide for identification of the methylation state of nucleotide loci by two methods: amplification and fragment detection. For example, the methylation state of loci located in the hybridization region can be determined by amplification of the target nucleic acid, and the methylation state of loci located in the region that does not hybridize to a primer (or amplification blocker) can be determined by the fragmentation and detection methods provided herein. Furthermore, both amplification methods and fragment detection methods can be used to identify the methylation state of two or more nucleotide loci, resulting in a large number of nucleotide loci of a target nucleic acid molecule whose methylation state can be identified using the methods provide herein.

In one embodiment, nucleotide loci that are located in the region that does not hybridize to a primer (or amplification blocker) are not used in methylation specific amplification steps provided herein. Thus, the methods provided herein can be used to identify the methylation state of one or more nucleotide loci where such determination is performed by mass peak analysis and not by hybridization or amplification methods. The number of nucleotide loci whose methylation state can be identified using mass peak analysis and not hybridization or amplification methods can be 2 or more, 3 or more, 5 or more, 7 or more, 9 or more, 11 or more, 13 or more, 15 or more, 17 or more, 20 or more, 25 or more, 30 or more, 35 or more, 40 or more, 45 or more, 50 or more, 60 or more, 70 or more, or 80 or more.

d. Confirmation of Specific Amplification

In another embodiment, the methods provided herein can be used to confirm specific amplification of a target nucleic acid molecule complementary to a methylation state specific amplification primer. The methods provided herein also can be used to distinguish between specific amplification of a target nucleic acid molecule complementary to a methylation state specific amplification primer and amplification resulting from a mismatch of a target nucleic acid molecule and a methylation state specific amplification primer. The methods provided herein also can be used to determine the methylation state of one or more nucleotides in the region of the target nucleic acid molecule to which one or more methylation specific primers can hybridize. For example, the methods provided herein can be used to measure the mass of amplification products or fragments thereof formed by amplification with methylation state specific amplification primers, and the measured masses can be used to confirm whether or not methylation state specific amplification resulted, or whether or not a mismatch between a methylation state specific primer and a target nucleic acid molecule resulted, or whether or not one or more nucleotides are methylated in the methylation specific primer binding region of the target nucleic acid molecule. In another example, the methods provided herein can be used to determine the number of fragmentation products formed by fragmentation of amplification products produced by amplification with methylation state specific amplification primers, and the number of fragmentation products can be used to confirm whether or not methylation state specific amplification resulted, or whether or not a mismatch between a methylation state specific primer and a target nucleic acid molecule resulted, or whether or not one or more nucleotides are methylated in the methylation specific primer binding region of the target nucleic acid molecule.

i. Distinguishing from Mismatch Hybridization

Traditional methylation specific PCR methods are prone to false positive results because phenomena such as mismatch hybridization or incomplete cytosine conversion can result in amplification of a target nucleic acid molecule that does not accurately reflect the methylation state of the target nucleic acid molecule. For example, when amplification occurs as a result of mismatch hybridization, each amplification product of methylation specific PCR no longer contains sequence information regarding the target nucleic acid molecule in the region to which the primer hybridized. After a few cycles of amplification, the number of amplified products is much greater than the number of target nucleic acid molecules, and information about the target nucleic acid molecule nucleotide sequence in the primer binding region is essentially lost. As a result, amplification products can result that do not accurately reflect the methylation state of the target nucleic acid molecule. Such a result is typically termed a false positive result.

The present methods can be used to distinguish between a false positive result and a true positive result in which amplification products result that do accurately reflect the methylation state of the target nucleic acid molecule. When methylation occurs in a nucleic acid region (e.g., a CpG island), it typically occurs at more than one nucleotide within the region. For example, a CpG island containing one methylated CpG will typically contain one or more additional methylated CpGs. The methods provided herein can be used to determine the methylation state of nucleotides in the region of the target nucleic acid molecule that does not hybridize to one or more methylation specific primers upon methylation specific amplification. By assessing the methylation state of nucleotides in the target nucleic acid molecule region not bound by a methylation specific primer, it is possible to determine the methylation state of one or more nucleotides in the target nucleic acid molecule region to which the primer binds.

For example, CpG islands can contain methylated cytosine nucleotides in a large percentage of the nucleotides of a target nucleic acid molecule, or in almost none of the nucleotides of a target nucleic acid molecule. In such an example, amplification of a target nucleic acid with a methylation specific primer can be identified as either a false positive amplification or a true positive amplification by identifying the methylation state of one or more nucleotide loci in the portion of the target nucleic acid to which methylation specific primer (or amplification blocker) did not hybridize.

For example, when a methylation state specific primer is used to amplify a bisulfite-treated target nucleic acid molecule by hybridizing to a target nucleic acid molecule nucleotide sequence containing one or more C nucleotides, if none of the C nucleotides in the target nucleic acid region not hybridized by a methylation state specific primer are methylated, the methylation state specific amplification reaction can be determined to be a false positive. That is, when methylation state specific amplification reaction yields a result where the only methylated C nucleotide is located at the methylation state specific primer hybridization region, the result from such methylation state specific amplification can serve to conclude that methylation state specific amplification did not occur, that instead a mismatch between a methylation state specific primer and a target nucleic acid molecule occurred, and that one or more C nucleotides in the methylation specific primer binding region of the target nucleic acid molecule are not methylated.

In another example, when a methylation state specific primer is used to amplify a bisulfite-treated target nucleic acid molecule by hybridizing to a target nucleic acid molecule nucleotide sequence containing one or more U or T nucleotides in the place of one or more C nucleotides (i.e., bisulfite converted unmethylated C nucleotides), if many of the C nucleotides in the target nucleic acid region not hybridized by a methylation state specific primer are methylated, the methylation state specific amplification reaction can be determined to be a false positive. That is, when methylation state specific amplification reaction yields a result where the only unmethylated C nucleotide is located at the methylation state specific primer hybridization region, the result from such methylation state specific amplification can serve to conclude that methylation state specific amplification did not occur, that instead a mismatch between a methylation state specific primer and a target nucleic acid molecule occurred, and that one or more C nucleotides in the methylation specific primer binding region of the target nucleic acid molecule are methylated.

In another example, when a methylation state specific primer is used to amplify a bisulfite-treated target nucleic acid molecule by hybridizing to a target nucleic acid molecule nucleotide sequence containing one or more C nucleotides, if many of the C nucleotides in the target nucleic acid region not hybridized by a methylation state specific primer are methylated, the methylation state specific amplification reaction can be a true positive. That is, when methylation state specific amplification reaction yields a result where numerous methylated C nucleotides are located outside of the methylation state specific primer hybridization region, the result from such methylation state specific amplification can serve to conclude that methylation state specific amplification occurred, and that a mismatch between a methylation state specific primer and a target nucleic acid molecule did not occur, and that one or more C nucleotides in the methylation specific primer binding region of the target nucleic acid molecule are methylated.

In another example, when a methylation state specific primer is used to amplify a bisulfite-treated target nucleic acid molecule by hybridizing to a target nucleic acid molecule nucleotide sequence containing one or more U or T nucleotides in the place of one or more C nucleotides (i.e., bisulfite converted unmethylated C nucleotides), if none of the C nucleotides in the target nucleic acid region not hybridized by a methylation state specific primer are methylated, the methylation state specific amplification reaction can be a true positive. That is, when methylation state specific amplification reaction yields a result where numerous unmethylated C nucleotides are located outside of the methylation state specific primer hybridization region, the result from such methylation state specific amplification can serve to conclude that methylation state specific amplification occurred, and that a mismatch between a methylation state specific primer and a target nucleic acid molecule did not occur, and that one or more C nucleotides in the methylation specific primer binding region of the target nucleic acid molecule are unmethylated.

Some of the above examples refer to situations in which the methylation state in none of the nucleotides in the region not bound by the methylation state specific primer are methylated or unmethylated, and when none of such nucleotides are methylated or unmethylated, the methylation state of the nucleotides in the methylation state specific primer binding region are determined to be the same. Also contemplated herein, as applied to the above examples, are situations in which a the methylation state of the nucleotides is the same in a large percentage of the nucleotides of a target nucleic acid molecule, or in almost none of the nucleotides of a target nucleic acid molecule. For example, when only one cytosine in a 100-nucleotide long non-hybridized region of a target nucleic acid molecule is determined to be methylated, it can be concluded that almost none of the nucleotides in the non-hybridized region are methylated, and, therefore, the nucleotides in the methylation state specific primer hybridization region also are unmethylated. Typically, for instances where almost none of the nucleotides are methylated or unmethylated, less than about 20% of the nucleotides (e.g., less than 20% of the cytosines) are methylated or unmethylated. Often, when almost none of the nucleotides are methylated or unmethylated, less than about 10% or less than about 5% of the nucleotides are methylated or unmethylated. Typically, for instances where most of the nucleotides are methylated or unmethylated, at least about 50% of the nucleotides (e.g., at least about 50% of the cytosines) are methylated or unmethylated. Often, when most of the nucleotides are methylated or unmethylated, more than about 70% or more than about 85% of the nucleotides are methylated or unmethylated.

In another embodiment, when there is a reference nucleic acid sequence having two or more loci with known methylation state, the methods provided herein can be used to confirm whether or not methylation state specific amplification resulted, or whether or not a mismatch between a methylation state specific primer and a target nucleic acid molecule resulted, or whether or not one or more nucleotides are methylated in the methylation specific primer binding region of the target nucleic acid molecule. In particular, when the methylation state of two or more loci are linked, the methods provided herein can be used to confirm whether or not methylation state specific amplification resulted, or whether or not a mismatch between a methylation state specific primer and a target nucleic acid molecule resulted, or whether or not one or more nucleotides are methylated in the methylation specific primer binding region of the target nucleic acid molecule. For example, when a linkage exists between a first methylated cytosine and a second methylated cytosine, identification of the first cytosine as methylated also can serve to identify the second cytosine as methylated. Thus, when a cytosine in the region of a target nucleic acid molecule not hybridized by a methylation state specific primer is identified as methylated, a cytosine in the region of the target nucleic acid molecule hybridized by a methylation state specific primer also can be identified as methylated. One skilled in the art can conclude, based on the methylation state of the cytosine loci and the methylation state specific primer used, whether or not methylation specific amplification occurred or whether or not mismatch hybridization occurred. Similarly, when a methylated cytosine is linked to an unmethylated cytosine, identification of either locus can identify both loci; and based on the methylation state of the cytosine loci and the methylation state specific primer used, one skilled in the art can conclude whether or not methylation specific amplification occurred or whether or not mismatch hybridization occurred. Similarly, when a unmethylated cytosine is linked to another unmethylated cytosine, identification of either locus can identify both loci; and based on the methylation state of the cytosine loci and the methylation state specific primer used, one skilled in the art can conclude whether or not methylation specific amplification occurred or whether or not mismatch hybridization occurred.

The methods for distinguishing between a false positive and a true positive can be performed using any of the methods provided herein. For example, fragment masses can be compared to reference masses and a shift in the fragment mass relative to a reference mass can be indicative of the methylation state of a nucleotide in the region of the target nucleic acid molecule not hybridized to the methylation state specific primer, and, thus can be used to conclude that false amplification occurred or that true amplification occurred, depending on the experimental design and the methylation state to be determined. In another example, fragment masses can be compared to reference masses and the same mass between a fragment mass and a reference mass can be indicative of the methylation state of a nucleotide in the region of the target nucleic acid molecule not hybridized to the methylation state specific primer, and, thus can be used to conclude that false amplification occurred or that true amplification occurred, depending on the experimental design. In another example, the number of sample fragments can be compared to the number of reference fragments and a difference in the number of sample fragments relative to the number of reference fragments can be indicative of the methylation state of a nucleotide in the region of the target nucleic acid molecule not hybridized to the methylation state specific primer, and, thus can be used to conclude that false amplification occurred or that true amplification occurred, depending on the experimental design. In another example, the number of sample fragments can be compared to the number of reference fragments and when the number of sample fragments relative to the number of reference fragments is the same, this can be indicative of the methylation state of a nucleotide in the region of the target nucleic acid molecule not hybridized to the methylation state specific primer, and, thus can be used to conclude that false amplification occurred or that true amplification occurred, depending on the experimental design. In another example, the number of sample fragments can be determined, and when three or more fragments are observed, this can indicate that the methylation state of a nucleotide in the region of the target nucleic acid molecule not hybridized to the methylation state specific primer is the same as the methylation state of a nucleotide in the region of the target nucleic acid molecule hybridized to the methylation state specific primer, and, thus can be used to conclude that true amplification occurred. In another example, the number of sample fragments can be determined, and when two or fewer fragments are observed, this can indicate that the methylation state of a nucleotide in the region of the target nucleic acid molecule not hybridized to the methylation state specific primer is different from the methylation state of a nucleotide in the region of the target nucleic acid molecule hybridized to the methylation state specific primer, and, thus can be used to conclude that false amplification occurred.

ii. Distinguishing from Incomplete Conversion

False positive amplification also can result from incomplete conversion. When incomplete conversion occurs, for example, incomplete conversion of unmethylated cytosines to uracil by bisulfite, methylation state specific primers can hybridize to unconverted nucleotides to yield amplified products that do not accurately reflect the methylation state of the target nucleic acid. The methods provided herein can be used to determine when incomplete conversion has occurred, can be used to distinguish between an incompletely converted nucleotide and a methylated or unmethylated nucleotide, and can be used to determine the extent to which incomplete conversion has occurred. In cases where incomplete conversion is determined to have occurred, one skilled in the art can determine the extent of the incomplete conversion and conclude the likelihood with which methylation specific amplification can have occurred as a result of incomplete conversion, resulting in a false positive amplification. For example, when more than about 5%, more than about 10% or more than about 20% of nucleotides are incompletely converted, the methylation specific amplification can be determined to be a false positive amplification. Thus, also provided herein are methods of determining whether or not false amplification of a target nucleic acid molecule occurred using a methylation state specific amplification primer as a result of incomplete conversion. The methods provided herein also can be used to distinguish between specific amplification of a completely converted target nucleic acid molecule complementary to a methylation state specific amplification primer and amplification resulting from hybridization of an incompletely converted target nucleic acid molecule and a methylation state specific primer; such methods include determining whether or no incomplete conversion occurred and, if incomplete conversion occurred, concluding that amplification resulted from hybridization of an incompletely converted target nucleic acid molecule and a methylation state specific primer.

The methods provided herein also can be used to determine the methylation state of one or more nucleotides in the region of the target nucleic acid molecule to which one or more methylation specific primers can hybridize. For example, the methods provided herein can be used to determine whether or not a nucleotide located in the portion of target nucleic acid molecule to which the methylation state specific primer did not hybridize is actually methylated or was merely incompletely converted, as described more fully elsewhere herein. If a nucleotide located in the portion of target nucleic acid molecule to which the methylation state specific primer did not hybridize is determined to be methylated, the methods provided herein can be used to determine that a nucleotide in the methylation state specific primer hybridization region also is methylated, and that true methylation specific amplification occurred despite the occurrence of incomplete conversion.

In another example, the methods provided herein can be used to determine whether or not a nucleotide located in the portion of target nucleic acid molecule to which the methylation state specific primer did not hybridize is actually unmethylated or was merely incompletely converted. If a nucleotide located in the portion of target nucleic acid molecule to which the methylation state specific primer did not hybridize is determined to be unmethylated, the methods provided herein can be used to determine that a nucleotide in the methylation state specific primer hybridization region also is unmethylated, and that true methylation specific amplification occurred despite the occurrence of incomplete conversion.

In another example, the methods provided herein can be used to determine whether or not a nucleotide located in the portion of target nucleic acid molecule to which the methylation state specific primer did not hybridize is actually methylated or was merely incompletely converted. If few or no nucleotides located in the portion of target nucleic acid molecule to which the methylation state specific primer did not hybridize are determined to be methylated, the methods provided herein can be used to determine that a nucleotide in the methylation state specific primer hybridization region is unmethylated, and that false methylation specific amplification occurred.

In another example, the methods provided herein can be used to determine whether or not a nucleotide located in the portion of target nucleic acid molecule to which the methylation state specific primer did not hybridize is actually unmethylated or was merely incompletely converted. If few or no nucleotides located in the portion of target nucleic acid molecule to which the methylation state specific primer did not hybridize are determined to be unmethylated, the methods provided herein can be used to determine that a nucleotide in the methylation state specific primer hybridization region is methylated, and that false methylation specific amplification occurred.

Measurements of the number of fragments, the number of fragments relative to reference fragments or the mass of fragments relative to relative masses, as disclosed herein, can be used to determine whether or not false amplification occurred as a result of incomplete conversion in the same manner as described in reference to determining whether or not false amplification occurred as a result of mismatch hybridization.

3. Analysis of Both Target Nucleic Acid Molecule Strands

When at least one nucleotide on a target nucleic acid molecule is methylated or unmethylated, treatment of a target nucleic acid molecule with a reagent that can modify the target nucleic acid molecule sequence as a function of the methylation state of the target nucleic acid molecule can result in the two strands of the treated target nucleic acid molecule being no longer perfectly complementary (i.e., having at least one mismatch). For example, a target nucleic acid containing at least one unmethylated cytosine that is treated with bisulfite will contain a U-G mismatched base pair at the site of the unmethylated cytosine. The two strands of post-treatment, pre-amplification target nucleic acid molecules are not to be confused with the two strands of post-treatment, post-amplification target nucleic acid molecules, because the former set of two strands are not complementary, whereas the latter set of two strands are complementary.

In one embodiment, both of the non-complementary post-treatment pre-amplification strands can be used to identify the methylation state of a target nucleic acid molecule. For example, both strands of a target nucleic acid molecule can contain methylated and/or unmethylated cytosines, and bisulfite treatment of the double stranded target nucleic acid molecule can result in sequence modification of each strand according to the methylation state of the respective strand, but not according to the methylation state of the complement strand. Accordingly, in order to identify the methylation state of each strand, each strand is independently examined according to the methods provided herein. Thus, also provided herein is a method for identifying the methylation state of a target nucleic acid molecule by treating a target nucleic acid molecule with a reagent that modifies one or more nucleotides of the target nucleic acid molecule as a function of the methylation state of the target nucleic acid molecule, then separating the two strands of the treated target nucleic acid molecule, and identifying the methylation state of each of the two strands using, for example, the amplification, fragmentation and mass measurement methods provided herein.

In another embodiment, use of both strands can serve a similar role as use of a reference nucleic acid. For example, when a target nucleic acid molecule is treated with bisulfite, unmethylated C nucleotides will be converted to U (or T in DNA) nucleotides, but the corresponding G nucleotide of the complementary strand and methylated C nucleotides will not be converted. Loci of C-G matched base pairs can indicate the presence of methylated cytosines, and loci of mismatched U-G (or T-G) base pairs can indicate the presence of unmethylated cytosines. In another example when a target nucleic acid molecule is treated with bisulfite, C-specific fragmentation of the first strand can indicate the number and loci of methylated C nucleotides on that strand, while G-specific fragmentation of the second strand can indicate the total number and loci of methylated and unmethylated C nucleotides on the first strand. Combining the cleavage information from both strands can result in a determination of both the number and loci of methylated and unmethylated C nucleotides in the first strand.

4. Information in Cleavage Patterns

The fragment measurements arising from the fragmentation and measurement methods provided herein, such as base specific cleavage, can provide information regarding the methylation state of a target nucleic acid molecule and the position of the methylated nucleotide on the target nucleic acid molecule.

In one embodiment all or almost all target nucleic acid molecule fragment masses provide redundant information on the presence or locus of methylated or unmethylated nucleotides. Fragmentation of a nucleic acid molecule, for example, by base specific cleavage, can yield numerous nucleic fragments, whose mass can be measured. Nucleic acid molecule fragments will contain a 5' end and a 3' end, where each end can arise as a result of fragmentation or can be the 5' or 3' end of the original uncleaved nucleic acid molecule. When both ends arise as a result of fragmentation, each end contains fragmentation information. For example, when both ends of a bisulfite-treated nucleic acid fragment arises from C-specific cleavage using RNase A, the 3' end will contain a C nucleotide corresponding to a first methylated C in the nucleic acid molecule, and the 5' end will contain the nucleotide immediately adjacent a C nucleotide corresponding to a second methylated C in the target nucleic acid molecule. Thus, the presence of such a fragment can identify the target nucleic acid molecule as having at least two methylated C nucleotides. Further, if the location of such a target nucleic acid molecule fragment in the nucleic acid molecule sequence is known, the fragment can indicate the presence and loci of the two methylated nucleotides in the nucleic acid molecule. Detection of adjacent target nucleic acid molecule fragments can give overlapping information, and thus, can serve to provide redundancy in the identification of methylated nucleotides. Such redundancy can be useful, for example, if one of two adjacent fragments cannot be detected using mass measurement methods. For example, when one fragment is too small or too large to be accurately measured by mass spectrometry, measurement of adjacent fragments can still permit the methylation state of the target nucleic acid molecule and the loci of methylated nucleotides on the target nucleic acid molecule to be determined.

An amplified target nucleic acid molecule sample can be divided into two or more fractions and a different fragmentation step can be performed on each fraction. For example, when two base specific cleavage reactions are performed on two different fractions of a target nucleic acid molecule sample, the information obtained from the mass peaks of a first fraction can be partially or fully redundant with the information obtained from the mass peaks of a second fraction, resulting in increased redundancy as a result of the overlapping information, and resulting in increased coverage as a result of the non-overlapping information (coverage as used in this context refers to completeness of methylation information for target nucleic acid loci in question). For example, two different base specific cleavage reactions can be performed on two separate target nucleic acid molecule sample fractions (one base specific cleavage per sample), and the fragment measurements from the two cleavage reactions, when combined, can provide information regarding the methylation state of all nucleotide loci under examination, and also can provide redundancy for one or more nucleotide loci under examination. In another embodiment, four base specific cleavage reactions on four target nucleic acid molecule samples can provide information regarding the methylation state of all nucleotide loci under examination and also can provide redundant information for 90% or more of all nucleotide loci under examination.

H. Applications

The methods provided herein can be used in a variety of applications, including those discussed above, identification of new methylation sites, identification of the methylation state of the DNA of a subject, determination of a fraction of total methylated DNA, and parallel determination of the methylation state of two or more target nucleic acid molecules.

1. Methylation Discovery

Methylated or unmethylated nucleotides in genomic DNA can influence structure of the DNA, including chromatin structure, and also can affect gene expression. Cytosine can be methylated in DNA. The majority of methylcytosine is located in transposons. Methylcytosine also is often observed with guanine nucleotides in forming "CpG" motifs. CpG motifs are uncommon in the genome, but often occur in clusters with other CpG motifs to form "CpG islands." CpG islands are typically 500 bases or longer and contain at least 55% G and C nucleotides and an observed over expected CpG frequency of at least 0.65. CpG islands have been found in promotor regions and these CpG islands are considered to influence gene expression, and to play a role in various diseases including various cancers. Methylated nucleotides such as methylated cytosines in CpG islands are still being discovered. The present methods provide rapid and sensitive ways to discover additional methylated nucleotides, particularly methylated cytosines such as those in CpG motifs and CpG islands. It also is possible that lack of methylation can play a role in DNA structure and/or gene expression. Thus, the present methods also provide for discovery of unmethylated nucleotide, particularly unmethylated cytosines such as those in CpG motifs and CpG islands.

Discovery of previously uncharacterized methylated nucleotides can be performed using the methods provided herein, where the primers used in amplification can have an intended, pre-determined sequence, or can have a random sequence. An intended or pre-determined sequence, for the purposes of this embodiment, refers to a sequence that is intended to hybridize with one or more known DNA region (e.g., a known location on a chromosome, a known promotor region, a known transposon or retrotransposon). A random sequence, for the purposes of this embodiment, refers to a sequence that is not intended to hybridized with any particular DNA region. In one example, one primer of a primer pair having either intended or random sequences can contain one or more G nucleotides, where the G nucleotide hybridizes with a C nucleotide of the sample DNA. When the sample DNA is treated with bisulfite prior to primer hybridization, the primers having G nucleotides can selectively hybridize to DNA sequences containing methylated C nucleotides. Amplification, fragmentation and mass measurement of the methylated DNA can be performed using the methods provided herein. Optionally, the methylated amplified DNA can be sequenced using known methods or methods provided herein. Alternatively, when sample DNA is treated with bisulfite prior to primer hybridization and the bisulfite treated DNA is amplified by at least one nucleic acid synthesis step, the primer sequences can contain one or more C nucleotides where the C nucleotide hybridizes with a G nucleotide in the newly synthesized strand which is complementary to the bisulfite treated strand.

In another example, one primer of a primer pair having either intended or random sequences can contain one or more A nucleotides, where the A nucleotide hybridizes with a U nucleotide of the sample DNA. When the sample DNA is treated with bisulfite prior to primer hybridization, the primers having A nucleotides can selectively hybridize to DNA sequences containing unmethylated C nucleotides. Amplification, fragmentation and mass measurement of the unmethylated cytosine-containing DNA can be performed using the methods provided herein. Optionally, the amplified DNA can be sequenced using known methods or methods provided herein. Alternatively, when sample DNA is treated with bisulfite prior to primer hybridization and the bisulfite treated DNA is amplified by at least one nucleic acid synthesis step, the primer sequences can contain one or more T or U nucleotides where the T or U nucleotide hybridizes with an A nucleotide in the newly synthesized strand which is complementary to the bisulfite treated strand.

In one embodiment, presence of one or more methylated nucleotides can be identified as abnormal or different from the typical nucleotides at those nucleotide loci in such an organism. In one embodiment, presence of one or more methylated nucleotides can be identified as normal or the same as typical nucleotides at those positions in such an organism. In another embodiment, presence of one or more unmethylated nucleotides can be identified as abnormal or different from the typical nucleotides at those nucleotide loci in such an organism. In one embodiment, presence of one or more unmethylated nucleotides can be identified as normal or the same as typical nucleotides at those positions in such an organism.

a. Disease-Related Discovery

In one embodiment, presence or absence of one or more methylated or unmethylated nucleotides can be identified as indicative of a disease state associated with methylated or unmethylated DNA, such as a neoplastic disease. In another embodiment, presence or absence of one or more methylated or unmethylated nucleotides can be identified as indicative of a normal, healthy or disease free state. In another embodiment, an abnormal ratio of methylated target nucleic acid molecules relative to unmethylated target nucleic acid molecules in a sample can be indicative of a disease state associated with methylated or unmethylated DNA, such as a neoplastic disease. For example, a relatively high number or a relatively low number of methylated target nucleic acid molecules compared to the relative amount in a normal individual can be indicative of a disease state associated with methylated or unmethylated DNA, such as a neoplastic disease. In another embodiment, an abnormal ratio of methylated nucleotide at a nucleotide locus relative to unmethylated nucleotide at a nucleotide locus in a target nucleic acid molecule can be indicative of a disease state associated with methylated or unmethylated DNA, such as a neoplastic disease. For example, a relatively high number or a relatively low number of methylated nucleotide loci compared to the relative amount in a normal individual can be indicative of a disease state associated with methylated or unmethylated DNA, such as a neoplastic disease.

Diseases associated with a modification of the methylation of one or more nucleotides include, for example: leukemia (Aoki E et al., "Methylation status of the p15INK4B gene in hematopoietic progenitors and peripheral blood cells in myelodysplastic syndromes" *Leukemia* 14(4):586-593 (2000); Nosaka, K. et al., "Increasing methylation of the CDKN2A gene is associated with the progression of adult T-cell leukemia" *Cancer Res* 60(4): 1043-1048 (2000); Asimakopoulos FA et al., "ABL1 methylation is a distinct molecular event associated with clonal evolution of chronic myeloid leukemia" *Blood* 94(7):2452-2460 (1999); Fajkusova L. et al., "Detailed Mapping of Methylcytosine Positions at the CpG Island Surrounding the Pa Promoter at the bcr-abl Locus in CML Patients and in Two Cell Lines, K562 and BV173" *Blood Cells Mol Dis* 26(3):193-204 (2000); Litz C E et al., "Methylation status of the major breakpoint cluster region in Philadelphia chromosome negative leukemias" Leukemia 6(1):35-41 (1992)), head and neck cancer (Sanchez-Cespedes M. et al. "Gene promoter hypermethylation in tumors and serum of head and neck cancer patients" *Cancer Res* 60(4):892-895 (2000)), Hodgkin's disease (Garcia J. F. et al. "Loss of p16 protein expression associated with methylation of the p16INK4A gene is a frequent finding in Hodgkin's disease" *Lab Invest* 79(12):1453-1459 (1999)), gastric cancer (Yanagisawa Y. et al., "Methylation of the hMLH1 promoter in familial gastric cancer with microsatellite instability" *Int J Cancer* 85(1):50-53 (2000)), prostate cancer (Rennie P. S. et al., "Epigenetic mechanisms for progression of prostate cancer" *Cancer Metastasis Rev* 17(4):401-409 (1998-99)), renal cancer (Clifford, S. C. et al., "Inactivation of the von Hippel-Lindau (VHL) tumor suppressor gene and allelic losses at chromosome arm 3p in primary renal cell carcinoma: evidence for a VHL-independent pathway in clear cell renal tumourigenesis" *Genes Chromosomes Cancer* 22(3):200-209 (1998)), bladder cancer (Sardi, I. et al., "Molecular genetic alterations of c-myc oncogene in superficial and locally advanced bladder cancer" *Eur Urol* 33(4):424-430 (1998)), breast cancer (Mancini, D. N. et al., "CpG methylation within the 5' regulatory region of the BRCA I gene is tumor specific and includes a putative CREB binding site" *Oncogene* 16(9):1161-1169 (1998); Zrihan-Licht S. et al., "DNA methylation status of the MUC1 gene coding for a breast-cancer-associated protein" *Int J. Cancer* 62(3):245-251 (1995); Kass, D. H. et al., "Examination of DNA methylation of chromosomal hot spots associated with breast cancer" *Anticancer Res* 13(5A): 1245-1251 (1993)), Burkitt's lymphoma (Tao, Q. et al., "Epstein-Barr virus (EBV) in endemic Burkitt's lymphoma: molecular analysis of primary tumor tissue" *Blood* 91(4):1373-1381 (1998)), Wilms tumor (Kleymenova, E. V. et al., "Identification of a tumor-specific methylation site in the Wilms tumor suppressor gene" *Oncogene* 16(6):713-720 (1998)), Prader-Willi/Angelman syndrome (Zeschnigh et al. "Imprinted segments in the human genome: different DNA methylation patterns in the Prader-Willi/Angelman syndrome region as determined by the genomic sequencing method" *Human Mol. Genetics* (6)3:387-395 (1997); Fang P et al. "The spectrum of mutations in UBE3A causing Angelman syndrome" *Hum Mol Genet* 8(1):129-135 (1999)), ICF syndrome (Tuck-Muller et al. "CMDNA hypomethylation and unusual chromosome instability in cell lines from ICF syndrome patients" *Cytogenet Cell Genet* 89(1-2):121-128 (2000)), dermatofibroma (Chen, T. C. et al., "Dermatofibroma is a clonal proliferative disease" *J Cutan Pathol* 27(1):36-39 (2000)), hypertension (Lee, S. D. et al., "Monoclonal endothelial cell proliferation is present in primary but not secondary pulmonary hypertension" *J Clin Invest* 101(5):927-934 (1998)), pediatric neurological disorders (Campos-Castello, J. et al., "The phenomenon of genomic "imprinting" and its implications in clinical neuropediatrics" *Rev Neurol* 28(1):69-73 (1999)), autism (Klauck, S. M. et al., "Molecular genetic analysis of the FMR-1 gene in a large collection of autistic patients" *Hum Genet* 100(2):224-229 (1997)), ulcerative colitis (Gloria, L. et al., "DNA hypomethylation and proliferative activity are increased in the rectal mucosa of patients with long-standing ulcerative colitis" *Cancer* 78(11):2300-2306 (1996)), fragile X syndrome (Hornstra, I. K. et al., "High resolution methylation analysis of the FMR1 gene trinucleotide repeat region in fragile X syndrome" *Hum Mol Genet* 2(10):1659-1665 (1993)), and Huntington's disease (Ferluga, J. et al., "Possible organ and age-related epigenetic factors in Huntington's disease and colorectal carcinoma" *Med Hypotheses* 29(1):51-54 (1998)). Additional disease associated with the epigenetic state of DNA include low grade astrocytoma, anaplastic astrocytoma, glioblastoma, medulloblastoma, colon cancer, lung cancer, pancreatic cancer, endometrial cancer, neuroblastoma, headaches, sexual malfunction, primary myxedema, pernicious anemia, Addison's disease, myasthenia gravis, juvenile diabetes, idiopathic thrombocytopenic purpura, multiple sclerosis, rheumatoid arthritis, scleroderma; and other disorders such as CNS malfunctions, damage or disease; symptoms of aggression or behavioral disturbances; clinical, psychological and social consequences of brain damage; psychotic disturbances and personality disorders; dementia and/or associated syndromes; cardiovascular disease, malfunction and damage; malfunction, damage or disease of the gastrointestinal tract; malfunction, damage or disease of the respiratory system; lesion, inflammation, infection, immunity and/or convalescence; malfunction, damage or disease of the body as an abnormality in the developmental process; malfunction, damage or disease of the skin, the muscles, the connective tissue or the bones; endocrine and metabolic malfunction, damage or disease; and also can be associated with undesired drug interactions.

b. Multiplex Analysis

Also contemplated herein, are methods for the high-throughput methylation state identification of nucleic acids from a plurality of target nucleic acid molecules. Multiplexing refers to the simultaneous identification of the methylation state of more than one target nucleic acid molecule. Methods for performing multiplexed reactions, particularly in conjunction with mass spectrometry, are known (see, e.g., U.S. Pat. Nos. 6,043,031, 5,547,835 and International PCT application No. WO 97/37041).

Multiplexing provides the advantage that a plurality of target-nucleic acids can be examined for methylation information in a few or even only a single mass spectrum, as compared to having to perform a separate mass spectrometry analysis for each individual target nucleic acid molecule. The methods provided herein lend themselves to high-throughput, highly-automated processes for elucidating nucleic acid methylation with high speed and accuracy.

Multiplexing can be used to identify the methylation state of two or more target nucleic acid molecules or identify the methylation state of one or more nucleotide loci of two or more target nucleic acid molecules. In one embodiment, the methods disclosed herein can be used to identify the methylation state of a target nucleic acid molecule from a variety of different samples including different cell types, different tissue types, different organisms, different strains, different species, or new cell types, new tissue types, new organisms, new strains or new species. Such multiplexing of samples from more than one source also can be referred to as pooling. Identification of the methylation state of a target nucleic acid molecule from different samples can be used, for example, to determine the neoplastic or metastatic state of cells, to diagnose a subject, including, for example, a patient with a genetic, infectious, autoimmune or neoplastic disease; to distinguish between cell types, tissue types, strain types or organism types; to determine linkage in expression between two or more genes, and a correlation between gene expression and cell morphology such as mitotic or meiotic state of a cell.

A mixture of biological samples from any two or more biological sources can be pooled into a single mixture for analysis herein. For example, the methods provided herein can be used for identifying the methylation state of multiple copies of a target nucleic acid molecules from different sources, and therefore identify methylation state variations in a target nucleic acid molecules in a mixture of nucleic acids in a biological sample. A mixture of biological samples also can include but is not limited to nucleic acid from a pool of individuals, different regions of nucleic acid from one or more individuals, a homogeneous tumor sample derived from a single tissue or cell type, or a heterogeneous tumor sample containing more than one tissue type or cell type, or a cell line derived from a primary tumor. Also contemplated are methods, such as haplotyping methods, in which the methylation state of each haplotype in the same region is detected.

In another embodiment, multiplexing methods that can be performed according to the methods provided herein include methylation state identification of two or more target nucleic acid molecules from a single subject. For example, the methylation state of two or more markers in a subject can be indicative of a disease state (such as a neoplastic state) of a subject or can be indicative of the propensity for disease or neoplasm of a subject. The methylation state of two or more markers also can serve to indicate the source of diseased cells. For example, methylation in CpG islands near genes such as p15, E-cadherin and calcitonin can indicate acute myeloid leukemia instead of prostate cancer, and methylation in CpG islands near the glutathione-S transferase protein-1 gene can indicate prostate cancer instead of acute myeloid leukemia. Thus, multiplexing methods that identify the methylation state of two or more target nucleic acids in an individual can be used to determine the disease state or propensity thereof in an individual, and also can be used to determine the type of disease likely present or likely to develop in an individual. Such multiplexing methods can include a panel of target nucleic acid markers where presence or absence of methylation in one or more target nucleic acid markers can be indicative of a disease state (such as a neoplastic state) of a subject, or can be indicative of the propensity for disease or neoplasm of a subject, or can serve to indicate the source of diseased cells.

c. Target Nucleic Acid Molecule Fragments as Markers

In other embodiments, target nucleic acid molecule fragments that reflect the methylation state of a target nucleic acid molecule can be used as markers or indicators of sequences or portions of a large target nucleic acid molecule. Such embodiments do not require determination of the sequence of the target nucleic acid molecule, but can include determining the sequence of portions of the target nucleic acid molecule, or simply determining the mass peak pattern of target nucleic acid molecule fragments. Such methods can include, for example, mapping, fingerprinting and fingerprinting related methods and other methods that can include use of target nucleic acid molecule fragments as indicators of the methylation state of a target nucleic acid molecule. For example, a particular sequence containing a methylated cytosine can occur only a few times in an entire organism's genome, and the location of the particular sequence containing methylated cytosine can serve as a unique identifier in a genomic map or DNA fingerprint. Fingerprinting methods that use amplification steps such as amplified ribosomal DNA restriction analysis (ARDRA), random amplified polymorphic DNA analysis (RAPD), restriction fragment length polymorphism (RFLP) and amplified fragment length polymorphism (AFLP), can be used in conjunction with the methylation detection methods disclosed herein.

In one embodiment, a target nucleic acid molecule can be treated with a reagent that modifies a target nucleic acid molecule as a function of the methylation state of the target nucleic acid molecule, fragments of the target nucleic acid molecule can be formed, and the mass of the fragments determined, to create a pattern of mass peaks characterized by one, two, three, or more characteristics such as the mass, the peak area, and the signal to noise ratio of the mass peak. Such a pattern of mass peaks can be used as an indicator of the methylation state of a target nucleic acid molecule.

In one embodiment, target nucleic acid molecule fragments can be from non-adjacent nucleotide sequences. Amplification and cleavage methods can be used to form target nucleic acid molecule fragments from broad regions of a chromosome or genome. A subset of these fragments can be further amplified and used as methylation fingerprint markers. As an alternative to further amplification, a subset of selected fragments can be separated from the remainder of the fragments by binding or hybridization methods, for example, hybridizing selected fragments to an array of capture oligonucleotide probes. This embodiment can use as a target nucleic acid molecule: a gene, a chromosome fragment, YAC, BAC, an entire chromosome, an entire genome, a plurality of genes, chromosome fragments, YACs, BACs, entire chromosomes and entire genomes, from one or more different organisms such as a population of a species or strains. Methods for amplifying subsets of nucleic acid fragments are known in the art, such as AFLP as disclosed in U.S. Pat. No. 6,045,994.

2. Methylation Analysis

Determination of the presence or absence of methylation in a particular target nucleic acid molecule can be used to provide a variety of information about a biological sample. For example, methylation analysis of a particular nucleic acid region can provide information about disease in a subject, can identify organisms or pathogens, can calculate frequency of methylation of a nucleic acid region or nucleotide locus, and can identify alleles linked to methylation.

a. Disease-Related Analysis

Increased or decreased levels of methylation have been associated with a variety of diseases. Methylation or lack of methylation at defined positions can be associated with a disease or a disease-free state. The methods disclosed herein can be used in methods of determining the propensity of a subject to disease, diagnosing a disease, and determining a treatment regimen for a subject having a disease.

The methylation state of a variety of nucleotide loci and/or nucleic acid regions are known to be correlated with a disease, disease outcome, and success of treatment of a disease, and also can be used to distinguish disease types that are difficult to distinguish according to the symptoms, histologic samples or blood or serum samples. For example, CpG island methylator indicator phenotype (CIMP) is present in some types of ovarian carcinomas, but not in other types (Strathdee, et al., Am. J. Pathol. 158:1121-1127 (2001)). In another example, methylation can be used to distinguish between a carcinoid tumor and a pancreatic endocrine tumor, which can have different expected outcomes and disease treatment regimens (Chan et al., Oncogene 22:924-934 (2003)). In another example, *H. pylori* dependent gastric mucosa associated lymphoid tissue (MALT) lymphomas are characterized as having several methylated nucleic acid regions, while those nucleic acid regions in *H. pylori* independent MALT lymphomas are not methylated Kaneko et al., Gut 52:641-646 (2003)). In another example, presence of CIMP in colorectal cancer typically does not contain abnormal p53 expression, and can be effectively treated using 5-fluorouracil, whereas such treatment is not as effective with CIMP-colorectal cancers (Van Rijnsoever et al., Clin. Cancer Res. 9:2898-2903 (2003)). Similar relationships with disease, disease outcome and disease treatment have been correlated with hypomethylation or unmethylated nucleic acid regions or unmethylated nucleotide loci.

Methods related to the disease state of a subject can be performed by collecting a sample from a subject, treating the sample with a reagent that modifies a target nucleic acid molecule sequence as a function of the methylation state of the target nucleic acid molecule, subjecting the sample to methylation specific amplification, then detecting one or more fragments that are associated with a disease or that are associated with a disease-free state. In one embodiment, the amplified target nucleic acid molecule is fragmented using the methods known in the art or disclosed herein. In another embodiment, the fragments are detected by measuring the mass of the target nucleic acid molecule or target nucleic acid molecule fragments. Target nucleic acid molecule or target nucleic acid molecule fragments also can be detected using hybridization-based detection methods known in the art or disclosed herein. Detection of a target nucleic acid molecule or target nucleic acid molecule fragment can identify the methylation state of a target nucleic acid molecule or the methylation state of one or more nucleotide loci of a target nucleic acid molecule. Identification of the methylation state of a target nucleic acid molecule or the methylation state of one or more nucleotide loci of a target nucleic acid molecule can indicate the propensity of the subject toward one or more diseases, the disease state of a subject, or an appropriate or inappropriate course of disease treatment or management for a subject.

A sample from a subject can be in any form, including a solid material such as a tissue, cells, a cell pellet, a cell extract, or a biopsy, or a biological fluid such as urine, blood, interstitial fluid, peritoneal fluid, plasma, lymph, ascites, sweat, saliva, follicular fluid, breast milk, non-milk breast secretions, serum, cerebral spinal fluid, feces, seminal fluid, lung sputum, amniotic fluid, exudate from a region of infection or inflammation, a mouth wash containing buccal cells, synovial fluid, or any other fluid sample produced by the subject. In addition, the sample can be collected from tissues, including, but are not limited to, bone marrow, epithelium, stomach, prostate, kidney, bladder, breast, colon, lung, pancreas, endometrium, neuron and muscle. Samples can include organs, and pathological samples such as a formalin-fixed sample embedded in paraffin. If desired, solid materials can be mixed with a fluid. Samples examined using the methods described herein can be treated in one or more purification steps in order to increase the purity of the desired cells or nucleic acid in the sample, Samples also can be examined using the methods described herein without any purification steps to increase the purity of desired cells or nucleic acid.

In one embodiment, detection of a methylated target nucleic acid molecule or one or more methylated nucleotide loci of a target nucleic acid molecule can indicate an increased propensity toward one or more diseases associated with methylated DNA. In another embodiment, detection of a methylated target nucleic acid molecule or one or more methylated nucleotide loci of a target nucleic acid molecule can indicate a decreased propensity toward one or more diseases associated with methylated DNA. In another embodiment, detection of an unmethylated target nucleic acid molecule or one or more unmethylated nucleotide loci of a target nucleic acid molecule can indicate a decreased propensity toward one or more diseases associated with methylated DNA. In yet another embodiment, detection of an unmethylated target nucleic acid molecule or one or more unmethylated nucleotide loci of a target nucleic acid molecule can indicate an increased propensity toward one or more diseases associated with methylated DNA.

Detection of a methylated target nucleic acid molecule or one or more methylated nucleotide loci of a target nucleic acid molecule can indicate the presence of a methylation state-associated disease in a subject. In another embodiment, detection of a methylated target nucleic acid molecule or one or more methylated nucleotide loci of a target nucleic acid molecule can indicate the absence of a methylation state-associated disease in a subject. In another embodiment, detection of an unmethylated target nucleic acid molecule or one or more unmethylated nucleotide loci of a target nucleic acid molecule can indicate the absence of a methylation state-associated disease in a subject. In yet another embodiment, detection of an unmethylated target nucleic acid molecule or one or more unmethylated nucleotide loci of a target nucleic acid molecule can indicate the presence of a methylation state-associated disease in a subject.

Detection of a methylated target nucleic acid molecule or one or more methylated nucleotide loci of a target nucleic acid molecule can indicate an increased effectiveness of a disease treatment regimen. In another embodiment, detection of a methylated target nucleic acid molecule or one or more methylated nucleotide loci of a target nucleic acid molecule can indicate a decreased effectiveness of a disease treatment regimen. In another embodiment, detection of an unmethylated target nucleic acid molecule or one or more unmethylated nucleotide loci of a target nucleic acid molecule can indicate an increased effectiveness of a disease treatment regimen. In yet another embodiment, detection of an unmethylated target nucleic acid molecule or one or more unmethylated nucleotide loci of a target nucleic acid molecule can indicate a decreased effectiveness of a disease treatment regimen. Treatment regimens can include administration of a pharmaceutical compound or composition, including a chemotherapeutic compound or composition, surgery or other medical procedure, physical therapy, occupational therapy, dietary modification, and behavioral modification.

b. Organism Identification

Methods provided herein can be used to identify an organism or to distinguish an organism as different from other organisms. In one embodiment, the identification of a human sample can be performed. Methylated regions can be useful markers for human identification, paternity and maternity testing, genetic mapping, immigration and inheritance disputes, zygosity testing in twins, tests for inbreeding in humans, quality control of human cultured cells, identification of human remains, and testing of semen samples, blood stains and other material in forensic medicine. Such methylated regions also can be useful markers in commercial animal breeding and pedigree analysis and in commercial plant breeding. Traits of economic importance in plant crops and animals can be identified through identifying methylated regions. The target nucleic acid molecules (e.g., genomic DNA) can be obtained from one long target nucleic acid molecule region and/or multiple short target nucleic acid molecule regions. In other embodiments, methods can be used for identifying non-human organisms such as non-human mammals, birds, plants, fungi and bacteria.

c. Pathogen Identification and Typing

Also contemplated herein is a process or method for identifying strains of microorganisms using the methylation identification methods provided herein. The microorganism(s) are selected from a variety of organisms including, but not limited to, bacteria, fungi, protozoa, ciliates, and viruses. The microorganisms are not limited to a particular genus, species, strain, or serotype. The microorganisms can be identified by determining methylation state and/or methylation state variations of a target microorganism nucleic acid relative to one or more reference nucleic acids. The reference nucleic acid(s) can be obtained from, for example, other microorganisms from the same or different genus, species strain or serotype, or from a host prokaryotic or eukaryotic organism.

Identification and typing of bacterial pathogens can be critical in the clinical management of infectious diseases. Precise identity of a microbe is used not only to differentiate a disease state from a healthy state, but to determine whether and which antibiotics or other antimicrobial therapies are suitable for treatment. Traditional methods of pathogen typing have used a variety of phenotypic features, including growth characteristics, color, cell or colony morphology, antibiotic susceptibility, staining, smell and reactivity with specific antibodies to identify bacteria. All of these methods require culture of the pathogen, which suffers from a number of serious shortcomings, including high material and labor costs, danger of worker exposure, false positives due to mishandling and false negatives due to low numbers of viable cells or due to the fastidious culture requirements of many pathogens. In addition, culture methods require a relatively long time to achieve diagnosis, and because of the potentially life-threatening nature of such infections, antimicrobial therapy is often started before the results can be obtained.

In many cases, the pathogens are very similar to the organisms that make up the normal flora, and can be indistinguishable from the innocuous strains by the phenotypic methods cited herein. In these cases, determination of the presence of the pathogenic strain can require the higher resolution afforded by the methylation detection methods provided herein. For example, methylation state-based sequence modification of a target nucleic acid molecule, followed by fragmentation and fragment detection using matrix-assisted laser desorption/ionization time-of-flight mass spectrometry, followed by screening for methylation state variations allows reliable discrimination of target nucleic acid molecules differing by only one methylated nucleotide, and combines the discriminatory power of methylation specific amplification with the speed and information provided through MALDI-TOF MS. Similarly, methods for identifying the methylation state of a nucleotide of a target nucleic acid molecule by comparing one or more mass peaks or mass peak patterns can be used to detect such sequence variations.

d. Haplotyping

The methods provided herein can be used to detect haplotypes. In any diploid cell, there are two haplotypes at any gene or other chromosomal segment that can contain one or more distinguishing methylation variations. Determination of haplotypes can be valuable for understanding the genetic basis of a variety of phenotypes including disease predisposition or susceptibility, response to therapeutic interventions, and other phenotypes of interest in medicine, animal husbandry, and agriculture.

Haplotyping procedures permit the selection of a portion of DNA from one of an individual's two homologous chromosomes and to identify linked potential methylation sites on that portion of DNA. Haplotyping procedures can be performed by separately identifying the methylation state of a target nucleic acid molecule or the methylation state of a nucleotide locus of a target nucleic acid molecule corresponding to each of the two haploid copies of DNA. Haplotyping also can be performed by pooling both haploid copies of DNA, and simultaneously identifying the methylation state of a target nucleic acid molecule or a nucleotide locus of a target nucleic acid molecule corresponding to both haploid copies of DNA. Simultaneous identification methods typically yields results indicating that both haploid copies are unmethylated, both haploid copies are methylated, or one haploid copy is unmethylated and one haploid copy is methylated. Such results can be determined by, for example, identifying mass peaks associated with methylated target nucleic acid molecule and/or mass peaks associated with unmethylated target nucleic acid molecule. Presence of only mass peaks associated with methylated nucleic acid can indicate both haploid copies are methylated. Presence of only mass peaks associated with unmethylated nucleic acid can indicate both haploid copies are unmethylated. Presence of both mass peaks associated with methylated nucleic acid and mass peaks associated with unmethylated nucleic acid can indicate one haploid copy is methylated and the other is unmethylated. When both mass peaks associated with methylated nucleic acid and mass peaks associated with unmethylated nucleic acid are present, the relative amount of nucleic acid fragments giving rise to the peaks can be determined using the methods provided herein; typically, haplotyping analysis will provide a ratio of about 50/50 when one haplotype is methylated and the other is not.

The direct resolution of haplotypes can yield increased information content, improving the diagnosis of any linked disease genes or identifying linkages associated with those diseases.

e. Determining Methylation Frequency

The methods herein described are useful for identifying one or more nucleic acid regions or nucleotides whose methylation state is correlated with a population grouped by age, ethnicity, sex, other disease, similar exposure to environmental conditions, similar intake (e.g., food, alcohol, tobacco), or other criteria. Methods disclosed herein for comparing the relative amount of methylation of a target nucleic acid molecule from a sample can be used to determine for a population the likelihood that a nucleic acid region or a nucleotide is methylated. For example, a sample can contain DNA from two or more members of a population, and the methylation state identification methods disclosed herein can be used to determine the amount of nucleic acid regions or nucleotides that are methylated relative to the amount of nucleic acid regions or nucleotides that are unmethylated. The methylation state of nucleic acid regions or nucleotides known to be associated at some level with disease also can be used to determine the susceptibility of a member of a population to being affected by a methylation-associated disease. Determining changes in methylation state in populations also can allow the identification of previously unknown methylation positions and ultimately a gene or pathway involved in the onset and progression of disease.

f. Identifying Alleles

Methylation state identification methods provided herein can be used to identify or provide a likelihood of the presence of one or more additional alleles. For example, identifying the methylation state of a particular locus can serve to identify or provide a likelihood of occurrence of a SNP at the same, proximal or distal locus. Alleles are known to be linked, or to be inherited at a higher rate than expected for random inheritance of alleles. The occurrence of alleles together more often than would be expected for random inheritance is referred to as linkage disequilibrium.

As is known in the art, the methylation state of nucleic acid regions (e.g., CpG islands) or nucleotide loci can be linked to a variety of different alleles. Types of alleles known to be linked to methylation include SNPs, microsatellites (e.g., microsatellite instability), deletions, loss of heterozygosity, imprinting or loss of imprinting, and other methylated or unmethylated regions. Alleles as used herein refers to a nucleotide locus or nucleotide loci of interest, and encompasses both commonly occurring or "wild type" loci and also encompasses variant loci (variant alleles). For example, p14 methylation is associated with the presence of microsatellite instability and the absence of p53 mutations in colon cancer (Shen et al., Gastroenterology 124:626-633 (2003)). In another example, hypermethylation of the hMLH1 gene promotor is associated with microsatellite instability (Kim et al., J. Pathol. 200:23-31 (2003)). In another example, mutations in the BRAF gene are correlated with hMLH1 promotor methylation (Deng et al., Clin. Cancer Res. 10:191-195 (2004)). In another example, hypermethylation of several genes is linked to microsatellite instability, G to A transitions, and double-strand breaks in DNA (Esteller, Eur. J. Cancer 36:2294-2300 (2000)). In another example, hypomethylation is correlated with an increase in loss of heterozygosity (Eden et al., Science 300:455 (2003)). In another example, loss of maternal allele-specific methylation of KvDMR1 is associated with the T382G SNP of DMRO (Murrell et al., Hum. Mol. Genet. 13:247-255 (2004)). In another example, presence of a SNP is correlated with a methylated locus (Ober et al., Am. J. Hum. Genet. 72:1425-1435 (2003)).

Included in the methods provided herein is a method for identifying or determining an increased likelihood of the presence or absence of an allele by identifying the methylation state of one or more nucleic acid regions (e.g., one or more CpG islands) or one or more nucleotide loci. Linkage disequilibrium can indicate the frequency with which the presence of a first genetic or epigenetic feature (e.g., methylation) is observed along with a second genetic or epigenetic feature (e.g., a SNP allele). Thus, according to the degree of linkage disequilibrium, identifying the methylation state of one or more nucleic acid regions or one or more nucleotide loci can be used to identify the likelihood that an allele is present or absent. The methods provided herein also can be used to identify the degree of linkage disequilibrium between one or more methylated or unmethylated nucleic acid regions or the methylation state of one or more nucleotide loci and a particular allele. Such methods can include selecting a particular allele, pooling two or more nucleic acid samples containing the allele, and determining the frequency with which the allele is observed along with one or more methylated or unmethylated nucleic acid regions or the methylation state of one or more nucleotide loci. Methods for determining the presence of linked alleles are known in the art, as exemplified in U.S. 20030190644, and can be used in conjunction with the methylation state identification methods provided herein.

3. Combinations and Kits

In another embodiment, there are provided diagnostic systems, typically in combination or kit form, containing at least one primer and at least one reagent for performing one or more of the fragmentation methods described herein, in a suitable packaging material. In one embodiment, for example, the diagnostic system, combination or kit contains one or more methylation specific primers, and reagents for performing one or more base specific cleavage reactions, such as the methylation specific primers and one or more RNases, DNases or chemical reagents described in the methods provided herein. Diagnostic systems, combinations and kits can be useful for identifying the methylation state of a target nucleic acid molecule or the methylation state of a nucleotide locus of a target nucleic acid molecule.

A diagnostic system, combination or kit can include at least one primer, typically two or more primers, including at least one methylation specific primer; and proteins such as enzymes for performing amplification, transcription, and/or fragmentation steps; as separately packaged chemical reagents in amounts sufficient for at least one assay. A diagnostic system, combination or kit also can include one or more amplification blockers, one or more dNTPs, one or more rNTPs, combinations of dNTPs and rNTPs, one or more compositions for conditioning target nucleic acid molecule fragments prior to mass spectrometric measurement, one or more MALDI matrix compounds, one or more mass spectrometry substrates, as known in the art or provided in the methods described herein.

One exemplary combination can contain a reagent that modifies one or more nucleotides of the target nucleic acid molecule as a function of the methylation state of the target nucleic acid molecule, such as bisulfite; one or more methylation specific primers for specifically hybridizing to a reagent-treated target nucleic acid molecule, such as one or more methylation specific PCR primers; and one or more compounds for fragmenting amplified target nucleic acid molecule, such as RNases, including RNase A or RNase T1.

Also provided herein are combinations that include the kits provided herein, and one or more devices such as a mass spectrometer, a thermal cycler, an apparatus for sample preparation such as a tissue homogenizer, as known in the art or provided herein. A kit also can include the appropriate buffers and solutions for performing the methylation identification methods described herein.

The packaging material used in the kit can be one or more physical structures used to house the contents of the kit, and can be constructed by well known methods, typically to provide a sterile, contaminant-free environment. The packaging material can have a label which indicates the components of the kit. In addition, the packaging material contains instructions indicating how the materials within the kit are employed to identify the methylation state of a target nucleic acid molecule or the methylation state of a nucleotide locus of a target nucleic acid molecule. Instructions typically include a tangible expression describing the reagent concentration or at least one assay method parameter, such as the relative amounts of reagent and sample to be admixed, maintenance time periods for reagent/sample admixtures, temperature, buffer conditions and other parameters. The kit can include one or more containers capable of holding within fixed limits a primer, enzyme or other reactant or buffer solution used in the methods of methylation identification. For example, a kit can include a glass vial used to contain milligram quantities of a primer or enzyme. A kit also can include substrates, supports or containers for performing the methylation identification methods, including vials or tubes, or a mass spectrometry substrate such as a Sequenom SpectroCHIP® substrate.

The following example is included for illustrative purposes only and are not intended to limit the scope of the invention.

I. Example

The following example demonstrates a method for identifying the methylation state of a target nucleic acid molecule.

Methods

Bisulphite Treatment

Bisulphite treatment was performed according to the method provided in Paulin et al., *Nucl. Acids Res.* 26:5009-5011 (1998). Genomic DNA (2 µg) was digested with restriction endonucleases, then denatured by adding 3 M sodium hydroxide and incubating for 15 min at 37° C. A 6.24 M urea/2 M sodium metabisulphite (4 M bisulphite) solution and a 10 mM hydroquinone solution were added to the denatured DNA to achieve final concentrations of 5.36 M urea, 3.44 M bisulfite and 0.5 mM hydroquinone. The DNA solution was placed in a 0.5 ml tube and overlaid with mineral oil. For 20 cycles in a PCR machine (MJ Tetrad), the tube was repeatedly heated to 95° C. for 30 seconds and incubated at 55° C. for 15 minutes. Bisulphite treated DNA was further processed as described in Clark et al., *Nucl. Acids Res.* 22:2990-2997 (1994), with the exception that a Bresaclean DNA purification step (Geneworks, Adelaide, Australia) was used to desalt the DNA.

PCR and in vitro Transcription

The target nucleic acid molecule of interest, MGMT, was PCR-amplified from bisulphite treated human genomic DNA using methylation specific primers that incorporate the T7 [5'-CAG TAA TAC GAC TCA CTA TAG GGA GA] promoter sequence (SEQ ID NO: 1). The PCR product can be optionally cloned into a pGEM-T vector system (Promega) and reamplified from the cloned DNA.

For amplification specific to non-methylated DNA, we used the following gene specific primer sequences:
MGMT_U T7_REV: cagtaatacgactcactatagggagaag-gcttttcctatcacaaaaataatccac (SEQ ID NO: 2)
MGMT_U_10MER_FOR: aggaagagagggattttat-taagtgggtgttg (SEQ ID NO: 3).

For methylation specific amplification, we used these primer sequences:
MGMT_M_T7_REV: cagtaatacgactcactatagggagaag-gctctificctatcacaaaaataatccg (SEQ ID NO: 4)
MGMT_M_10MER_FOR: aggaagagaggattttat-taagcgggcgtc ISEQ ID NO: 5).

The PCR reactions were carried out in a total volume of 5 µl using 1 pmol of each primer, 40 µM dNTP, 0.1 U µl Hot Star Taq DNA polymerase (Qiagen), 1.5 mM $MgCl_2$ and a buffer supplied with the enzyme. This reaction mix was preactivated for 15 minutes at 95° C. The reactions were amplified in 45 cycles of 95° C. for 20 seconds, 62° C. for 30 seconds and 72° C. for 30 seconds, and after the cycles were complete, the reaction was incubated at 72° C. for 3 minutes. Unused dNTPs were dephosphorylated by adding 1.7 µl $H_2O$ and 0.3 µl Shrimp Alkaline Phosphatase (0.3 U) and incubated at 37° C. for 20 minutes.

A two µl aliquot of the PCR reaction (25 to 250 ng amplicon) was directly used as template in a 4-µl transcription reaction. A mutant polymerase (20 units T7 R&DNA polymerase; Epicentre, Madison, Wis.) was used to incorporate either dCTP or dUTP/dTTP in the transcripts. Ribonucleotides were used at 1 mM and the (optional) dNTP substrate at 5 mM; other components in the reaction are as recommended by the enzyme supplier. Following transcription, RNase was added to cleave the in vitro transcript. The mixture was then further diluted with $H_2O$ to a final volume of 27 µl.

The protocol is known in the art, as demonstrated in Stanssens et al., Genome Res. 14:126-133 (2004).

Sample Conditioning and Mass Spectrometry Measurements.

Conditioning of the phosphate backbone was achieved by the addition of 6 mg CLEAN Resin (Sequenom Inc., San Diego, Calif.) to the transcription sample. A 15 nl aliquot of the cleavage reaction was robotically dispensed onto a silicon chip preloaded with matrix (SpectroCHIP; Sequenom Inc., San Diego, Calif.). Mass spectra were collected using a MassARRAY mass spectrometer (Bruker-SEQUENOM).

Discovery of Genomic Methylation Profiles

The test amplicon can be a 400 to 500 base pair target nucleic acid molecule including 25-30 CpG sites. The top strand and bottom strand of this region can be separately examined. To achieve a segregation into methylated and non-methylated templates the bisulphite treated genomic DNA can be amplified, and the amplification products can be cloned. A difference in mass signal patterns will be observed in reactions that cleave C-specific on the forward or G-specific on the reverse strand. A single cleavage reaction generates a mass signal pattern that allows discrimination between methylated and non-methylated template DNA. Those strands in which methylation has protected the cytosine from conversion into uracil will carry cleavage sites in the amplification product. These cleavage sites result in fragmentation of the transcription product with fragment lengths that are determined by the distance of the neighboring methylated CpG sites. A non-methylated template does not contain cytosine and therefore carries no cleavage sites. The resulting full-length transcription product is not detected by MALDI-TOF. These reactions provide mass patterns useful for discovery of methylation and discrimination between methylated and non-methylated samples, because the difference of fragments derived from non-methylated and methylated DNA is readily measurable. In addition, these patterns are suited to identify methylation in mixtures that contain only 5% methylated DNA after selective PCR amplification.

Methylation Ratio Analysis

Another base-specific cleavage reaction is suited for determination of methylation ratios. Methylation induced C/T changes on the forward strand are represented as G/A changes on the reverse strand. These changes lead to a mass shift of 16 Daltons (G/A mass shift) or a multitude thereof, when multiple CpGs are enclosed in one cleavage product. In reactions where methylation results in a mass shift of signals, one signal represents the methylated template and a second signal represents the non-methylated template. The intensities of these signals can be compared to determine the ratio of methylated vs. non-methylated template. Also, the base composition of the measured fragments differs only by one or a few nucleotides, which assures equal desorption and ionization behavior during MALDI-TOF measurement. Methods for signal intensity estimation such as "area-under the peak" and "signal to noise" can yield similar results. Depending on the sequence of the target nucleic acid molecule, multiple signal pairs can be used in determining the ratio between signal intensities. This information can be used to assess the degree of methylation for each CpG site independently, or, if all CpG sites are methylated approximately to the same degree, to average the methylation content over the complete target region. A direct correlation between signal intensity ratios and the ratio of the deployed DNAs can be determined for ranges of 10%-90% of methylated template. If the ratio between methylated and non-methylated template is below 10% or exceeds 90%, the signals that represent the lower amount of template can still be detected, but the quantitation can be subject to higher error.

Methylation Pattern Analysis

Base specific cleavage can determine the methylation status of every CpG within a given target nucleic acid molecule. A C-specific forward reaction generates a cleavage site for each methylated CpG within the amplicon. Therefore, in theory, each methylated CpG generates a specific fragment resulting in at least one indicative mass signal in the mass spectrum. Some of these signals might not be detectable because their masses fall outside of the high or low mass cutoff. Current MALDI-TOF equipment allows detection of cleavage products with a mass between about 1000 to 11000 Da, which is equivalent to a fragment of about 3 to about 35 nucleotides in length. The analysis of one reaction alone can be used in determining the methylation status of around 75% (which can be greater or smaller depending on the target nucleic acid molecule size and sequence and degree of methylation) of all CpG sites within the target nucleic acid molecule. To obtain the information about all CpG sites two reactions can be sufficient. Using four reactions provides the benefit of redundant information. For example, more than 90% of all CpG sites can be represented by more than one signal when four reactions are carried out. This means that most or all methylation events are independently confirmed by more than one observation. This redundancy can be useful in diagnostic applications.

Results

Provided below is an example of a method used to analyze base cleavage fragments derived from PCR reactions that were intended to be specific for amplification of methylated versus non-methylated template DNA. The method allows for the elimination of false positive results that arise when a PCR reaction using methylation specific primers results in amplification of non-methylated DNA. In brief, the mass signal pattern was recorded and compared to an in silico calculated fragmentation pattern. The methylation status was determined by comparing the obtained mass signal pattern to the in silico calculated mass signals for methylated and non-methylated template DNA.

FIGS. 1 and 2 show an overlay of two mass spectra: the upper spectrum is derived from a "U" reaction specific for amplification of non-methylated DNA (where "U" corresponds to unmethylated), and the lower spectrum is derived from a "M" reaction specific for the amplification of methylated DNA (where "M" corresponds to methylated). In FIGS. 1 and 2, the dotted lines indicate reference mass signals for cleavage products derived from the non-methylated template (FIG. 1) and the methylated template (FIG. 2) respectively. FIG. 1 shows that the cleavage products derived form the non-methylated template are found at their expected masses. All signals of the upper spectrum were found at their expected mass, as calculated by in silico simulation, thus indicating that the specific amplification of non-methylated template DNA was successful. On the contrary, FIG. 2 shows that cleavage product derived from the amplification specific for methylated template DNA does not align with the expected masses. The signals at 3913 Daltons and 2878 Daltons are not affected by methylation and remain aligned, however, the signals at 2525 Daltons and 3473 Daltons correspond to 2509 Daltons and 3457 Daltons in the non-methylated reference. By comparing FIG. 1 and FIG. 2, it is apparent that the cleavage products from the methylation specific reaction are detected at masses specific for non-methylated template DNA. This demonstrates that the methylation specific amplification reaction actually amplified non-methylated DNA and yielded a false positive result by gel electrophoresis, which could be corrected by mass spectrometric analysis.

\* \* \*

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Incorporation by reference of these documents, standing alone, should not be construed as an assertion or admission that any portion of the contents of any document is considered to be essential material for satisfying any national or regional statutory disclosure requirement for patent applications. Notwithstanding, the right is reserved for relying upon any of such documents, where appropriate, for providing material deemed essential to the claimed subject matter by an examining authority or court.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

What is claimed is:

1. A method for determining the methylation state of one or more nucleotide loci in a target nucleic acid molecule, which comprises:
   (a) generating by mass spectrometry mass signals of a fragmented target nucleic acid molecule,
   wherein the target nucleic acid molecule has been (i) treated with a reagent that modifies a nucleotide according to whether the nucleotide is methylated, (ii) amplified and (iii) contacted with a base-specific cleavage reagent that cleaves the target nucleic acid into fragments,
   (b) comparing the mass signals of fragments of at least three nucleotides in length of the target nucleic acid molecule to the corresponding reference mass signals of fragments of at least three nucleotides in length derived from base-specific cleavage or simulated cleavage of a reference nucleic acid molecule in which each of the one or more nucleotide loci are methylated and/or the corresponding reference mass signals fragments of at least three nucleotides in length derived from base-specific cleavage or simulated cleavage of a reference nucleic acid molecule in which each of the one or more nucleotide loci are unmethylated to determine fragment mass patterns, wherein a fragment mass pattern includes determining: (i) the presence of a fragment, (ii) the absence of a fragment, and (iii) the mass of a fragment relative to a reference, and
   (c) determining the methylation state of the one or more nucleotide loci in the target nucleic acid molecule based on the fragment mass patterns determined in (b).

2. The method of claim 1, wherein the reference mass signals are calculated mass signals.

3. The method of claim 1, wherein the reference mass signals are of methylated nucleic acid molecule fragments.

4. The method of claim 1, wherein the reference mass signals are of unmethylated nucleic acid molecule fragments.

5. The method of claim 1, wherein the methylation state of one or more nucleotide loci are identified in two or more target nucleic acids.

6. The method of claim 5, wherein each of the two or more target nucleic acids are from different biological samples.

7. The method of claim 6, wherein the target nucleic acids are pooled.

8. The method of claim 6, wherein the methylation state of one or more nucleotide loci in each target nucleic acid is determined.

9. The method of claim 8, which further comprises calculating a ratio of methylated nucleotide to unmethylated nucleotide at the one or more nucleotide loci.

10. The method of claim 1, wherein the base-specific cleavage reagent is a guanine-specific cleavage reagent.

11. The method of claim 1, wherein the base-specific cleavage reagent is a cytosine-specific cleavage reagent.

12. The method of claim 1, wherein the mass signals are detected by mass spectrometry.

13. The method of claim 1, wherein the mass signals are detected by MALDI-TOF mass spectrometry.

14. The method of claim 1, wherein the base-specific cleavage reagent is selected from the group consisting of an RNase, a DNase, an alkaline compound, piperidine formate, piperidine, dimethyl sulfate and hydrazine.

15. The method of claim 14, wherein the RNase is selected from the group consisting of RNase A, RNase T1 and RNase U2.

16. The method of claim 1, wherein amplified target nucleic acid is divided into two aliquots, and the base-specific cleavage reagent applied to the first aliquot is different from the base-specific cleavage reagent applied to the second aliquot.

17. The method of claim 16, wherein the first aliquot is treated with RNase A and the second aliquot is treated with RNase T1.

18. The method of claim 1, wherein the target nucleic acid is amplified by a process comprising transcription.

19. The method of claim 1, wherein the target nucleic acid is amplified by a process comprising a polymerase chain reaction.

20. The method of claim 1, wherein a target nucleic acid comprises a gene promoter region or portion thereof.

21. The method of claim 20, wherein the gene promoter region is a tumor suppressor promoter region.

22. The method of claim 1, wherein the reagent that modifies a nucleotide according to whether the nucleotide is methylated deaminates unmethylated cytosine.

23. The method of claim 22, wherein the unmethylated cytosine is modified to produce uracil.

24. The method of claim 1, wherein the reagent that modifies a nucleotide according to whether the nucleotide is methylated comprises bisulfite.

25. The method of claim 1, wherein the product of (a) (ii) is contacted with a base-specific cleavage reagent in (a) (iii).

26. The method of claim 1, wherein amplification is with a methylation specific primer.

27. The method of claim 26, wherein one or more methylated nucleotides are located in regions of the target nucleic acid molecule to which the methylation-specific primer does not hybridize.

* * * * *